US006087160A

United States Patent [19]
Yuan et al.

[11] Patent Number: 6,087,160
[45] Date of Patent: Jul. 11, 2000

[54] PROGRAMMED CELL DEATH GENES AND PROTEINS

[75] Inventors: Junying Yuan, Newton, Mass.; Masayuki Miura, Tsukuba, Japan

[73] Assignee: The General Hospital Corporation, Boston, Mass.

[21] Appl. No.: 08/368,704

[22] Filed: Jan. 4, 1995

Related U.S. Application Data

[63] Continuation-in-part of application No. 08/258,287, Jun. 10, 1994, which is a continuation-in-part of application No. 08/080,850, Jun. 24, 1993, abandoned.

[51] Int. Cl.[7] .................................................. C12N 15/63
[52] U.S. Cl. .................... 435/320.1; 435/69.1; 435/226; 435/219; 536/23.2; 536/23.5
[58] Field of Search ................. 536/23.2, 23.5; 435/69.1, 172.3, 226, 320.1, 219

[56] References Cited

FOREIGN PATENT DOCUMENTS

| 0 533 350 A1 | 3/1993 | European Pat. Off. . |
|---|---|---|
| WO 91/15577 | 10/1991 | WIPO . |
| WO 93/05071 | 3/1993 | WIPO . |
| WO 93/11246 | 6/1993 | WIPO . |
| WO 93/25685 | 12/1993 | WIPO . |
| WO 93/25694 | 12/1993 | WIPO . |
| 9600297 | 1/1996 | WIPO . |

OTHER PUBLICATIONS

Eddington (1993) Looking Death in the Eye: Apoptosis and Cancer Research. Bio/Technology, vol. 11, pp. 787–792, 1993.
Black, R.A., et al., "A Pre–aspartate–specific Protease from Human Leukocytes That Cleaves Pro–interleukin–1β,"*J. Biol. Chem.* 264(10):5323–5326 (1989).
Bruno, S., et al., "Inhibitors of Proteases Prevent Endonucleolysis Accompanying Apoptotic Death of HL–60 Leukemic Cells and Normal Thymocytes," *Leukemia* 6(11):1113–1120 (Nov. 1992).
Hockenbery, D., et al., "Bcl–2 is an inner mitochondrial membrane protein that blocks programmed cell death," *Nature* 348:334–336 (1990).
Komiyama, T., et al., "Inhibition of Interleukin–1β Converting Enzyme by the Cowpox Virus Serpin CrmA," *J. Biol. Chem.* 269(30):19331–19337 (Jul. 1994).
Kumar, S., et al., "Identification of a Set of Genes with Developmentally Down–regulated Expression in the Mouse Brain," *Biochem. Biophys. Res. Comm.* 185(3):1155–1161 (Jun. 1992).
Tewari, M., and Dixit, V.M., "Fas—and Tumor Necrosis Factor–induced Apoptosis Is Inhibited by the Poxvirus crmA Gene Product," *J. Biol. Chem.* 270(7):3255–3260 (Feb. 1995).
Supplementary European Search Report for European Application No. EP 94 92 1950.5.
Miura, M., et al., "Tumor necrosis factor–induced apoptosis is mediated by a CrmA–sensitive cell death pathway," *Proc. Natl. Acad. Sci. USA* 92:8318–8322 (Aug. 1995).

Wang, L., et al., "Ich–1, an Ice/ced–3–Related Gene, Encodes Both Positive and Negative Regulators of Programmed Cell Death," *Cell* 78:739–750 (Sep. 1994).
Dinarello, C.A., "Interleukin–1ª," *Ann N.Y. Acad. Sci.*, 546:122–132 (Dec. 1998).
Sarih, M., et al., "Silica induces apoptosis in macrophages and the release of interleukin–1α and interleukin–1β," *J. Leukoc. Biol.*, 54(3):407–113 (Nov. 1993).
Zychlinsky, A., et al., "Interleukin–1 is released by Murine Macrophages during Apoptosis Induced by Shigella flexneri," *J. Clin. Invest.*, 94(3):1328–1332 (Sep. 1994).
International Search Report for Patent Application No. PCT/US94/06630 (attached cited reference: UEMBL, Accession No. D28492 and D10713, issued Jun. 4, 1994, Kumar et al., "Mouse mRNA for Nedd2 protein"; sequence).
Barinaga, M., Cell Suicide: By ICE, Not Fire, *Science* 263:754–756 (1994).
Barinaga, M., Death Gives Birth to the Nervous System. But How?, *Science* 259:762–763 (1993).
Black, R.A. et al., Activation of interleukin–1β by a co–induced protease, *FEBS Letters* 247 (2):386–390 (Apr. 1989).
Cerretti, D.P. et al., Molecular Cloning of the Interleukin–1β Converting Enzyme, *Science* 256:97–100 (Apr. 3, 1992).
Ellis, H.M. et al., Genetic Control of Programmed Cell Death in the Nematode C. elegans, *Cell* 44:817–829 (Mar. 28, 1986).
Ellis, R.E. et al., Genes Required for the Engulfment of Cell Corpses During Programmed Cell Death in *Caenorhabditis elegans, Genetics* 129:79–94 (Sep. 1991).
Ellis, R.E. et al., Two C. elegans genes control the programmed deaths of specific cells in the pharynx, *Development* 112:591–603 (1991).
Gagliardini, V. et al., Prevention of Vertebrate Neuronal Death by the crmA Gene, *Science* 263:826–828 (1994).
Hengartner, M.O. et al., *Caenorhabditis elegans* gene ced–9 protects cells from programmed cell death, *Nature* 356:494–499 (Apr. 9, 1992).
Hogquist, K.A. et al., Interleukin 1 is processed and released during apoptosis, *Proc. Natl. Acad. Sci. USA* 88:8485–8489 (Oct. 1991).
Jacobson, M.D. et al., Bcl–2 blocks apoptosis in cells lacking mitochondrial DNA, *Nature* 361:365–369 (Jan. 28, 1993).
Kostura, M.J. et al., Identification of a monocyte specific pre–interleukin 1β convertase activity, *Proc. Natl. Acad. Sci. USA* 86:5227–5231 (Jul. 1989).
Marx, J., Cell Death Studies Yield Cancer Clues, *Science* 259:760–761 (1993).

(List continued on next page.)

*Primary Examiner*—Bradley Sisson
*Assistant Examiner*—Enrique D. Longton
*Attorney, Agent, or Firm*—Sterne, Kessler, Goldstein & Fox P.L.L.C.

[57] ABSTRACT

This invention relates to genes involved in regulating programmed cell death, the proteins encoded by such genes and methods for controlling programmed cell death by regulating the activity of the cell death gene products.

15 Claims, 46 Drawing Sheets

OTHER PUBLICATIONS

Miura, M. et al., Induction of Apoptosis in Fibroblasts by IL–1β–Converting Enzyme, a Mammalian Homolog of the C. elegans Cell Death Gene ced–3, *Cell* 75:653–660 (1993).

Nett, M.A. et al., Molecular Cloning of the Murine IL–1β Converting Enzyme cDNA, *J. Immunol.* 149 (10) : 3254–3259 (Nov. 15, 1992).

Nuñez, G. et al., Deregulated Bcl–2 Gene Expression Selectively Prolongs Survival of Growth Factor–Deprived Hempoietic Cell Lines, *J. Immunol.* 144(9) :3602–3610 (May 1, 1990).

Oltvai, Z.N. et al., Bcl–2 Heterodimerizes In Vivo with a Conserved Homolog, Bax, That Accelerates Programmed Cell Death, *Cell* 74:609–619 (1993).

Ray, C.A. et al., Viral Inhibition of Inflammation: Cowpox Virus Encodes an Inhibitor of the Interleukin–1β Converting Enzyme, *Cell* 69:597–604 (May 15, 1992).

Sentman, C.L. et al., bcl–2 Inhibits Multiple Forms of Apoptosis but not Negative Selection in Thymocytes, *Cell* 67:879–888 (Nov. 29, 1991).

Strasser, A. et al., bcl–2 Transgene Inhibits T Cell Death and Perturbs Thymic Self–Censorship, *Cell* 67:889–899 (Nov. 29, 1991).

Thornberry, N.A. et al., A novel heterodimeric cysteine protease is required for interleukin–1β processing in monocytes, *Nature* 356:768–774 (Apr. 30, 1992).

Vaux, D.L. et al., Prevention of Programmed Cell Death in *Caenorhabditis elegans* by Human bcl–2, *Science* 258:1955–1957 (Dec. 18, 1992).

Yuan, J. et al., The *Caenorhabditis elegans* cell death gene ced–4 encodes a novel protein and is expressed during the period of extensive programmed cell death, *Development* 116:309–320 (1992).

Yuan, J. et al., The *Caenorhabditis elegans* Genes ced–3 and ced–4 Act Cell Autonomously to Cause Programmed Cell Death, *Developmental Biology* 138:33–41 (1990).

Yuan, J. et al., The C. elegans Cell Death Gene ced–3 encodes a protein similar to mammalian Interleukin–1β–converting enzyme, cell 75:641–652 (1993).

```
   1 AGATCTGAAATAAGGTGATAAATTAATAAATTAAGTGTATTTCTGAGGAAATTTGACTGT
  61 TTTAGCACAATTAATCTTGTTTCAGAAAAAAAGTCCAGTTTTCTAGATTTTTCCGTCTTA
 121 TTGTCGAATTAATATCCCTATTATCACTTTTTCATGCTCATCCTCGAGCGGCACGTCCTC
 181 AAAGAATTGTGAGAGCAAACGCGCTCCCATTGACCTCCACACTCAGCCGCCAAAACAAAC
 241 GTTCGAACATTCGTGTGTTGTGCTCCTTTTCCGTTATCTTGCAGTCATCTTTTGTCGTTT
 301 TTTTCTTTGTTCTTTTTGTTGAACGTGTTGCTAAGCAATTATTACATCAATTGAAGAAAA
 361 GGCTCGCCGATTTATTGTTGCCAGAAAGATTCTGAGATTCTCGAAGTCGATTTTATAATA
 421 TTTAACCTTGGTTTTTGCATTGTTTCGTTTAAAAAAAACCACTGTTTATGTGAAAAACGAT
 481 TAGTTTACTAATAAAACTACTTTTAAACCTTTACCTTTACCTCACCGCTCCGTGTTCATG
 541 GCTCATAGATTTTCGATACTCAAATCCAAAAATAAATTTACGAGGGCAATTAATGTGAAA
 601 CAAAAACAATCCTAAGATTTCCACATGTTTGACCTCTCCGGCACCTTCTTCCTTAGCCCC
 661 ACCACTCCATCACCTCTTTGGCGGTGTTCTTCGAAACCCACTTAGGAAAGCAGTGTGTAT
 721 CTCATTTGGTATGCTCTTTTCGATTTTATAGCTCTTTGTCGCAATTTCAATGCTTTAAAC
 781 AATCCAAATCGCATTATATTTGTGCATGGAGGCAAATGACGGGGTTGGAATCTTAGATGA
 841 GATCAGGAGCTTTCAGGGTAAACGCCCGGTTCATTTGTACCACATTTCATCATTTTCCT
 901 GTCGTCCTTGGTATCCTCAACTTGTCCCGGTTTTGTTTTCGGTACACTCTTCCGTGATGC
 961 CACCTGTCTCCGTCTCAATTATCGTTTAGAAATGTGAACTGTCCAGATGGGTGACTCATA
1021 TTGCTGCTGCTACAATCCACTTTCTTTTCTCATCGGCAGTCTTACGAGCCCATCATAAAC
1081 TTTTTTTTCCGCGAAATTTGCAATAAACCGGCCAAAAACTTTCTCCAAATTGTTACGCAA
1141 TATATACAATCCATAAGAATATCTTCTCAATGTTTATGATTTCTTCGCAGCACTTTCTCT
1201 TCGTGTGCTAACATCTTATTTTTATAATATTTCCGCTAAAATTCCGATTTTTGAGTATTA
1261 ATTTATCGTAAAATTATCATAATAGCACCGAAAACTACTAAAAATGGTAAAAGCTCCTTT
                                                Repeat 1a
                                  ──────────────────────────────
1321 TAAATCGGCTCGACATTATCGTATTAAGGAATCACAAAATTCTGAGAATGCGTACTGCGC ─────────────────────────────────────────────────────────────
1381 AACATATTTGACGGCAAAATATCTCGTAGCGAAAACTACAGTAATTCTTTAAATGACTAC
                                 ──────────>  <─── Repeat 1a
1441 TGTAGCGCTTGTGTCGATTTACGGGCTCAATTTTTGAAAATAATTTTTTTTTCGAATTT ────────────────────────────────────────────────────────────
1501 TGATAACCCGTAAATCGTCACAACGCTACAGTAGTCATTTAAAGGATTACTGTAGTTCTA
```

FIG.2A

```
1561 GCTACGAGATATTTTGCGCGCCAAATATGACTGTAATACGCATTCTCTGAATTTTGTGTT
1621 TCCGTAATAATTTCACAAGATTTTGGCATTCCACTTTAAAGGCGCACAGGATTTATTCCA
1681 ATGGGTCTCGGCACGCAAAAAGTTTGATAGACTTTTAAATTCTCCTTGCATTTTTAATTC
1741 AATTACTAAAATTTTCGTGAATTTTTCTGTTAAAATTTTTAAAATCAGTTTTCTAATATT
1801 TTCCAGGCTGACAAACAGAAACAAAAACACAACAAACATTTTAAAAATCAGTTTTCAAAT
1861 TAAAAATAACGATTTCTCATTGAAAATTGTGTTTTATGTTTGCGAAAATAAAAGAGAACT
1921 GATTCAAAACAATTTTAACAAAAAAAAACCCCAAAATTCGCCAGAAATCAAGATAAAAAA
1981 TTCAAGAGGGTCAAAATTTTCCGATTTTACTGACTTTCACCTTTTTTTTCGTAGTTCAGT
2041 GCAGTTGTTGGAGTTTTTGACGAAAACTAGGAAAAAAATCGATAAAAAATTACTCAAATCG
2101 AGCTGAATTTTGAGGACAATGTTTAAAAAAAAACACTATTTTTCCAATAATTTCACTCAT

2161 TTTCAGACTAAATCGAAAATCAAATCGTACTCTGACTACGGGTCAGTAGAGACGGTCAACC
             ▼
2221 ATCAGCCGAAGATGATGCGTCAAGATAGAAGGAGCTTGCTAGAGAGGAACATTATGATGT
              M  M  R  Q  D  R  R  S  L  L  E  R  N  I  M  M  F
              1                           T(n1060) 10
2281 TCTCTAGTCATCTAAAAGTCGATGAAATTCTCGAAGTTCTCATCGCAAAACAAGTGTTGA
      S  S  H  L  K  V  D  E  I  L  E  V  L  I  A  K  Q  V  L  N
            20                         30
2341 ATAGTGATAATGGAGATATGATTAATGTGAGTTTTTAATCGAATAATAATTTTAAAAAAA
      S  D  N  G  D  M  I  N
                  40
2401 AATTGATAATATAAAGAATATTTTTGCAGTCATGTGGAACGGTTCGCGAGAAGAGACGGG
                                  S  C  G  T  V  R  E  K  R  R  E
                            A(n716)              50
2461 AGATCGTGAAAGCAGTGCAACGACGGGGAGATGTGGCGTTCGACGCGTTTTATGATGCTC
       I  V  K  A  V  Q  R  R  G  D  V  A  F  D  A  F  Y  D  A  L
         60                                    70
2521 TTCGCTCTACGGGACACGAAGGACTTGCTGAAGTTCTTGAACCTCTCGCCAGATCGTAGG
       R  S  T  G  H  E  G  L  A  E  V  L  E  P  L  A  R  S
         80                                    90
2581 TTTTTAAAGTTCGGCGCAAAAGCAAGGGTCTCACGGAAAAAAGAGGCGGATCGTAATTTT
2641 GCAACCCACCGGCACGGTTTTTTCCTCCGAAAATCGGAAATTATGCACTTTCCCAAATAT
2701 TTGAAGTGAAATATATTTTATTTACTGAAAGCTCGAGTGATTATTTATTTTTTAACACTA
2761 ATTTTCGTGGCGCAAAAGGCCATTTTGTAGATTTGCCGAAAATACTTGTCACACACACAC
2821 ACACACATCTCCTTCAAATATCCCTTTTTCCAGTGTTGACTCGAATGCTGTCGAATTCGA
                                           V  D  S  N  A  V  E  F  E
                                                            100
2881 GTGTCCAATGTCACCGGCAAGCCATCGTCGGAGCCGCGCATTGAGCCCCGCCGGCTACAC
      C  P  M  S  P  A  S  H  R  R  S  R  A  L  S  P  A  G  Y  T
```

FIG.2B

2941 TTCACCGACCCGAGTTCACCGTGACAGCGTCTCTTCAGTGTCATCATTCACTTCTTATCA
     S  P  T  R  V  H  R  D  S  V  S  S  V  S  S  F  T  S  Y  Q
                       130                            140
3001 GGATATCTACTCAAGAGCAAGATCTCGTTCTCGATCGCGTGCACTTCATTCATCGGATCG
     D  I  Y  S  R  A  R  S  R  S  R  A  L  H  S  S  D  R
                       150                         160
3061 ACACAATTATTCATCTCCTCCAGTCAACGCATTTCCCAGCCAACCTTCTATGTTGATGCG
     H  N  Y  S  S  P  P  V  N  A  F  P  S  Q  P  S
         Repeat 1b   170
3121 AACACTAAATTCTGAGAATGCGCATTACTCAACATATTTGACGCGCAAATATCTCGTAGC
3181 GAAAAATACAGTAACCCTTTAAATGACTATTGTAGTGTCGATTTACGGGCTCGATTTTCG
3241 AAACGAATATATGCTCGAATTGTGACAACGAATTTTAATTTGTCATTTTTGTGTTTTCTT
                              <  Repeat 1b
3301 TTGATATTTTTGATCAATTAATAAATTATTTCCGTAAACAGACACCAGCGCTACAGTACT
3361 CTTTTAAAGAGTTACAGTAGTTTTCGCTTCAAGATATTTTGAAAAGAATTTTAAACATTT
3421 TGAAAAAAAATCATCTAACATGTGCCAAAACGCTTTTTTCAAGTTTCGCAGATTTTTTGA
                      Repeat 2
3481 TTTTTTTCATTCAAGATATGCTTATTAACACATATAATTATCATTAATGTGAATTTCTTG
3541 TAGAAATTTTGGGCTTTTCGTTCTAGTATGCTCTACTTTTGAAATTGCTCAACGAAAAAA
3601 TCATGTGGTTTGTTCATATGAATGACGAAAAATAGCAATTTTTTATATATTTTCCCCTAT
3661 TCATGTTGTGCAGAAAAATAGTAAAAAAGCGCATGCATTTTTCGACATTTTTTACATCGA
3721 ACGACAGCTCACTTCACATGCTGAAGACGAGAGACGCGGAGAAATACCACACATCTTTCT
         <  Repeat 2
3781 GCGTCTCTCGTCTTCAGCATGTGAAATGGGATCTCGGTCGATGTAAAAAAATGTCGAATA
3841 ATGTAAAAAATGCATGCGTTTTTTTACACTTTTCTGCACAAATGAATAGGGGGAAAATGT
3901 ATTAAAATACATTTTTTGTATTTTTCAACATCACATGATTAACCCCATTATTTTTTCGTT
3961 GAGCAACTTAAAAAGTAGAGAATATTAGAGCGAAAACCAAAATTTCTTCAAGATATTACC
4021 TTTATTGATAATTATAGATGTTAATAAGCATATCTTGAATGAAAGTCAGCAAAAATATGT
4081 GCGAAACACCTGAAAAAAATCAAAAATTCTGCGAAAATTGAAAAAATGCATTAAAATACA
4141 TTTTTGCATTTTTCTACATCACATGAATGTAGAAAATTAAAAGGGAAATCAAAATTTCTA
4201 GAGGATATAATTGAATGAAACATTGCGAAATTAAAATGTGCCGAAACGTCAAAAAAGAGGA
4261 AATTTGGGTATCAAAATCGATCCTAAAACCAACACATTTCAGCATCCGCCAACTCTTCAT
                                                       S  A  N  S  S  F
                                                                180
4321 TCACCGGATGCTCTTCTCTCGGATACAGTTCAAGTCGTAATCGCTCATTCAGCAAAGCTT
     T  G  C  S  S  L  G  Y  S  S  S  R  N  R  S  F  S  K  A  S
                       190                            200
4381 CTGGACCAACTCAATACATATTCCATGAAGAGGATATGAACTTTGTCGATGCACCAACCA
     G  P  T  Q  Y  I  F  H  E  E  D  M  N  F  V  D  A  P  T  I
                       210                            220
4441 TAAGCCCGTGTTTTCGACGAGAAAACCATGTACAGAAACTTCTCGAGTCCTCGTGGAATGT
     S  R  V  F  D  E  K  T  M  Y  R  N  F  S  S  P  R  C  M  C
                       230                            240
4501 GCCTCATCATAAATAATGAACACTTTGAGCAGATGCCAACACGGAATGGTACCAAGGCCG
     L  I  I  N  N  E  H  F  E  Q  M  P  T  R  N  G  T  K  A  D
                       250                            260

FIG.2C

```
4561 ACAAGGACAATCTTACCAATTTGTTCAGATGCATGGGCTATACGGTTATTTGCAACGACA
      K  D  N  L  T  N  L  F  R  C  M  G  Y  T  V  I  C  K  D  N
                     270                        280
4621 ATCTGACGGGAAGGGTACGGCGAAATTATATTACCCAAACGCGAAATTTGCCATTTTGCG
      L  T  G  R
                 Repeat 3                >
4681 CCGAAAATGTGGCGCCCCGGTCTCGACACGACAATTTGTGTTAAATGCAAAAATGTATAAT
4741 TTTGCAAAAAACAAAATTTTGAACTTCCGCGAAAATGATTTACCTAGTTTCGAAATTTTC
4801 GTTTTTTCCGGCTACATTATGTGTTTTTTCTTAGTTTTTCTATAATATTTGATGTAAAAA
4861 ACCGTTTGTAAATTTTCAGACAATTTTCCGCATACAAAACTTGATAGCACGAAATCAATT
4921 TTCTGAATTTTCAAAATTATCCAAAAATGCACAATTTAAAATTTGTGAAAATTGGCAAAC
4981 GGTGTTTCAATATGAAATGTATTTTTAAAAACTTTAAAAACCACTCCCGAAAAGCAATAA
5041 AAATCAAAACAACGTCACAATTCAAATTCAAAAGTTATTCATCCGATTTGTTTATTTTTG
5101 CAAAATTTGAAAAAATCATGAAGGATTTAGAAAAGTTTTATAACATTTTTTCTAGATTTT
5161 TCAAAATTTTTTTTAACAAATCGAGAAAAAGAGAATGAAAAATCGATTTTAAAAATATCC
       < Repeat 3
5221 ACAGCTTCGAGAGTTTGAAATTACAGTACTCCTTAAAGGCGCACACCCCATTTGCATTGG
5281 ACCAAAAATTTGTCGTGTCGAGACCAGGTACCGTAGTTTTTGTCGCAAAAATTGCACCAT
5341 TGGACAATAAACCTTCCTAATCACCAAAAAGTAAAATTGAAATCTTCGAAAAGCCAAAAA
5401 ATTCAAAAAAAAAGTCGAATTTCGATTTTTTTTTTGGTTTTTTGGTCCCAAAAACCAAAA
5461 AAATCAATTTTCTGCAAAATACCAAAAAGAAACCCGAAAAAATTTCCCAGCCTTGTTCCT
5521 AATGTAAACTGATATTTAATTTCCAGGGAATGCTCCTGACAATTCGAGACTTTGCCAAAC
                                              G  M  L  L  T  I  R  D  F  A  K  H
                                                          290                     300
5581 ACGAATCACACGGAGATTCTGCCATACTCGTGATTCTATCACACGGAGAAGAGAATGTGA
      E  S  H  G  D  S  A  I  L  V  I  L  S  H  G  E  E  N  V  I
                     310                        320
5641 TTATTGGAGTTGATGATATACCGATTAGTACACACGAGATATATGATCTTCTCAACGCGG
      I  G  V  D  D  I  P  I  S  T  H  E  I  Y  D  L  L  N  A  A
                     330                        340
                                                              A(n2433)
                                                               |
5701 CAAATGCTCCCCGTCTCGCCGAATAAGCCGAAAATCGTTTTTGTGCAGGCTTGTCGAGGCG
      N  A  P  R  L  A  N  K  P  K  I  V  F  V  Q  A  C  R  G  E
                     350                        360
5761 GTTCGTTTTTTATTTTAATTTTAATATAAATATTTTAAATAAATTCATTTTCAGAACGTC
                                                              R  R
5821 GTGACAATGGATTCCCAGTCTTGGATTCTGTCGACGGAGTTCCTGCATTTCTTCGTCGTG
      D  N  G  F  P  V  L  D  S  V  D  G  V  P  A  F  L  R  R  G
                     370                        380
                                                              T(n1165)
                                                               |
5881 GATGGGACAATCGAGACGGGCCATTGTTCAATTTTCTTGGATGTGTGCCGGCCGCAAGTTC
      W  D  N  R  D  G  P  L  F  N  F  L  G  C  V  R  P  Q  V  Q
                     390                        400
```

FIG.2D

```
5941 AGCTTGCAATTTAATTTCTTGAATGAGAATATTCCTTCAAAAAATCTAAAATAGATTTTT
6001 ATTCCAGAAAGTCCCGATCGAAAAATTGCGATATAATTACGAAATTTGTGATAAAATGAC
         Repeat 4
6061 AAACCAATCAGCATCGTCGATCTCCGCCCACTTCATCGGATTGGTTTGAAAGTGGGCGGA
     ─────────────────────────────────────>
6121 GTGAATTGCTGATTGGTCGCAGTTTTCAGTTTAGAGGGAATTTAAAAATCGCCTTTTCGA 6181 AAATTAAAAATTGATTTTTTCAATTTTTTCGAAAAATATTCCGATTATTTTATATTCTTT
                                                           A(n717)
                                                              │
6241 GGAGCGAAAGCCCCGTCCTGTAAACATTTTTAAATGATAATTAATAAATTTTGCAGCAA
              T(n1949)                                        Q
                 │
6301 GTGTGGAGAAAGAAGCCGAGCCAAGCTGACATTCTGATTCGATACGCAACGACAGCTCAA
      V  W  R  K  K  P  S  Q  A  D  I  L  I  R  Y  A  T  T  A  Q
                        410                        420
          A(n1286)
             │
6361 TATGTTTCGTGGAGAAACAGTGCTCCTGGATCATCGTTCATTCAAGCCCGTCTGTGAAGTG
       Y  V  S  W  R  N  S  A  R  G  S  W  F  I  Q  A  V  C  E  V
                        430                        440
             T(n11129,n1164)
                │
6421 TTCTCGACACACGCAAAGGATATGGATGTTGTTGAGCTGCTGACTGAAGTCAATAAGAAG
       F  S  T  H  A  K  D  M  D  V  V  E  L  L  T  E  V  N  K  K
                        450                        460
        T(n2430)                                              A(n2426)
           │                                                     │
6481 GTCGCTTGTGGATTTCAGACATCACAGGGATCGAATATTTTGAAACAGATGCCAGAGGTA
      V  A  C  G  F  Q  T  S  Q  G  S  N  I  L  K  Q  M  P  E
                  470                        480
```

FIG.2E

```
                                           Repeat 5
6541 CTTGAAACAAACAATGCATGTCTAACTTTTAAGGACACAGAAAAATAGGCAGAGGCTCCT
     ────────────────────────────>
6601 TTTGCAAGCCTGCCGCGCGTCAACCTAGAATTTTAGTTTTTAGCTAAAATGATTGATTTT
6661 GAATATTTTATGCTAATTTTTTTGCGTTAAATTTTGAAATAGTCACTATTTATCGGGTTT
6721 CCAGTAAAAAATGTTTATTAGCCATTGGATTTTACTGAAAACGAAAATTTGTAGTTTTTC
6781 AACGAAATTTATCGATTTTTAAATGTAAAAAAAAATAGCGAAAATTACATCAACCATCAA
6841 GCATTTAAGCCAAAATTGTTAACTCATTTAAAAATTAATTCAAAGTTGTCCACGAGTATT
         <  Repeat 5
6901 ACACGGTTGGCGCGCGGCAAGTTTGCAAAACGACGCTCCGCCTGTTTTTCTGTGCGGCTT
                                                            T(n1163)
                                                            |
6961 GAAAACAAGGGATCGGTTTAGATTTTTCCCCAAAATTTAAATTAAATTTCAGATGACATC
                                                        M  T  S
7021 CCGCCTGCTCAAAAAGTTCTACTTTTGGCCGGAAGCACGAAACTCTGCCGTCTAAAATTC
      R  L  L  K  K  F  Y  F  W  P  E  A  R  N  S  A  V  *
         400                           500
7081 ACTCGTGATTCATTGCCCAATTGATAATTGTCTGTATCTTCTCCCCCAGTTCTCTTTCGC
7141 CCAATTAGTTTAAAACCATGTGTATATTGTTATCCTATACTCATTTCACTTTATCATTCT
7201 ATCATTTCTCTTCCCATTTTCACACATTTCCATTTCTCTACGATAATCTAAAATTATGAC
7261 GTTTGTGTCTCGAACGCATAATAATTTTAATAACTCGTTTTGAATTTGATTAGTTGTTGT
7321 GCCCAGTATATATGTATGTACTATGCTTCTATCAACAAAATAGTTTCATAGATCATCACC
7381 CCAACCCCACCAACCTACCGTACCATATTCATTTTTGCCGGGAATCAATTTCGATTAATT
7441 TTAACCTATTTTTTCGCCACAAAAAAATCTAATATTTGAATTAACGAATAGCATTCCCATC
7501 TCTCCCGTGCCGGAATGCCTCCCGGCCTTTTAAAGTTCGGAACATTTGGCAATTATGTAT
7561 AAATTTGTAGGTCCCCCCCATCATTTCCCGCCCATCATCTCAAATTGCATTCTTTTTTCG
7621 CCGTGATATCCCGATTCTGGTCAGCAAAGATCT
```

FIG.2F

Repeat 1

|            | 1         10        20        30        40        50        60        70 |
|---|---|
| ced-3(1a,for) | GTATTAA-GGAATCACAAAATTCTGAGAATGCCTACTGCCGCAACATATTTGACCG-CAAAATATCTCGTAGCG |
| ced-3(1a,rev) | AAAATTCAGAGAATGCGTATTACAGTC-ATATTTGGCGCGCAAAATATCTCGTAGCT |
| ced-3(1b,for) | AAATTCTGAGAATGCGCATTACTCAACATATTTGACCGGC-AAATATCTCGTAGCG |
| ced-3(1b,rev) | TATCTTGAAGCG |
| fem-1(for) | GTATTAC-GGCAAGAAATAATTATGAGAATGCCTATTGCGCACCATAGTTGACGCGCAAAATATCTCGTAGCG |
| fem-1(rev) | GTATAAC-GGTAACACACAATTCTGAGAATGCGTATTGCACAACACATTTGACCGCAAAATATCTCGTAGCG |
| hlh-1(for) | CTATTAC-GGGAGTACAAAATTCTGAGAATGCCTACTGCCGCAACATATTTGACCGCCAAAATATTTCGTATCG |
| hlh-1(rev) | GGGAGCACAAAATTCTGACTATGAGAAT-GCGTATAA GCACAAAATATTTCGTAGCG | consensus  -TAT-A--GG-A--A-A-AATT--GA--ATG---A-T-C------A-A-TTG-CG--CAAATAT-T-G-A-C-

|            | 80        90       100       110       120       130       140 |
|---|---|
| ced-3(1a,for) | AAAACTACAGTAATTCTTTAAATGACTACTGTAGCG TTGTGTCGA-TTTACGGGCTCAATT |
| ced-3(1a,rev) | AGAACTACAGTAATCCTTTAAATGACTACTGTAGCC TTGTGACCA-TTTACGGGTTATCAAAATTCGAAA |
| ced-3(1b,for) | AAAA-TACAGTAACCCTTTAAATGACTATTGTAG TGTCGA-TTTACGGGC—TCGATTTTCGAAA |
| ced-3(1b,rev) | AAAACTACTGTAACTCTTTAAAAGAGTACTGTAGCG TGGTGTCTG-TTTACGGAAATAATT |
| ced-3(2b,rev) | AAAACTACAGTGATTCCCTGAATGAATACGGTAGGGTCG TTGTTTCGA-TTTACGGGCTCGTT |
| fem-1(for) | AAAACTACAGTAATTCGTTTATTGCCTACTGT-GCG TGTTGA-TTTACGGGC |
| fem-1(rev) | AAAACTACAGTAATTGTCAAGGGACTACTGTAGCTAGCG-CTTGTGTCGA-TTTACGGAGC-TCGATTTT |
| hlh-1(for) | |
| hlh-1(rev) | TTTACCG TT-GAAA | consensus  A--AACTAC--GT-A-------A--G--TA--GTAG--------T--GT---------TTTACCG

FIG.2G

Repeat 2

```
              1        10         20         30         40         50         60         70         80
ced-3(for)    TCATTCAAGATATGCTTATTAACACATATAATTATCATTAATGTGAATTTCTTCTGTAGAAATTTGGGCTTTTCCTTCTAG
ced-3(rev)    TCATTCAAGATATGCTTATTAACATCTATAATTATCAATAAAGGTAATATCTTGAAGAAATTTTGG---TTTTCCTCTAA consensus     TCATTCAAGATATGCTTATTAACA--TATAATTATCA-TAA-G--AAT-TCTTG-AGAAATTTTGG---TTTTCG-TCTA- 90        100       110       120       130       140       150       160
ced-3(for)    TATGCTCTACTTTTGAAATTGCTCAACGAAAAAT---------CATGTGGTTTGTTCATATGAATGACGAAAAATA
ced-3(rev)    TATTCTCTACTTTTAAGTTGCCTCAACAAAAAATAATGGGGTTAATCATGTG-----------ATGTGAAAAATA consensus     TAT-CTCTACTTTT--AA-TTGCCTCAACGAAAAAT---------CATGTG-----------ATG--GAAAAATA 170       180       190       200       210       220       230       240
ced-3(for)    GCAA------T-TTTTATATATTTT--CCCTATTCATGTTGTGCAGAAAAATAGTAAAAACCGCCATGCATTTT---
ced-3(rev)    CAAAAAATGTATTTTACATTTCCCCCTATTCAT--TTGTGCAGAAAGT-GTAAAAAAACGCATGCATGCATTTTACAT consensus     -AA------T-TTTT-ATA-ATTTT--CCCTATTCAT-TTGTGCAGAAAA-T-GTAAAAAA-CGCATGCATTTT---

250       260       270       280       290
ced-3(for)    ------CCGACA-TTTTTTACATCGA-CGA-A-C-CA-TTCACATGCTGAAGACGAGAGACG
ced-3(rev)    TATTCGACATTTTTTTTACATCGACCGAGATCCCATTTCACATGCTGAAGACGAGAGACG consensus     ------CCGACA-TTTTTTACATCGA-CGA-A-C-CA-TTCACATGCTGAAGACGAGAGACG
```

FIG. 2H

Repeat 3

```
                    1         10        20        30        40        50        60
ced-3(for)      CAGCTTCGAGAGTTTG-AAATTACAGTACTCCTTAAAGGCGCACACCCCATTTGCATTGG
ced-3(rev)      ------------------------------------------------------------
lin-12(for)     CAGCAACAAATGTTTG-AAATTACAGTAATCTTTAAAGGCGCACACC-------------
lin-12(rev)     ------------------------------------------------------------
B0303(1)        CTGCAACGAAAGTCTG-AAATTACAGTACCCCTTAAAGGCGCATA---------------
B0303(2)        ---------------GTTAG-AAACTAGAGTACCTCTTAAAGGCGCACAT--CCTTTCCCACCT
ZK643(1)        CAGCAACAAAAGTTTG-AAATTACAGTGCTCTTAAAGGCACACACC-TTTTTACATT-T
ZK643(2,for)    CAGAAGCGAAAATTTG-AAATTACAGTACTCTTAAACGCTCAA-CCCCGTTTCTATTCA
ZK643(2,rev)    -------GATTGTT-GAAAATTACAGTAATCTTTAAAGGCGCACACA-CGTTTGTATTTT
ZK643(3)        ------------------------------------------------------------
glp-1(for)      -----------TTTTTAAACTACAGTACTCTTTAGGAGCGCACA--TTTTTTCGCATTT
glp-1(rev)      ---------ACCGTTTG-AAACTACAGTACTCTTTAAAGGCGC-----------------
consensus       C-G----C-------T----AAA-TA-AGT-----TTA---GC-CA-A-------TTT-----

70        80        90        100       110
ced-3(for)      ACCAAAAATTTGTCGTGTCGAGA-CCAGGTA-CCGTAGTTTTTG-TC-------GCAAA
ced-3(rev)      --ACAAA-TTGTCGTGTCGAGA-CCGGGCG-CCACA-----------------------
lin-12(for)     ------------------------------------------------------------
lin-12(rev)     AACAAAACTTGTCGTGTCGAGA-CCGGGTA-CCGTATTTTTAATT--------GCAAA
B0303(1)        ------------------------------------------------------------
B0303(2)        ATCGAAAATTTGTCGTGTCGAGA-CCGGGTAGC-TAATTTTATGC-CAAAAA--------
ZK643(1)        AACAAAAAAGTGTCGCTTCGAGA-CCGGGTA-CCGTGTTTTTGGCGCAAAAATCGCTAT
ZK643(2,for)    ATAGAAAG-TTGTCGTTTCGAGA-CCGGACA-CCGTATTTTTGGCGCAAAATATACCTG
ZK643(2,rev)    ACAGAAAA-TTCTCGTTTCGAGA-CCGAACA-CAGTATTTTTGGCGGAGAAATTCTAAA
ZK643(3)        --------TTTGTCGTGTCGAGA-CCTGG-------------------------------
glp-1(for)      AACAAATTTTTGTCGTGGCGAGA-CCTGATA-CCGTATTTTTAGGTCAAGATTACTAGG
glp-1(rev)      ------GTTTGTCGT---------------------------------------------
consensus       A----A-----T-TCG---CGAGA-CC--------C----TTT-------A--A-------
```

FIG.21

Repeat 4

```
              1          10         20         30         40         50         60         70
ced-3      AACCAATCAGACTCGTCGATCTCCGCCCACTTCATCGGATTGGTTGAAAGTGGGCGGAGTGAATTGCTGATTGGTC
lin-12     AACCAATTAGGGACTTCGGAATTCCATACTTAATCTGATTGGTTGAAGAATGGGCAGAGCGAATTGCTGATTGGCC consensus  AACCAAT-AGC--C-TCG-----T---C--ACTT-ATC-GATTGGTT--A-A-TGGGC-GAG-GAATTGCTGATTGG-C
```

FIG. 2J

Repeat 5

```
                1          10         20         30         40         50         60
ced-3(for)   TTTTAAG-GACACAGAAAAATAGGCAGAGGCTCCTTTGCAAGCCTGCCGCGCGTCAACC
ced-3(rev)   TTTCAAGCCGCACAGAAAAGAGGCGGAGCGTCGTTTGCAAACTTGCCGCGCGCCAACC consensus    TTT-AAG---CACAGAAAAA-AGGC-GAG--TC-TTTTGCAA-C-TGCCCGCCG-CAACC
```

FIG. 2K

```
  1 AACCATCAGCCGAAGATGATGCGTCAAGATAGAAGGAGCTTGCTAGAGAGAACATTATGATGTTCTCTAGTCATCTAAAAGTCGATGAAATTCTCGAAG
         M  M  R  Q  D  R  R  S  L  L  E  R  N  I  M  M  F  S  S  H  L  K  V  D  E  I  L  E  V

101 TTCTCATCGCAAAACAAGTGTTGAATAGTCGATGATAATGGAGATATGATTAATTCATGTGGAACCGGTTCGGCAGAAGAGACCGGAGATCGTGAAAGCAGTCCA
      L  I  A  K  Q  V  L  N  S  D  N  G  D  M  I  N  S  C  G  T  V  R  E  K  R  R  E  I  V  K  A  V  Q

201 ACGACCGGGAGATGTGGCGTTCGACGCGTTTTATGATCCTCTTCGCTCTACGGGACACGAAGACTTGCTGAAGTTCTTGAACCTCGCCAGATCTGTT
      R  P  G  D  V  A  F  D  A  F  Y  D  A  L  R  S  T  G  H  E  G  L  A  E  V  L  E  P  L  A  R  S  V

301 GACTCGAATGCTGTCGAATTCGAGTGTCCAATGTCACCGGCCAACCATCGTCGGAGCCCGGCATTGAGCCCCGGCTACACTTCACCGACCCAGTTC
      D  S  N  A  V  E  F  E  C  P  M  S  P  A  S  H  R  R  S  R  A  L  S  P  A  G  Y  T  S  P  T  R  V  H

401 ACCGTGACAGGTCTCTTCAGTGTCATCATTCACTCTTCATCAGGATATCTACTCAAGAGCAAGATCTGTTCTCGATGGCGTGCACTTCATTCATCGGA
      R  D  S  V  S  S  V  S  S  F  T  S  Y  Q  D  I  Y  S  R  A  R  S  R  S  R  A  L  H  S  S  D

501 TCGACACAATTATTCATCTCCTCCAGTCAACGCCATTTCCAGCCAACCTTCATCCGCCATGCTCTTCTCCTCGGATACAGTTCA
      R  H  N  Y  S  S  P  P  V  N  A  F  P  S  Q  P  P  S  S  A  N  S  S  F  T  G  C  S  S  L  G  Y  S  S

601 AGTCGTAATCGCTCATTCAGCAAAGCTTCTGGACCAACTCAATACATATTCCATGAAGAGGATATGAACTTTGTCGATGCACCAACCATAAGCCGTGTTT
      S  R  N  R  S  F  S  K  A  S  G  P  T  Q  Y  I  F  H  E  E  D  M  N  F  V  D  A  P  T  I  S  R  V  F
```

```
1301 GAAACAGTGCTCGTGGATCATGGTTCATTCAAGCCCGTCTGTGAAGTGTTCTCGACACACGCAAAGGATATGGATGTTGTGGAGCTGCTGACTGAAGTCAA
           N  S  A  R  G  S  W  F  I  Q  A  V  C  E  V  F  S  T  H  A  K  D  M  D  V  V  E  L  L  T  E  V  N

1401 TAAGAAGGTCGCTTGTGGCGATTCAGACATCACAGGATCACAGGGATCCAATATTTGAAACAGATGCCAGAGATGACATCCCCGCTCAAAAAGTTCTACTTTTGG
           K  K  V  A  C  G  F  Q  T  S  Q  G  S  N  I  L  K  Q  M  P  E  M  T  S  R  L  L  K  K  F  Y  F  W

1501 CCCGAAGCACGCAAACTCTGCCGTCTAAAATTCACTCGTGATTCATTGCCCAATTGATAATGTCTGTATCTCTCCCCAGTTCTCTTTCGCCCAATTAG
           P  E  A  R  N  S  A  V  *

1601 TTTAAAACCATGTGTATATTGTTATCCTATACTCATTTCACTTTATCATTCTCTCCATTTCACACATTCCATTTCTAGATAATC

1701 TAAAATTATGACGTTTGTGTCTCGAACCCATAATAATTTAATAACTCGTTTTGAATTGATTAGTTGTGTGCCCAGTATATGTATGTACTATGCTT

1801 CTATCAACAAATAGTTTCATAGATCATCACCCCAACCTACGTACCCATATTCATTTTTGCCGGGAATCAATTCGATTAATTTTAACCTA

1901 TTTTTCGCCACAAAAAATCTAATATATTGAATTAACGAATAGCATTCCATCTCTCCCGTGCCGAACTCCCGGCCCTTTTAAAGTTCGGAACATTTGGCC

2001 AATTATGTATAAAATTTGTAGGTCCCCCCCATCATTTCCCGCCCCATCATCTCAAATTGCATTCTTTTTCGCCGTGATATCCCGATTCTGGTCAGCAAA
```

FIG.20

```
2101 GATCTTTCTCATAGCCCATTCCATTCGAGCTTTCTAATAGGAATTTGAAAATTTCGAAAATAATATATGGAAATAATATTGGATTTTTCGAGTTTT

2201 CAGCAACACAAATTTACTTGAAACCCATTTTCCAAATTTCAATTTTTTCAAATTTCCCGCTATCTTCCAAAATACTCTTGTACGTTTATTATATTCC

2301 CTCGTTTTCTTCGATTCCTCCTCTCCGGCCACCCAATAAGTTTTATATATGTTGAGATTATATAGCTGTTATTATAATTATATATTTATAGATTATT

2401 ATAGTTGCTTTCTCGCCGTATGTTTGTGTGTGTGATTGGTATACATAGATAAAAGAAAACAAGTAAAAAAGGAATTC
```

```
                                                                                    n1129,n1164
                                        *  *                                   *         v
C. elegans Ced-3    ------VPAFL-----RRGMDNRCG-PLFNFLGCVRPQV--QQVWFKK-FSQADILIRYA-TTAQYVSWRNSARGSWF-IQAVCEVFSTHAKDMDVVELLIEVNKK    464
C. briggsae Ced-3   ------VPSLI-----FRGMONRCG-PLFNFLGCVRPQV--QQVWFKK-FSQADMLIAYA-TTAQYVSWRNSARGSWF-IQAVCEVFSLHAKDMDVVELLIEVNKK    462
C. vulgaris Ced-3   ------VPALI-----FRGMDXGDG-P--NFLGCVRPQA--QQVWFKK-FSQADILIAYA-TTAQYVSWRNSARGSWF-IQAVCEVFSLHAKDMDVVELLIEVNKK    455
Mouse ICE           ------------RDSEE----DE-LIDAIFED--DGI-KKA-HIEKDFIAFCSSTPDNVSWRH-PVRGSLFIESLIKHMKEYAWSCDLEDIFRKVRF-         373
Human ICE           ------------     ---GVSGNL--SLPTIEEFED-DAI-KKA-HIEKDFIAFCSSTPDNVSWRH-PTIMGSVFIGRLIEHMQEYACSCDVEEIFRKVRF-      375
NEDD2               CSLLPPPLLLYETDRGVDQDDGKNHTQSPGCEESDAGKEELMKWRIPTRSDMICGYACLKGNAAMRNTKRGSWYJEALTQVFSERACDMHVADMLVKVNAL         131 n2430         n2426  n1163
                         v                 K   F
C. elegans Ced-3    VA---CGFQTSQCSNILKQMPEMTSRLLKKFYTWPEAR---NSAV    503
C. briggsae Ced-3   VA---CGFQTSQGSNILKQMPELTSRLLKKFYTWPEDRG RNSAV    503
C. vulgaris Ced-3   VA---CGFQTSQGANILKQMPELTSRLLKKFYTWPEDRN RSSAV    496
Mouse ICE           ------SFE-QPEFRLQMPTADRVT--LIKKFYLFPGH--         402
Human ICE           ------SFE-QPDGRAQMPTTERVT--LITRCFYLFPGH--        404
NEDD2               IKEREGYAPGTEFHRCEMSEYCSTLCQQLMLFPG------YPPT     171
```

FIG.3B

```
  1 TCTTCACAGTGCCGAAAGAACTGAGGCTTTTTCTCATGCTGAAAACAAACACCCTGACAAACCACTTAAGGTGTTGGAACAGCTGGGCAAAGAAGTCCTT
                                  M  A  E  N  K  H  P  D  K  P  L  K  V  L  E  Q  L  G  K  E  V  L

101 ACGGAGTACCTAGAAAAATTAGTACAAAGCAATGTACTGAAATTAAAGGAGGAAGATAAACAAAAATTTAACAATGCTGAACGCAGTGACAAGCGTTGGG
     T  E  Y  L  E  K  L  V  Q  S  N  V  L  K  L  K  E  E  D  K  Q  K  F  N  N  A  E  R  S  D  K  R  W  V

201 TTTTTGTAGATGCCATGAAAAAGAAACAGCAAAGTAGGTGAAATGCTTCTCCAGACATTCTTCAGTGTGGACCCAGGCAGCCACCATGGTGAAGCTAA
     F  V  D  A  M  K  K  K  H  S  K  V  G  E  M  L  L  Q  T  F  F  S  V  D  P  G  S  H  H  G  E  A  N

301 TCTGGAAATGGAGGAACCAGAAGAATCATTGAACACTCTCAAGCTTTGTTCCCTGAAGAGTTCACAGAGTTCACAAGGCCTTTGCAGAGAAAGACACAAGAAATTTAC
     L  E  M  E  E  P  E  E  S  L  N  T  L  K  L  C  S  P  E  E  F  T  R  L  C  R  E  K  T  Q  E  I  Y

401 CCAATAAAGGAGGCCAATGCCCGTACGAAAGGCTCTTATCATATGCAATACAGAGTTCAAACATCTCTCACTGAGGTATGGGCTAAATTTGACATCA
     P  I  K  E  A  N  G  R  T  R  K  A  L  I  I  C  N  T  E  F  K  H  L  S  L  R  Y  G  A  K  F  D  I  I
```

FIG.6A

```
501  TTGGTATGAAAGGCCTTCTTGAAGACTTAGGCTACGATGTGGTGGTGAAAGAGGAGCTTACAGCAGAGGGCATGGAGTCAGAGATGAAAGACTTTGCTGC
      G  M  K  G  L  L  E  D  L  G  Y  D  V  V  V  K  E  E  L  T  A  E  G  M  E  S  E  M  K  D  F  A  A

601  ACTCTCAGAACACCAGACACAGCACACTGCATTCCTGGTGCTAATGTCTCATGGCACACTGCATTGTGTGAACAGTGCACAGTGAAAAAACTCCA
      L  S  E  H  Q  T  S  D  S  T  F  L  V  L  M  S  H  G  T  L  H  G  I  C  G  T  M  H  S  E  K  T  P

701  GATGTGCTACAGTATGATACCATCTATCAGATATTCAACAATTGCCACTGTCCAGGTCTACGAGACAAACCCAAAGTCATCATTGTGCAGGCCTGCAGAG
      D  V  L  Q  Y  D  T  I  Y  Q  I  F  N  N  C  H  C  P  G  L  R  D  K  P  K  V  I  I  V  Q  A  C  R  G

801  GTGGGAACTCTGGAGAAATGTGGATCAGAGAGTCTTCAAAACCCCAGTGTGCAGAGGGTAGATCTACCTAGGAATATGGAAGCTGATGCTGTCAAGCT
      G  N  S  G  E  M  W  I  R  E  S  S  K  P  Q  L  C  R  G  V  D  L  P  R  N  M  E  A  D  A  V  K  L

901  GAGCCACGTGGAGAAGGACTTCATTGCCTTCTACGCTACAACCCCACATCACTTGTCCTACCGAGACAAAACACGGAGGCTCTTACTTCATCACTAGACTC
      S  H  V  E  K  D  F  I  A  F  Y  A  T  T  P  H  H  L  S  Y  R  D  K  T  G  G  S  Y  F  I  T  R  L
```

FIG.6B

```
1001 ATTCCTCCTTCCGGAAACATGCTTGCTCTTGTCATCTCTTGATATATCCTGAAGGTGCAACAATCATTGAAAAGGCAAGTATTCATTCCCAGATGC
      I  S  C  F  R  K  H  A  C  S  C  H  L  F  D  I  F  L  K  V  Q  Q  S  F  E  K  A  S  I  H  S  Q  M  P

1101 CCACCATTGATGGGCAACCTTGACAAGATATATTCTACCTCTTTCCTGGCAACTGAGAACAAGCAACAACTGAATCTCATTTCTTCAGCTTGAAG
      T  I  D  R  A  T  L  T  R  Y  F  Y  L  F  P  G  N  *

1201 AAGTGATCTTGGCCAAGATACACATTCTATTCCTGAAATTAAGGAAAGATACTTATGAATTCAAGACCAGCTAAGCAACAC

1301 AGTGGGATTCTGTTCGATAGACAAGCAAACAAGCAAAAATAAAAAAAAAA
```

FIG.6C

```
         1                                                                50
mICE1    MADKILRAKR KQFINS..... .VSIGTINGL LDELLEKRVL NQEEMDKIKL
hICE     MADKVLKEKR KLFIRS..... .MGEGTINGL LDELLQTRVL NKEEMEKVKR
mICH2    MAENKHPDKP LKVLEQ..... .LGKEVLTEY LEKLVQSNVL KLKEEDKQKF
Ced3     ....MMRQDR RSLLERNIMM FSSHLKVDEI LEVLIAKQVL NSDNGDMIN.

51                                                               100
mICE1    ANITAMDKAR NLCDHVSKKG APASQ.IFIT YICNEDCYLA GLLELQSAPS
hICE     ENATVMDKTR ALIDSVIPKG AQACQ.ICIT YICEEDSYLA GTLGLSADQT
mICH2    NNAERSDKRW VFVDAMKKKH SKVGE.MLL. .......... ..........
Ced3     SCGTVREKRR EIVKAVQRPG DVAFDAFYDA LRSTGHEGLA EVLEPLARSV 101                                                              150
mICE1    AETFVATEDS KGGHPSSSET KE.EQNKEDG TFPGLTGTLK FCPLEKAQKL
hICE     SGNYLNMQDS QGVLSSFPAP QAVQDNPAMP TSSGSEGNVK LCSLEEAQRI
mICH2    .......... QTFFSVDPGS HHGEANLEME EPEESLNTLK LCSPEEFTRL
Ced3     DSNAVEFECP MSPASHRRSR ALSPAGYTSP TRVHRDSVSS VSSFTSYQDI 151                                                              200
mICE1    WKE....... .......... .......... .......... ..........
hICE     WKQ....... .......... .......... .......... ..........
mICH2    CRE....... .......... .......... .......... ..........
Ced3     YSRARSRSRS RALHSSDRHN YSSPPVNAFP SQPSSANSSF TGCSSLGYSS 201                                                              250
mICE1    .......... .......... .....NPSEI YPIMNTTTRT R.......LA
hICE     .......... .......... .....KSAEI YPIMDKSSRT R.......LA
mICH2    .......... .......... .....KTQEI YPIKEANGRT R.......KA
Ced3     SRNRSFSKAS GPTQYIFHEE DMNFVDAPTI SRVFDEKTMY RNFSSPRGMC 251                                                              300
mICE1    LIICNTEFQH LSPRVGAQVD LREMKLLLED LGYTVKVKEN LTALEMVKEV
hICE     LIICNEEFDS IPRRTGAEVD ITGMTMLLQN LGYSVDVKKN LTASDMTTEL
mICH2    LIICNTEFKH LSLRYGAKFD IIGMKGLLED LGYDVVVKEE LTAEGMESEM
Ced3     LIINNEHFEQ MPTRNGTKAD KDNLTNLFRC MGYTVICKDN LTGRGMLLTI
```

FIG.7

```
          301                                                              350
mICE1  KEFAACPEHK TSDSTFLVFM SHGIQEGICG TTYSNEVSDI .LKVDTIFQM
hICE   EAFAHRPEHK TSDSTFLVFM SHGIREGICG KKHSEQVPDI .LQLNAIFNM
mICH2  KDFAALSEHQ TSDSTFLVLM SHGTLHGICG TMHSEKTPDV .LQYDTIYQI
Ced3   RDFAKHESH. .GDSAILVIL SHGEENVIIG ......VDDI PISTHEIYDL 351                                                              400
mICE1  MNTLKCPSLK DKPKVIILQA CRGEKQGVVL LKDSVRDSEE .DFLTDAIFE
hICE   LNTKNCPSLK DKPKVIIIQA CRGDSPGVVW FKDSVGVSGN LSLPTTEEFE
mICH2  FNNCHCPGLR DKPKVIIVQA CRGGNSGEMW IRESSKPQLC RGVDLPRNME
Ced3   LNAANAPRLA NKPKIVFVQA CRGERRDNGF PVLDSVDGVP AFLRRGWDNR 401                                                              450
mICE1  DDGI...... .........K KAHIEKDFIA FCSSTPDNVS WRHPVRGSLF
hICE   DDAI...... .........K KAHIEKDFIA FCSSTPDNVS WRHPTMGSVF
mICH2  ADAV...... .........K LSHVEKDFIA FYATTPHHLS YRDKTGGSYF
Ced3   DGPLFNFLGC VRPQVQQVWR KKPSQADILI RYATTAQYVS WRNSARGSWF 451                                                              500
mICE1  IESLIKHMKE YAWSCDLEDI F....RKVRF SFEQPEFRLQ MPTADRVT..
hICE   IGRLIEHMQE YACSCDVEEI F....RKVRF SFEQPDGRAQ MPTTERVT..
mICE2  ITRLTSCFRK HACSCHLFDI F....LKVQQ SFEKASIHSQ MPTIDRAT..
Ced3   IQAVCEVFST HAKDMDVVEL LTEVNKKVAC GFQTSQGSNI LKQMPEMTSR 501         517
mICE1  LTKRFYLFPG H......
hICE   LTRCFYLFPG H......
mICH2  LTRYFYLFPG N*.....
Ced3   LLKKFYFWPE ARNSAV*
```

FIG.7A

```
          TTCTGGTAGCTCCAAGAGGTTTTTCGACTTTTTGACAATGCTAACTGTCCAAGTCTACAG
   1141 ───────┼─────────┼─────────┼─────────┼─────────┼─────────┼ 1200 a        F W * L Q E V F R L F D N A N C P S L Q   -
b          S G S S K R F F D F L T M L T V Q V Y R -
c            L V A P R G F S T F * Q C * L S K S T E -

AACAAGCCAAAAATGTTCTTCATCCAAGCATGTCGTGGAGGTGCTATTGGATCCCTTGGG
   1201 ───────┼─────────┼─────────┼─────────┼─────────┼─────────┼ 1260 a        N K P K M F F I Q A C R G G A I G S L G   -
b          T S Q K C S S S K H V V E V L L D P L G -
c            Q A K N V L H P S M S W R C Y W I P W A -
```

FIG.8

```
Ced-3   1................MMRQDRRSLLERNIMMFSSHLKVDEILEVLI        31
              |:.:...  |.:|  :::..:|  :.|:|| |:
ICH-1_L 1 IPHKELMAADRGRRILGVCGMHPHHQETLKKNRVVLAKQLLLSELLEHLL      50

Ced-3   32 AKQVLNSDNGDMINSCGTVREKRREIVKAVQRPGDVAFDAFYDALRSTGH    81
           .|:::.  :  ::|.. ..  ... |::. :.:.|. ||||::|||.| :
ICH-1_L 51 EKDIITLEMRELIQAKVGSFSQNVELLNLLPKRGPQAFDAFCEALRETKQ    100

Ced-3   82 -EGLAEVLEPLARSVDSNAVEFECPMSPASHRRSRALSPAGYTSPTRVHRD  131
              :|.::|
ICH-1_L 101 GHLEDML.........................................  107

Ced-3   132 SVSSVSSFTSYQDIYSRARSRSRSRALHSSDRHNYSSPPVNAFPSQPSSA  181
              :..:.:.|.:                              :|. .:.
ICH-1_L 108 ....LTTLSGLQHV..........................LPPLSCDY   125

Ced-3   182 NSSFTGCSSLGYSSSRNRSFSKASGPTQYIFHEEDMNFVDAPTISRVFDE  231
            : |:.  . :::.  :. ..:|...... .  .:::.:  |... .::
ICH-1_L 126 DLSLPFPVCESCPLYKKLRLSTDTVEHSLDNKDGPVCLQVKPCTPEFYQT  175

Ced-3   232 ..KTMYRNFSSPRGMCLIINNEHF...EQMPTRNGTKADKDNLTNLFRCM  276
             . ||  |.|||:.|:::.| ||   .:::  |.|...|...|..||: :
ICH-1_L 176 HFQLAYRLQSRPRGLALVLSNVHFTGEKELEFRSGGDVDHSTLVTLFKLL  225

Ced-3   277 GYTVICKDNLTGRGMLLTIRDFAKHESH..GDSAILVILSHGEENVIIGV  324
            ||.| . : |:.:|  .:.:||. ..|  .||.|.|::|||| |..|.||
ICH-1_L 226 GYDVHVLCDQTAQEMQEKLQNFAQLPAHRVTDSCIVALLSHGVEGAIYGV  275

Ced-3   325 DDIPISTHEIYDLLNAANAPRLANKPKIVFVQACRGERRDNGFPVLDSVD  374
            |:  :  :|:::.||.|.|.||||:.|:||||:  |.|..   |
ICH-1_L 276 DGKLLQLQEVFQLFDNANCPSLQNKPKMFFIQACRGDETDRGVDQQD...  322

Ced-3   375 GVPAFLRRGWDNRDGPLFNFLGCVRPQVQQVWRKKPSQADILIRYATTAQ  424

ICH-1_L 323 ........GKNHAGSPGCEESDAGKEKLPKMR..LPTRSDMICGYACLKG  362

Ced-3   425 YVSWRNSARGSWFIQAVCEVFSTHAKDMDVVELLTEVNK..KVACGFQTS  472
            .. ||. ||||:|:|...|||.:| ||.|.|::|..||    |:...:
ICH-1_L 363 TAAMRNTKRGSWYIEALAQVFSERACDMHVADMLVKVNALIKDREGYAPG  412

Ced-3   473 QGSNILKQMPEMTSRLLKKFYFWPEARNSAV*        504
            : : |:|.| .| | |:|::::|:..
ICH-1_L 413 TEFHRCKEMSEYCSTLCRHLYLFPGHPPT*..        442
```

FIG.9

```
hICE    1  ........................MADKVLKEKRKLFIRSMGEGTINGLLD        27
              :..II..:  ::  : :      :,.:II:
Ich-1   1  IPHKELMAADRGRRILGVCGMHPHHQETLKKNRVVLAKQL...LLSELLE           47 hICE   28  ELLQTRVLNKEEMEKVKRENATVMDKTRALIDSVIPKGAQACQICITYIC              77
              .II:, ::. II .: ...... :... .I:: : .:I:II :  .. :
Ich-1  48  HLLEKDIITL.EMRELIQAKVGSFSQNVELLNLLPKRGPQAFDAFCEALR               96 hICE   78  E.EDSYLAGTLGLSADQTSGNYLNMQDSQGVLSSFPAPQAVQDNPAMPTS              126
              I .::.I.: I            , .: : I II,.:... .:   ::..:
Ich-1  97  ETKQGHLEDML..........LTTLSGLQHVLPPLSCDYDLSLPFPVCES              136 hICE  127  SGSEGNVKLCSLEEAQRIWKQKSAEIYPIMDKS................S              160
              :.   ,::I I :,,:: :..I.:,:: :,.:                  I
Ich-1 137  CPLYKKLRL.STDTVEHSLDNKDGPVCLQVKPCTPEFYQTHFQLAYRLQS              185 hICE  161  RTR.LALIICNEEFDS...IPRRTGAEVDITGMTMLLQNLGYSVDVKKNL              206
              I.I III:::I .I.:   :, I.I::II ,.:. I:. III.I.I   :
Ich-1 186  RPRGLALVLSNVHFTGEKELEFRSGGDVDHSTLVTLFKLLGYDVHVLCDQ              235 hICE  207  TASDMTTELEAFAHRPEHKTSDSTFLVFMSHGIREGICGKKHSEQVPDIL              256
              II :I ..I:.II: I.I:..II,::.:::III: ::I:I .    ..:I
Ich-1 236  TAQEMQEKLQNFAQLPAHRVTDSCIVALLSHGVEGAIYGVD.....GKLL              280 hICE  257  QLNAIFNMLNTKNCPSLKDKPKVIIIQACRGDSPGVVWFKDSVGVSGNLS              306

Ich-1 281  QLQEVFQLFDNANCPSLQNKPKMFFIQACRGDETD..RGVDQQDGKNHAG              328 hICE  307  LPTTEEFEDDAIK....KAHIEKDFIAFCSSTPDNVSWRHPTMGSVFIGR              352

Ich-1 329  SPGCEESDAGKEKLPKMRLPTRSDMICGYACLKGTAAMRNTKRGSWYIEA              378 hICE  353  LIEHMQEYACSCDVEEIFRKVRFSFEQPDGRAQMPTTERV........TL              394
              I : : I II. .I.::: II.  :.:.:I I. .. .I.        II
Ich-1 379  LAQVFSERACDMHVADMLVKVNALIKDREGYAPGTEFHRCKEMSEYCSTL              428 hICE  395  TRCFYLFPGH.... 404
              .I :IIIIII
Ich-1 429  CRHLYLFPGHPPT* 442
```

FIG.9A

```
  1  GCACAAGGAGCTGATGGCCGCTGACAGGGGACGCAGGATATTGGGAGTGTGTGGCATGCATCCTCATCATCAGGAAACTC
     ---------|---------|---------|---------|---------|---------|---------|---------|
              M  A  A  D  R  G  R  R  I  L  G  V  C  G  M  H  P  H  H  Q  E  T  L

81  TAAAAAAGAACCGAGTGGTGCTAGCCAAACAGCTGTTGTTGAGCGAATTGTTAGAACATCTTCTGGAGAAGGACATCATC
     ---------|---------|---------|---------|---------|---------|---------|---------|
       K  K  N  R  V  V  L  A  K  Q  L  L  L  S  E  L  L  E  H  L  L  E  K  D  I  I

161  ACCTTGGAAATGAGGGAGCTCATCCAGGCCAAAGTGGGCAGTTTCAGCCAGAATGTGGAACTCCTCAACTTGCTGCCTAA
     ---------|---------|---------|---------|---------|---------|---------|---------|
       T  L  E  M  R  E  L  I  Q  A  K  V  G  S  F  S  Q  N  V  E  L  L  N  L  L  P  K

241  GAGGGGTCCCCAAGCTTTTGATGCCTTCTGTGAAGCACTGAGGGAGACCAAGCAAGGCCACCTGGAGGATATGTTGCTCA
     ---------|---------|---------|---------|---------|---------|---------|---------|
       R  G  P  Q  A  F  D  A  F  C  E  A  L  R  E  T  K  Q  G  H  L  E  D  M  L  L  T

321  CCACCCTTTCTGGGCTTCAGCATGTACTCCCACCGTTGAGCTGTGACTACGACTTGAGTCTCCCTTTTCCGGTGTGTGAG
     ---------|---------|---------|---------|---------|---------|---------|---------|
       T  L  S  G  L  Q  H  V  L  P  P  L  S  C  D  Y  D  L  S  L  P  F  P  V  C  E

401  TCCTGTCCCCTTTACAAGAAGCTCCGCCTGTCGACAGATACTGTGGAACACTCCCTAGACAATAAAGATGGTCCTGTCTG
     ---------|---------|---------|---------|---------|---------|---------|---------|
       S  C  P  L  Y  K  K  L  R  L  S  T  D  T  V  E  H  S  L  D  N  K  D  G  P  V  C

481  CCTTCAGGTGAAGCCTTGCACTCCTGAATTTTATCAAACACACTTCCAGCTGGCATATAGGTTGCAGTCTCGGCCTCGTG
     ---------|---------|---------|---------|---------|---------|---------|---------|
       L  Q  V  K  P  C  T  P  E  F  Y  Q  T  H  F  Q  L  A  Y  R  L  Q  S  R  P  R  G

561  GCCTAGCACTGGTGTTGAGCAATGTGCACTTCACTGGAGAGAAAGAACTGGAATTTCGCTCTGGAGGGGATGTGGACCAC
     ---------|---------|---------|---------|---------|---------|---------|---------|
       L  A  L  V  L  S  N  V  H  F  T  G  E  K  E  L  E  F  R  S  G  G  D  V  D  H

641  AGTACTCTAGTCACCCTCTTCAAGCTTTTGGGCTATGACGTCCATGTTCTATGTGACCAGACTGCACAGGAAATGCAAGA
     ---------|---------|---------|---------|---------|---------|---------|---------|
       S  T  L  V  T  L  F  K  L  L  G  Y  D  V  H  V  L  C  D  Q  T  A  Q  E  M  Q  E

721  GAAACTGCAGAATTTTGCACAGTTACCTGCACACCGAGTCACGGACTCCTGCATCGTGGCACTCCTCTCGCATGGTGTGG
     ---------|---------|---------|---------|---------|---------|---------|---------|
       K  L  Q  N  F  A  Q  L  P  A  H  R  V  T  D  S  C  I  V  A  L  L  S  H  G  V  E

801  AGGGCGCCATCTATGGTGTGGATGGGAAACTGCTCCAGCTCCAAGAGGTTTTTCAGCTCTTTGACAACGCCAACTGCCCA
     ---------|---------|---------|---------|---------|---------|---------|---------|
       G  A  I  Y  G  V  D  G  K  L  L  Q  L  Q  E  V  F  Q  L  F  D  N  A  N  C  P
```

FIG.10A

```
 881 AGCCTACAGAACAAACCAAAAATGTTCTTCATCCAGGCCTGCCGTGGAGATGAGACTGATCGTGGGGTTGACCAACAAGA
     |-------|-------|-------|-------|-------|-------|-------|-------|
      S  L  Q  N  K  P  K  M  F  F  I  Q  A  C  R  G  D  E  T  D  R  G  V  D  Q  Q  D

961 TGGAAAGAACCACGCAGGATCCCCTGGGTGCCGAGGAGAGTGATGCCGGTAAAGAAAAGTTGCCGAAGATGAGACTGCCCA
     |-------|-------|-------|-------|-------|-------|-------|-------|
      G  K  N  H  A  G  S  P  G  C  E  E  S  D  A  G  K  E  K  L  P  K  M  R  L  P  T

1041 CGCGCTCAGACATGATATGCGGCTATGCCTGCCTCAAAGGGACTGCCGCCATGCGGAACACCAAACGAGGTTCCTGGTAC
     |-------|-------|-------|-------|-------|-------|-------|-------|
      R  S  D  M  I  C  G  Y  A  C  L  K  G  T  A  A  M  R  N  T  K  R  G  S  W  Y

1121 ATCGAGGCTCTTGCTCAAGTGTTTTCTGAGCCGGCTTGTGATATGCACGTGGCCGACATGCTGGTTAAGGTGAACGCACT
     |-------|-------|-------|-------|-------|-------|-------|-------|
      I  E  A  L  A  Q  V  F  S  E  R  A  C  D  M  H  V  A  D  M  L  V  K  V  N  A  L

1201 TATCAAGGATCGGGAAGGTTATGCTCCTGGCACAGAATTCCACCGGTGCAAGGAAATGTCTGAATACTGCAGCACTCTGT
     |-------|-------|-------|-------|-------|-------|-------|-------|
      I  K  D  R  E  G  Y  A  P  G  T  E  F  H  R  C  K  E  M  S  E  Y  C  S  T  L  C

1281 GCCGCCACCTCTACCTGTTCCCAGGACACCCTCCCACATGATGTCACCTCCCCATCATCCACGCCAAGTGGAAGCCACTG
     |-------|-------|-------|-------|-------|-------|-------|-------|
      R  H  L  Y  L  F  P  G  H  P  P  T  *

1361 GACCACAGGAGGTGTGATAGAGCCTTTGATCTTCAGGATGCACGGTTTCTGTTCTGCCCCCTCAGGGATGTGGGAATCTC
     |-------|-------|-------|-------|-------|-------|-------|-------|

1441 CCAGACTTGTTTCCTG
     |-------|-------
```

FIG.10B

```
  1  AGAGGGAGGGAACGATTTAAGGAGCGAATACTACTGGTAAACTAATGGAAGAAATCTGCTGCACCACTGGATATTGGGAG
     ----|----|----|----|----|----|----|----|

81  TGTGTGGCATGCATCCTCATCATCAGGAAACTCTAAAAAAGAACCGAGTGGTGCTAGCCAAACAGCTGTTGTTGAGCGAA
     ----|----|----|----|----|----|----|----|
              M  H  P  H  H  Q  E  T  L  K  K  N  R  V  V  L  A  K  Q  L  L  L  S  E

161  TTGTTAGAACATCTTCTGGAGAAGGACATCATCACCTTGGAAATGAGGGAGCTCATCCAGGCCAAAGTGGGCAGTTTCAG
     ----|----|----|----|----|----|----|----|
      L  L  E  H  L  L  E  K  D  I  I  T  L  E  M  R  E  L  I  Q  A  K  V  G  S  F  S

241  CCAGAATGTGGAACTCCTCAACTTGCTGCCTAAGAGGGGTCCCCAAGCTTTTGATGCCTTCTGTGAAGCACTGAGGGAGA
     ----|----|----|----|----|----|----|----|
      Q  N  V  E  L  L  N  L  L  P  K  R  G  P  Q  A  F  D  A  F  C  E  A  L  R  E  T

321  CCAAGCAAGGCCACCTGGAGGATATGTTGCTCACCACCCTTTCTGGGCTTCAGCATGTACTCCCACCGTTGAGCTGTGAC
     ----|----|----|----|----|----|----|----|
      K  Q  G  H  L  E  D  M  L  L  T  T  L  S  G  L  Q  H  V  L  P  P  L  S  C  D

401  TACGACTTGAGTCTCCCTTTTCCGGTGTGTGAGTCCTGTCCCCTTTACAAGAAGCTCCGCCTGTCGACAGATACTGTGGA
     ----|----|----|----|----|----|----|----|
      Y  D  L  S  L  P  F  P  V  C  E  S  C  P  L  Y  K  K  L  R  L  S  T  D  T  V  E

481  ACACTCCCTAGACAATAAAGATGGTCCTGTCTGCCTTCAGGTGAAGCCTTGCACTCCTGAATTTTATCAAACACACTTCC
     ----|----|----|----|----|----|----|----|
      H  S  L  D  N  K  D  G  P  V  C  L  Q  V  K  P  C  T  P  E  F  Y  Q  T  H  F  Q

561  AGCTGGCATATAGGTTGCAGTCTCGGCCTCGTGGCCTAGCACTGGTGTTGAGCAATGTGCACTTCACTGGAGAGAAAGAA
     ----|----|----|----|----|----|----|----|
      L  A  Y  R  L  Q  S  R  P  R  G  L  A  L  V  L  S  N  V  H  F  T  G  E  K  E

641  CTGGAATTTCGCTCTGGAGGGGATGTGGACCACAGTACTCTAGTCACCCTCTTCAAGCTTTTGGGCTATGACGTCCATGT
     ----|----|----|----|----|----|----|----|
      L  E  F  R  S  G  G  D  V  D  H  S  T  L  V  T  L  F  K  L  L  G  Y  D  V  H  V

721  TCTATGTGACCAGACTGCACAGGAAATGCAAGAGAAACTGCAGAATTTTGCACAGTTACCTGCACACCGAGTCACGGACT
     ----|----|----|----|----|----|----|----|
      L  C  D  Q  T  A  Q  E  M  Q  E  K  L  Q  N  F  A  Q  L  P  A  H  R  V  T  D  S

801  CCTGCATCGTGGCACTCCTCTCGCATGGTGTGGAGGGCGCCATCTATGGTGTGGATGGGAAACTGCTCCAGCTCCAAGAG
     ----|----|----|----|----|----|----|----|
      C  I  V  A  L  L  S  H  G  V  E  G  A  I  Y  G  V  D  G  K  L  L  Q  L  Q  E
```

FIG.10C

```
881  GTTTTTCAGCTCTTTGACAACGCCAACTGCCCAAGCCTACAGAACAAACCAAAAATGTTCTTCATCCAGGCCTGCCGTGG
     ----|----|----|----|----|----|----|----|----|----|----|----|----|----|----|----|
      V  F  Q  L  F  D  N  A  N  C  P  S  L  Q  N  K  P  K  M  F  F  I  Q  A  C  R  G

961  AGGTGCTATTGGATCCCTTGGGCACCTCCTTCTGTTCACTGCTGCCACCGCCTCTCTTGCTCTATGAGACTGATCGTGGG
     ----|----|----|----|----|----|----|----|----|----|----|----|----|----|----|----|
      G  A  I  G  S  L  G  H  L  L  L  F  T  A  A  T  A  S  L  A  L  *

1041 GTTGACCAACAAGATGGAAAGAACCACGCAGGATCCCCTGGGTGCCAGGAGAGTGATGCCCGGTAAAGAAAAGTTGCCCGAA
     ----|----|----|----|----|----|----|----|----|----|----|----|----|----|----|----|

1121 GATGAGACTGCCCACGCGCTCAGACATGATATGCCGGCTATGCCTGCCTCAAAGGGACTGCCGCCATGCGGAACACCAAAC
     ----|----|----|----|----|----|----|----|----|----|----|----|----|----|----|----|

1201 GAGGTTCCTGGTACATCGAGGCTCTTGCTCAAGTGTTTTCTGAGCGGGCTTGTGATATGCACGTGGCCGACATGCTGGTT
     ----|----|----|----|----|----|----|----|----|----|----|----|----|----|----|----|

1281 AAGGTGAACGCACTTATCAAGGATCGGGAAGGTTATGCTCCTGGCACAGAATTCCACCGGTGCAAGGAGATGTCTGAATA
     ----|----|----|----|----|----|----|----|----|----|----|----|----|----|----|----|

1361 CTGCAGCACTCTGTGCCGCCACCTCTACCTGTTCCCAGGACACCCTCCCACATGATGTCACCTCCCCATCATCCACGCCA
     ----|----|----|----|----|----|----|----|----|----|----|----|----|----|----|----|

1441 AGTGGAAGCCACTGGACCACAGGAGGTGTGATAGAGCCTTTGATCTTCAGGATGCACGGTTTCTGTTCTGCCCCCTCAGG
     ----|----|----|----|----|----|----|----|----|----|----|----|----|----|----|----|

1521 GATGTGGGAATCTTCCAGACTTGTTTCCTGTGCCCATCATCTCTGCCTTTGAGTGTGGGACTCCAGGCCAGCTCCTTTTC
     ----|----|----|----|----|----|----|----|----|----|----|----|----|----|----|----|

1601 TGTGAAGCCCTTTGCCTGTAGAGCCAGCCTTGGTTGGACCTATTGCCAGGAATGTTTCAGCTGCAGTTGAAGAGCCTGAC
     ----|----|----|----|----|----|----|----|----|----|----|----|----|----|----|----|

1681 AAGTGAAGTTGTAAACACAGTGTGGTTATGGGGACAGGGCATATAAAATTCCCCATATTTGTGTTCAGTTCCAGCTTTTGT
     ----|----|----|----|----|----|----|----|----|----|----|----|----|----|----|----|

1761 AGATGGCACTTTAGTGATTGCTTTTATTACATTAGTTAAGATGTCTTGAGAGACCATCTCCTATCTTTTATTTCATTCAT
     ----|----|----|----|----|----|----|----|----|----|----|----|----|----|----|----|
```

FIG.10D

1841 ATCCTCCGCCCTTTTTGTCCTAGAGTGAGAGTTTGGAAGGTGTCCAAATTTAATGTAGACATTATCTTTTGGCTCTGAAG
     ----|--------|--------|--------|--------|--------|--------|--------|

1921 AAGCAAACATGACTAGAGACGCACCTTGCTGCAGTGTCCAGAAGCGGCCTGTGCGTTCCCTTCAGTACTGCAGCGCCACC
     ----|--------|--------|--------|--------|--------|--------|--------|

2001 CAGTGGAAGGACACTCTTGGCTCGTTTGGGCTCAAGGCACCGCAGCCTGTCAGCCAACATTGCCTTGCATTTGTACCTTA
     ----|--------|--------|--------|--------|--------|--------|--------|

2081 TTGATCTTTGCCCATGGAAGTCTCAAAGATCTTTCGTTGGTTGTTTCTCTGAGCTTTGTTACTGAAATGAGCCTCGTGGG
     ----|--------|--------|--------|--------|--------|--------|--------|

2161 GAGCATC
     -------

FIG.10E

```
ICH-1S  ..........................MHPHHQETLKKNRVVLAKQLLSELLEHLLEKDIITLEMRELIQ.AKVGSFSQNVELLNLL         60
ICH-1L  MAADRGRRILGVCGMHPHHQETLKKNRVVLAKQLLSELLEHLLEKDIITLEMRELIQ.AKVGSFSQNVELLNLL                     74
hICE    MAD..........KVLKEKRKLFIRS.....MGEGTINGLLDELLQTRVLNKEEMEKVKRENATVMDKTRALIDSV                    61
mICE    MAD..........KILRAKRKQFINS.....VSIGTINGLLDELLEKRVLNQEEMDKIKLANITAMDKARNLCDHV                   61
Ced-3   ...........MRFQDRRSLLERNIMMFSSHLKVDEILEVLIAKQVLNSDNGDMIN.SCGTVREKRREIVKAV                      61

ICH-1S  PKRGPQAFDAFCEALRETKQGHLEDML.........................................L                         88
ICH-1L  PKRGPQAFDAFCEALRETKQGHLEDML.........................................L                        102
hICE    IPKGAQACQ.ICITYICEEDSYLAGTLGLSADQTSGNYLNMQ..........................DSQGVL                    108
mICE    SKKGAPASQ.IFITYICNEDCYLAGILELQSAPSAETFVATE..........................DSKGGH                    108
Ced-3   QRPGDVAFDAFYDALRSTGHEGLAEVLEPLARSVDSNAVEFECPMSPASHRRSRALSPAGYTSPTRVHRDSVSSV                   136

ICH-1S  TTLSGLQHVL..............................................PPLSCDYDLSLPFPVCESCPLYKKLRLSTDTVEHS    133
ICH-1L  TTLSGLQHVL..............................................PPLSCDYDLSLPFPVCESCPLYKKLRLSTDTVEHS    147
hICE    SSFPAPQAVQ..............................................DNPAMPTSSGSEGNVKLC.....SLEEA....QRI    144
mICE    PSSSETKE.E..............................................QNKEDGTFPGLIGTLKFC......PLEKA....QKL    143
Ced-3   SSFTSYQDIYSRARSRSRSRALHSSDRHNYSSPPVNAFPSQPSSANSSFTGCSSLGYSSSRNRSFSKASGPTQYI                   211
                                                                  F
ICH-1S  LDNKDGPVCLQVKPCTPEFYQTHFQLAYRLQSRPRGLALVLSNVHFTGEKELEFRSGGDVDHSTLVTLFKLLGYD                    208
ICH-1L  LDNKDGPVCLQVKPCTPEFYQTHFQLAYRLQSRPRGLALVLSNVHFTGEKELEFRSGGDVDHSTLVTLFKLLGYD                    222
hICE    WKQ......KSAEIYPIMDKSSR....TR.......LALIICNEEF...DSIPRRTGAEVDITGMTMLQNLGYS                    199
mICE    WKE......NPSEIYPIMNTTTR....TR.......LALIICNTEF...QHLSPRVGAQVDLREMKLLLEDLGYT                   198
Ced-3   FHEEDMNFVDAPTISRVFDEKTM......YRNFSSPRGMCLIINNEHF...EQMPTRNGTKADKDNLTNLFRCMGYT                 279
```

FIG.12A

```
Nedd-2                                                MLTVQV.YRTSQK........CSSSKHVVEVLLDPLGTSFC..SL      34
ICH-1S  VHVLCDQTAQEMQEKLQNFAQLPAHRVTDSCIVALLSHGVEGAIYG........VDGKLLQLQEVFQLFDNANCPSL                   277
ICH-1L  VHVLCDQTAQEMQEKLQNFAQLPAHRVTDSCIVALLSHGVEGAIYG........VDGKLLQLQEVFQLFDNANCPSL                   291
hICE    VDVKKNLTASDMTTELEAFAHRPEHKTSDSTFLVFMSHGIREGICCKKHSEQVPDI.LQLNAIFNMLNTKNCPSL                     273
mICE    VKVKENLTALEMVKEVKEFAACPEHKTSDSTFLVFMSHGIQEGICGTTYSNEVSDI.LKVDTIFQMMNTLKCPSL                     272
Ced-3   VICKDNLTGRGMLLTIRDFAKHESH..GDSAILVILSHGEENVIIG........VDDIPISTHEIYDLLNAANAPRL                   346

T
Nedd-2  LPPPLLLY........ETDRGVDQDGKNHTQSP..........GCEESDAG......KEELMKMRLPTRSDMICGYAC                    89
ICH-1S  QNKPKMFFIQACRGGAIGSLGHLLLFTAATASL..........AL*                                                  312
ICH-1L  QNKPKMFFIQACRGDETDRGVDQDGKNHAGSP...........GCEESDAG......KEKLPKMRLPTRSDMICGYAC                  353
hICE    KDKPKVIIIQACRGDSPGVVW.FKDSV................GVSGNLSLPTTEEFEDDAI.KKAHIEKDFIAFCSS                  333
mICE    KDKPKVIIIQACRGEKQGVVL.LKDSV................RDSEE.DFLTDAIFEDDGI.KKAHIEKDFIAFCSS                  331
Ced-3   ANKPKIVFVQACRGERRDNGFPVLDSVDGVPAFLRRGWDNRDGPLFNFLGCVRPQVQQVWRKKPSQADILIRYAT                      421

S
Nedd-2  LKGNAAMRNTKRGSWYIEALTQVFSERACDMHVADMLVKVNALIK.EREGYAPGTEFHRCKEMSEYCSTLCQQLY                      163
ICH-1L  LKGTAAMRNTKRGSWYIEALAQVFSERACDMHVADMLVKVNALIK.DREGYAPGTEFHRCKEMSEYCSTLCRHLY                      427
hICE    TPDNVSWRHPTMGSVFIGRLIEHMQEYACSCDVEEIF.....RKVRFSFEQPDGRAQMPTTERVT......LTRCFY                    399
mICE    TPDNVSWRHPVRGSLFIESLIKHMKEYAWSCDLEDIF.....RKVRFSFEQPEFRLQMPTADRVT......LTKRFY                    397
Ced-3   TAQYVSWRNSARGSMFIQAVCEVFSTHAKDMDVVELLTEVNKKVACGFQTSQGSNILKQMPEMTSR...LLKKFY                      493

Nedd-2  LFPGYPPT*      171
ICH-1L  LFPGHPPT*      435
hICE    LFPGH*         404
mICE    LFPGH*         402
Ced-3   FWPEARNSAV*    503
```

FIG.12B

```
  1  CTTTTTTTTTTTTTTTTTTTTATGTCCTGGAGTCCTGCACAGCCATGGCGGCCAGGAGGA
     ----|----|----|----|----|----|----|----|----|----|----|----|  60
       F  F  F  F  F  F  Y  V  L  E  S  C  T  A  M  A  A  R  R  T

61  CACATGAAAGAGATCCAATCTACAAGATCAAAGGTTTGGCCAAGGACATGCTGGATGGGG
     ----|----|----|----|----|----|----|----|----|----|----|----| 120
       H  E  R  D  P  I  Y  K  I  K  G  L  A  K  D  M  L  D  G  V

121  TTTTTGATGACCTGGTGGAGAAGAATGTTTTAAATGGAGATGAGTTGCTCAAAATAGGGG
     ----|----|----|----|----|----|----|----|----|----|----|----| 180
       F  D  D  L  V  E  K  N  V  L  N  G  D  E  L  L  K  I  G  E

181  AAAGTGCGAGTTTCATCCTGAACAAGGCTGAGAATCTGGTTGAGAACTTCTTAGAGAAAA
     ----|----|----|----|----|----|----|----|----|----|----|----| 240
       S  A  S  F  I  L  N  K  A  E  N  L  V  E  N  F  L  E  K  T

241  CAGACATGGCAGGAAAAATATTTGCTGGCCACATTGCCAATTCCCAGGAACAGCTGAGTT
     ----|----|----|----|----|----|----|----|----|----|----|----| 300
       D  M  A  G  K  I  F  A  G  H  I  A  N  S  Q  E  Q  L  S  L

301  TACAATTTTCTAATGATGAGGATGATGGACCTCAGAAGATATGTACACCTTCTTCTCCAT
     ----|----|----|----|----|----|----|----|----|----|----|----| 360
       Q  F  S  N  D  E  D  D  G  P  Q  K  I  C  T  P  S  S  P  S

361  CAGAATCCAAGAGAAAAGTAGAGGATGATGAAATGGAGGTAAATGCTGGATTGGCCCATG
     ----|----|----|----|----|----|----|----|----|----|----|----| 420
       E  S  K  R  K  V  E  D  D  E  M  E  V  N  A  G  L  A  H  E

421  AATCACATCTAATGCTGACAGCTCCTCATGGACTCCAGAGCTCAGAAGTCCAAGATACAC
     ----|----|----|----|----|----|----|----|----|----|----|----| 480
       S  H  L  M  L  T  A  P  H  G  L  Q  S  S  E  V  Q  D  T  L

481  TGAAGCTTTGTCCACGTGATCAGTTTTGTAAGATAAAGACAGAAAGGGCAAAAGAGATAT
     ----|----|----|----|----|----|----|----|----|----|----|----| 540
       K  L  C  P  R  D  Q  F  C  K  I  K  T  E  R  A  K  E  I  Y

541  ATCCAGTGATGGAGAAGGAGGGACGAACACGTCTGGCTCTCATCATCTGCAACAAAAAGT
     ----|----|----|----|----|----|----|----|----|----|----|----| 600
       P  V  M  E  K  E  G  R  T  R  L  A  L  I  I  C  N  K  K  F

601  TTGACTACCTTTTTGATAGAGATAATGCTGATACTGACATTTTGAACATGCAAGAACTAC
     ----|----|----|----|----|----|----|----|----|----|----|----| 660
       D  Y  L  F  D  R  D  N  A  D  T  D  I  L  N  M  Q  E  L  L

661  TTGAAAATCTTGGATACTCTGTGGTGTTAAAAGAAAACCTTACAGCTCAGGAAATGGAGA
     ----|----|----|----|----|----|----|----|----|----|----|----| 720
       E  N  L  G  Y  S  V  V  L  K  E  N  L  T  A  Q  E  M  E  T
```

FIG.14

```
721  CAGAGTTAATGCAGTTTGCTGGCCGTCCAGAGCACCAGTCCTCAGACAGCACACCTGGTG
     ———|————|————|————|————|————|  780
      E  L  M  Q  F  A  G  R  P  E  H  Q  S  S  D  S  T  P  G  V

781  TTTATGTCCCATGGCATCCTGGAAGGAATCTGTGGGGTGAAGCACCGAAACAAAAGCCAG
     ———|————|————|————|————|————|  840
      Y  V  P  W  H  P  G  R  N  L  W  G  E  A  P  K  Q  K  P  D

841  ATGTTCTTCATGATGACACTATCTTCAAAATTTTCAACAACTCTAACTGTCGGAGTCTGA
     ———|————|————|————|————|————|  900
      V  L  H  D  D  T  I  F  K  I  F  N  N  S  N  C  R  S  L  R

901  GAAACAAACCCAAGATTCTCATCATGCAGGCCTGCAGAGGCAGATATAATGGAACTATTT
     ———|————|————|————|————|————|  960
      N  K  P  K  I  L  I  M  Q  A  C  R  G  R  Y  N  G  T  I  W

961  GGGTATCCACAAACAAAGGGATAGCCACTGCTGATACAGATGAGGAACGTGTGTTGAGCT
     ———|————|————|————|————|————|  1020
      V  S  T  N  K  G  I  A  T  A  D  T  D  E  E  R  V  L  S  C

1021 GTAAATGGAATAATAGTATAACAAAGGCCCATGTGGAGACAGATTTCATTGCTTTCAAAT
     ———|————|————|————|————|————|  1080
      K  W  N  N  S  I  T  K  A  H  V  E  T  D  F  I  A  F  K  S

1081 CTTCTACCCCACATAATATTTCTTGGAAGGTAGGCAAGACTGGTTCCCTCTTCATTTCCA
     ———|————|————|————|————|————|  1140
      S  T  P  H  N  I  S  W  K  V  G  K  T  G  S  L  F  I  S  K

1141 AACTCATTGACTGCTTCAAAAAGTACTGTTGGTGTTATCATTTGGAGGAAATTTTTCGAA
     ———|————|————|————|————|————|  1200
      L  I  D  C  F  K  K  Y  C  W  C  Y  H  L  E  E  I  F  R  K

1201 AGGTTCAACACTCATTTGAGGTCCCAGGTGAACTGACCCAGATGCCCACTATTGAGAGAG
     ———|————|————|————|————|————|  1260
      V  Q  H  S  F  E  V  P  G  E  L  T  Q  M  P  T  I  E  R  V

1261 TATCCATGACACGCTATTTCTACCTTTTTCCCGGGAATTAGCACAGGCAACTCTCATGCA
     ———|————|————|————|————|————|  1320
      S  M  T  R  Y  F  Y  L  F  P  G  N  *

1321 GTTCACAGTCAAGTATTGCTGTAGCTGAGAAGAAAAGAAAATTCCAAGATCCCAGGATTT
     ———|————|————|————|————|————|  1380

1381 TTAAATGTGTAAAACTTTT
     ———|———  1399
```

FIG.14A

```
            1                                                    50
   ICH-3    .......... ..........M AARRTHERDP IYKIKGLAKD MLDGVFDDLV
    mIce    .......... .......... MADKILRAKR KQFINSVSIG TINGLLDELL
   mICH-2   .......... .......... MAENKHPDKP LKVLEQLGKE VLTEYLEKLV
   ICH-1ₗ   IPHKELMAAD RGRRILGVCG MHPHHQETLK KNRVVLAKQL LLSELLEHLL
    Ced3    .......... .........M MRQDRRSLLE RNIMMFSSHL KVDEILEVLI 51                                                   100
   ICH-3    EKNVLNGDEL LKIGESASFI LNKAENLVEN FLEKTDMAGK IFAGHI.ANS
    mIce    EKRVLNQEEM DKIKLANITA MDKARNLCDH VSKKGAPASQ IFITYI.CNE
   mICH-2   QSNVLKLKEE DKQKFNNAER SDKRWVFVDA MKKKHSKVGE MLL.......
   ICH-1ₗ   EKDIITLEMR ELIQ.AKVGS FSQNVELLNL LPKRGPQAFD AFCEALRETK
    Ced3    AKQVLNSDNG DMIN.SCGTV REKRREIVKA VQRPGDVAFD AFYDALRSTG 101                                                  150
   ICH-3    QEQLSLQF.. .......... .......... .......... ..........
    mIce    DCYLAGIL.. .......... .......... .......... ..........
   mICH-2   .......... .......... .......... .......... ..........
   ICH-1ₗ   QGHLEDML.. .......... .......... .......... ..........
    Ced3    HEGLAEVLEP LARSVDSNAV EFECPMSPAS HRRSRALSPA GYTSPTRVHR 151                                                  200
   ICH-3    ....SNDEDD GPQKICTPSS PS........ .......... ....ESKRKV
    mIce    ....ELQSAP SAETFVATED SK........ .......... ....GGHPSS
   mICH-2   .......... ..QTFFSVD. .P........ .......... ....GSHHGE
   ICH-1ₗ   .....LTTLS GLQHV..... .......... .......... ...LPPLSCD
    Ced3    DSVSSVSSFT SYQDIYSRAR SRSRSRALHS SDRHNYSSPP VNAFPSQPSS 201                                                  250
   ICH-3    EDDEMEVNAG LAHESHL... MLTAPHGLQS SEVQDTLKLC PRDQFCKIKT
    mIce    SETKEEQNKE DGTFPGL... T......... ....GTLKFC PLEKAQKLWK
   mICH-2   ANLEMEEPEE S......... L......... ....NTLKLC SPEEFTRLCR
   ICH-1ₗ   YDLSLPFPVC ESCPLYKKLR LSTDTVEHSL DNKDGPVCLQ VKPCTPEFYQ
    Ced3    ANSSFTGCSS LGYSSSRNRS FSKASGPTQY IFHEEDMNFV DAPTISRVFD 251                                                  300
   ICH-3    ERAKEIYPVM EKEGRTRLAL IICNKKF... DYLFDRDNAD TDILNMQELL
    mIce    ENPSEIYPIM NTTTRTRLAL IICNTEF... QHLSPRVGAQ VDLREMKLLL
   mICH-2   EKTQEIYPIK EANGRTRKAL IICNTEF... KHLSLRYGAK FDIIGMKGLL
   ICH-1ₗ   THFQLAYRLQ SR..PRGLAL VLSNVHFTGE KELEFRSGGD VDHSTLVTLF
    Ced3    E..KTMYRNF SS..PRGMCL IINNEHF... EQMPTRNGTK ADKDNLTNLF
```

FIG. 15

```
              301                                                       350
     ICH-3    ENLGYSVVLK  ENLTAQEMET  ELMQFAGRPE  HQSSDSTPGV  YVPWHPGRNL
      mIce    EDLGYTVKVK  ENLTALEMVK  EVKEFAACPE  HKTSDSTFLV  FMSHGIQEGI
    mICH-2    EDLGYDVVVK  EELTAEGMES  EMKDFAALSE  HQTSDSTFLV  LMSHGTLHGI
    ICH-1_L   KLLGYDVHVL  CDQTAQEMQE  KLQNFAQLPA  HRVTDSCIVA  LLSHGVEGAI
      Ced3    RCMGYTVICK  DNLTGRGMLL  TIRDFAKHES  H..GDSAILV  ILSHGEENVI 351                                                       400
     ICH-3    WGEAPKQK.P  DVLHDDTIFK  IFNNSNCRSL  RNKPKILIMQ  ACRGRYNGTI
      mIce    CGTTYSNEVS  DILKVDTIFQ  MMNTLKCPSL  KDKPKVIIIQ  ACRGEKQGVV
    mICH-2    CGTMHSEKTP  DVLQYDTIYQ  IFNNCHCPGL  RDKPKVIIVQ  ACRGGNSGEM
    ICH-1_L   YGVD.....G  KLLQLQEVFQ  LFDNANCPSL  QNKPKMFFIQ  ACRGDETDRG
      Ced3    IGVD.....D  IPISTHEIYD  LLNAANAPRL  ANKPKIVFVQ  ACRGERRDNG 401                                                       450
     ICH-3    WVSTNKGIAT  A....DTDEE  RVLSCKWNNS  ITKAHVET..  .......DFI
      mIce    LLKDSVRD..  .....SEEDF  LTDAIFEDDG  IKKAHIEK..  .......DFI
    mICH-2    WIRESSKPQL  C....RGVDL  PRN..MEADA  VKLSHVEK..  .......DFI
    ICH-1_L   VDQQD.....  ......GKNH  AGSPGCEESD  AGKEKLPKMR  ..LPTRSDMI
      Ced3    FPVLDSVDGV  PAFLRRGWDN  RDGPLFNFLG  CVRPQVQQVW  RKKPSQADIL 451                                                       500
     ICH-3    AFKSSTPHNI  SWKVGKTGSL  FISKLIDCKF  KYCWCYHLEE  IFRKVQHSFE
      mIce    AFCSSTPDNV  SWRHPVRGSL  FIESLIKHMK  EYAWSCDLED  IFRKVRFSFE
    mICH-2    AFYATTPHHL  SYRDKTGGSY  FITRLISCFR  KHACSCHLFD  IFLKVQQSFE
    ICH-1_L   CGYACLKGTA  AMRNTKRGSW  YIEALAQVFS  ERACDMHVAD  MLVKVNALIK
      Ced3    IRYATTAQYV  SWRNSARGSW  FIQAVCEVFS  THAKDMDVVE  LLTEVNK..K 501                                               540
     ICH-3    VPGELTQMPT  IERV......  ...SMTRYFYL  FPGN*.....
      mIce    QPEFRLQMPT  ADRV......  ...TLTKRFYL  FPGH......
    mICH-2    KASIHSQMPT  IDRA......  ...TLTRYFYL  FPGN*.....
    ICH-1_L   DREGYAPGTE  FHRCKEMSEY  CSTLCRHLYL  FPGHPPT...
      Ced3    VACGFQTSQG  SNILKQMPEM  TSRLLKKFYF  WPEARNSAV*
```

FIG.15A

PROGRAMMED CELL DEATH GENES AND PROTEINS

CROSS-REFERENCE TO RELATED APPLICATIONS

This application is a continuation-in-part application of U.S. application Ser. No. 08/258,287, filed Jun. 10, 1994, which is a continuation-in-part application of U.S. application Ser. No. 08/080,850, filed Jun. 24, 1993, now abandoned.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The invention is in the field of molecular biology as related to the control of programmed cell death.

2. Description of the Background Art

Programmed Cell Death

Cell death occurs as a normal aspect of animal development as well as in tissue homeostasis and aging (Glucksmann, A., *Biol. Rev. Cambridge Philos. Soc.* 26:59–86 (1950); Ellis et al., *Dev.* 112:591–603 (1991); Vaux et al., *Cell* 76:777–779 (1994)). Naturally occurring cell death acts to regulate cell number, to facilitate morphogenesis, to remove harmful or otherwise abnormal cells and to eliminate cells that have already performed their function. Such regulated cell death is achieved through an endogenous cellular mechanism of suicide, termed programmed cell death or apoptosis (Wyllie, A. H., in *Cell Death in Biology and Pathology*, Bowen and Lockshin, eds., Chapman and Hall (1981), pp. 9–34). Programmed cell death or apoptosis occurs when a cell activates this internally encoded suicide program as a result of either internal or external signals. The morphological characteristics of apoptosis include plasma membrane blebbing, condensation of nucleoplasm and cytoplasm and degradation of chromosomal DNA at inter-nucleosomal intervals. (Wyllie, A. H., in *Cell Death in Biology and Pathology*, Bowen and Lockshin, eds., Chapman and Hall (1981), pp. 9–34). In many cases, gene expression appears to be required for programmed cell death, since death can be prevented by inhibitors of RNA or protein synthesis (Cohen et al., *J. Immunol.* 32:38–42 (1984); Stanisic et al., *Invest. Urol.* 16:19–22 (1978); Martin et al., *J. Cell Biol.* 106:829–844 (1988)).

The genetic control of programmed cell death has been well-elucidated by the work on programmed cell death in the nematode *C. elegans*. Programmed cell death is characteristic and widespread during *C. elegans* development. Of the 1090 somatic cells formed during the development of the hermaphrodite, 131 undergo programmed cell death. When observed with Nomarski microscopy, the morphological changes of these dying cells follow a characteristic sequence. (Sulston et al., *Dev. Biol.* 82:110–156 (1977); Sulston et al., *Dev. Biol.* 100:64–119 (1983)).

Fourteen genes have been identified that function in different steps of the genetic pathway of programmed cell death in *C. elegans* (Hedgecock et al., *Science* 220:1277–1280 (1983); Ellis et al., *Cell* 44:817–829 (1986); Ellis et al., *Dev.* 112:591–603 (1991); Ellis et al., *Genetics* 112:591–603 (1991b); Hengartner et al., *Nature* 356:494–499 (1992); Ellis et al., *Dev.* 112:591–603 (1991)). Two of these genes, ced-3 and ced-4, play essential roles in either the initiation or execution of the cell death program. Recessive mutations in these genes prevent almost all of the cell deaths that normally occur during *C. elegans* development.

The ced-4 gene encodes a novel protein that is expressed primarily during embryogenesis, the period uring which most programmed cell deaths occur (Yuan et al., *Dev.* 116:309–320 (1992)). The 549 amino acid sequence of ced-4, deduced from cDNA and genomic clones, contain two regions that are similar to the calcium-binding domain known as the EF-hand (Kretsinger, 1987); however, it is still not clear at present whether calcium plays a role in regulating ced-4 or programmed cell death in *C. elegans*.

A gain-of-function mutation in ced-9 prevents normal programmed cell death, while mutations that inactivate ced-9 are lethal. This suggest that ced-9 acts by suppressing programmed cell death genes in cells that normally do not undergo programmed cell death (Hengartner, M., et al., *Nature* 356:494–499 (1992)). The ced-9 gene encodes a protein product that shares sequence similarity with the mammalian prot-oncogene and cell death suppressor bcl-2 (Hengartner, M., et al., *Cell* 76:665–676 (1994)). The lethality of ced-9 loss-of-function mutations can be suppressed by mutations in ced-3 and ced-4, indicating that ced-9 acts by suppressing the acitivity of ced-3 and ced-4.

Genetic mosaic analyses indicated that ced-3 and ced-4 likely act in a cell-autonomous fahsion within dying cells, suggesting that they might be cytotoxic proteins and/or control certain cytotoxic proteins in the process of programmed cell death (Yuan, J., et al., *Dev. Bio.* 138:33–41 (1190)).

nedd2

Cell death also occurs in mammals. nedd2 is a mouse gene which is preferentially expressed during early embryonic brain development (Kumar et al., *Biochem. Biophys. Res. Commun.* 185:1155–1161 (1992)). Since many neurons die during early embryonic brain development, it is possible that nedd-2 is a cell death gene. Nedd-2 mRNA is downregulated in the adult brain (Kumar et al., *Biochem. & Biophys. Res. Comm.* 185:1155–1161 (1992); Yuan, J., et al., *Cell* 75:641–752 (1993)).

bcl-2 bcl-2 is an oncogene known to inhibit programmed cell death and to be overexpressed in many follicular and B cell lymphomas. Overexpression of bcl-2 as a result of chromosomal translocation occurs in 85% of follicular and 20% of diffuse B cell lymphomas, Fukuhara et al., *Cancer Res.* 39:3119 (1979); Levine et al., *Blood* 66:1414 (1985); Yunis et al., *N. Engl. J. Med.* 316:79–84 (1987).

Overexpression of bcl-2 protects or delays the onset of apoptotic cell death in a variety of vertebrate cell types as well as in *C. elegans* (Vaux et al., *Science* 258:1955–1957 (1992); Nunez et al., *J. Immun.* 144:3602–3610 (1990); Vaux et al., *Science* 258:1955–1957 (1992); Sentman et al., *Cell* 67:879–888 (1992); Strasser et al., *Cell* 67:889–899 (1991)). Expression of bcl-2 in the nematode *C. elegans* has been shown to partially prevent programmed cell death. Thus, bcl-2 is functionally similar to the *C. elegans* ced-9 gene (Vaux et al., *Science* 258:1955–1957 (1992); Hengartner et al., *nature* 356:494–499 (1992)).

Interleukin-1β Converting Enzyme

Interleukin-1β converting enzyme (ICE) is a substrate-specific cysteine protease that cleaves the inactive 31 KD prointerleukin-1β at $Asp^{116}$-$Ala^{117}$, releasing a carboxy-terminal 153 amino-acid peptide to produce the mature 17.5 kD interleukin-1β (IL-1β) (Kostura et al., *Proc. Natl. Acad. Sci., USA* 86:5227–5231 (1989); Black et al., *FEBS Lett.* 247:386–390 (1989); Cerretti et al., *Science* 256:97–100 (1992); Thornberry et al., *Nature* 356:768–774 (1992)). IL-1β is a cytokine involved in mediating a wide range of biological responses including inflammation, septic shock, wound healing, hematopoiesis and growth of certain leukemias (Dinarello, C. A., *Blood* 77:1627–1652 (1991); diGiovine et al., *Today* 11:13 (1990)). A specific inhibitor of ICE, the crmA gene product of cowpox virus, prevents the proteolytic activation of IL-1β(Ray et al., *Cell* 69:597–604 (1992)) and inhibits host inflammatory response (Ray et al., *Cell* 69:597–604 (1992)). Cowpox virus carrying a deleted crmA gene is unable to suppress the inflammatory response of chick embryos, resulting in a reduction in the number of virus-infected cells and less damage to the host (Palumbo et al., *Virology* 171:262–273 (1989)). This observation indicates the importance of ICE in bringing about the inflammatory response.

Tumor Necrosis Factor

Tumor necrosis factor-α (TNF-α) is a pleiotropic tumoricidal cytokine (Tracey, K. J. et al., *Ann. Rev. Cell. Biol.* 9:317–343 (1993)). One of the striking functions of TNF-α is to induce apoptosis of transformed cells. In the case of non-transformed cells, TNFα can also induce apoptosis in the presence of metabolic inhibitors (Tracey, K. J., et al., *Ann. Rev. Cell. Biol.* 9:317–343 (1993). Apoptosis induced by TNF-α is also suppressed by bcl-2.

One of the most extensively studied functions of TNF-α is its cytotoxicity on a wide variety of tumor cell lines in vitro (Laster, S. M. et al., *J. Immunol.* 141:2629–2634 (1988)). However, the mechanism of cell death induced by TNF has been largely unknown. HeLa cells express predominantly p55 TNF receptor which is thought to be responsible for cell death signaling (Englemann, H. et al., *J. Biol. Chem.* 265:14497–14504 (1990); Thoma, B. et al., *J. Exp. Med.* 172:1019–1023 (1990)).

HeLa cells are readily killed by TNF-α in the presence of the metabolic inhibitor cycloheximide (CHX). The cell death induced by TNF-α/CHX shows DNA fragmentation and cytolysis, which are typical features of apoptosis (White, E. et al., *Mol. Cell. Biol.* 12:2570–2580 (1992)). Expression of adenovirus E1B 19K protein, which is functionally similar to bcl-2, inhibits apoptosis induced by TNF in HeLa cells (White, E. et al., *Mol. Cell. Biol.* 12:2570–2580 (1992)).

SUMMARY OF THE INVENTION

In the present invention, the ced-3 gene (SEQ ID NO: 1) has been cloned and sequenced and the amino acid sequence (SEQ ID NO: 2) of the protein encoded by this gene is disclosed. Structural analysis of the ced-3 gene revealed that it is similar to the enzyme interleukin-1β converting enzyme ("ICE") and that overexpression of the murine interleukin-1β converting enzyme ("mICE") causes programmed cell death in vertebrate cells. Based upon these results, a novel method for controlling programmed cell death in vertebrates by regulating the activity of ICE is claimed. "Caspase" is the official designation for all members of the ICE family. Therefore, the most recent designation for: ICE is "caspase-1," Ich-3 is "caspase-11" and Ich-1 is "caspase-2."

The amino acid sequence of ced-3 was also found to be similar to another murine protein, nedd-2, which is detected during early embryonic brain development, a period when many cells die. The results suggest that ced-3, ICE and nedd-2 are members of a gene family which function to cause programmed cell death.

A new cell death gene, mIch-2 (murine ICE-ced-3 homolog), has been discovered which appears to be in the same family as ced-3, ICE, and nedd-2. mIch-2 is distinguished from other previously identified cell death genes in that it is preferentially expressed in the thymus and placenta of vertebrates. Thus, the invention is also directed to a newly discovered gene, mIch-2, which is preferentially expressed in thymus and placenta and which encodes a protein causing programmed cell death. Thus, the present invention is directed to both the mIch-2 gene sequence (SEQ ID NO: 41) and the protein (SEQ ID NO: 42) encoded by mIch-2. Also encompassed are vectors expressing mIch-2 and host cells transformed with such vectors. The invention also encompasses methods of regulating cell death by expressing mIch-2.

A comparison of the nucleotide sequences of ced-3, mICE, human ICE ("hICE"), nedd-2 and mIch-2 indicates that they are members of a gene family that promotes programmed cell death. The identification of this family facilitated the isolation of the newly discovered cell death gene Ice-ced 3 homolog-1 (Ich-1).

Ich-1 is homologous to the other cell death genes described above and particularly to nedd2. Based upon its structure and the presence of DNA encoding the QACRG sequence characteristic of the active center of cell death genes, Ich-1 was identified as a new member of the ced-3/ICE family. Thus, the present invention is directed to both the Ich-1 gene sequence and the protein encoded by Ich-1. Also encompassed are vectors expressing Ich-1 and host cells transformed with such vectors. Alternative splicing results in two distinct Ich-1 mRNA species. Thus, the invention also encompasses these species, proteins produced from them, vectors containing and expressing the genes, and the uses described herein.

The inventors have also identified a further member of the ICE/ced-3 family, Ich-3(SEQ ID NO: 54). Ich-3 has at least two alternative splicing products. A full length cDNA of one of them from a mouse thymus cDNA library has been identified. It encodes a protein of 418 amino acids that is 38% identical with mICE, 42% identical with mIch-2, 25% with Ich-1, and 24% identical with *C. elegans* ced-3.

The invention is thus directed to genomic or cDNA nucleic acids having genetic sequences which encode ced-3, mIch-2, Ich-1, and Ich-3. The invention also provides for vectors and expression vectors containing such genetic sequences, the host cells transformed with such vectors and expression vectors, the recombinant nucleic acid or proteins made in such host/vectors systems and the functional derivatives of these recombinant nucleic acids or proteins. The use of the isolated genes or proteins for the purpose of regulating, and especially promoting cell death is also part of the invention.

The invention is also directed to methods for controlling the programmed death of vertebrate cells by regulating the activity of interleukin-1β converting enzyme. Such regulation may take the form of inhibiting the enzymatic activity, e.g. through the use of specific antiproteases such as crmA, in order to prevent cell death. In this way, it may be possible to develop cell lines which remain viable in culture for an extended period of time or indefinitely. Certain cells can only be maintained in culture if they are grown in the presence of growth factors. By blocking cell death, it may be possible to make such cells growth factor independent. Alternatively, ICE activity may be increased in order to promote cell death. Such increased activity may be used in cancer cells to antagonize the effect of oncogenes such as bcl-2.

The present invention is also based on the discovery that TNF-α activates endogenous ICE activity in HeLa cells and that TNF-α-induced apoptosis is suppressed by crmA, which can specifically inhibit ICE-mediated cell death. Thus, certain embodiments of the invention are based on the activation of the ICE/ced-3-mediated cell death pathway by TNF-α.

BRIEF DESCRIPTION OF THE FIGURES

FIG. 1 shows the genetic map of C. elegans in the region near ced-3 with the cosmid clones representing this region depicted below the map. nP33, nP34, nP35, nP36, and nP37 are restriction fragment length polymorphisms (RFLP) between Bristol and Bergerac wild type C. elegans strains. C43C9, W07H6 and C48D1 are three cosmid clones tested for rescue of the ced phenotype of ced-3(n717) animals. The ability of each cosmid clone to rescue ced-3 mutants and the fraction of independently obtained transgenic lines that were rescued are indicated on the right of the figure (+, rescue; -, no rescue; see text for data). The results indicate that ced-3 is contained in the cosmid C48D1.

FIG. 1A is a restriction map of C48D1 subclones. C48D1 was digested with BamHI and self-ligated to generate subclone C48D1-28. C48D1-43, pJ40 and pJ107 were generated by partial digesting C48D1-28 with BglII. pJ7.5 and pJ7.4 were generated by ExoIII deletion of pJ107. These subclones were assayed for rescue of the ced phenotype of ced-3(n717) animals (+, rescue; -, no rescue, -/+, weak rescue). The numbers in parentheses indicate the fraction of independently obtained transgenic lines that were rescued. The smallest fragment that fully rescued the ced-3 mutant phenotype was the 7.5 kb pJ7.5 subclone.

FIGS. 2A–2P Genomic Organization, Nucleotide Sequence, and Deduced Amino Acid Sequence of ced-3

FIGS. 2A–2F shows the genomic sequence of the ced-3 region (SEQ ID NO: 1), as obtained from plasmid pJ107. The deduced amino acid sequence of ced-3 (SEQ ID NO: 2) is based on the DNA sequence of ced-3 cDNA pJ87 and upon other experiments described in the text and in Experimental Procedures. The 5' end of pJ87 contains 25 bp of poly-A/T sequence (not shown), which is probably a cloning artifact since it is not present in the genomic sequence. The likely start site of translation is marked with an arrowhead. The SL1 splice acceptor site of the ced-3 transcript is boxed. The positions of 12 ced-3 mutations are indicated. Repetitive elements are indicated as arrows above the relevant sequences. Numbers on the left indicate nucleotide positions, beginning with the start of pJ107. Numbers below the amino acid sequence indicate codon positions. Five types of imperfect repeats were found: repeat 1, also found in fem-1 (Spence et al., Cell 60:981–990 (1990)) and hlh-I (Krause et al., Cell 63:907–919 (1990)); repeat 2, novel; repeat 3, also found in lin-12 and fem-1; repeat 4, also found in lin-12; and repeat 5, novel. Numbers on the sides of the figure indicate nucleotide positions, beginning with the start of pJ107. Numbers under the amino acid sequence indicate codon positions.

FIG. 2G–FIG. 2K contain comparisons of the repetitive elements in ced-3 with the repetitive elements in the genes ced-3, fem-1, hlh-1, lin-12, glp-1, and the cosmids B0303 and ZK643 (see text for references). In the case of inverted repeats, each arm of a repeat ("for" or "rev" for "forward" or "reverse", respectively) was compared to both its partner and to individual arms of the other repeats. 2G: Repeat 1 (SEQ ID NOS: 3–11); 2A: Repeat 2 (SEQ ID NOS: 12–14); 2I: Repeat 3 (SEQ ID NOS: 15–27); 2J: Repeat 4 (SEQ ID NOS: 28–30); and 2K; Repeat 5 (SEQ ID NOS: 31–33). The different ced-3 sequences which appear in the comparisons are different repeats of the same repetitive element. The numbers "1a", "1b" etc. are different repeats of the same class of repetitive element.

FIGS. 2M–2P shows the cDNA sequence (SEQ ID NO: 34) and deduced amino acid sequence (SEQ ID NO: 35) of ced-3 as obtained from plasmid pJ87.

FIGS. 3 and 3A–3B: Comparison of the Structure of the ced-3 Protein and hICE Protein FIG. 3 shows a comparison of structural features of ced-3 with those of the hICE gene. The predicted proteins corresponding to the hICE proenzyme and ced-3 are represented. The active site in hICE and the predicted active site in ced-3 are indicated by the black rectangles. The four known cleavage sites in hICE flanking the processed hICE subunits (p24, which was detected in low quantities when hICE was purified (Thornberry et al. (1992), p20, and p10) and two conserved presumptive cleavage sites in ced-3 are indicated with solid lines and linked with dotted lines. Five other potential cleavage sites in ced-3 are indicated with dashed lines. The positions of the aspartate (D) residues at potential cleavage sites are indicated below each diagram.

FIGS. 3A–3B contains a comparison of the amino acid sequences of ced-3 from C. elegans (SEQ ID NO: 35), C. briggsae (SEQ ID NO: 36) and C. vulgaris (SEQ ID NO: 37) with hICE (SEQ ID NO: 38), mICE (SEQ ID NO: 39), and mouse nedd-2 (SEQ ID NO: 40). Amino acids are numbered to the right of each protein. Dashes indicate gaps in the sequence made to allow optimal alignment. Residues that are conserved among more than half of the proteins are boxed. Missense ced-3 mutations are indicated above the comparison blocks showing the residue in the mutant ced-3 and the allele name. Asterisks indicate potential aspartate self-cleavage sites in ced-3. Circles indicate known aspartate self-cleavage sites in hICE. Residues indicated in boldface correspond to the highly conserved pentapeptide containing the active cysteine.

FIG. 4 shows several expression cassettes used in studying the cellular effects of ICE and ced-3 expression. The cassettes are as follows: pβactM10Z contains intact mICE fused to the E. coli lacZ gene (mICE-lacZ). pβactM11Z contains the P20 and P10 subunits of mICE fused to the E. coli lacZ gene (P20/P10-lacZ). pβactM19Z contains the P20 subunit of mICE fused to the E. coli lacZ gene (P20-lacZ). pβactM12Z contains the P10 subunit of mICE fused to the E. coli lacZ gene (P10-lacZ). pβactced38Z contains the C. elegans ced-3 gene fused to the lacZ gene (ced-3-lacZ).

pJ485 and pβactced37Z contain a Gly to Ser mutation at the active domain pentapeptide "QACRG" in mICE and ced-3 respectively. pβactM17Z contains a Cys to Gly mutation at the active domain pentapeptide "QACRG" in mICE. pactβgal' is a control plasmid (Maekawa et al., *Oncogene* 6:627–632 (1991)). All plasmids use the β-actin promoter.

Figure 5:
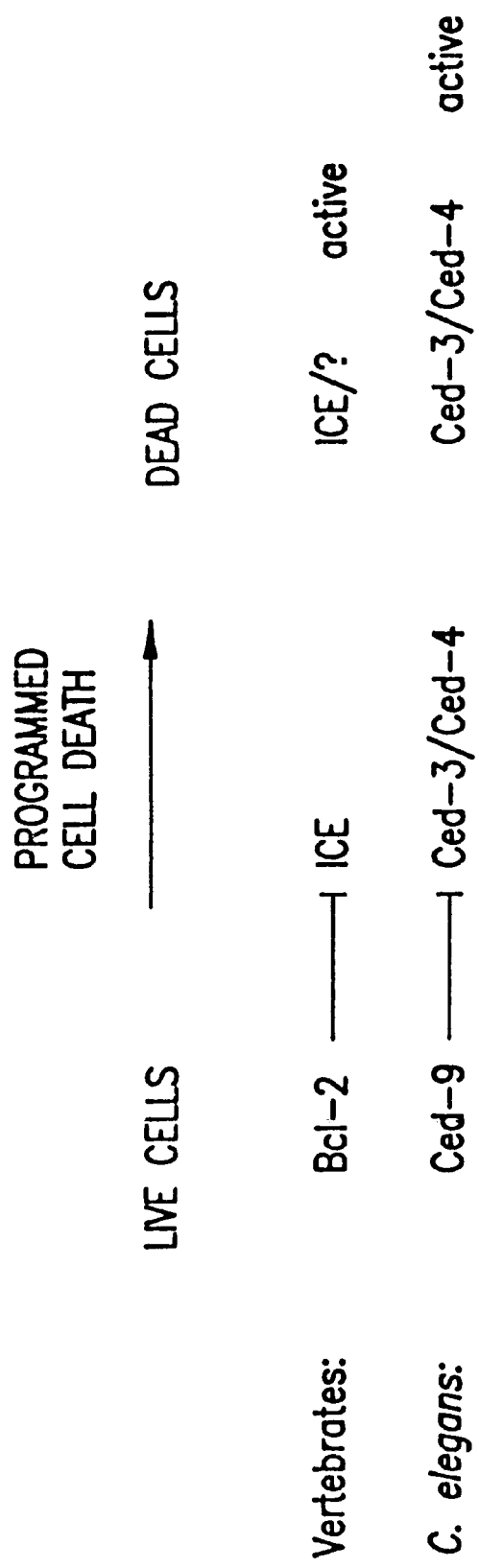

FIG. 5: Genetic Pathways of Programmed Cell Death in the Nematode *C. elegans* and in Vertebrates In vertebrates, bcl-2 blocks the activity of ICE thereby preventing programmed cell death. Enzymatically active ICE causes vertebrate cell death. In *C. elegans*, ced-9 blocks the action of ced-3/ced-4. Active ced-3 together with active ced-4 causes cell death.

FIGS. 6A–6C: mIch-2 cDNA Sequence and Deduced Amino Acid Sequence

FIGS. 6A–6C shows the nucleotide sequence of the mIch-2 cDNA sequence (SEQ ID NO: 41) and the amino acid sequence (SEQ ID NO: 42) deduced therefrom.

FIGS. 7 and 7A: mIch-2 Amino Acid Sequence

FIGS. 7 and 7A contain a comparison of the amino acid sequences of mICE, hICE, mIch-2 and ced-3.

FIG. 8: Potential QACRG Coding Region in the Mouse nedd2 cDNA

The reading frame proposed by Kumar et al. (*Biochem. & Biophys. Res. Comm.* 185:1155–1161 (1992)) is b. In reading frame a, a potential QACRG coding region (SEQ ID NOS: 44–49) is underlined.

FIGS. 9 and 9A: Comparison of the Amino Acid Sequences of ced-3, hICE and Ich-1

FIG. 9 contains a comparison of the amino acid sequences of ced-3 (SEQ ID NO: 35) and Ich-1 (SEQ ID NO: 43). There is a 52% similarity between the sequences and a 28% identity.

FIG. 9A contains a comparison of the amino acid sequences of hICE (SEQ ID NO: 39) and Ich-1 (SEQ ID NO: 43). There is a 52% similarity between the sequences and a 27% identity.

FIGS. 10A–10B: The cDNA Sequence of Ich-1$_L$ (SEQ ID NO: 50) and the Deduced Amino Acid Sequence of Ich-1$_L$ (SEQ ID NO: 51) Protein Product The putative active domain is underlined.

FIGS. 10C–10E: The cDNA Sequence of Ich-1$_S$ (SEQ ID NO: 52) and the Deduced Amino Acid Sequence of (SEQ ID NO: 53) Ich-1$_S$ Protein Product The intron sequence is underlined.

Figure 11A:
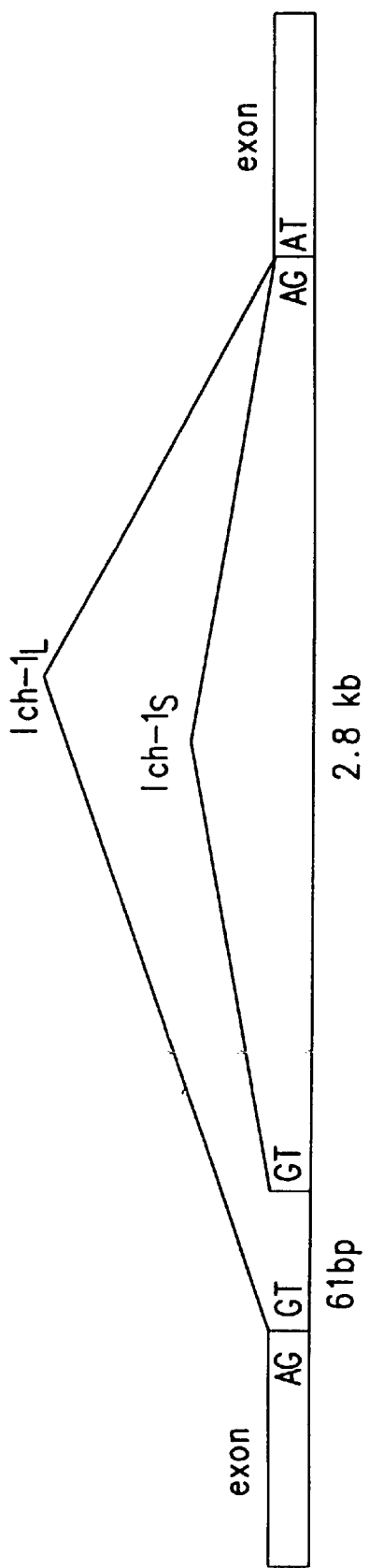

FIG. 11A: The Alternative Splicing of Ich-1 mRNA

The exons are shown in bars. The intron is shown in a line. Nucleotides at the exon-intron borders are indicated.

Figure 11B:
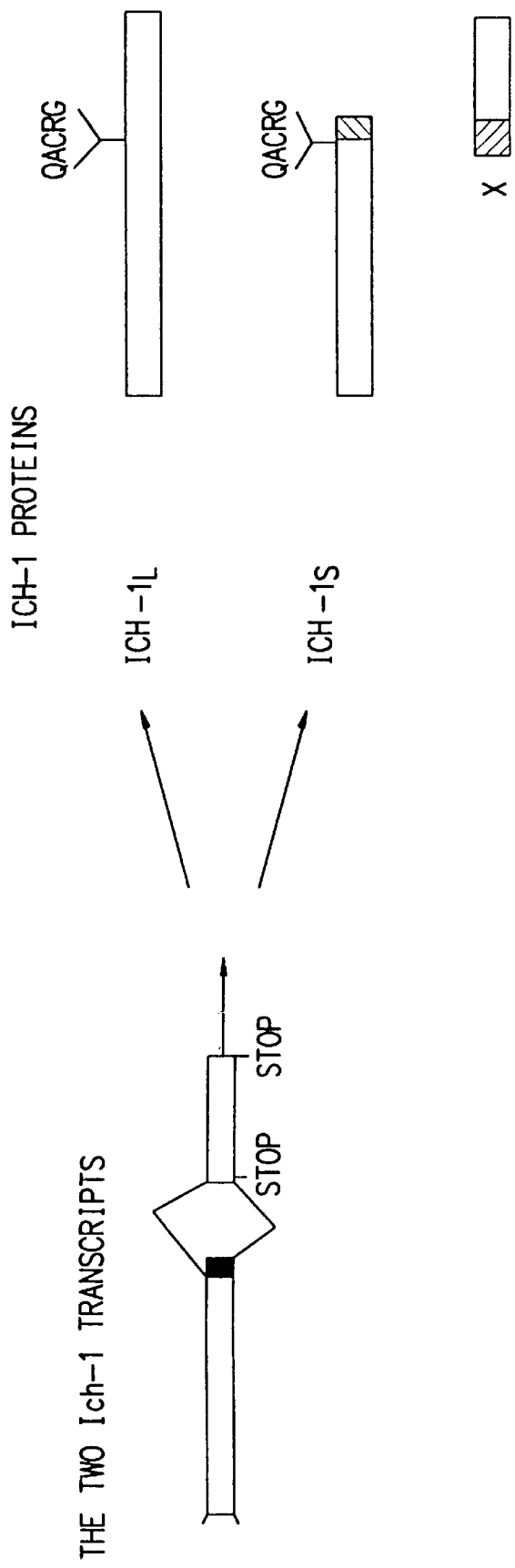

FIG. 11B: The Schematic Diagram of the Two Alternatively Spliced Ich-1 Transcripts and Ich-1$_L$ and Ich-1$_S$ Proteins The peptide marked with X may not be translated in vivo. The open reading frames and proteins are shown in bars. Untranslated regions and introns are shown in lines. The positions of Ich-1$_S$ and Ich-1$_L$ stop codons are indicated on the transcript diagram as "stop". Amino acid sequences in Ich-1$_S$ that are different from Ich-1$_L$ are shaded.

FIGS. 12A–12B: A Comparison of the Ich-1 Protein Sequence with the Mouse nedd-2 Protein, the hICE Protein, the mICE Protein, and *C. elegans* ced-3 Protein Amino acids are numbered to the right of each sequence. Any residues in nedd-2 (SEQ ID NO: 40), hICE (SEQ ID NO: 39), mICE (SEQ ID NO: 38), and ced-3 (SEQ ID NO: 35) that are identical with Ich-1 (SEQ ID NOS: 51,53) are highlighted. The two point mutations made by site-directed mutagenesis are marked on the top of the sequence.

Figure 12C:
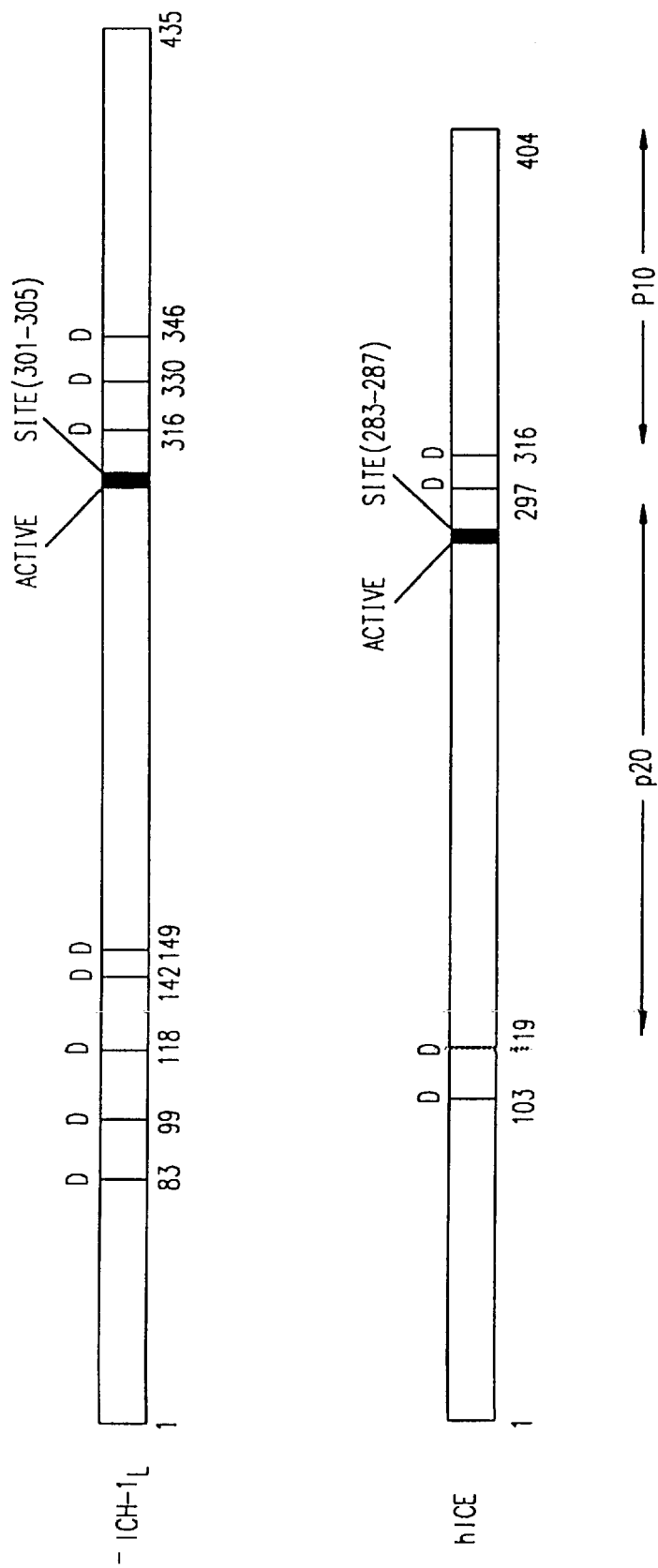

FIG. 12C: A Schematic Comparison of Structural Features of Ich-1$_L$ and hICE

The active site of hICE and predicted active site of Ich-1$_L$ are indicated. The four known cleavage sites of hICE and potential cleavage sites of Ich-1$_L$ are marked.

Figure 13:
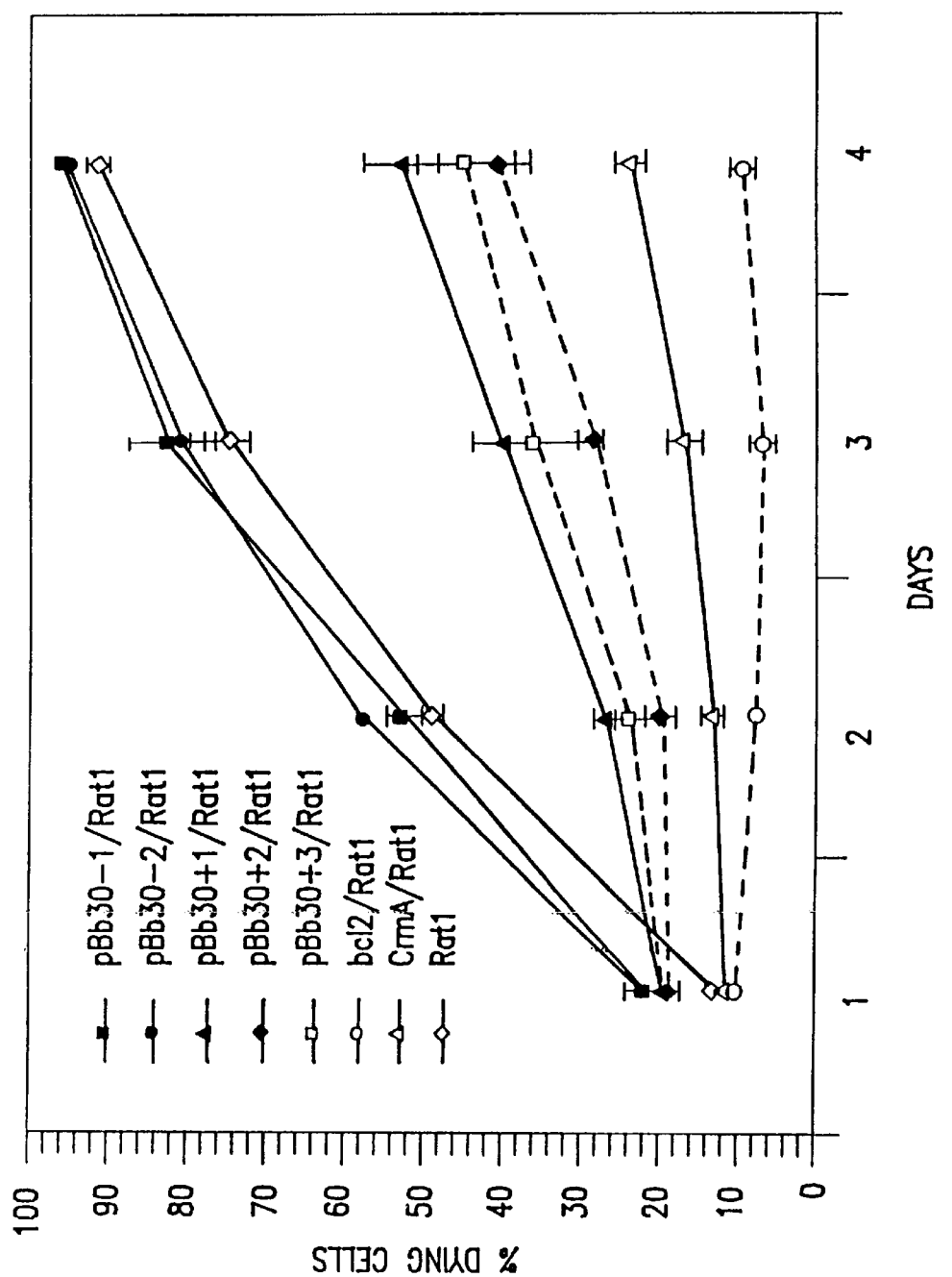

FIG. 13: Stable Expression of Ich-1$_S$ Prevents Cell Death of Rat-1 Cells Induced by Serum Removal Stable transfectants of Rat-1 cells expressing bcl-2, crmA or Ich-1$_S$ were prepared as described in Experimental Procedures. Independent Ich-1$_S$-positive and Ich-1$_S$-negative clones were used. At time 0, exponentially growing cells were washed with serum-free DMEM and dead cells were counted over time by trypan blue staining.

FIGS. 14–14A: The cDNA Sequence (SEQ ID NO: 54) and Putative Ich-3 Protein Sequence (SEQ ID NO: 55)

The putative first Met is marked with a dot.

FIGS. 15–15A: Companson of Amino Acid Sequences of Ich-3 (SEQ ID NO: 56) with hICE (SEQ ID NO: 38), mIch-2 (SEQ ID NO: 42), Ich-1 (SEQ ID NO: 43) and ced-3 (SEQ ID NO: 35)

Several amino acid sequences are compared.

Figure 16:
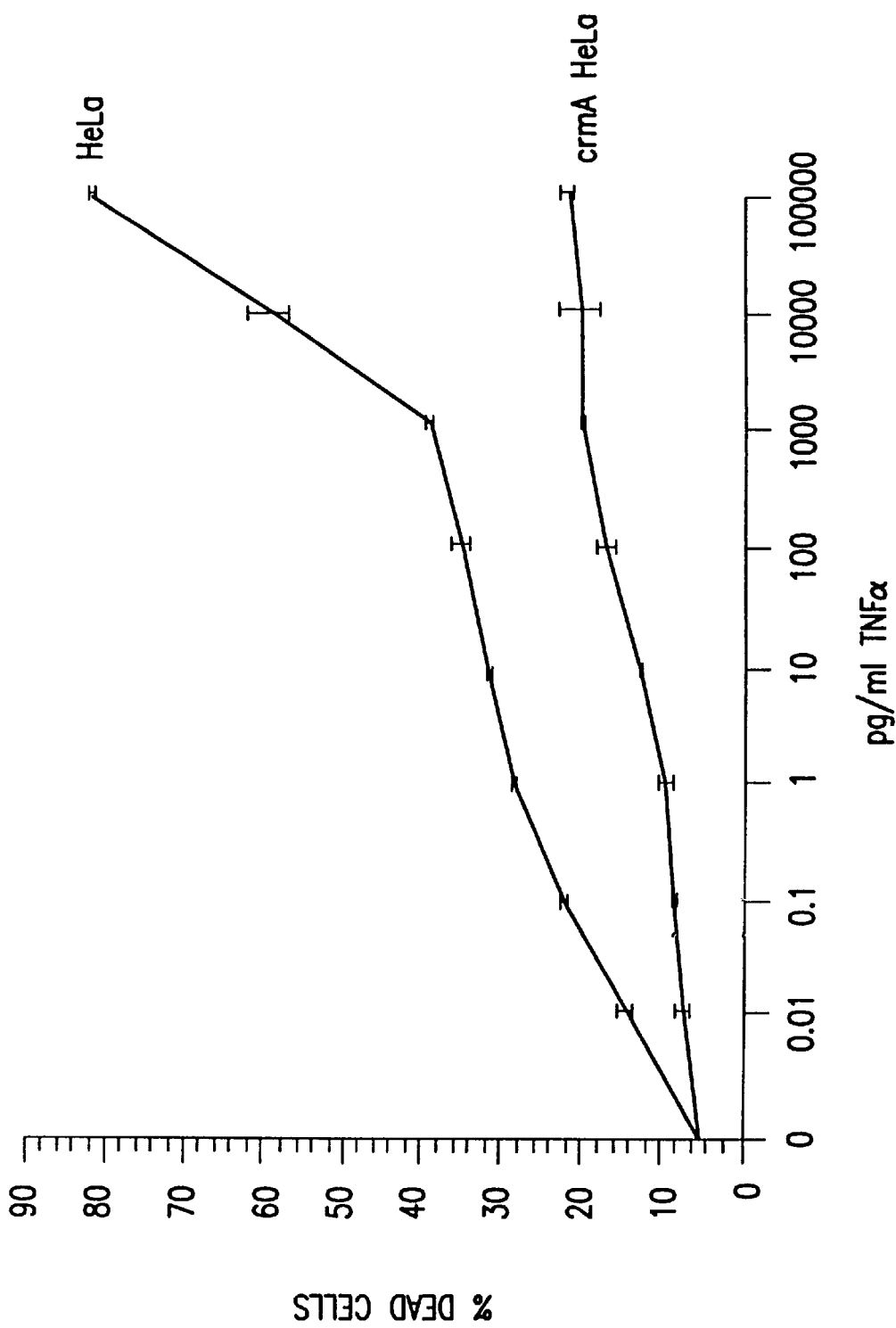

FIG. 16: Suppression of TNF-lnduced Cytotoxicity by Overexpression of CrmA

The results are from three separate experiments with each condition done in duplicate.

DEFINITIONS

In the description that follows, a number of terms used in recombinant DNA (rDNA) technology or in the research area of programmed cell death are extensively utilized. In order to provide a clear and consistent understanding of the specification and claims, including the scope to be given such terms, the following definitions are provided.

Gene

A DNA sequence containing a template for a RNA polymerase. The RNA transcribed from a gene may or may not code for a protein. RNA that codes for a protein is termed messenger RNA (mRNA). It is understood, however, that a gene also encompasses non-transcribed regulatory sequences including, but not limited to, such sequences as enhancers, promoters, and poly-A addition sequences.

A "complementary DNA" or "cDNA" gene includes recombinant genes synthesized by reverse transcription of mRNA and from which intervening sequences (introns) have been removed. Of course, cDNA may also include any complementary part of any gene sequence. The complement could be synthesized, for example, and may not exclude DNA sequences not found in the naturally occurring mRNA.

Cloning vector

A plasmid or phage DNA or other DNA sequence which is able to replicate autonomously in a host cell, and which is characterized by one or a small number of endonuclease recognition sites at which such DNA sequences may be cut in a determinable fashion without loss of an essential biological function of the vehicle, and into which DNA may be spliced in order to bring about its replication and cloning. The cloning vector may further contain a marker suitable for use in the identification of cells transformed with the cloning vehicle. Markers, for example, are tetracycline resistance or ampicillin resistance. The term "cloning vehicle" is sometimes used for "cloning vector."

9

Expression vector

A vector similar to a cloning vector but which is capable of expressing a gene which has been cloned into it, after transformation into a host. The cloned gene is usually placed under the control of (i.e., operably linked to) certain control sequences such as promoter sequences. Control sequences will vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

Programmed cell death

The process in which cell death is genetically programmed. Programmed cell death allows organisms to eliminate cells that have served a developmental purpose but which are no longer beneficial.

Functional Derivative

A "functional derivative" of mIch-2, Ich-1 (Ich-1$_L$ and Ich-1$_S$), or Ich-3 is a protein, or DNA encoding a protein, which possesses a biological activity that is substantially similar to the biological activity of the non-recombinant. A functional derivative of may or may not contain post-translational modifications such as covalently linked carbohydrate, depending on the necessity of such modifications for the performance of a specific function. The term "functional derivative" is intended to include the "fragments," "variants," "analogues," or "chemical derivatives" of a molecule. The derivative retains at least one of the naturally-occurring functions of the parent gene or protein. The function can be any of the regulatory gene functions or any of the function(s) of the finally processed protein. The degree of activity of the function need not be quantitatively identical as long as the qualitative function is substantially similar.

Fragment

A "fragment" is meant to refer to any subgenetic sequence of the molecule, such as the peptide core, or a variant of the peptide core.

DETAILED DESCRIPTION OF THE
PREFERRED EMBODIMENTS

Description

The present invention relates, inter alia, to isolated DNA encoding ced-3 of C. elegans, mIch-2, Ich-1, and lch-3. The invention also encompasses nucleic acids having the cDNA sequence of ced-3, mIch-2, Ich-1, and Ich-3. The invention also encompasses related sequences in other species that can be isolated without undue experimentation. It will be appreciated that trivial variations in the claimed sequences and fragments derived from the full-length genomic and cDNA genes are encompassed by the invention as well. The invention also encompasses protein sequences encoded by ced-3, mIch-2, Ich-1, and Ich-3. It should also be understood that Ich-1 encompasses both Ich-1$_S$ and Ich-1$_L$.

ced-3

Figure 2L:
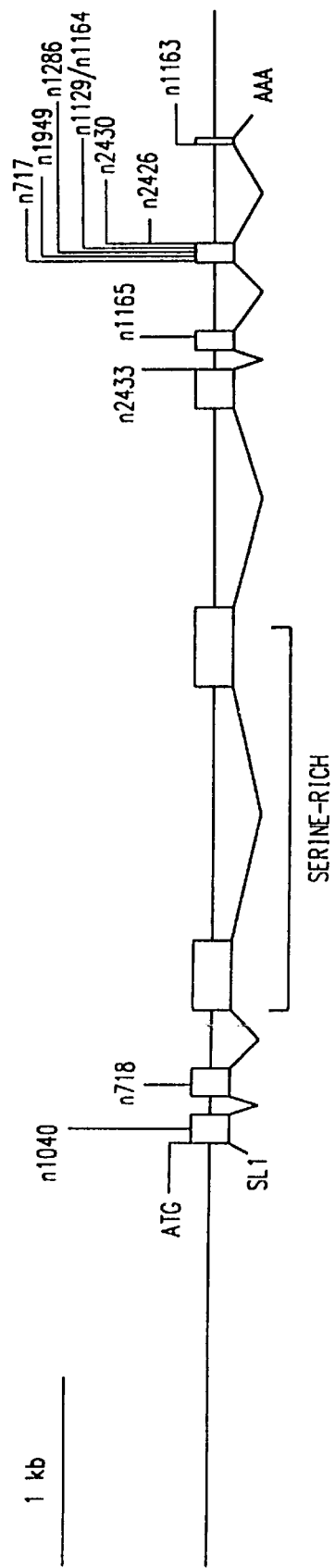
FIG. 2L shows the locations of the introns (lines) and exons (open boxes) of the ced-3 gene as well as the positions of 12 ced-3 mutations analyzed. The serine-rich region, the trans-spliced leader (SL1), the possible start of translation (ATG) and polyadenlyation (AAA) site are also indicated.
Figure 2N:
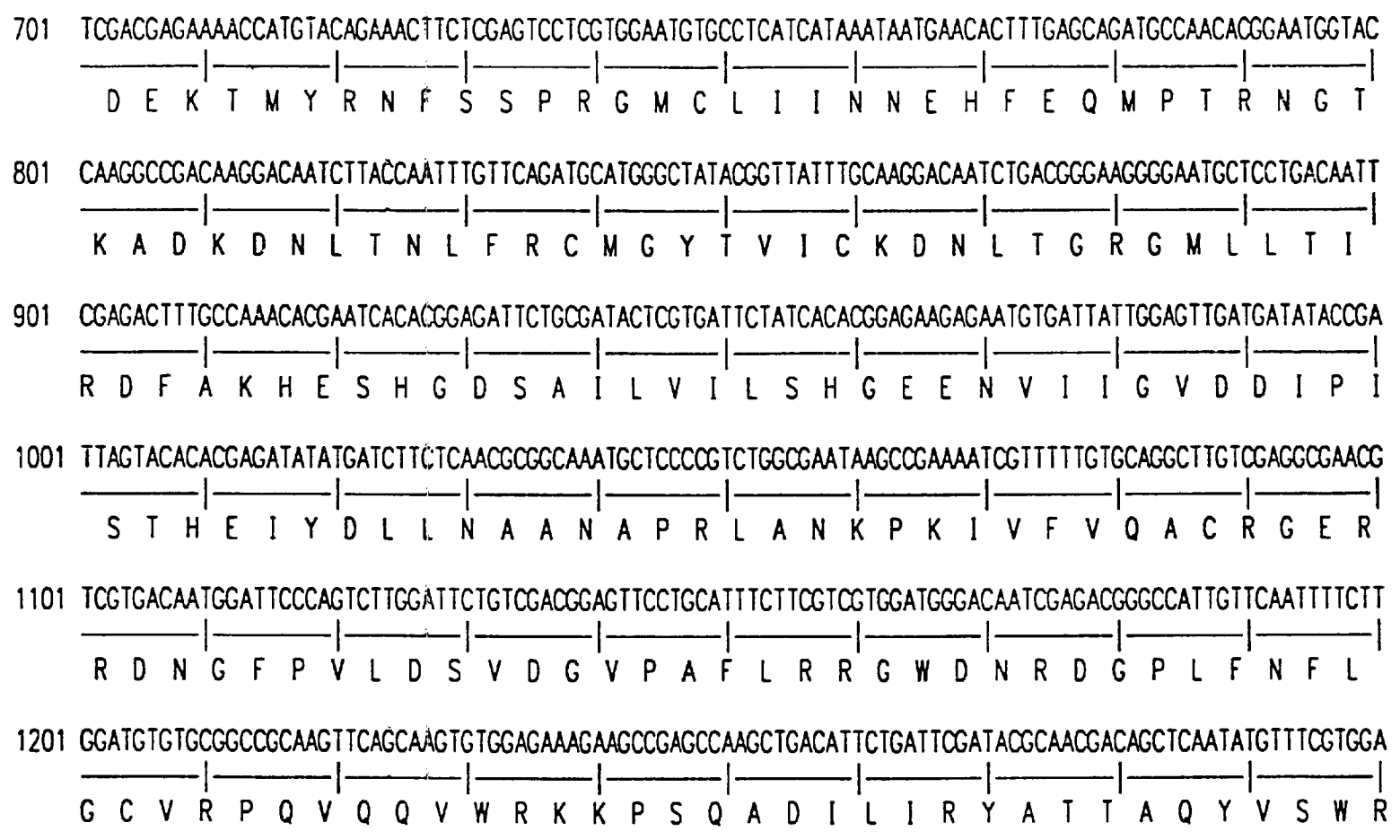

The genomic sequence of the claimed gene encoding ced-3 is shown in FIGS. 2A–2F. The gene is 7,656 base pairs in length and contains seven introns ranging in size from 54 base pairs to 1,195 base pairs. The four largest introns as well as sequences 5' to the START codon contain repetitive elements, some of which have been previously characterized in the non-coding regions of other C. elegans genes such as fem-1 (Spence et al., Cell 60:981–990 (1990)) and hlh-I (Krause et al., Cell 63:907–919 (1990)). A comparison of the repetitive elements in ced-3 with previously characterized repetitive elements is shown in FIGS. 2A(i)–2A(v) (SEQ ID NOS: 3–33). The START codon of ced-3 is the methionine at position 2232 of the genomic sequence shown in FIGS. 2A–2F.

The cDNA sequence of ced-3 shown in FIGS. 2M–2P (SEQ ID NO: 34). The cDNA is 2,482 base pairs in length with an open reading frame encoding 503 amino acids (SEQ ID NO: 35) and 953 base pairs of 3' untranslated sequence. The last 380 base pairs of the 3' sequence are not essential for the expression of ced-3.

In addition to encompassing the genomic and cDNA sequences of ced-3 from C. elegans, the present invention also encompasses related sequences in other nematode species which can be isolated without undue experimentation. For example, the inventors have shown that ced-3 genes from C. briggsae and C. vulgaris may be isolated using the ced-3 cDNA from C. elegans as a probe (see Example 1).

The invention also encompasses protein products from the ced-3 gene, gene variants, derivatives, and related sequences. As deduced from the DNA sequence, ced-3 is 503 amino acids in length and contains a serine-rich middle region of about 100 amino acids. The amino acid sequence comprising the claimed ced-3 is shown in FIGS. 2A–2F and FIGS. 2M–2P (SEQ ID NO: 2). A comparison of ced-3 of C. elegans with the inferred ced-3 sequences from the related nematode species C. briggsae (SEQ ID NO: 36) and C. vulgaris (SEQ ID NO: 37) indicates that the non-serine-rich region is highly conserved and that the serine-rich region is more variable. The non-serine-rich portion of ced-3 is also homologous with hICE (SEQ ID NO: 39). The C-terminal portions of both ced-3 and hICE are similar to the mouse nedd-2 (SEQ ID NO: 40). The results suggest that ced-3 acts as a cysteine protease in controlling the onset of programmed cell death in C. elegans and that members of the ced-3/ICE/nedd-2 gene family function in programmed cell death in a wide variety of species.

mIch-2

The cDNA sequence (SEQ ID NO: 41) and deduced amino acid sequence (SEQ ID NO: 42) of mIch-2 are shown in FIG. 6. As expected, mIch-2 shows homology to both hICE and mICE as well as to C. elegans ced-3 (see FIGS. 7 and 7A). In contrast to other cell-death genes that have been identified, mIch-2 is preferentially expressed in the thymus and placenta. Example 3 describes how the gene was obtained by screening a mouse thymus cDNA library with a DNA probe derived from hICE under conditions of low stringency. Given the amino acid sequence and cDNA sequence shown in FIGS. 6A–6C, preferred methods of obtaining the mIch-2 gene (either genomic or cDNA) are described below.

Ich-1 nedd2, hICE, mIch-2 and ced-3 are all members of the same gene family. This suggested that new genes might be isolated based upon their homology to identified family members.

Ich-1 is 1456 base pairs in length and contains an open reading frame of 435 amino acids (FIGS. 10A–10B (SEQ ID NOS: 50, 51)). The C-terminal 130 amino acids of Ich-1 are over 87% identical to mouse nedd2. However, Ich-1 contains a much longer open reading frame and has the pentapeptide QACRG which is the active center of the proteins of the ced-3/ICE family. The results indicate that the cDNA isolated by Kumar et al. may not have been synthesized from a fully processed mRNA and that the 5' 1147 base pairs which Kumar et al. reported for nedd2 cDNA may actually represent the sequence of an intron. The sequence reported by Kumar et al. contains a region which could potentially code for QACRG but these amino acids are encoded in a different reading frame (SEQ ID NOS: 44, 49) than that indicated by Kumar et al. (FIG. 8). This suggests that Kumar et al. made an error in cloning.

The coding regions of nedd2 and Ich-1$_L$ are highly homologous. The amino acid sequence of the deduced Ich-1$_L$ protein shares 28% identity with ced-3 and 27% identity with hICE (FIGS. 9, 9A).

Ich-1 mRNA is alternatively spliced into two different forms. One mRNA species encodes a protein product of 435 amino acids, designated Ich-1$_L$ (SEQ ID NO: 51), which contains amino acid sequence homologous to both P20 and P10 subunits of hICE as well as entire ced-3 (28% identity). The other mRNA encodes a 312 amino-acid truncated version of Ich-1, designated Ich-1$_S$ (SEQ ID NO: 53), that terminates 21 amino acid residues after the QACRG active domain of Ich-1. Expression of Ich-1$_L$ and Ich-1$_S$ has opposite effects on cell death. Overexpression of Ich-1$_L$ induces Rat-1 fibroblast cells to die in culture, while overexpression of the Ich-1$_S$ suppresses Rat-1 cell death induced by serum deprivation. Results herein suggest that Ich-1 may play an important role in both positive and negative regulation of programmed cell death in vertebrate animals.

Ich-3

Ich-3 (SEQ ID NO: 54) was identified based on its sequence homology with hICE and other isolated ICE homologs. Since the Ich-3 clone isolated by PCR only contains the coding region for the C-terminal half of Ich-3, a mouse thymus cDNA library was screened using the Ich-3 insert. Among 2 million clones screened, 9 positive clones were isolated. The sequence herein is from one clone (deposited at the American Type Culture Collection, Rockville, Md., on Sep. 26, 1997 and given accession number ATCC 209304) that contains the complete coding region for Ich-3 gene.

Methods of Making ced-3

There are many standard procedures for cloning genes which are well-known in the art and which can be used to obtain the ced-3 gene (see e.g., Sambrook et al., *Molecular Cloning, a Laboratory Manual*, 2nd edition, vol. 1–3, Cold Spring Harbor Laboratory Press, 1989). In Example 1, a detailed description is provided of two preferred procedures. The first preferred procedure does not require the availability of ced-3 gene sequence information and is based upon a method described by Ruvkun et al. (*Molecular Genetics of Caenorhabditis Elegans Heterochromic Gene lin-14* 121: 501–516 (1988)). In brief, Bristol and Bergerac strains of nematode are crossed and restriction fragment length polymorphism mapping is performed on the DNA of the resulting inbred strain. Restriction fragments closely linked to ced-3 are identified and then used as probes to screen cosmid libraries for cosmids carrying all or part of the ced-3 gene. Positive cosmids are injected into a nematode strain in which ced-3 has been mutated. Cosmids carrying active ced-3 genes are identified by their ability to rescue the ced-3 mutant phenotype A second method for cloning ced-3 genes relies upon the sequence information which has been disclosed herein. Specifically, DNA probes are constructed based upon the sequence of the ced-3 gene of *C. elegans*. These probes are labelled and used to screen DNA libraries from nematodes or other species. Procedures for carrying out such cloning and screening are described more fully below in connection with the cloning and expression of mIch-2, Ich-1, and Ich-3, and are well-known in the art (see, e.g., Sambrook et al., *Molecular Cloning, a Laboratory Manual*, 2nd edition (1988)). When hybridizations are carried out under conditions of high stringency, genes are identified which contain sequences corresponding exactly to that of the probe. In this way, the exact same sequence as described by the inventors herein may be obtained. Alternatively, hybridizations may be carried out under conditions of low stringency in order to identify genes in other species which are homologous to ced-3 but which contain structural variations (see Example 1 for a description of how such hybridizations may be used to obtain the ced-3 genes from *C. briggsae* and *C. vulgaris*).

The results in Example 2 demonstrate that the products of cell-death genes may be tolerated by cells provided they are expressed at low levels. Therefore, ced-3 may be obtained by incorporating the ced-3 cDNA described above into any of a number of expression vectors well-known in the art and transferring these vectors into appropriate hosts (see Sambrook et al., *Molecular Cloning, a Laboratory Manual*, vol. 3 (1988)). As described below in connection with the expression of mIch-2, Ich-1, and Ich-3, expression systems may be utilized in which cells are grown under conditions in which a recombinant gene is not expressed and, after cells reach a desired density, expression may be induced. In this way, the tendency of cells which express ced-3 to die may be circumvented.

mIch-2, Ich-1, and Ich-3

DNA encoding mIch-2, lch-1, and Ich-3 may be obtained from either genomic DNA or from cDNA. Genomic DNA may include naturally occurring introns. Moreover, such genomic DNA may be obtained in association with the 5' promoter region of the sequences and/or with the 3' transcriptional termination region. Further, such genomic DNA may be obtained in association with the genetic sequences which encode the 5' non-translated region of the mIch-2, Ich-1, and Ich-3 mRNA and/or with the genetic sequences which encode the 3' non-translated region. To the extent that a host cell can recognize the transcriptional and/or translational regulatory signals associated with the expression of the mRNA and protein, then the 5 and/or 3' non-transcribed regions of the native gene, and/or, the 5' and/or 3 non-translated regions of the mRNA, may be retained and employed for transcriptional and translational regulation.

Genomic DNA can be extracted and purified from any cell containing mouse chromosomes by means well known in the art (for example, see *Guide to Molecular Cloning Techniques*, S. L. Berger et al., eds., Academic Press (1987)). Alternatively, mRNA can be isolated from any cell which expresses the genes, and used to produce cDNA by means well known in the art (Id.). The preferred sources for mIch-2 are thymus or placental cells. The mRNA coding for any of the proteins may be enriched by techniques commonly used to enrich mRNA preparations for specific sequences, such as sucrose gradient centrifugation.

For cloning into a vector, DNA prepared as described above (either human genomic DNA or preferably cDNA) is randomly sheared or enzymatically cleaved, and ligated into appropriate vectors to form a recombinant gene library. A DNA sequence encoding the protein or its functional derivatives may be inserted into a DNA vector in accordance with conventional techniques. Techniques for such manipulations are disclosed by Sambrook, et al., supra, and are well known in the art.

In a preferred method, oligonucleotide probes specific for the gene are designed from the cDNA sequences shown in the FIGS. 6A–6C, 10A–10B, 10C, and 14–14A. The oligonucleotide may be synthesized by means well known in the art (see, for example, *Synthesis and Application of DNA and RNA*, S. A. Narang, ed., Academic Press, San Diego, Calif.

(1987)) and employed as a probe to identify and isolate the cloned gene by techniques known in the art. Techniques of nucleic acid hybridization and clone identification are disclosed by Maniatis, T., et al. (In: *Molecular Cloning, A Laboratory Manual*, Cold Spring Harbor Laboratories, Cold Spring Harbor, N.Y. (1982)), and by Hames, B. D., et al. (In: *Nucleic Acid Hybridization, A Practical Approach*, IRL Press, Washington, D.C. (1985)). Those members of the above-described gene library which are found to be capable of such hybridization are then analyzed to determine the extent and nature of the coding sequences which they contain.

To facilitate the detection of the desired coding sequence, the above-described DNA probe is labeled with a detectable group. This group can be any material having a detectable physical or chemical property. Such materials are well-known in the field of nucleic acid hybridization and any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. The oligonucleotide may be radioactively labeled, for example, by "nick-translation" by well-known means, as described in, for example, Rigby, P. J. W., et al., *J. Mol. Biol.* 113:237(1977) or by T4 DNA polymerase replacement synthesis as described in, for example, Deen, K.C., et al., *Anal. Biochem.* 135:456 (1983).

Alternatively, oligonucleotide probes may be labeled with a non-radioactive marker such as biotin, an enzyme or a fluorescent group. See, for example, Leary, J. J., et al., *Proc. Natl. Acad. Sci. USA* 80:4045 (1983); Renz, M., et al., *Nucl. Acids Res.* 12:3435 (1984); and Renz, M., *EMBO J.* 6:817 (1983).

For Ich-1, the isolation shown in the Examples was as follows. Two primers were used in the polymerase chain reaction to amplify nedd2 cDNA from embryonic day 15 mouse brain cDNA (Sambrook et al., *Molecular Cloning, a Laboratory Manual*, vol. 3 (1988)). One primer had the sequence (SEQ ID NO: 57): ATGCTAACTGTC-CAAGTCTA and the other primer had the sequence (SEQ ID NO: 58): TCCAACAGCAGGAATAGCA. The cDNA thus amplified was cloned using standard methodology. The cloned mouse nedd2 cDNA was used as a probe to screen a human fetal brain cDNA library purchased from Stratagene. Such methods of screening and isolating clones are well known in the art (Maniatis, T., et al., *Molecular Cloning, A Laboratory Manual*, Cold Spring Harbor Laboratories, Cold Spring Harbor, N.Y. (1982)); Hames, B. D., etal., *Nucleic Acid Hybridization, A Practical Approach*, IRL Press, Washington, D.C. (1985)). A human nedd-2 cDNA clone was isolated that encodes a protein much longer than the mouse nedd-2 and contains amino acid sequences homologous to the entire hICE and ced-3. The isolated clone was given the name Ice-ced 3 homolog or Ich-1.

The Ich-1 cDNA may be obtained using the nucleic acid sequence information given in FIGS. 10A–10B or 10C–10E. DNA probes constructed from this sequence can be labeled and used to screen human gene libraries as described herein. Also as discussed herein, Ich-1 may be cloned into expression vectors and expressed in systems in which host cells are grown under conditions in which recombinant genes are not expressed and, after cells reach a desired density, expression is induced. In this way, a tendency of cells which express Ich-1 to die may be circumvented.

One method of making Ich-3 is as follows. mRNA was isolated from embryonic day 14 mouse embryos using Invitrogen's microfast track mRNA isolation kit. The isolated mRNA was reverse transcribed to generate template for PCR amplification. The degenerate PCR primers were: cICEB (SEQ ID NO: 59) {TG(ATCG)CC(ATCG)GGGAA (ATCG)AGGTAGAA} and cICEAs (SEQ ID NO: 60) {ATCAT(ATC)ATCCAGGC(ATCG)TGCAG(AG)GG}. The PCR cycles were set up as follows: 1. 94° C., 3 min; 2. 94° C., 1 min; 3. 48° C., 2 min; 4. 72° C., 3 min; 5. return to "2" 4 cycles; 6. 94° C., 1 min; 7. 55° C., 2 min; 8. 72° C., 3 min; 9. return to "6" 34 cycles; 10. 72° C., 10 min; 11. end. Such PCR generated a band about 400 bp, the predicted size of ICE homologs. The PCR products were cloned into T-tailed blunt-ended pBSKII plasmid vector (Stratagene). Plasmids that contain an insert were analyzed by DNA sequencing.

The Ich-3 cDNA may also be obtained using the nucleic acid sequence information given in FIGS. 14–14A. DNA probes constructed from this sequence can be labeled and used to screen human gene libraries as described herein. Also as discussed herein, Ich-3 may be cloned into expression vectors and expressed in systems in which host cells are grown under conditions in which recombinant genes are not expressed and, after cells reach a desired density, expression is induced.

The methods discussed herein are capable of identifying genetic sequences which encode mIch-2, Ich-1, and Ich-3. In order to further characterize such genetic sequences, and, in order to produce the recombinant protein, it is desirable to express the proteins which these sequences encode.

To express any of the genes herein or their derivatives, transcriptional and translational signals recognizable by an appropriate host are necessary. The cloned coding sequences, obtained through the methods described herein, may be operably linked to sequences controlling transcriptional expression in an expression vector and introduced into a host cell, either prokaryote or eukaryote, to produce recombinant protein or a functional derivative thereof. Depending upon which strand of the sequence is operably linked to the sequences controlling transcriptional expression, it is also possible to express antisense RNA or a functional derivative thereof.

Expression of the protein in different hosts may result in different post-translational modifications which may alter the properties of the protein. Preferably, the present invention encompasses the expression of mIch-2, Ich-1, and Ich-3 or a functional derivative thereof, in eukaryotic cells, and especially mammalian, insect and yeast cells. Especially preferred eukaryotic hosts are mammalian cells either in vivo, or in tissue culture. Mammalian cells provide post-translational modifications which should be similar or identical to those found in the native protein. Preferred mammalian host cells include rat-1 fibroblasts, mouse bone marrow derived mast cells, mouse mast cells immortalized with Kirsten sarcoma virus, or normal mouse mast cells that have been co-cultured with mouse fibroblasts (Razin et al., *J. of Immun.* 132:1479 (1984); Levi-Schaffer et al., *Proc. Natl. Acad. Sci.* (*USA*) 83:6485 (1986) and Reynolds et al., *J. Biol. Chem.* 263:12783–12791 (1988)).

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a coding sequence is connected to a regulatory sequence (or sequences) in such a way as to place expression of the coding sequence under the influence or control of the regulatory sequence. Two DNA sequences (e.g. the coding sequence of protein and a promoter) are said to be operably linked if induction of promoter function results in the transcription of the coding sequence and if the nature of the linkage between the two DNA sequences does not (1) result in the introduction of a frame-shift mutation; (2) interfere with the ability of regulatory sequences to direct the expression of the coding sequence, antisense RNA, or protein; or (3) interfere with the ability of the coding sequence template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively, such as the TATA box, capping sequence, CAAT sequence, and the like. Especially, such 5' non-transcribing control sequences will include a region which contains a promoter for transcriptional control of the operably linked gene.

Expression of proteins of the invention in eukaryotic hosts requires the use of regulatory regions functional in such hosts, and preferably eukaryotic regulatory systems. A wide variety of transcriptional and translational regulatory sequences can be employed, depending upon the nature of the eukaryotic host. The transcriptional and translational regulatory signals can also be derived from the genomic sequences of viruses which infect eukaryotic cells, such as adenovirus, bovine papilloma virus, simian virus, herpesvirus, or the like. Preferably, these regulatory signals are associated with a particular gene which is capable of a high level of expression in the host cell.

In eukaryotes, where transcription is not linked to translation, control regions may or may not provide an initiator methionine (AUG) codon, depending on whether the cloned sequence contains such a methionine. Such regions will, in general, include a promoter region sufficient to direct the initiation of RNA synthesis in the host cell. Promoters from heterologous mammalian genes which encode mRNA capable of translation are preferred, and especially, strong promoters such as the promoter for actin, collagen, myosin, etc., can be employed provided they also function as promoters in the host cell. Preferred eukaryotic promoters include the promoter of the mouse metallothionein I gene (Hamer, D., et al., *J. Mol. Appl. Gen.* 1:273–288 (1982)); the TK promoter of herpesvirus (McKnight, S., *Cell* 31:355–365 (1982)); the SV40 early promoter (Benoist, C., et al., *Nature (London)* 290:304–310 (1981)); in yeast, the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)) or a glycolytic gene promoter may be used.

It is known that translation of eukaryotic mRNA is initiated at the codon which encodes the first methionine. For this reason, it is preferable to ensure that the linkage between a eukaryotic promoter and a DNA sequence which encodes the proteins of the invention or functional derivatives thereof, does not contain any intervening codons which are capable of encoding a methionine. The presence of such codons results either in the formation of a fusion protein or a frame-shift mutation.

If desired, a fusion product of the proteins may be constructed. For example, the sequence coding for the proteins may be linked to a signal sequence which will allow secretion of the protein from, or the compartmentalization of the protein in, a particular host. Such signal sequences may be designed with or without specific protease sites such that the signal peptide sequence is amenable to subsequent removal. Alternatively, the native signal sequence for this protein may be used.

Transcriptional initiation regulatory signals can be selected which allow for repression or activation, so that expression of operably linked genes can be modulated. Of interest are regulatory signals which are temperature-sensitive so that by varying the temperature, expression can be repressed or initiated, or are subject to chemical regulation, e.g., metabolite.

If desired, the non-transcribed and/or non-translated regions 3' to the sequence coding for the proteins can be obtained by the above-described cloning methods. The 3'-non-transcribed region may be retained for transcriptional termination regulatory sequence elements; the 3'-non-translated region may be retained for translational termination regulatory sequence elements, or for those elements which direct polyadenylation in eukaryotic cells. Where native expression control signals do not function satisfactorily in a host cell, functional sequences may be substituted.

The vectors of the invention may further comprise other operably linked regulatory elements such as enhancer sequences, or DNA elements which confer tissue or cell-type specific expression on an operably linked gene.

To transform a mammalian cell with the DNA constructs of the invention many vector systems are available, depending upon whether it is desired to insert the DNA construct into the host cell chromosomal DNA, or to allow it to exist in extrachromosomal form. If the protein encoding sequence and an operably linked promoter are introduced into a recipient eukaryotic cell as a non-replicating DNA (or RNA) molecule, the expression of the protein may occur through the transient expression of the introduced sequence.

In a preferred embodiment, genetically stable transformants may be constructed with vector systems, or transformation systems, whereby mIch-2, Ich-1, or Ich-3 DNA is integrated into the host chromosome. Such integration may occur de novo within the cell or, in a most preferred embodiment, through the aid of a cotransformed vector which functionally inserts itself into the host chromosome, for example, retroviral vectors, transposons or other DNA elements which promote integration of DNA sequences in chromosomes.

Cells which have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transfection.

In another embodiment, the introduced sequence is incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, vaccinia virus, SV40, and, in yeast, plasmids containing the 2-micron circle, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982); Bollon, D. P., et al., *J. Clin. Hematol. Oncol.* 10:39–48 (1980); Maniatis, T., In: *Cell Biology: A Comprehensive Treatise*, Vol. 3, *Gene Expression*, Academic Press, N.Y., pp. 563–608 (1980)), and are commercially available.

Once the vector or DNA sequence containing the construct(s) is prepared for expression, the DNA construct (s) is introduced into an appropriate host cell by any of a variety of suitable means, including transfection. After the introduction of the vector, recipient cells are grown in a medium which selects for the growth of vector-containing cells. Expression of the cloned gene sequence(s) results in the production of the protein, or in the production of a fragment of this protein. This expression can take place in a continuous manner in the transformed cells, or in a controlled manner, for example, expression which follows induction of differentiation of the transformed cells (for example, by administration of bromodeoxyuracil to neuroblastoma cells or the like). The latter is preferred for the expression of the proteins of the invention. By growing cells under conditions in which the proteins are not expressed, cell death may be avoided. When a high cell density is reached, expression of the proteins may be induced and the recombinant protein harvested immediately before death occurs.

The expressed protein is isolated and purified in accordance with conventional procedures, such as extraction, precipitation, gel filtration chromatography, affinity chromatography, electrophoresis, or the like.

The mIch-2, Ich-1, and Ich-3 sequences, obtained through the methods above, will provide sequences which not only encode proteins but which also provide for transcription of mIch-2, Ich-1, and Ich-3 antisense RNA; the antisense DNA sequence will be that sequence found on the opposite strand of the strand transcribing the mRNA. The antisense DNA strand may also be operably linked to a promoter in an expression vector such that transformation with this vector results in a host capable of expression of the antisense RNA in the transformed cell. Antisense DNA and RNA may be used to interact with endogenous mIch-2, Ich-1, or Ich-3 DNA or RNA in a manner which inhibits or represses transcription or translation of the genes in a highly specific manner. Use of antisense nucleic acid to block gene expression is discussed in Lichtenstein, C., *Nature* 333:801–802 (1988).

Methods of Using ced-3

The ced-3 gene (as well as ced-3 homologs and other members of the ced-3 gene family) may be used for a number of distinct purposes. First, portions of the gene may be used as a probe for identifying genes homologous to ced-3 in other strains of nematode (see Example 1) as well as in other species (see Examples 2 and 3). Such probes may also be used to determine whether the ced-3 gene or homologs of ced-3 are being expressed in cells.

The cell death genes will be used in the development of therapeutic methods for diseases and conditions characterized by cell death. Among diseases and conditions which could potentially be treated are neural and muscular degenerative diseases, myocardial infarction, stroke, virally induced cell death and aging. The discovery that ced-3 is related to ICE suggests that cell death genes may play an important role in inflammation (IL-1β is known to be involved in the inflammatory response). Thus therapeutics based upon ced-3 and related cell death genes may also be developed.

mIch-2, Ich-1, and Ich-3 mIch-2, Ich-1, and Ich-3 will have the same uses as those described in connection with ced-3 (above) and ICE (see below). The gene sequences may be used to construct antisense DNA and RNA oligonucleotides, which, in turn, may be used to prevent programmed cell death in thymus or placental cells. Techniques for inhibiting the expression of genes using antisense DNA or RNA are well-known in the art (Lichtenstein, C., *Nature* 333:801–802 (1988)). Portions of the claimed DNA sequence may also be used as probes for determining the level of expression. Similarly the protein may be used to generate antibodies that can be used in assaying cellular expression.

Portions of the mIch-2, Ich-1, and Ich-3 genes described above may be used for determining the level of expression of the proteins (mIch-2 in thymus or placental cells as well as in other tissues and organs). Such methods may be useful in determining if these cells have undergone a neoplastic transformation. Probes based upon the gene sequences may be used to isolate similar genes involved in cell death. A portion of the gene may be used in homologous recombination experiments to repair defective genes in cells or, alternatively, to develop strains of mice that are deficient in the gene. Antisense constructs may be transfected into cells, according to the native cellular expression patterns of each gene (placental or thymus cells for mIch-2, for example) in order to develop cells which may be maintained in culture for an extended period of time or indefinitely. Alternatively antisense constructs may be used in cell culture or in vivo to block cell death.

The protein may be used for the purpose of generating polyclonal or monoclonal antibodies using standard techniques well known in the art (Klein, J., *Immunology: The Science of Cell-Noncell Discrimination*, John Wiley & Sons, N.Y. (1982); Kennett et al., *Monoclonal Antibodies, Hybridoma: A New Dimension in Biological Analyses*, Plenum Press, N.Y. (1980); Campbell, A., "Monoclonal Antibody Technology," In: *Laboratory Techniques in Biochemistry and Molecular Biology* 13, Burdon et al. eds., Elseiver, Amsterdam (1984); Harlow and Lane, *Antibodies, A Laboratory Manual*, Cold Spring Harbor Laboratory, N.Y. (1988)). Such antibodies may be used in assays for determining the expression of the genes. Purified protein would serve as the standard in such assays.

Based upon the sequences of FIGS. 6A–6C, probes may be used to determine whether the mIch-2 gene or homologs of mIch-2 are being expressed in cells. Such probes may be utilized in assays for correlating mIch-2 expression with cellular conditions, e.g. neoplastic transformation, as well as for the purpose of isolating other genes which are homologous to mIch-2.

mIch-2 will be used in the development of therapeutic methods for diseases and conditions characterized by cell death. The diseases and conditions which could potentially be treated include neural and muscular degenerative diseases, myocardial infarction, stroke, virally induced cell death and aging.

Antisense nucleic acids based upon the sequences shown in FIGS. 6A–6C may be used to inhibit mIch-2 expression. Such inhibition will be useful in blocking cell death in cultured cells.

mIch-2 may be used to generate polyclonal or monoclonal antibodies using methods well known in the art (see above).

The antibodies may be used in assays for determining the expression of mIch-2. Purified mIch-2 would serve as the standard in such assays.

Based upon the sequences of FIGS. 10A–10B and 10C–10E, probes may be used to determine whether the Ich-1 gene or homologs of Ich-1 are being expressed in cells. Such probes may be utilized in assays for correlating Ich-1 expression with cellular conditions, e.g. neoplastic transformation, as well as for the purpose of isolating other genes which are homologous to Ich-1.

Ich-1 will be used in the development of therapeutic methods for diseases and conditions characterized by cell death. The diseases and conditions which could potentially be treated include neural and muscular degenerative diseases, myocardial infarction, stroke, virally induced cell death and aging.

Antisense nucleic acids based upon the sequences shown in FIGS. 10A–10B and 10C–E, may be used to inhibit Ich-1 expression. Such inhibition will be useful in blocking cell death in cultured cells.

Ich-1 protein may be used to generate polyclonal or monoclonal antibodies using methods well known in the art (see above). The antibodies may be used in assays for determining the expression of Ich-1. Purified Ich-1 would serve as the standard in such assays.

Based upon the sequence of FIGS. 14–14A, probes may be used to determine whether the Ich-3 gene or homologs of Ich-3 are being expressed in cells. Such probes may be utilized in assays for correlating Ich-3 expression with cellular conditions, e.g. neoplastic transformation, as well as for the purpose of isolating other genes which are homologous to Ich-3.

Ich-3 will be used in the development of therapeutic methods for diseases and conditions characterized by cell death. The diseases and conditions which could potentially be treated include neural and muscular degenerative diseases, myocardial infarction, stroke, virally induced cell death and aging.

Antisense nucleic acids based upon the sequence shown in FIGS. 14–14A may be used to inhibit Ich-3 expression. Such inhibition will be useful in blocking cell death in cultured cells.

Ich-3 protein may be used to generate polyclonal or monoclonal antibodies using methods well known in the art (see above). The antibodies may be used in assays for determining the expression of Ich-3. Purified Ich-3 would serve as the standard in such assays.

Method for Preventing Programmed Cell Death in Vertebrate Cells by Inhibiting the Enzymatic Activity of ICE The present invention is directed to preventing the programmed death of vertebrate cells by inhibiting the action of ICE. The detailed structural analysis performed on the ced-3 gene from *C. elegans* revealed a homology to human and murine ICE which is especially strong at the QACRG active domain of hICE (see FIGS. 3A–3B).

In order to determine if ICE functions as a cell death gene in vertebrates, the mICE gene was cloned, inserted into an expression vector and then transfected into rat cells. A close correlation was found between ICE expression and cell death (see Example 2).

Further support for the function of ICE as a cell death gene was obtained from inhibition studies. In order to determine whether cell death can be prevented by inhibiting the enzymatic action of ICE, cell lines were established which produced a high level of crmA. When these cells were transfected with mICE, it was found that a large percentage of the cells expressing mICE maintained a healthy morphology and did not undergo programmed cell death (Example 2 herein).

Evidence that ICE has a physiological role as a vertebrate cell death gene was also obtained by examining cells engineered to over-express bcl-2, an oncogene known to inhibit programmed cell death and to be overexpressed in many follicular and B cell lymphomas. It was found that cells expressing bcl-2 did not undergo cell death despite the high levels of ICE expression (Example 2 herein). These results suggest that bcl-2 may promote malignancy by inhibiting the action of ICE.

Any method of specifically regulating the action of ICE in order to control programmed cell death in vertebrates is encompassed by the present invention. This would include using not only inhibitors specific to ICE, e.g. crmA, or the inhibitors described by Thornberry et al. (*Nature* 356:768–774 (1992)), but also any method which specifically prevented the expression of the ICE gene. Thus, antisense RNA or DNA comprised of nucleotide sequences complementary to ICE and capable of inhibiting the transcription or translation of ICE are within the scope of the invention (see Lichtenstein, C., *Nature* 333:801–802 (1988)).

The ability to prevent vertebrate programmed cell death is of use in developing cells which can be maintained for an indefinite period of time in culture. For example, cells over-expressing crmA may be used as hosts for expressing recombinant proteins. The ability to prevent programmed cell death may allow cells to live independent of normally required growth factors. It has been found that microinjecting crmA mRNA or a crmA-expressing nucleic acid construct into cells allows chicken sympathetic neurons to live in vitro after the removal of neural growth factor.

Method for Promoting Programmed Cell Death in Vertebrate Cells by Increasing or Inducing the Activity of ICE The expression of ICE can be increased in order to cause programmed cell death. For example, homologous recombination can be used to replace a defective region of an ICE gene with its normal counterpart. The level of regulation amenable to manipulation to either increase or decrease the expression of ICE include DNA, RNA, or protein. Genomic DNA, for example, can be mutated by the introduction of selected DNA sequences introduced into the genome by homologous recombination. Any desired mutation can be introduced in vitro and, through gene replacement, either decoding or regulatory sequences of the gene can be manipulated. Extrachromosomal DNA with the appropriate gene sequence can also be introduced into cells to compete with the endogenous product. At the level of RNA, antisense RNA molecules can be introduced, as well as RNA having more or less affinity for the translational apparatus or greater or lesser tendency to be transcribed. At the level of protein, protein counterparts can be designed having a higher or lower activity.

In addition to direct regulation, and particularly an increase in gene expression of ICE, the possibility also exists for indirect regulation by regulating those cellular components that either induce or suppress the expression of ICE. The inventors have found, for example, that TNF-α induces a program of cell death via the activation of hICE genetic sequences. Thus, a further level of regulation is that of modulating the expression of TNF-α and its functional counterparts. Thus, any cellular component regulating programmed cell death by means of the ICE/ced-3 pathway can itself be regulated rather than directly regulating the ICE-gene. Regulation can occur by any of the means discussed above, for example. The genes in the bcl-2 family, p53 and the genes that are regulated by p53 (such as p21), the proteins in the ras pathway (ras, raf 14-3-3), Fas and the proteins in the cytotoxic T cell granules (such as granzyme B) may all directly and indirectly influence the activity of the ICE family. Accordingly, the regulation can also occur by means of any of these genes and others in such pathways. In this way, it may be possible to prevent the uncontrolled growth of certain malignant cells.

Methods of increasing ICE activity may be used to kill undesired organisms such as parasites. crmA is a viral protein that is important for cowpox infection. This suggests that the prevention of cell death may be important for successful infection and that the promotion of ICE expression may provide a means for blocking infection. Activation of ICE family genes may be used to eliminate cancerous cells or any other unwanted cells. Prevention of cell death by inactivating the ICE family of genes could prevent neuronal degenerative diseases, such as Alzheimer's disease, amylotrophic lateral sclerosis, and cell death associated with stroke, ischemic heart injury, and aging.

Having now generally described this invention, the same will be further described by reference to certain specific examples which are provided herein for purposes of illustration only and are not intended to be limiting unless otherwise specified. All references cited throughout the specification are incorporated by reference in their entirety.

EXAMPLE 1

Experimental Procedures

General methods and strains

The techniques used for culturing *C. elegans* have been described by Brenner (Brenner, S., *Genetics* 77:71–94 (1974)). All strains were grown at 20° C. The wild-type parent strains were *C. elegans* variety Bristol strain N2, Bergerac strain EM1002 (Emmons et al., *Cell* 32:55–65 (1983)), *C. briggsae* and *C. vulgaris*. The genetic markers used are described below. These markers have been previously described (Brenner, S., *Genetics* 77:71–94 (1974)); and Hodgkin et al., *Genetics in the Nematode Caenorhabditis Elgens* (Wood et al. eds.) pp. 491–584, Cold Spring Harbor, N.Y. (1988)). Genetic nomenclature follows the standard system (Horvitz et al., *Mol. Gen. Genet.* 175:129–133 (1979)).

LG I: ced-1 (ei 735); unc-54 (r323)

LG VI: unc-31 (e928), unc-30 (e191), ced-3 (n717, n718, n1040, n1129, n11634, n1164, n1165, n1286, n1949, n2426, n2430, n2433), unc-26 (e205), dpy-4 (e1166)

LG V: eg-1(n986); unc-76 (e911)

LG X: dpy-3(e27)

Isolation of additional alleles of ced-3

A non-complementation screen was designed to isolate new alleles of ced-3. Because animals heterozygous for ced3(n717) in trans to a deficiency are viable (Ellis et al., *Cell* 44:817–829 (1986)), it was expected that animals carrying a complete loss-of-function mutant ced-3 allele in trans to ced-3(n717) would be viable even if homozygotes for the allele were inviable. EMS mutagenized egl-1L4 males were mated with ced-3(n717) unc-26(e205); egl-1 (n487); dpy-3(e27) hermaphrodites. egl-1 was used as a marker in this screen. Dominant mutations in egl-1 cause the two hermaphrodite-specific neurons, the HSNs, to undergo programmed cell death (Trent et al., *Genetics* 104:619–647 (1983)). The HSNs are required for normal egg-laying, and egl-1(n986) hermaphrodites, which lack HSNs are egg-laying defective (Trent et al., *Genetics* 104:619–647)). The mutant phenotype of egl-1 is suppressed in a ced-3; egl-1 strain because mutations in ced-3 block programmed cell deaths. egl-1 males were mutagenized with EMS and crossed with ced3(n717) unc-26(e205); egl-1(n487); dpy-3 (e27). Most cross progeny were egg-laying defective because they were heterozygous for ced-3 and homozygous for egl-1. Rare egglaying competent animals were picked, those animals being candidates for carrying new alleles of ced-3. Four such animals were isolated from about 10,000 F1 cross progeny of EMS-mutagenized animals. These new mutations were made homozygous to confirm that they carried mutations of ced-3.

RFLP mapping

Two cosmid libraries were used extensively in this work—a Sau3A I partial digest genomic library of 7000 clones in the vector pHC79 and a Sau3A I partial digest genomic library of 6000 clones in the vector pJB8 (Coulson et al., *Proc. Natl. Acad. Sci. U.S.A.* 83:7821–7825 (1986).

Bristol (N2) and Bergerac (EM1002) DNA was digested with various restriction enzymes and probed with different cosmids to look for RFLPs. nP33 is a HindIII RFLP detected by the "right" end of Jc8. The "right" end of Jc8 was made by digesting Jc8 with EcoRI and self-ligating. nP34 is a HindIII RFLP detected by the "left" end of Jc8. The "left" end of Jc8 was made by digesting Jc8 by SalI and self ligating. nP36 and nP37 are both HindIII RFLPs detected by T10H5 and B0564, respectively.

Germ line transformation

The procedure used for microinjection basically follows that of A. Fire (Fire, A., *EMBO J.* 5:2673–2680 (1986)). Cosmid DNA was twice CsCl gradient purified. Miniprep DNA was used when deleted cosmids were injected and was prepared from 1.5 ml overnight bacterial culture in super-broth. Superbroth was prepared by combining 12 g Bacto tryptone, 24 g yeast extract, 8 ml 50% glycerol and 900 ml $H_2O$. The mixture was autoclaved and then 100 ml of 0.17 M $KH_2PO_4$ and 0.72 M $K_2HPO_4$ were added. The bacterial culture was extracted by the alkaline lysis method as described in Maniatis et al. (*Molecular Cloning, A Laboratory Manual*, Cold Spring Harbor Press, Cold Spring Harbor, N.Y. (1983)). DNA was treated with RNase A (37° C., 30 min) and then with protease K (55° C., 30 min). The preparation was phenol- and then chloroform-extracted, precipitated twice (first in 0.3 M Na acetate and second in 0.1 M K acetate, pH 7.2), and resuspended in 5 1 injection buffer as described by A. Fire (Fire, A., *EMBO J.* 5:2673–2680 (1986)). The DNA concentration for injection was in the range of 100 $\mu$g to 1 mg per ml.

All transformation experiments used the ced-1(e1735); unc-31(e928) ced-3(n717) strain. unc-31 was used as a marker for co-transformation (Kim et al., *Genes & Dev.* 4:357–371 (1990)). ced-1 was present to facilitate scoring of the ced-3 phenotype. The mutations in ced-1 block the engulfment process of cell death, which makes the corpses of the dead cells persist much longer than that in the wild-type (Hedgecock et al., *Science* 220:1277–1280 (1983)). ced-3 phenotype was scored as the number of dead cells present in the head of young L1 animals. The cosmid C10D8 or the plasmid subclones of C10D8 were mixed with C14G10 (unc-31(+)-containing) at a ratio of 2:1 or 3:1 to increase the chances that an Unc-31(+) transformant would contain the cosmid or plasmid being tested. Usually, 20–30 animals were injected in one experiment. Non-Unc F1 progeny of injected animals were isolated three to four days later. About ½ to ⅓ of the non-Unc progeny transmitted the non-Unc phenotype to F2 and established a line of transformants. The young L₁ progeny of such non-Unc transformants were checked for the number of dead cells present in the head using Nomarski optics.

Determination of ced-3 transcript initiation site

Two primers,
Pex 1 (SEQ ID NO: 61): (5'GTTGCACTGCTTTCACGATCTCCCGTCTCT3') and Pex2 (SEQ ID NO: 62): (5'TCATCGACTTTTAGATGACTAGAGAACATC3'), were used for primer extension. The primers for RT-PCR were:
SL1 (SEQ ID NO: 63) (5'GTTTAATTACCCAAGTTTGAG3') and log-5 (SEQ ID NO: 64) (5'CCGGTGACATTGGACACTC3'). The products were reamplified using the primers SL1 and oligo10 (5'ACTATTCAACACTTG3'). A product of the expected length was cloned into the PCR1000 vector (Invitrogen) and sequenced.

Determination and analysis of DNA sequence

For DNA sequencing, serial deletions were made according to a procedure developed by Henikoff (Heinkoff, S., *Gene* 28:351–359 (1984)). DNA sequences were determined using Sequenase and protocols obtained from U.S. Biochemicals with minor modifications.

The ced-3 amino acid sequence was compared with amino acid sequences in the GenBank, PIR and SWISS-PROT databases at the National Center for Biotechnology Information (NCBI) using the blast network service.

Cloning of ced-3 genes from other nematode species

*C. briggsae* and *C. vulgaris* ced-3 genes were isolated from corresponding phage genomic libraries using the ced-3 cDNA subclone pJ118 insert as a probe under low stringency conditions (5×SSPE, 20% formamide, 0.02% Ficoll, 0.02% BSA, 0.02% polyvinylpyrrolidone, and 1% SDS) at 40° C. overnight and washed in 1×SSPE and 0.5% SDS twice at room temperature and twice at 42° C. for 20 min each time.

Results ced-3 is not essential for viability

All previously described ced-3 alleles were isolated in screens designed to detect viable mutants in which programmed cell death did not occur (Ellis et al., *Cell* 44:817–829 (1986)). Such screens might systematically have missed classes of ced-3 mutations that result in inviability. Since animals with the genotype of ced-3/deficiency are viable (Ellis et al., *Cell* 44:817–829 (1986)), a noncomplementation-screening scheme was designed that would allow the isolation of recessive lethal alleles of ced-3. Four new ced-3 alleles (n1163, n1164, n1165, and n1286) were obtained which were viable as homozygotes. These new alleles were isolated at a frequency of about 1 in 2500 mutagenized haploid genomes, approximately the frequency expected for the generation of null mutations in an average *C. elegans* gene (Brenner, S., *Genetics* 77:71–94 (1974); Meneely et al., *Genetics* 92:99–105 (1990); Greenwald et al., *Genetics* 96:147–160 (1980)).

These results suggest that animals lacking ced-3 gene activity are viable. In support of this hypothesis, molecular analysis has revealed that three ced-3 mutations are nonsense mutations that prematurely terminate ced-3 translation and one alters a highly conserved splice acceptor site (see below). These mutations would be expected to eliminate ced-3 activity completely. Based upon these considerations, it was concluded that ced-3 gene activity is not essential for viability.

ced-3 is contained within a 7.5 kb genomic fragment

The ced-3 gene was cloned using the approach of Ruvkun et al., (*Molecular Genetics of the Caenorhabditis elegan Heterochronic Gene lin*-14 121:501–516 (1988)). Briefly (For further details, see Experimental Procedures), the *C. elegans* Bristol strain N2 contains 30 dispersed copies of the transposable element Tc1, whereas the Bergerac strain contains more that 400 copies (Emmons et al., *Cell* 32:55–65 (1983); Finney M., Ph. D. Thesis, "The Genetics and Molecular Biology of unc-86, a *Caenorhabditis elegans* Cell Lineage Gene, " Cambridge, Mass. (1987)). By crossing Bristol and Bergerac strains, a series of recombinant inbred strains were generated in which chromosomal material was mostly derived from the Bristol strain with varying amounts of Bergerac-specific chromosome IV-erived material in the region of the ced-3 gene. By probing DNA from these strains with plasmid pCe2001 which contains Tc1 (Emmons et al., *Cell* 32:55–65 (1983), a 5.1 kb EcoRI Tc1-containing restriction fragment specific to the Bristol strain (restriction fragment length polymorphism nP35) and closely linked to ced-3 was identified.

Figure 1:
FIGS. 1 and 1A: Genetic and Physical Maps of the ced-3 Region on Chromosome IV

Cosmids that contained this 5.1 kb restriction fragment were identified and it was found that these cosmids overlapped an existing cosmid contig that had been defined as part of the *C. elegans* genome project (Coulson et al., *Proc. Natl. Acad. Sci.* 83:7821–7825 (1986). Four other Bristol-Bergerac restriction fragment length polymorphisms were defined by cosmids in this contig (nP33, np34, nP36, nP37). By mapping these restriciton fragment length polymorphisms with respect to the genes unc-30, ced-3 and unc-26, the physical contiguity was oriented with respect to the genetic map and the region containing the ced-3 gene was narrowed to an interval spanned by three cosmids (FIG. 1).

On Southern blot, three of three+Berg unc-26 recombinants showd the Bristol nP33 pattern while two of two ced-3 +Berg recombinants showd the Bergerac pattern (data not shown). thus, nP33 maps very close or to the right of unc-26. For nP34, two of two ced-3+Berg recombinants and two of three+Berg unc-26 recombinants showed the Bergerac pattern; one of the three+Berg unc-26 recombinant showed the Bristol pattern (data not shown). The genetic distance between ced-3 and unc-26 is about 0.2 mu. Thus, nP34 maps between ced-3 and unc-26, about 0.1 mu to the right of ced-3. Similar experiments mapped nP35, the 5.1 kb Bristol specific Tc1 element, to about 0.1 mu to the right of ced-3.

Figure 1A:
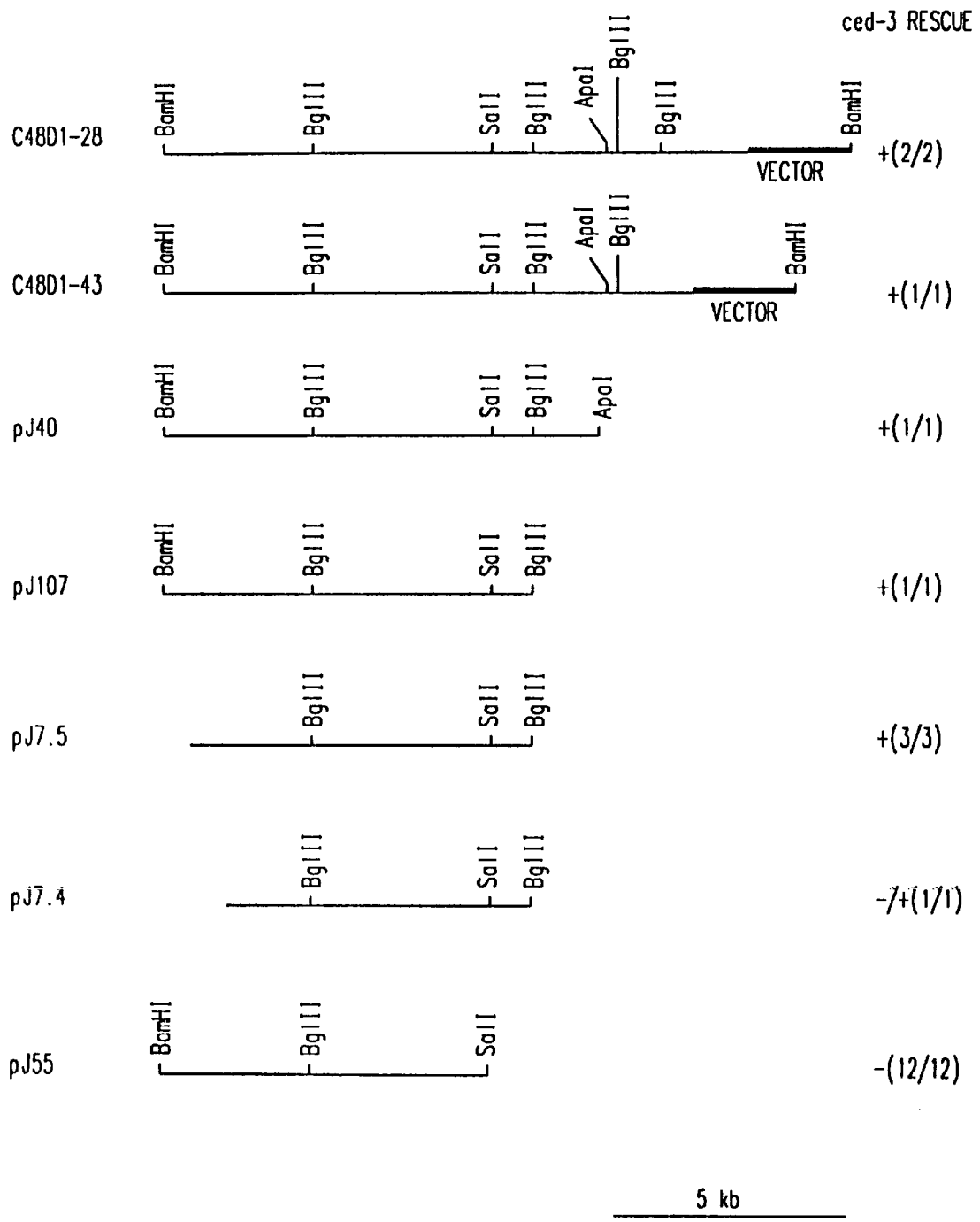

In order to map n36 and n37, Bristol unc-30 ced-3/++ males were crossed with Bergerac hermaphrodites. From the progeny of heterozygotes of genotype unc-30 ced-3 (Bristol)/++ (Bergerac), Unc-30/non-ced-3 and non-Unc-30/ced-3 animals were picked and DNA was prepared from these strains. nP36 maps very close or to the right of unc-30 since two of two unc-30+Berg recombinants showed Bristol pattern and two of two+Berg ced-3 recombinants showed the Bergerac pattern (data not shown). Similarly, nP37 maps very close or to the right of unc-30 since four of the four+Berg ced-3 showed Bergerac pattern and six of six unc-30+Berg recombinants showed the Bristol pattern (data not shown). These experiments narrowed the region containing the ced-3 gene to an interval spanned by the three cosmids (FIG. 1A).

Cosmids that were candidates for containing the ced-3 gene were microinjected (Fire, A., *EMBO J.* 5:2673–2680 (1986)) into ced-3 mutant animals to test for rescue of the mutant phenotype. Specifically, cosmid C14G10, which contains the wild-type unc-31 gene and a candidate cosmid were coinjected into ced-1(e1375); unc-31(e928) ced-3 (n717) hermaphrodites. Non-unc progeny were isolated and observed to see if the non-Unc phenotype was transmitted to the next generation, thus establishing a line of transformed animals. Young L1 progeny of such transformant lines were examined for the presence of cell deaths using Nomarski optics to see whether the ced-3 phenotype was complemented (see Experimental Procedures). Cosmid C 14G10 alone does not confer ced-3 activity when injected into a ced-3 mutant.

unc-31 was used as a marker for co-transformation (Kim et al., *Genes & Devel.* 4:357–371 (1990)). ced-1 was present to facilitate scoring of the ced-3 phenotype. Mutations in ced-1 block the engulfment process of programmed cell death, causing the corpses of dead cells to persist much longer than in the wild-type (Hedgecock et al., *Science* 220:1277–1280 (1983)). Thus, the presence of a corpse indicates a cell that has undergone programmed cell death. The ced-3 phenotype was scored as the number of corpses present in the head of young L1 animals.

As indicated in FIG. 1, of the three cosmids injected (C43C9, W07H6 and C48D1), only C48D1 rescued the ced-3 mutant phenotype. Both non-Unc transformed lines obtained, nisl and nEx2, were rescued. Specifically, L1 ced-1 animals contain an average of 23 cell corpses in the head, and L1 ced-1; ced3 animals contain an average of 0.3 cell corpses in the head (Ellis et al., *Cell* 44:817–829 (1986)). By contrast, ced-1; unc-31 ced-3; nIs1; and ced-1; unc-31 ced-3; nEx2 animals contained an average of 16.4 and 14.5 cell corpses in the head, respectively. From these results, it was concluded that C48D1 contains the ced-3 gene.

To locate ced-3 more precisely within the cosmid C48D1, this cosmid was subcloned and the subclones tested for their ability to rescue the ced-3 mutant phenotype (FIG. 1A). From these experiments, ced-3 was localized to a DNA fragment of 7.5 kb (pJ7.5).

A 2.8 kb ced-3 transcript is expressed primarily during embryogenesis and independently of ced-4 function The 7.6 kb pJ107 subclone of C48D1 (FIG. 1A) was used as a probe in a northern blot of polyA+RNA derived from the wild-type *C. elegans* strain N2. This probe hybridized to a 2.8 kb transcript. Although this transcript is present in 11 different EMS-induced ced-3 mutant strains, subsequent analysis has shown that all 11 tested ced-3 mutant alleles contain mutations in the genomic DNA that encodes this mRNA (see below), thus establishing this RNA as a ced-3 transcript.

The developmental expression pattern of ced-3 was determined by hybridizing a northern blot of RNA from animals at different stages of development with the ced-3 cDNA subclone pJ118 (see below). The ced-3 transcript was found to be most abundant during embryogenesis, when most programmed cell deaths occur, but was also detected during the L1 through L4 larval stages. It is present in relatively high levels in young adults.

Since ced-3 and ced-4 are both required for programmed cell death in *C. elegans*, and since both are highly expressed during embryonic development (Yuan et al., *Dev.* 116:309–320 (1992), the possibility existed that one of the genes might regulate the mRNA level of the other. Previous studies have revealed that ced-3 does not regulate ced-4 mRNA levels (Yuan et al., *Dev.* 116:309–320 (1992)). To determine if ced-4 regulates ced-3 mRNA levels, a northern blot of RNA prepared from ced-4 mutant embryos was probed with the ced-3 cDNA subclone pJ118. It was found that the amount and size of the ced-3 transcript was normal in the ced-4 mutants n1162, n1416, n1894 and n1920. Thus, ced-4 does not appear to affect the steady-state levels of ced-3 mRNA.

ced-3 cDNA and genomic Sequences

To isolate ced-3 cDNA clones, ced-3 genomic DNA pJ40 (FIG. 1A) was used as a probe to screen a cDNA library of the *C. elegans* wild-type strain N2 (Kim et al., *Genes & Dev.* 4:357–371 (1990)). The 2.5 kb cDNA clone pJ87 was isolated in this way. On northern blots, pJ87 hybridized to a 2.8 kb transcript and on Southern blots, it hybridized only to bands to which pJ40 hybridizes (data not shown). Thus, pJ87 represents an mRNA transcribed entirely from pJ40 which can rescue the ced-3 mutant phenotype when microinjected into ced-3 mutant animals. To confirm that pJ87 contains the ced-3 cDNA, a frameshift mutation in the SalI site of pJ40 was made corresponding to the SalI site in the pJ87 cDNA. Constructs containing the frameshift mutation failed to rescue the ced-3 phenotype when microinjected into ced-3 mutant animals (6 transformant lines; data not shown), suggesting that ced-3 activity had been eliminated by mutagenizing a region of genomic DNA that corresponds to the pJ87 cDNA.

The DNA sequence of pJ87 is shown in FIGS. 2M–2P. pJ87 contains an insert of 2482 bp with an open reading frame of 503 amino acids. It has 953 bp of 3' untranslated sequence, not all of which is essential for ced-3 expression; genomic constructs that do not contain 380 bp of the 3'-most region (pJ107 and its derivatives, see FIG. 1a) were capable of rescuing ced-3 mutant phenotype. The cDNA ends with a poly-A sequence, suggesting that the complete 3' end of the ced-3 transcript is present.

To confirm the DNA sequence obtained from the ced-3 cDNA and to study the structure of the ced-3 gene, the genomic sequence of the ced-3 gene from the plasmid pJ107 was determined. The insert in pJ107 is 7656 bp in length (FIGS. 2A–2F).

To determine the location and nature of the 5' end of the ced-3 transcript, a combination of primer extension and amplification using the polymerase chain reaction (PCR) was used. Two primers, Pex1 and Pex2, were used for primer extension. The Pex1 reaction yielded two major bands, whereas the Pex2 reaction gave one band. The Pex2 band corresponds in size to the smaller band from the Pex1 reaction, and agrees in length with a possible transcript that is trans-spliced to a *C. elegans* splice leader (Bektesh et al., *Genes & Dev.* 2:1277–1283 (1988)) at a consensus splice acceptor at position 2166 of the genomic sequence. The nature of the larger Pex1 band is unclear.

To confirm these observations, wild-type total RNA was reverse-transcribed and then amplified using the primers SL1 and log-5 followed by reamplification using the primers SL1 and oligo10. A product of the expected length was cloned into the PCR1000 vector (Invitrogen) and sequenced. The sequence obtained confirmed the presence of a ced-3 message trans-spliced to SL1 at position 2166 of the genomic sequence. These experiments suggest that a ced-3 transcript is trans-spliced to the *C. elegans* splice leader SL1 (Bektesh et al., *Genes & Dev.* 2:1277–1283 (1988)) at a consensus splice acceptor at position 2166 of the genomic sequence. Based upon these observations, it is concluded that the start codon of ced-3 is the methionine encoded at position 2232 of the genomic sequence and that ced-3 is 503 amino acids in length.

The predicted ced-3 is hydrophilic (256/503 residues are charged or polar) and does not contain any obvious potential trans-membrane domains. One region of ced-3 is rich in serines: from amino acid 107 to amino acid 205, 32 of 99 amino acids are serine residues.

The sequences of 12 EMS-induced ced-3 mutations (Table 1) were determined. Eight are missense mutations, three are nonsense mutations, and one alters a conserved G at the splice acceptor site of intron 6. Interestingly, nine of these 12 mutations alter residues within the last 100 amino acids of the protein, and none occurs within the serine-rich region.

TABLE 1

Sites of mutations in the ced-3 gene

| Allele | Mutation | Nucleotide | Codon | Consequence |
|---|---|---|---|---|
| n717 | G to A | 6297 | | Altered splicing |
| n718 | G to A | 2487 | 65 | G to R |
| n1040 | C to T | 2310 | 27 | L to F |
| n1129 & n164 | C to T | 6434 | 449 | A to V |
| n1163 | C to T | 7020 | 486 | S to F |
| n1165 | C to T | 5940 | 403 | Nonsense |
| n1286 | G to A | 6371 | 428 | Nonsense |
| n1949 | C to T | 6222 | 412 | Nonsense |
| n2426 | G to A | 6535 | 483 | E to K |
| n2430 | C to T | 6485 | 466 | A to V |
| n2433 | G to A | 5757 | 360 | G to S |

Nucleotide and codon positions correspond to the numbering in FIGS. 2A–2F

Figure 3:
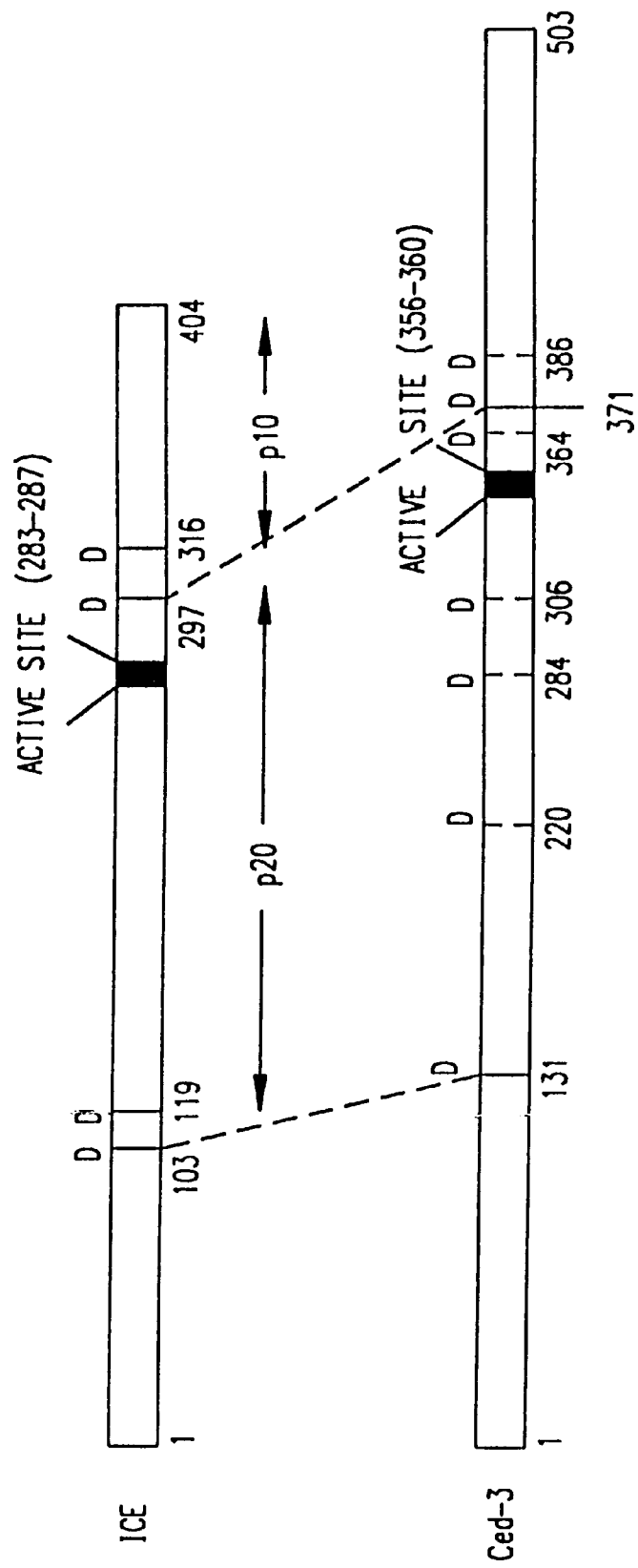
Figure 3A:
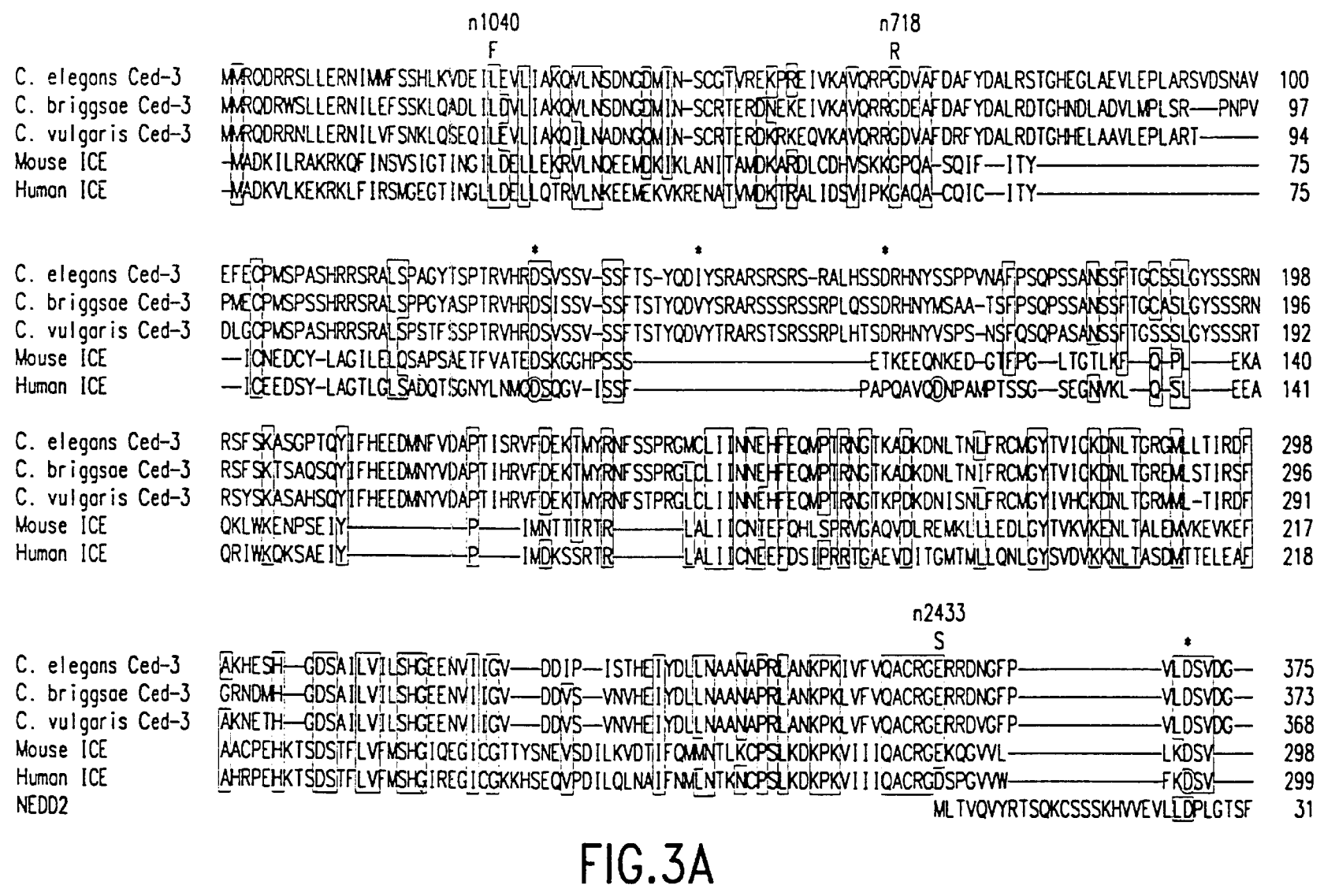

To identify functionally important regions of ced-3, the genomic sequences of the ced-3 genes from the related nematode species *C. briggsae* and *C. vulgaris* were cloned and sequenced. Sequence comparison of the three ced-3 genes showed that the relatively non-serine-rich regions of the proteins are more conserved than are serine-rich regions (FIGS. 3A–3B). All 12 EMS-induced ced-3 mutations altered residues that are conserved among the three species. These results suggest that the non-serine-rich region is important for ced-3 function and that the serine rich region is either unimportant or that residues within it are functionally redundant.

ced-3 protein is similar to the mammalian ICE and nedd-2 proteins

A search of the GenBank, PIR and SWISS-PROT databases revealed that the non-serine-rich regions of ced-3 are similar to hICE and mICE (FIGS. 3A–3B). The most highly conserved region among the proteins shown in FIGS. 3A–3B consists of amino acids 246–360 of ced-3 and amino acids 166–287 of the hICE: 49 residues are identical (43% identity). The active site cysteine of hICE is located at cysteine 285 (Thornberry et al., *Nature* 356:768–774 (1992)). The five-amino-acid peptide (QACRG) around this active cysteine is the longest conserved peptide among mICE and hICE and ced-3.

hICE is composed of two subunits (p20 and p10) that appear to be proteolytically cleaved from a single proenzyme to the mature enzyme (Thornberry et al., *Nature* 356:768–774 (1992)). Two cleavage sites in the proenzyme, Asp-Ser at positions 103 and 297 of hICE, are conserved in ced-3 (position 131 and 371, respectively).

The C-terminal portion of ced-3 and the p10 subunit of hICE are similar to the protein product of the murine nedd-2 gene. ced-3, nedd-2 and hICE are 27% identical (FIGS. 3A–3B). nedd-2 does not contain the QACRG peptide at the active site of hICE and mICE (FIG. 3A). Seven of eight point mutations that were analyzed (n718, n1040, n1129, n1164, n2430, n2426 & n2433) result in alterations of amino acids that are conserved or semi-conserved among the three nematode ced-3 proteins, hICE and nedd-2. In particular, the mutation, n2433, introduces a Gly to Ser change near the putative active cysteine (FIGS. 2A–2F, Table 1).

Discussion

The genes ced-3 and ced-4 are the only genes known to be required for programmed cell death to occur in *C. elegans* (Ellis et al., *Cell* 44:817–829 (1986)). Genetic and molecular studies have revealed that the ced-3 gene shares a number of features with ced-4 (see Yuan et al., *Dev.* 116:309–320 (1992)). Like ced-4, ced-3 is not required for viability. It appears to contain the sequence for a single mRNA which is expressed mostly in the embryo, the stage during which most programmed cell death occurs. Furthermore, just as ced-3 gene function is not required for ced-4 gene expression (Yuan et al., Dev. 116:309–320 (1992)), ced-4 gene function is not required for ced-3 gene expression. Thus, these two genes do not appear to control the onset of programmed cell death by acting sequentially in a regulatory transcriptional cascade. Unlike ced-4 (Yuan et al., *Dev. Biol.* 138:33–41 (1992)), ced-3 is expressed at a substantial level in young adults. This observation suggests that ced-3 expression is not limited to cells undergoing programmed cell death.

The ced-4 amino acid sequence is novel. Two regions show similarity to the EF-hand motif, which binds calcium (Yuan et al., *Dev.* 116:309–320 (1992)). For this reason it has been suggested that ced-4 protein and hence, programmed cell death in *C. elegans*, might be regulated by calcium. ced-3 contains a region of 99 amino acids that contain 32 serines. Since serines are common phosphorylation sites (Edelman et al., *Ann. Rev. Biochem.* 56:567–613 (1987)), ced-3 and hence, programmed cell death in *C. elegans*, may be regulated by phosphorylation. Phosphorylation has previously been suggested to function in cell death (McConkey et al., *J. Immunol.* 145:1227–1230 (1990)). McConkey et al. have shown that several agents that elevate cytosolic cAMP level induce thymocyte death. This suggests that protein kinase A may mediate cell death by phosphorylating certain proteins. Although the precise sequence of the serine-rich region varies among the three Caenorhabditis species studied, the relatively high number of serines is conserved in *C. elegans, C. briggsae* and *C. vulgaris*. None of the mutations in ced-3 affect the serine-rich region. These observations are consistent with the hypothesis that the presence of serines is more important than the precise amino acid sequence within this region.

Much more striking than the presence of the serine-rich region in ced-3 is the similarity between the non-serine-rich regions of ced-3 and hICE and mICE.

The carboxy half of ced-3 is the region that is the most similar to ICE. A stretch of 115 residues (amino acids 246–360 of ced-3) is 43% identical between ced-3 and hICE. This region in ICE contains a conserved pentapeptide QACRG (positions 361–365 of ced-3), which surrounds the active cysteine. Specific modification of this cysteine in hICE results in complete loss of activity (Thornberry et al., *Nature* 356:768–774 (1992)). The ced-3 mutation n2433 alters the conserved glycine in this pentapeptide and eliminates ced-3 function. This suggests that this glycine is important for ced-3 activity and is an integral part of the active site of ICE. Interestingly, while the mutations n718 (position 67 of ced-3) and n1040 (position 27 of ced-3) eliminate ced-3 function in vivo, they contain alterations in conserved residues which are outside of the mature P20 subunit of hICE (Thornberry et al., *Nature* 356:768–774 (1992)). These residues may have a non-catalytic role in both ced-3 and ICE function, e.g., they may maintain a proper conformation for proteolytic activation. The hICE precursor (p45) is proteolytically cleaved at 4 sites (Asp103, Asp19, Asp297 and Asp316) to generate p24, p20, and p10 (Thronberry et al., *Nature* 356:768–774 (1992)). At least two of the cleavage sites are conserved in ced-3. This indicates that the ced-3 protein is processed.

The similarity between ced-3 and ICE suggests that ced-3 functions as a cysteine protease, controlling programmed cell death by proteolytically activating or inactivating a substrate protein. A substrate for ced-3 could be the product of the ced-4 gene which contains 6 Asp residues. These could be the target of ced-3 (Asp25, Asp151, Asp185, Asp192, Asp459 and Asp541). Alternatively, ced-3 could directly cause cell death by proteolytically cleaving certain proteins or subcellular structures that are crucial for cell viability.

ced-3 and ICE are part of a novel protein family. Thornberry et al. suggested that the sequence GDSPG at position 287 of hICE resembles a GX(S/C)XG motif found in serine and cysteine protease active sites (*Nature* 356:768–774 (1992)). However, in the three nematode ced-3 proteins examined, only the first glycine is conserved, and in mICE, the S/C is not present. This suggests that the ced-3/ICE family shares little sequence similarity with known protease families.

The similarity between ced-3 and ICE suggests not only that ced-3 functions as a cysteine protease, but also that ICE functions in programmed cell death in vertebrates. Thus, it has been observed that after murine peritoneal macrophages are stimulated with lipopolysaccharide (LPS) and induced to undergo programmed cell death by exposure to extracellular ATP, mature active IL-1β is released into the culture supernatant. In contrast, when cells are injured by scraping, IL-1β is released exclusively as the inactive proform (Hogoquist et al., *Proc. Natl. Acad. USA* 88:8485–8489 (1991)). These results suggest that ICE is activated upon induction of programmed cell death. ICE transcript has been detected in cells that do not make IL-1β (Cerretti et al., *Science* 256:97–100 (1992)), suggesting that other ICE substrates exist. This suggests that ICE could mediate programmed cell death by cleaving a substrate other than IL-1β.

The carboxy-terminal portions of both ced-3 and the p10 subunit of hICE are similar to the protein encoded by nedd-2. Since nedd-2 lacks the QACRG active domain, it might function to regulate ICE or ICE-like p20 subunits. Interestingly, four ced-3 mutations alter residues conserved between nedd-2 and ced-3. Further, nedd-2 gene expression is high during embryonic brain development, when much programmed cell death occurs. These observations suggest that nedd-2 functions in programmed cell death.

The *C. elegans* gene ced-9 protects cells from undergoing programmed cell death by directly or indirectly antagonizing the activities of ced-3 and ced-4 (Hengartner et al., *Nature* 356:494–499 (1992)). bcl-2 also affects the onset of apoptotic cell death. Thus, if hICE or another ced-3/ICE family member is involved in vertebrate programmed cell death, bcl-2 might act by modulating its activity. The fact that bcl-2 is a dominant oncogene suggests that hICE and other ced-3/ICE family members might be recessive oncogenes. The elimination of such cell death genes would prevent normal cell death and promote malignancy, just as overexpression of bcl-2 does.

EXAMPLE 2

The mouse ICE homolog (mICE) from a mouse thymus cDNA library (Stratagene) was cloned by low stringency hybridization using hICE as a probe. The clone is identical to the clone isolated by Nett et al. (*J. Immun.* 149:3245–3259 (1992)) except that base pair 166 is an A and encodes Asn rather than Asp. This may be a DNA polymorphism because the clone was derived from a B6/CBAF1J (C57Black×CBA) strain cDNA library (Stratagene), while the Nett et al. clone was derived from a WEHI3 cDNA library (Stratagene). Subsequent experiments have shown that this variation is not in a region essential for ICE function (see below).

Figure 4:
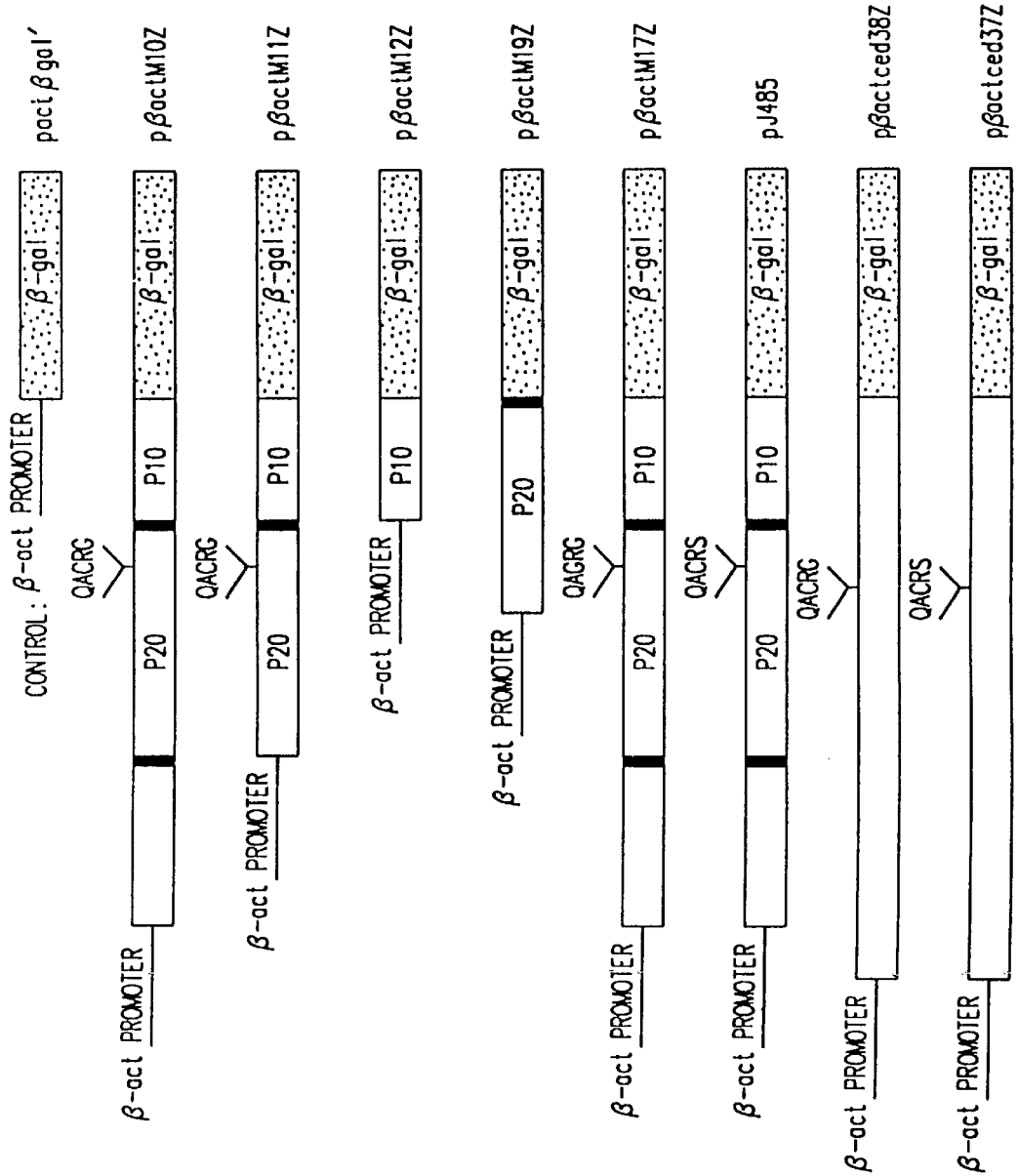
FIG. 4: Construction of Expression Cassettes of mICE-lacZ and ced-3-lacZ Fusion Genes

A transient expression system was developed to determine if overexpression of mICE kills cells. MICE cDNA was fused with the *E. coli* lac-Z gene and placed under the control of the chicken β-actin promoter (FIG. 4). To test the function of the subunits, P20 and P10, which are processed from a precursor peptide, two additional fusion genes were made (P20/P10-lacZ and P10-lacZ).

The constructs, shown in FIG. 4, were transfected into Rat-1 cells by calcium phosphate precipitation. 24 hours after transfection, cells were fixed and X-gal was added. Healthy living rat cells are flat and well-attached to plates, while dying cells are round and often float into the medium. After 3 hours of color development, most blue cells transfected with intact mICE-lacZ or P20/P10-lacZ were round. However, most blue cells transfected with P10-lacZ or the control lac-Z construct were normal flat cells (Table 2). Similar results were obtained with NG108-15 neuronal cells (not shown).

TABLE 2

Overexpression of mICE causes Rat-1 cells to undergo programmed cell death
The constructs shown in FIG. 4 were transiently transfected into Rat-1 cells, Rat-1 cells expressing bcl-2 (Rat-1/bcl-2) or Rat-1 cells expressing crmA (Rat-1/crmA). 24 hrs after transfection, cells were fixed and stained with X-gal for 3 hrs. The data shown are the percentage of round blue cells among total number of blue cells. The data were collected from at least three different experiments.

| Construct | Rat-1 | Rat-1/bcl-2 | Rat-1/crmA |
|---|---|---|---|
| pactβgal' | 1.44 ± 0.18 | 2.22 ± 0.53 | 2.89 ± 0.79 |
| pβactM10Z | 80.81 ± 2.33 | 9.91 ± 2.08 | 18.83 ± 2.86 |
| pβactM11Z | 93.33 ± 2.68 | 13.83 ± 4.23 | 24.48 ± 2.78 |
| pβactM19Z | 2.18 ± 0.54 | — | — |
| pβactM12Z | 2.44 ± 0.98 | 3.33 ± 1.45 | 2.55 ± 0.32 |
| pβact17Z | 2.70 ± 1.07 | — | — |
| pJ485 | 1.32 ± 0.78 | — | — |
| pβactced38Z | 46.73 ± 4.65 | 35.28 ± 1.36 | 34.40 ± 2.38 |
| pβactced37Z | 3.67 ± 1.39 | — | — |

Methods: a: Construction of bcl-2 expression vector (pJ415): pJ415 was constructed by first inserting 5', the 400 bp BglII/BamHI crmA fragment into the BamHI site of the pBabe/puro vector and then inserting the remaining 1 kb BamHI crmA fragment into the 3'BamHI site in the sense direction.
b: Construction of the bcl-2 expression vector (pJ436): pJ436 was constructed by inserting an EcoRI/SalI bcl-2 fragment into the EcoRI/SalI sites of the pBabe/puro vector.
c: Establishing Rat-1 cell lines that overexpress crmA and bcl-2: pJ415 and pJ436 were electroporated into ΨCRE retroviral packaging cells (Danos et al., Proc. Natl. Acad. Sci. (USA) 85:6460–6464 (1988)) using a BioRad electroporating apparatus. Supernatant either from overnight transiently transfected ΨCRE cells or from stable lines of ΨCRE cells expressing either crmA or bcl-2 were used to infect Rat-1 cells overnight in the presence of 8 μg/ml of polybrene. Resistant cells were selected using 30 μg/ml puromycin for about 10 days. Resistant colonies were cloned and checked for expression using both Northern and Western blots. Bcl-2 antibodies were from S. J. Korsmeyer and from DAKO. crmA antiserum was made by immunizing rabbits with an *E. coli*-expressed crmA fusion protein (pJ434). pJ434 was made by inserting an EcoRI/SalI fragment of crmA cDNA into EcoRI/SalI sites of pET21a (Novagen) and fusion protein was expressed in the *E. coli* BL21 (*DE3*) strain. Multiple lines that express either bcl-2 or crmA were checked for suppression of mICE induced cell death and all showed similar results.

When cells were stained with rhodamine-coupled anti-β galactosidase antibody and Hoechst dye, it was found that β-galactosidase-positive round cells had condensed, fragmented nuclei. Such nuclei are indicative of programmed cell death. When observed with an electron microscope, the X-gal reaction product was electron dense, allowing cells expressing mICE-lacZ to be distinguished from other cells (Snyder et al., *Cell* 68:33–51 (1992)). The cells expressing the chimeric gene showed condensed chromatin and membrane blebbing. These are characteristics of cells undergoing programmed cell death (Wyllie, A. H., in *Cell Death in Biology and Pathology*, 9–34 (1981); Oberhammer et al., *Proc. Natl. Acad. Sci. U.S.A.* 89:5408–5412 (1992); Jacobson et al., *Nature* 361:365–369 (1993)). Thus, the results indicate that overexpression of mICE induces programmed cell death and that induction depends on both P20 and P10 subunits.

When color development in Rat-1 cells transfected with mICE-lacZ or P20/P10-lacZ is allowed to proceed for 24 hours, a greater number of flat cells become blue. This result indicates that cells tolerate lower levels of ICE activity.

If mICE is a vertebrate homolog of ced-3, then ced-3 might also be expected to cause cell death in vertebrates. This hypothesis was tested by making a ced-3-lacZ fusion construct and examining its ability to cause cell death using the assay as described above. As expected, the expression of ced-3 caused the death of Rat-1 cells (Table 2).

If mICE functions in a similar way to ced-3, mutations eliminating ced-3 activity in *C. elegans* should also eliminate its activity in vertebrates. This hypothesis was tested by mutating the Gly residue in the pentapeptide active domain of hICE, QACRG, to Ser. It was found that this mutation eliminated the ability of both mICE and ced-3 to cause rat cell death in Rat-1 cells (Table 2).

crmA specifically inhibits ICE activity (Ray et al., above). To demonstrate that cell death associated with overexpression of mICE is due to the enzymatic activity of mICE, Rat-1 cells were infected with a pBabe retroviral construct (Morgenstern et al., *Nucl. Acids Res.* 18:3587–3596 (1990)) expressing crmA and cell lines identified which produce high levels of crmA. When the mICE-lacZ construct was transfected into these cell lines, it was found that a large percentage of blue cells had a healthy, flat morphology (Table 2). In addition, a point mutation that changes the Cys residue in the active site pentapeptide, QACRG to a Gly eliminates the ability of mICE to cause cell death (construct pβactM17Z, FIG. 4, Table 2). This result indicates that the proteolytic activity of mICE is essential to its ability to kill cells.

bcl-2 can also prevent or inhibit cell death (Vaux et al., Nuñez et al., Strasser et al., Sentman et al., above). Rat-1 cells were infected with the pBabe retroviral construct expressing bcl-2. Transfection of the mICE-lacZ fusion construct into the cells lines overexpressing bcl-2 showed that a high percentage of blue cells were now healthy (Table 2). Thus, cell death induced by overexpression of mICE can be suppressed by bcl-2. This result indicates that cell death induced by overexpression of mICE is probably caused by activation of a normal programmed cell death mechanism. Thus, taken together, the results all suggest that vertebrate animals have a genetic pathway of programmed cell death similar to that of *C. elegans* (FIG. 5).

EXAMPLE 3

As described above, the genes in the ICE/ced-3 family would be expected to function during the initiation of programmed cell death. In order to identify additional members of this gene family, cDNA encoding hICE was used to screen a mouse thymus cDNA library (Stratagene) under conditions of low stringency. Using this procedure, a new gene was identified and named "mIch-2" (see FIGS. 6A–6C for the cDNA sequence and deduced amino acid sequence of mIch-2).

FIGS. 7 and 7A show that the protein encoded by mIch-2 contains significant homology to hICE, mICE, and ced-3. The sequence homology indicates that mIch-2, like mICE, is a vertebrate cell death gene.

Northern blot analyses showed that the expression of mIch-2, unlike mICE, which is broadly expressed during embryonic development, is restricted to the thymus and placenta, areas in which cell death frequently occurs. In addition, it was found that the expression of mIch-2 in the thymus can be induced by dexamethasone, an agent which causes thymus regression. It is concluded that mIch-2 is a thymus/placenta specific vertebrate cell death gene.

EXAMPLE 4

Extensive cell death occurs in the developing nervous system (Oppenheim, R. W., *Ann. Rev. Neurosci.* 145:453–501 (1991)). Many neurons die during the period of synapse formation. During this critical period, the survival of neurons depends on the availability of neural trophic factors. The survival of isolated primary neurons in vitro depends critically on the presence of such trophic factors (Davies, A. M., *Development* 100:185–208 (1987)). Removal of such factors induces neuronal cell death, usually within 48 hrs. The death of the sympathetic neurons and sensory neurons whose survival depends on one or more members of the nerve growth factor family (nerve growth factor, brain-derived neurotrophic factor, and neurotrophin-3) can be prevented by microinjection of a bcl-2 expression vector (Garcia, I., et al., *Science* 258:302–304 (1993); Allsopp et al., 1993). To examine if the genes in the ICE/ced-3 family are involved in neuronal cell death, the ability of crmA (which inhibits ICE) to inhibit the death of chicken dorsal root ganglionic neurons induced by NGF removal was examined. It was found that microinjection of an expression vector containing crmA inhibits the death of DRG neurons as effectively as that of a bcl-2 expression vector (Gagliardini, V., et al., *Science* 263:826–828 (1994)). This result demonstrates that the genes in the ICE/ced-3 family play a role in regulating neuronal cell death during development.

EXAMPLE 5

Results

Cloning of Ich-1

The protein product of the *C. elegans* cell death gene, ced-3, is homologous to the product of the mouse gene, nedd-2. The nedd-2 cDNA in the data bank has an open reading frame of 171 amino acids and has long 3' and 5' untranslated regions. This 171-amino acid nedd-2 protein does not contain the active domain (SEQ ID NO: 66), QACRG, of ICE and ced-3 proteins and is homologous only to the P10 subunit of mammalian ICE and the C-terminal part of ced-3. While analyzing nedd-2 cDNA, the inventors discovered that it contains a sequence that can potentially encode a QACRG pentapeptide, but that the sequence is in another reading frame. The inventors considered the possibility that the nedd-2 cDNA isolated by Kumar et al. contains cloning artifacts and that another nedd-2 transcript encodes a protein homologous to both the P20 and P10 subunits of ICE.

A mouse nedd-2 probe was made by polymerase chain reaction (PCR). Using this probe, three cDNA libraries were screened: a mouse embryonic day 11.5 cDNA library from CLONTECH (one million clones screened), a human fetal brain cDNA library from James Gusella's laboratory (10 million clones screened), and a human fetal brain cDNA library from Stratagene (one million clones screened). The longest positive cDNA clones were obtained from the Stratagene cDNA library. From the Stratagene library, two cDNA species (pBSH37 and pBSH30) (Deposited on Nov. 8, 1999 at the American Type Culture Collection (ATCC), 10801 University Blvd., Manassas, VA. 20110–2209 ) and assigned numbers PTA-924 and PTA-925 respectively were identified that encode two closely related proteins homologous to the mouse nedd-2 (FIGS. 10A–10E, 11A–11B, and 12A–12C).

The insert of pBSH37 (2.5 kb) encodes a protein of 435 amino acids that contains amino acid sequence similarities to both the P20 and P10 subunits of hICE and the entire ced-3. The insert of pBSH30 (2.2 kb) has an open reading frame of 512 amino acids and contains an additional 61 bp one basepair after the sequence encoding QACRG. This causes an early termination of protein translation. The Northern blot analysis showed that expression of this human gene is different than expression of nedd-2 (Kumar et al.); thus, the sequences were renamed Ich-$1_L$ (pBSH37) (FIGS. 10A–10B) and Ich-$1_S$ (pBSH30) (FIGS. 10C–10E).

A comparison of cDNA sequences revealed that Ich-$1_S$ cDNA differs from Ich-$1_L$ at the 5' end, around the beginning of the initiation of translation, and by the presence of an additional intron in the middle of Ich-$1_S$ cDNA (FIG. 11B). The first difference is at the beginning of the coding region. The putative first methionine of Ich-$1_S$ is 15 amino acids downstream from the first methionine of Ich-$1_L$; the first 35 bp of Ich-$1_S$ are different from Ich-$1_L$ and include a stop codon (FIGS. 10A–10B and 10C). PCR analysis using primers specific to the first 35 bp of Ich-1 and the Ich-$1_S$-specific intron (see below), and human placenta cDNA as template, amplified a DNA fragment of predicted size. This suggests that the 35 bp Ich-$1_S$-specific sequence is not a cloning artifact and is present in the endogenous Ich-$1_S$ mRNA.

The second difference is distal to the active domain QACRG. Ich-$1_S$ begins to differ from Ich-$1_L$ one basepair after the coding region of the active site QACRG. The difference is caused by a 61 bp insertion, which results in a termination codon 21 amino acids downstream from the insertion. The last two identical basepairs of Ich-$1_S$ and Ich-$1_L$ are AG, the general eukaryotic splicing donor consensus sequence (Mount, 1982).

To eliminate the possibility that the 61 bp insertion in pBSH30 is a result of incomplete RNA processing, both forms of murine Ich-1 were cloned from adult mouse brain mRNA by PCR using primers flanking the insertion site as described (Experimental Procedure). The resulting 233 and 172 bp fragments (FIG. 11B) were cloned separately and sequenced. Three murine Ich-$1_L$ clones and two murine Ich-$1_S$ clones were sequenced. Sequencing confirmed that the murine Ich-$1_S$ contains the same 61 bp insertion as in human Ich-$1_S$ at the same position (FIG. 11A).

Chicken Ich-1 from an embryonic chicken cDNA library (Clontech) was also cloned using a chicken Ich-1 probe obtained by PCR (see Experimental Procedures). Two clones were isolated. One encodes Ich-$1_L$ and the other encodes Ich-$1_S$ which contains a 62 bp insertion at the same position. The DNA sequence of the 62 bp insertion is 72% identical to that of human and murine Ich-$1_S$ and also caused premature termination of protein translation. The extra basepair in the intron of chicken Ich-$1_S$ causes the amino acid sequence of the last 41 amino acids of chicken Ich-$1_S$ to differ from human and murine Ich-$1_S$; however, truncation of the protein may be the important point.

To examine the origin of the 61 bp insertion in murine and human Ich-$1_S$, mouse genomic Ich-1 DNA was cloned. Analysis showed that the 61 bp is from an intron whose sequence is identical in human and mouse Ich-1. The difference between Ich-$1_S$ and Ich-$1_L$ is caused by alternative splicing from the two different 5' splicing donor sequences. The first two basepairs of the 61 bp intron and the two basepairs after the 61 bp intron are GT (FIG. 11A). This sequence is the 100% conserved general eukaryotic splicing donor consensus sequence (Mount, 1982). The DNA sequence at the 3' splicing acceptor site is AG. This sequence is the 100% conserved eukaryotic splicing acceptor sequence (FIG. 11A). Thus, the DNA sequences at the splicing junction are completely consistent with alternative splicing of Ich-$1_S$.

As the result of an insertion of an intron between coding regions, the open reading frame of Ich-$1_S$ is divided into two: the first encodes a 312 amino acid peptide homologous to the P20 subunit of hICE. The second encodes a 235 amino acid peptide homologous to a part of the P20 subunit and the P10 subunit of hICE. The second is nearly identical to mouse nedd-2 (FIGS. 10–10E). The data suggest that only the first open reading frame is translated in cells. A schematic diagram of Ich-$1_L$ and Ich-$1_S$ is shown in FIG. 11B.

Ich-$1_L$ contains similarities to both ICE (27% identity and 52% similarity) and ced-3 (28% identity and 52% similarity) (FIGS. 12A–12B and 12C). Thus, the homology between Ich-1 and ced-3, Ich-1 and ICE is about equal.

Ich-1 is expressed in many tissues and THP-1 cells which express interleukin-1β converting enzyme To characterize the function of Ich-1, the expression pattern of Ich-1 was examined. Northern blot analysis of human fetal heart, brain, lung, liver and kidney tissue was done using the insert of pBSH37 as a probe. The probe hybridizes to both Ich-$1_S$ and Ich-$1_L$ transcripts. The analysis showed that 4 kb Ich-1 mRNA is expressed at the same low levels in all tissues examined. When the same Northern blot (completely stripped of the previous probe) was analyzed using the Ich-$1_S$ 61 bp intron as a probe (which hybridizes to Ich-$1_S$ transcript only), it showed that Ich-$1_S$ is expressed in a larger amount in the embryonic heart and brain than in the lung, liver, and kidney. This result demonstrates that in the embryonic lung, liver and kidney, Ich-$1_L$ is expressed to a greater extent than Ich-$1_S$ is. In Northern blot analysis of adult RNA with the pBSH37 probe, Ich-1 is detected in all the tissues examined. The level is higher in placenta, lung, kidney and pancreas than in heart, brain, liver and skeletal muscle.

To study the expression of Ich-$1_L$ and Ich-$1_S$ during mouse embryonic development, a quantitative RT-PCR analysis was developed using specific primers that differentiate between Ich-$1_L$ and Ich-$1_S$. Primers were synthesized that flank the 61 bp intron sequence of Ich-$1_S$. The two primers are located in separate exons separated by a 2.8 kb intron in genomic DNA. Thus, the possibility of genomic DNA contamination was eliminated. Ich-$1_L$ and Ich-$1_S$ were amplified simultaneously to produce DNA fragments of 172 bp and 233 bp, respectively. The cDNA templates were reverse-transcribed from mRNA isolated from thymus, adult heart, adult kidney, embryonic 15d brain, and adult brain. Negative (no DNA template) and positive (Ich-$1_S$ and Ich-$1_L$) controls were used. Acting primers were used on one set of each sample. Analyses showed that only expression of Ich-$1_L$ can be detected in thymus while the expression of both Ich-$1_L$ and Ich-$1_S$ can be detected in heart, kidney, and both embryonic and adult brain. The expression of Ich-$1_S$ was found to be highest in embryonic brain by this PCR analysis. The results are consistent with Northern blot analysis described above. The results were reproducible among multiple mRNA preparations.

To examine whether Ich-1 and hICE are expressed in the same cells, a Northern blot of THP-1 and U937 cells was analyzed with the Ich-1 probe, pBSH37. hICE expression has been detected in these cells (Thornberry, N. A., et al., Nature 356:768–774 (1992); Cerretti, D. P., et al., Science 256:97–100 (1992)). The inventors found that Ich-1 can be detected in THP.1 and U937 cells. Thus, both Ich-1 and hICE are expressed in THP.1 and U937 cells.

Ich-1$_S$, Ich-1$_L$ and hICE expression were compared in human cell lines. Using a similar quantitative RT-PCR analysis, the expression of Ich-1$_L$, Ich-1$_S$ and hICE were compared in HeLa, Jurkat, THP.1 and U937 cells. Ich-1$_L$ and Ich-1$_S$ were amplified simultaneously to produce DNA fragments of 234 bp and 295 bp, respectively. hICE was amplified as a fragment of 191 bp. cDNA templates were reversed-transcribed from mRNA isolated from HeLa, Jurkat, THP.1 and U937 cells. Negative (no DNA template) and positive (hICE cDNA) controls were used. pBSH37 and pBSH30 were used as positive controls for Ich-1$_L$ and Ich-1$_S$ expression. Chicken actin cDNA was used as a positive contraol for actin. Expression of Ich-1$_S$ was detected in HeLa and Jurkat cells but no in THP.1 and U937 cells. Bothe hICE and Ich-1 transcripts are present in relatively high level in HeLa cells. The level of Ich-1 transcrip is higher than that of hICE transcript in Jurkat cells. Both hICE and Ich-1 expression is detected in THP.1 and U937 cells.

Using a quantitative RT-PCR analysis, the inventors examined the expression of hICE and Ich-1 in the normal living T-cell hybridoma DO11.10 cells (Haskins, K., et al., Exp. Med 157:1149–1169 (1983)) and dying DO11.10 cells (serum-dprived). The expression of bothe hICE and Ich-1 can be detected in DO11.10 cells. Interestingly, the expression levels of both Ich-1$_L$ and hICE appear to increase in dying DO11.10 cells.

Overexpression of Ich-1$_L$ induces rat-1 fibroblast death

To examine the function of Ich-1$_L$, the same transient expression system used for ICE (Miura., M., et al., Cell 75:653–660 (1993)) was use dot determine if overexpression of Ich-1 induces programmed cell death. The human Ich-1$_L$ cDNA was fused with the E. coli lacZ gene and fused gene was placed under the control of the chicken β-actin promotor (pβactH37Z). This fusion gene was trasfected into Rat-1 cells by lopfectamine-mediated gene transfer and the expression of the gene was eaxamined using the X-gal reaction. Results showed that most of the blue (X-gal-positive) Rat-1 cells transfected with pBactH37Z were round. these reults are similar to those obtained with cells transfected with mICE-lacZ fusion sequence shown in Table 2. In contract, most blue cells transfected with vector along were falt and healty. This result suggest that the expression of Ich-1$_L$ induces Rat-1 cells to die.

To examine whether the cell death induced by Ich-1 has any cell type specificity and to compalre its effect with that of mICE, mICE-lacZ and Ich-1-lacZ fusion contructs were transfected to HeLa cell, NG108-15 cells, Rat-1 cells, and COS cells. these cells thus expressed mICE-lacZ (pβactM10Z) Ich-1$_L$-LacZ (pβactH37Z) and Ich-1$_S$-lac-Z (pβactH30Z1 and lacZ control (pactβgal'). The cell killing effect was assayed as for Table 2. The results are shown in Table 3.

TABLE 3

EFFECTS OF ICH-1 OVEREXPRESSION ON CELLS IN CULTURE

| Expression cassettes | COS | HeLa | NG108-15 | Rat-1 | Rat-1/bcl-2 | Rat-1/crmA |
|---|---|---|---|---|---|---|
| pactβgal' | • 1.3 + 0.1(983) | 2.9 ± 0.2(1020) | 4.2 ± 0.2(1535) | 2.9 ± 0.2(1470) | 3.4 ± 0.2(1446) | 3.7 ± 0.1(1459) |
| pβactM10Z | • 11.0 ± 0.2(1080) | 93.9 ± 0.3(1003) | 80.2 ± 0.5(1545) | 94.2 ± 1.1(978) | 28.8 ± 0.5(691) | 45.8 ± 1.6(233) |
| pβactH37Z | 8.3 ± 0.9(1053) | 91.4 ± 0.2(1076) | 68.7 ± 1.5(1605) | 92.1 ± 0.3(1079) | 21.5 ± 3.2(1335) | 80.7 ± 0.9(1010) |
| pβactH37ZCS | ND | 5.6 ± 0.1(1039) | 5.9 ± 0.9(707) | 4.1 ± 0.2(1477) | ND | ND |
| pβactH37ZAT | ND | 8.2 ± 0.7(435) | 5.2 ± 0.2(640) | 5.4 ± 0.3(1356) | ND | ND |
| pβactH30Z1 | 1.3 ± 0.2(676) | 0.0 ± 0.0(40) | 0.0 ± 0.0(61) | 1.8 ± 0.4(785) | ND | ND |

The mICE-LacZ (pβactM10Z), Ich-1$_L$-lacZ (pβactH37Z), Ich-1$_L$(S303C)-lacZ (pβactH37ZCS), Ich-1$_L$(T352A)-lacZ (pβactH37ZAT), Ich-1$_S$-lacZ (pβactH30Z1) and control vector alone (pactβgal') were transiently transfected into Rat-1 cells, Rat-1 cells expressing human bcl-2, Rat-1 cells expressing cowpox virus crmA gene, HeLa cells, NG108-15 cells and COS cells. Cells were fixed lightly 24 hr after transfection and stained with X-Gal for 3 hr. The data (mean ± SEM) shown are the percentage of round blue cells among total number of blue cells counted. The numbers in the parentheses are the number of blue cells counted. The data were collected from at least three independent experiments. ND = not determined.

Compared to controls, the cytotoxic effect of Ich-1 and mICE exhibit certain cell type specificities. Expression of Ich-1 or mICE kills Rat-1 cells and HeLa cells effectively (>90% dead). NG108 cells are more resistant to Ich-1 and mICE expression than Rat-1 cells and HeLa cells (68–80% dead). Expression of Ich-1 or mICE cannot kill COS cells.

To confirm that the cell death caused by Ich-1$_L$ expression is apoptosis, the inventors examined the nuclear morphology of the cell death induced by Ich-1 expression. Rat-1 cells were transiently transfected with control pactβgal' vector and 24 hours later, fixed and stained by anti-β-galactosidase antibody or by Hoechst dye 33258 using a protocol from Miura et al. (1993). The nuclear morphology in β-galactosidase-expressing cells is normal and non-condensed. Rat-1 cells were also transiently transfected with pβactH37Z expressing Ich-1$_L$. The nuclei of round cells expressing the Ich-1$_L$-lacZ chimeric gene were condensed and fragmented. This is one of the characteristics of cells undergoing apoptosis. Thus, the results suggest that overexpression of Ich-1$_L$, like that of mICE, causes Rat-1 cells to undergo programmed cell death.

To determine the structure and function of Ich-1$_L$ protein, two mutant Ich-1$_L$ fusion proteins were made: the first is a Ser→Cys 303 in the active site of Ich-1$_L$; the second is a Thr→Ala 352 in the putative P10 subunit (FIGS. 12A–12B). The Ala 352 in P10 is an amino acid residue of ced-3 that is conserved in Ich-1$_L$ but not in ICE. The mutant Ich-1$_L$-lacZ fusion constructs were transfected into Rat-1 cells and expression was examined by the X-gal reaction.

The analysis revealed that the S303C (pβactH37ZCS) and T352A (pβactH37ZAT) mutations eliminated the activity of Ich-1$_L$ completely (Table 3). These results suggest that the ability of Ich-1$_L$ to cause cell death depends upon its enzymatic activity and that only some characteristics of ced-3 are conserved in Ich-1$_L$.

The cell death induced by overexpression of ICE can be inhibited by bcl-2 and crmA (Miura, M., et al., Cell 75:653–660 (1993)). To examine if the cell death induced by expression of Ich-$1_L$ could also be inhibited by bcl-2 and crmA, Ich-$1_L$-lacZ fusion construct (pβactH37Z) was transfected into Rat-1 cells that overexpress either bcl-2 or crmA. Cell death was assayed as described for Table 3. The results showed that the cell death induced by overexpression of Ich-$1_L$ could be inhibited effectively by bcl-2 but only marginally by crmA.

Expression of Ich-$1_S$ protects Rat-1 fibroblast death induced by serum removal Since Ich-$1_S$ contains two open reading frames, it was important to determine which reading frame is functionally translated (FIG. 11A). Ich-$1_S$ was translated in the presence of $^{35}$S-methionine using in vitro transcribed RNA in a reticulocyte lysate as described in Experimental Procedures. The translated products were run on an SDS-polyacrylamide gel with molecular weight standards. Ich-$1_S$ antisense RNA was used as a negative control. Results showed that only the first reading frame was translated.

Second, E. coli lacZ gene was fused to the ends of the first (pβactH30Z1) and second (pβactH30Z2) open reading frames. The constructs were separately transfected into Rat-1 cells and the cells were assayed for color using the X-gal reaction. Results showed that when the lacZ gene was fused to the end of the first open reading frame, blue cells could be detected. Blue cells were not detected when the lacZ gene was fused to the second open reading frame. Thus, it is likely that only the first open reading frame is used in vivo.

To characterize the function of Ich-$1_S$, the ability of pβactH30Z1 to cause cell death was examined. pβactH30Z1 was transfected into Rat-1 cells, COS cells, HeLa cells and NG108-15 cells, and the X-gal reaction was developed as before. The analysis showed that the expression of pβactH30Z1 did not cause cell death (Table 3).

To examine if Ich-$1_S$ has any protective effect against cell death, a stable Rat-1 cell line that expresses Ich-$1_S$ was established. The cDNA Ich-$1_S$ was cloned into pBabepuro retroviral expression vector (Morgenstern et al., Nucl. Acids Res. 18:3587–3596 (1990)) and transfected into Rat-1 cells. The stable transfectants were selected in puromycin and individual clones were assayed for expression of Ich-$1_S$ by Northern blot analysis. The clones that expressed Ich-$1_S$ were used for analysis and the clones that did not express Ich-$1_S$ were used as negative controls together with untransfected Rat-1 cells. Nomarski micrographs were taken on days 0, 2, 3, and 4 of control Rat-1 cells, Ich-$1_S$ non-expressing Rat-1 cells, crmA expressing Rat-1 cells, and bcl-2 expressing Rat-1 cells in serum-free medium. Trypan blue assay was also performed.

When plated to non-confluent density and washed carefully, 90% of Rat-1 cells die in serum-free medium. However, under these conditions, Rat-1 cells expressing bcl-2 or crmA are resistant to death (FIG. 13). When the ability of the stable Rat-1 cell lines that express human Ich-$1_S$ was tested under serum-free conditions, it was found that they are more resistant to serum deprivation than parental Rat-1 cells and negative control transfectants not expressing Ich-$1_S$ (FIG. 13). These experiments suggest that Ich-$1_S$ has the ability to prevent cell death.

Ich-$1_S$ may prevent cell death by inhibiting Ich-$1_L$. The inventors thus examined whether Rat-1 cells express Ich-1. Using mouse Ich-1 cDNA as a probe, an mRNA species predictive of the Ich-1 transcript was detected in Rat-1 cells under low stringency conditions.

Discussion

The isolation and characterization of Ich-1, a mammalian gene belonging to the cell death gene family of ICE/ced-3, has been described. Two distinct Ich-1 mRNA species have been identified (Ich-$1_L$ and Ich-$1_S$). These two cDNAs differ in the 5' region around the translation initiation and in the middle region. The difference in the middle is the result of alternative use of two different 5' splicing donor sites.

The Ich-1 gene is expressed at low levels in embryonic and adult tissues. Ich-$1_S$ is expressed at higher levels than Ich-$1_L$ in embryonic heart and brain. The converse is true in embryonic lung, liver and kidney. Expression of Ich-$1_S$ can be detected in all tissues examined except thymus. The expression of both hICE and Ich-1 can be detected in THP.1 cells, HeLa cells, Jurkat cells, U937 cells, and DO11.10 cells. The expression of both hICE and Ich-$1_L$ appears to increase in dying cells under serum deprived conditions. Overexpression of Ich-$1_L$ in rat fibroblast cells caused programmed cell death prevented by bcl-2. This suggests that Ich-1 is a programmed cell death gene. Overexpression of Ich-$1_S$, however, did not cause cell death. Stable expression of Ich-$1_S$ prevented Rat-1 cell death induced by serum deprivation. The collective results show that Ich-1 encodes protein products that regulate cell death positively and negatively.

The mouse nedd-2 gene was originally isolated by Kumar et al. (Biochem. & Biophy. Res. Comm. 185:1155–1161 (1992)). The nedd-2 gene was identified as having a transcript of 3.7 kb that is abundantly expressed in embryonic day 10 mouse brain and almost undetectable in adult brain. The nedd-2 cDNA isolated contained an open reading frame of 171 amino acids and long 5' and 3' untranslated regions with stop codons in all reading frames. The 171-amino-acid open reading frame is homologous to P10 subunit of hICE and the C-terminal part of ced-3 (Yuan, J., et al., Cell 75:641–752 (1993)). The amino acid sequence of the C-terminal part of Ich-$1_L$ is 87% identical to the amino acid sequence of the mouse nedd-2 protein from residues 42 to 172 (the first 41 amino acids are different because of the presence of the 61 bp intron). In mouse, nedd-2 is a unique gene (L. Wang, unpublished data). Thus, human Ich-1 and mouse nedd-2 must be the same gene.

In the Northern blot analysis described herein, Ich-1 expression in human fetal brain is not high compared to other tissues tested (heart, lung, liver and kidney) and does not appear to be significantly down-regulated in adult brain. Part of the difference could be explained by the different developmental stages tested: mouse E10 versus human 20–26 week old fetuses. However, Ich-1 expression can be detected in human and mouse adult tissues.

In the studies herein, amplification of the 5' untranslated regions of the mouse nedd-2 cDNA that Kumar et al. reported was not achieved. It is possible that the 5' untranslated region in the Kumar et al. clone was a product of incompletely processed nedd-2 mRNA. Both Ich-1 mRNAs are about 4 kb; since the cDNA clones described herein are 2.5 kb and 2.2 kb for Ich-$1_L$ and Ich-$1_S$, respectively, these cDNAs are incomplete. However, since they are fully functional in the assay reported herein, the complete coding regions should be encoded in these two cDNAs.

Ich-1 is a new member of the ICE/ced-3 family of cell death genes. Thus, unlike C. elegans, mammals must have multiple members of ICE/ced-3. Ich-1 is even slightly more homologous to ced-3 than mICE. The cell death induced by overexpression of Ich-1 was poorly inhibited by crmA. This result is similar to that with ced-3 (Miura, M., et al., Cell 75:653–660 (1993)).

The nucleotides corresponding to the two amino acid residues of ced-3 that are conserved in Ich-1, but not in ICE, were mutagenized. Results showed that T352A completely eliminated the ability of Ich-1 to cause cell death, despite the fact that the corresponding amino acid in ICE is a Ser. These data also suggest that Ich-1 is mechanistically more similar to ced-3 than ICE, and that Ich-1 and ICE may have evolved independently from ced-3.

The overexpression of ICE and Ich-1 can kill Rat-1 cells and HeLa cells effectively but NG108 cells only moderately. It is possible that NG108 cells express a higher level of ICE and Ich-1 inhibitors. COS cells are completely resistant to the cell killing activity of ICE and Ich-1. COS cells may lack either the activator or the substrates of ICE and Ich-1. This result also suggests that the cytotoxic effects of ICE and Ich-1 have certain specificity and are unlikely to be caused by random cleavage activities of proteases.

Ich-1 encodes protein products that prevent or cause cell death, depending on how the mRNA is processed. Similar regulation has been observed with bcl-x, a bcl-2 related gene (Boise et al., 1993). The bcl-x transcripts can also be processed in two different ways: the larger mRNA, bcl-$x_L$, encodes a bcl-2 related protein product that can inhibit cell death. Alternative splicing of bcl-x transcript generates another smaller transcript, bcl-$x_S$. This encodes an internal truncated version of bcl-x that inhibits the ability of bcl-2 to enhance the survival of growth factor-deprived cells. Control of the RNA splicing may be an important regulatory point in programmed cell death.

Ich-$1_S$ could act to prevent cell death by inactivating the activator of cell death or by directly inactivating Ich-$1_L$. In the transient transfection assay, the expression of Ich-$1_L$-lacZ fusion gene and the ICE-lacZ fusion gene kill the stable Ich-$1_S$-expressing cells as efficiently as the control Rat-1 cells (L. Wang, unpublished data). Thus, unlike crmA or bcl-2, the inhibition of cell death by Ich-$1_S$ may be highly dosage-dependent. This could explain why the expression of Ich-$1_S$ provided only partial protection of serum deprived Rat-1 cells. Possibly, only cells expressing high levels of Ich-1s are protected.

crmA has the ability to suppress cell death induced by overexpression of Ich-$1_L$. The amino acid sequence of crmA is homologous to the members of the serpin superfamily (Pickup et al., 1986), which usually inhibit serine proteases by acting as pseudosubstrates. The nature of interaction of ICE and crmA protein is likely to be similar to the interaction of other serpin and serine proteases. The inhibition of ICE family members by crmA may depend upon both the affinity and relative concentration of ICEs and crmA. The fact that crmA can suppress a certain percentage of cell deaths induced by overexpression of the Ich-$1_L$ suggests that crmA and Ich-1 can bind to each other. It is possible that when the Ich-1 concentration is lower, crmA may be able to suppress cell death induced by Ich-1 to a greater extent. Microinjection of crmA expression construct can effectively suppress the death of dorsal root ganglia neurons induced by nerve growth factor deprivation (Gagliardini, V., et al., Science 263:826–828 (1994)). One or more ICE/ced-3 family members may be responsible for neuronal cell death. When crmA expression construct is microinjected into neurons, the transient concentration of crmA may be very high. Thus, it is possible that crmA may be able to suppress multiple members of ICE/ced-3 family under such conditions despite the fact that their affinity to crmA is not very high.

Since the expression of Ich-1 and ICE can be detected in the same cells, the results described herein suggest that multiple members of ICE/ced-3 family may contribute to cell death induced by a single signal. There are three possible ways that Ice and Ich-1 may act to cause cell death. First, Ich-1 may activate ICE, directly or indirectly, to cause cell death. Second, ICE may inactivate Ich-1, directly or indirectly, to cause cell death. Third, ICE and Ich-1 may act in parallel to cause cell death. In the first scenario, the inhibitor of ICE should inhibit cell death induced by Ich-1. In the second scenario, the inhibitor of Ich-1 should inhibit the cell death induced by ICE. To test this hypothesis, specific inhibitors for each member of ICH are necessary. For the reasons discussed above, it seems likely that crmA can inhibit other members of ICE/ced-3 family as well. These models can be tested directly by "knock-out" mutant mice in which a specific member of the ICE/ced-3 family is mutated.

Experimental Procedures

Cloning and construction of plasmids

The mouse nedd-2 cDNA was isolated using embryonic mouse brain cDNA and the primer pairs specific for the 5' and 3' untranslated regions and the coding region. Primers nedd2/1 (SEQ ID NO: 67) (5'-CAACCCTGTAACTCTTGATT-3') and nedd2/2 (SEQ ID NO: 68) (5'-ACCTCTTTGGAGCTACCAGAA-3') were used for amplifying the 5' untranslated region. Primers nedd2/3 (SEQ ID NO: 69) (5'-CCAGATCTATGCTAACTGTCCAAGTCTA-3') and nedd2/4 (SEQ ID NO: 70) (5'AAGAGCTCCTCCAACAGCAGGAATAGCA-3') were used for amplifying the nedd-2 coding region. Primer nedd2/5 (SEQ ID NO: 71) (AGAAGCACTTGTCTCTGCTC) and nedd2/6 (SEQ ID NO: 72) (5'TTGGCACCTGATGGCAATAC-3') were used for amplifying the 3' untranslated region. 0.5 kb PCR product of nedd-2 coding region was cloned into pBluescript plasmid vector to be used as a probe (Stratagene).

Two human fetal brain cDNA libraries and one mouse embryonic 11.5d cDNA library were screened with murine nedd-2 cDNA probe at low stringency and one mouse embryonic 11.5d cDNA library. The filters were hybridized in 5×SSPE, 30% formamide, 1×Denhardt's solution, 1% SDS at 42° C. overnight and washed in 1×SSPE and 0.5% SDS, twice at room temperature and twice at 45° C. (20 min). The human Ich-$1_S$ (pBSH30) was isolated from the positive clones using a BamHI-SalI fragment of the murine nedd-2 cDNA, a 70 bp fragment which contains 52 bp of the 61 bp intron, as a probe under the same hybridization and washing conditions described above. The phage clones (pBSH37 for Ich-$1_L$, pBSH30 for Ich-$1_S$) were excised in vivo to obtain plasmids by an in vivo excision protocol (Stratagene). To construct expression constructs, PCR was performed using synthetic primers. H1 (SEQ ID NO: 73) (5'-GATATCCGCACAAGGAGCTGA-3') and H2 (SEQ ID NO: 74) (5'-CTATAGGTGGGAGGGTGTCC-3') were used for Ich-$1_L$ construction. H3 (SEQ ID NO: 75) (5'-GATATCCAGAGGGAGGGAACGAT-3'), corresponding to sequences in the 5' region of Ich-$1_S$ cDNA and H4 (SEQ ID NO: 76) (5'-GATATCAGAGCAAGAGAGGCGGT-3'), corresponding to the sequences in the 3' region of the first open reading frame (ORF) of Ich-$1_S$ were used for the first ORF of Ich-$1_S$ construction. H3 and H5 (SEQ ID NO: 77) (5'-GATATCGTGGGAGGGTGTCCT-3'), corresponding to the sequences in the 3' region of the second ORF of Ich-$1_S$ were used for the second ORF of Ich-$1_S$ construction. pBSH37 and pBSH30 were used as templates where appropriate. The three PCR products were inserted into the EcoRV site of pBluescript II, and the inserts of these subclones, pβSIIh37, pβSIIh30.1, and pβSIIh30.2, were isolated by digestion with SmaI and KpnI and cloned into SmaI-KpnI sites of BSLacZ (Miura, M., et al., Cell 75:653–660 (1993)).

NotI linkers were added to the KpnI site by digesting with KpnI, blunt-ending by T4 polymerase and ligating in the presence of excess NotI linker. These constructs, BSh37Z, BSh30Z1, and BSh30Z2, were digested with NotI and individually cloned into pβactstneoB (which uses the chicken β-actin promoter) (Miyawaki, A., et al., *Neuron* 5:11–18 (1990)). The final plasmids were designated pβactH37Z, pβactH30Z1 and pβactH30Z2, respectively. pBabeH30 plasmid, used for establishing stable Rat-1 cell lines carrying Ich-$1_S$, was constructed by inserting the full length Ich-$1_S$ cDNA into the SalI site of pBabe/puro vector (Morgenstern, J. P., et al., *Nucl. Acids Res.* 18:3587–3596 (1990)).

To mutagenize Cys 303 to a Ser residue in the active domain of Ich-$1_L$ and Ala 352 to a Thr residue in the P10 subunit of Ich-$1_L$, primers containing mutant sites were synthesized as follows:

HM1 5'-ATCCAGGCCTCTAGAGGAGAT-3' (SEQ ID NO: 78)

HM2 5'-ATCTCCTCTAGAGGCCTGGAT-3' (SEQ ID NO: 79)

HM3 5'-TGCGGCTATACGTGCCTCAAA-3' (SEQ ID NO: 80)

HM4 5'-TTTGAGGCACGTATAGCCGCA-3' (SEQ ID NO: 81)

(HM1 corresponds with HM2 and HM3 corresponds with HM4. PCRs were performed in two steps. To make the Cys 303 to Ser mutation, in the first round of PCR, the fragments from the N-terminus to the mutation site of Ich-$1_L$ and from the mutant site to the C-terminus of Ich-$1_L$ were synthesized using two primer pairs, T3 and HM1, HM2 and T7, and PBSH37 as a template. In the second round of PCR, the two PCR fragments generated in the first reaction were used as templates and T7 and T3 were used as primers. Two such rounds of PCR generated a full length Ich-$1_L$ mutant. The other mutation was generated in a similar way, using T3 and HM3, HM4 and T7, for the Ala 352 to Thr mutation, as primers for the first PCR. The PCR products were inserted into the EcoRV site of pBluescript II and sequenced. The mutant cDNA inserts were cloned into expression vectors as described above. The mutated clones were designated pβactH37ZCS and pβactH37ZAT.

Cell culture and functional studies

COS cells, Rat-1 cells, HeLa cells, and NG108-15 cells were maintained in Dulbecco's modified Eagle's medium (DMEM) supplemented with 10% fetal calf serum (FCS). The day before transfection, cells were seeded at a density of about $2.5 \times 10^5$ in each of the 6-well dishes. For each well, 0.7-1 µg of the lacZ chimeric construct and 10 µg of lipofectamine reagent were used according to a protocol from GIBCO BRL (Gaithersburg, Md.). The cells were incubated for 3 hr in serum-free medium containing DNA and lipofectamine. Then an equal volume of growth medium containing 20% serum was added without removing the transfection mixture and incubation was continued for 24 hr. The expression of the chimeric gene in cells in culture was detected as previously described (Miura, M., et al., *Cell* 75:653–660 (1993)).

To establish Rat-1 cell lines overexpressing Ich-$1_S$, pBabeH30 was transfected into Rat-1 cells using lipofectamine mediated gene transfer. Resistant cells were selected using 3 µg/ml puromycin for about 10 days. Cells were assayed for expression of Ich-$1_S$ by Northern blot analysis. To examine whether Ich-$1_S$ can render Rat-1 cells resistant to apoptosis under conditions of serum deprivation, Rat-1 cells overexpressing Ich-$1_S$, untransfected control Rat-1 cells, transfected negative control Rat-1 cells, and Rat-1 cells overexpressing bcl-2 or crmA, were seeded in 24-well dishes at $5 \times 10^4$ cells in 500 µl of DMEM containing 10% FCS for 24 hr, washed once with serum-free DMEM, and transferred into 500 µl of serum-free DMEM. The cells were harvested at daily intervals and stained with 0.4% trypan blue for 5 min. at room temperature. The numbers of dead and living cells were counted using a haemocytometer.

Jurkat cells, THP.1 cells, and U937 cells were cultured in RPMI 1640 medium (GIBCO) with 10% fetal calf serum.

RNA analysis

The Multiple Tissue Northern (MTN) blots membrane of human fetal and adult tissues (CLONTECH) were probed using human Ich-$1_L$ cDNA or the intron of Ich-$1_S$ cDNA (for fetal tissue) in 5×SSPE, 10×Denhardt's solution, 50% formamide, 2% SDS, and 100 µg/ml salmon sperm DNA at 42° C. overnight. The blots were washed twice in 2×SSPE and 0.05% SDS at room temperature, and twice in 0.1× SSPE, and 0.1% SDS for 20 min. at 50° C.

The Multiple Tissue Northern (MTN) blot membrane of human fetal tissue was first probed with a 1.3 kb fragment from the insert of pBSH37, which hybridizes to both Ich-$1_L$ and Ich-$1_S$. The blot was exposed for two days and developed. Then the blot was stripped by boiling the filter in H$_2$O twice for 20 min. After stripping, the filter was re-exposed for three days to ensure that the stripping was complete. Then the filter was re-hybridized with the 70 bp BamHI-SalI fragment derived from mouse nedd-2 gene. This fragment contains 52 bp of the 61 bp intron (which is identical to the human Ich-$1_S$ intron; the remaining 18 bp are from an exon and 5 out of the 18 bp are different from the human Ich-1 sequence). The Northern blot of THP.1 cells and U936 cells was carried out under the same conditions. To detect Ich-$_1$ expression in Rat-1 cells, hybridization was carried out in 25% formamide and under otherwise identical conditions.

Cloning of murine Ich-1

A murine Ich-1 cDNA was cloned in two steps by PCR. A 5' murine Ich-1 cDNA fragment was amplified using a primer derived from the pBSH37 5' end sequence (SEQ ID NO: 82) (5' ATTCCGCACAAGGAGCTGATGGCC 3') and a primer from the mouse nedd-2 after the active site sequence (SEQ ID NO: 83) (5' GCTGGTCGACACCTC-TATC 3') using a mouse embryo cDNA library as template (a gift from D. Nathan). The resulting 945 bp fragment was cloned into the EcoRV site of plasmid pBSKII (Stratagene) and sequenced. A 3' murine Ich-1 cDNA frament was amplified using a human Ich-1 primer further downstream (SEQ ID NO: 84) (5' CAGCTTTTGATGCCTTCTGTGA 3' and a nedd-2 primer downstream from the coding region (SEQ ID NO: 85) (5' CTCCAACAGCAGGAATAGA 3'). The resulting fragment was also cloned in pBSKII and sequenced. The two fragments were then joined together using an unique SalI site at nucleotide 930 from the beginning of the coding region.

Cloning of Chicken Ich-1

A chicken Ich-1 cDNA fragment was obtained using murine Ich-1 degenerate primers. The 5' primer was from murine Ich-1 mucleotide 241 to 268 bp (SEQ ID NO: 86): 5'GC(GATC)TT(TC)GA(TC)GC(GATC)TT(TC)(TCG)GA (AG)GC3'. The 3' primer was from murine Ich-1 nucleotide 883 to 908 bp (SEQ ID NO: 87): 5'CA(GATC)GC(CT)TG (TAG)AT(AG)AA(AG)AACAT(CT)TT(GATC)GG3'. The resulting DNA fragment was used as a probe to screen a chicken embryonic library (CLontech) by high stringency hybridization.

Quantitative PCR Analysis mRNA was isolated using the MicroFast mRNA isolation kit from Invitrogen. 1 to 2 ug of mRNA was used from reverse transcription by randon priming (Invitrogen) using MMLV (Moloney Murin Leukemia Virus) revesrse transcriptase (Invitrogen). The primers used to amplify murine Ich-1: 5' primer, (SEQ ID NO: 88)5' ATGCTAACTGTC-CAAGTCTA 3') and 3' primer (SEQ ID NO: 89) (5' GTCT-CATCTTCATCAACTCC 3'). The primers used to amplify human Ich-1: 5' primer (SEQ ID NO: 90) (5'GTTACCTGCACACCGAGTCACG 3') and 3' primer (SEQ ID NO: 91) (5' GCGTGGTTCTTTCCATCTTGTTG-GTCA 3'). The primers used to amplify hICE: 5' primer (SEQ ID NO: 92) (5' ACCTTAATATGCAAGACTCT-CAAGGAG 3') and 3' primer (SEQ ID NO: 93) (5' GCG-GCTTGACTTGTCCATTATTGGATA 3'). Mouse β-actin primers were used as controls to amplify a 350 bp actin fragment from mouse and human tissue. 5' β-actin primer (SEQ ID NO: 94): 5' GACCTGACAGACTACCTCAT 3'. 3' β-actin primer (SEQ ID NO: 95): 5' AGACAGCACTGT-GTTGGCAT 3'. The following conditions were used for the PCR reactions: 1×reaction buffer (Promega), 1.5 mM MgCl$_2$, 200 μM dNTP, 2 μM each primers, 1 unit of Taq DNA polymerase (Promega) in a total volume of 50 μl. The DNA was denatured for 4 min at 94° C. prior to 26 PCR cycles (94° C., 1 min/55° C., 1 min/72° C., 2 min). In some of the experiments, Vent polymerase (Biolab) was used.

In vitro transcription and translation of Ich-1$_S$

To determine which open reading frame of Ich-1$_S$ was expressed, pBluescript plasmid containing Ich-1$_S$ (pBSH30) was linearized at the 3' multiple cloning site with XhoI, purified, and transcribed with T3 RNA polymerase for 2 hr at 37° C. using a protocol from Stratagene. The plasmid was also linearized at the 5' multiple cloning site with NotI, purified, and transcribed with T7 polymerase as an antisense control. The resulting runoff transcripts were extracted with phenol-chloroform and ethanol precipitated. In vitro translation was performed with rabbit reticulocyte lysate (Promega) in the presence of $^{35}$S-methionine for 1 hr. at 30° C. 5 μl lysate was mixed with equal volume of 2×SDS gel loading buffer and subjected to SDS-polyacrylamide gel electrophoresis (12%). The gel was dried and exposed to X-ray film.

EXAMPLE 6

Experimental Procedures

Cells and tissue culture

HeLa cells were grown in Dulbecco's modified Eagle's medium (DMEM) with 10% fetal bovine serum (FBS). HeLa cells were transfected with pHD1.2 crmA expression vector (Gagliardini, V. et al., Science 263:826–828 (1994)) by calcium phosphate precipitation and two days after transfection, 600 μg/ml of G418 (Gibco) was added for selection. Resistant colonies were cloned by limiting dilution. Dosage response of HeLa and HeLa/crmA cells to TNF-α treatment was tested as follows. Cells were seeded in DMEM plus 10% fetal calf serum in a 24-well plate at a density of 4×10$^4$ cells per well. After overnight incubation, the cells were washed twice with serum-free DMEM. Drugs were then added to a total volume of 0.2 ml of serum-free DMEM and the cells were incubated for 24 hours. Cells were then trypsinized and dead cells scored on a hemocytometer by trypan blue exclusion (Sigma, St. Louis, Mo.). At least 200 cells were scored per well. Each concentration was tested in duplicate each time.

Western blotting

Cells were lysed in SDS sample buffer and cell lysates were subjected to 15% SDS-PAGE. After electroblotting the proteins to an Immobilon nylon membrane (Millipore), the membrane was blocked with 4% nonfat milk in 25 mM Tris-HCl pH7.5, 150 mM NaCl, 0.2% Tween (TBST). The membrane was incubated with anti-crmA antibody (Gagliardini et al., Science 263:826–828 (1994)) (5 μg/ml) for 1 hour at room temperature and then washed five times with TBST. The membrane was incubated with HRP-conjugated goat anti-rabbit IgG (1/1000 dilution, Amersham) for 30 minutes and washed five times with TBST. crmA protein was detected with an ECL detection kit (Amersham).

DNA transfection

One day before transfection, cells were seeded at a density of about 2×10$^5$ per well in 6-well dishes. For each well, 1 μg of plasmid DNA and 10 μg of lipofectamine reagent was added according to a protocol from Gibco BRL. Cells were incubated for 3 hours in serum-free medium containing DNA and lipofectamine, and then medium was changed to DMEM containing 10% FBS and incubation was continued for 24 hours. The expression of chimeric gene was detected as previously described (Muira et al., Cell 75:653–660 (1993)).

Detection of IL-1β production from HeLa cells

HeLa cells were grown overnight in medium containing 10% fetal calf serum and then the medium was changed to a serum-free DMEM with or without drugs. After 24 hours, cells were scraped off and precipitated. Conditioned medium was collected, dialyzed against distilled water at 4° C. overnight, lyophilized, and the residue dissolved in distilled water. Cell precipitates were extracted with extraction buffer (20 mM HEPES-NaOH pH7.4, 10 mM KCl, 1.5 mM MgCl2, 0.5 mM EDTA, 10 μg/ml PMSF, 10 μg/ml E64, 2 μg/ml pepstatin, 1 μg/ml leupeptin, 0.5 μg/ml aprotinin, 1% NP-40). Insoluble materials were removed by centrifugation. Proteins were separated by 15% SDS-PAGE and IL-1β was detected by immunoblotting using anti-human IL-1β antibody (1/300 dilution, Calbiochem).

Results

Establishment of crmA-expressing HeLa cells

To test the hypothesis that activation of ICE is responsible for TNF-α induced apoptosis, the inventors first established HeLa cell lines constitutively expressing cowpox virus crmA protein. This protein is a viral serpin that can specifically inhibit ICE activity (Ray, C. A. et al., Cell 69:597–604 (1992)).

HeLa cell clones expressing crmA were analyzed by Western blot analysis with affinity-purified anti-crmA. HeLa cells were transfected with crmA expression vector and selected for G418 resistance as described in "Experimental Procedures" above. Six different G418 resistant HeLa cell clones were analyzed. As a positive control, cell lysate of a Rat-1 cell clone expressing crmA (Miura, H. et al., Cell 75:653–660 (1993)) was applied to the gel. Several HeLa cell clones stably expressing crmA were established.

Overexpression of Ice/ced-3 family gene in HeLa/crmA cells

The cell lines were tested for resistance to cell death induced by ICE overexpression. The overexpression of crmA in HeLa cells suppressed ICE-induced cell death. HeLa cells constitutively expressing crmA were transfected with a chimeric expression vector expressing both the lacZ and the mICE gene (pβactM10Z). Transfection is described above in "Experimental Procedures". One of the HeLa/crmA clones expressing high levels of crmA could efficiently suppress ICE induced cell death. A clone expressing crmA at low levels also could efficiently suppress the ICE induced cell death under the same conditions (viability 69.8±1.2%, Table 4.)

TABLE 4

Prevention of apoptosis by CrmA

| | % round blue cells | |
|---|---|---|
| Expression cassettes | HeLa | Hela/CrmA |
| pactβGal' | 3.2 ± 0.8 | 1.1 ± 0.4 |
| pβactM10Z | 85.5 ± 3.0 | 46.9 ± 7.0 |
| pβactH37Z | 91.4 ± 4.9 | 87.5 ± 3.0 |

| Drug treatments | % dead cells | |
|---|---|---|
| control | 1.5 ± 0.3 | 5.5 ± 1.8 |
| CHX | 2.9 ± 0.7 | 3.8 ± 0.5 |
| TNF | 2.7 ± 1.2 | 2.8 ± 1.0 |
| CHX + TNF | 68.2 ± 1.9 | 9.7 ± 1.2 |

Cells were transfected and stained as described herein. Plasmid pactβGal' is a control LacZ gene expression vector and plasmid pβactM10Z is a mouse Ice/lacZ chimeric gene expression vector (Muira, M. et al., Cell 75:653–66 (1993)). Plasmid pβactH37Z is a Ich-1/lacZ chimeric gene expression vector (Lin, W. et al., Cell 78:739–750 (1994). The data (mean ± SEM) shown are the percentage of round blue cells among total number of blue cells counted. To see the effects of CHX (20 μg/ml) and the TNF-α (5 ng/ml), cells were treated with drugs for 24 h and cell viabilities were measured by typan blue dye exclusion. The data (mean ± SEM) shown are the percentage of dead cells. The data were collected from at least three independent experiments.

CrmA is a potent and highly specific serpin for ICE. However, cell death induced by overexpression of ced-3 is poorly suppressed by crmA (Miura, M. et al., Cell 75:653–660 (1993)). Ich-1 (nedd-2) has been described above as third member of the ICE/Ced-3 gene family (see also, Kumar, S. et al., Genes Dev. 8:1613–1626 (1994)). As with ICE, overexpression of Ich-1 induces Rat-1 and HeLa cell death efficiently. However, Ich-1 induced cell death is weakly suppressed by overexpression of crmA in HeLa cells (Table 4) and Rat-1 cells. Thus, crmA does not appear to be a general inhibitor of ICE/Ced-3 family protease.

Suppression of TNFα-induced apoptosis by crmA

The effect of crmA expression on TNF-induced apoptosis was tested. TNF induced cytotoxicity was suppressed by overexpression of crmA. HeLa cells or HeLa/crmA cells were treated with cycloheximide (CHX) (20 μg/ml, Sigma), TNF-α (5 ng/ml, Sigma), or a combination of both drugs. Cells were photographed 24 hours after drug treatment. Control HeLa and HeLa/crmA cells were tested for the ability to resist increasing amounts of TNF-α in the presence of 10 μg/ml CHX (FIG. 16). In the presence of CHX, TNF-α efficiently induced HeLa cell death (White, E. et al., Mol. Cell. Biol. 12:2570–2580 (1992)). Under the same conditions, HeLa cells expressing crmA at high levels are resistant to the TNF-α cell death stimulus (Table 4). A clone of HeLa/crmA cells that expresses lower levels of crmA was also resistant under the same conditions (% dead cells= 30.2±1.2%). The dose response of crmA-expressing HeLa cells to increasing amounts of TNF-α in the presence of 10 μg/ml of CHX was tested. HeLa/crmA cells are resistant to 0.01 pg/ml to 100 ng/ml of TNF-α (FIG. 16). After a 24 hour incubation in the presence of 100 ng/ml TNF-α, 83% of the control HeLa cells died compared to 23% of HeLa/crmA cells.

Activation of endogenous ICE after TNF stimulation

The inventors have detected the expression of both ICE and Ich-1 in HeLa cells (Lin, W. et al., Cell 78:739–750 (1994)). Since Ich-1-induced cell death is only weakly suppressed by crmA and crmA appears to be very effective in preventing cell death induced by TNF and CHX treatment, the ICE-mediated cell death pathway may be activated by TNF stimulation and may play a role in HeLa cell death. If this is the case, TNF stimulation should activate endogenous ICE in HeLa cells.

Pro-IL-1β is the only known endogenous substrate for ICE. Active ICE is an oligometric enzyme with p20 and p10 subunits (Thornberry, N. A. et al., Nature 356:768–774 (1992); Cerretti, D. P. et al., Science 256:97–100 (1992)). These subunits are derived from a p45 precursor form of ICE (Thornberry, N. A. et al., Nature 356:768–774 (1992); Cerretti, D. P. et al., Science 256:97–100 (1992)). If ICE is activated after TNF stimulation, the endogenous 33 kd pro-IL-1β should be processed and mature 17.5 kd IL-1βsecreted into the medium.

To detect mature IL-1β, conditioned medium was collected from HeLa cells with or without TNF stimulation. The processing of pro-IL-1β was analyzed by Western blot. Processing of IL-1β was observed only after induction of apoptosis by TNF-α/CHX in HeLa cells. The following samples were compared: purified mature human IL-1β, cell lysates (10 μg protein/lane), conditioned medium (5 μg/lane), serum-free controls, LPS (10 μg/ml, Sigma) treatment, cycloheximide (20 μg/ml) and TNF (5 ng/ml).

The procedure for detecting IL-1β is described above under "Experimental Procedures". Cell viabilities were measured by trypan blue dye exclusion (97.4±1.5% for serum free control, 97.4±0.2% for LPS treatment, 56.3±2.2% for CHX/TNF-α treatment). The data showed that mature IL-1β was only observed after induction of apoptosis by TNF. These results strongly suggest that TNF stimulation induces apoptosis by activation of an ICE-dependent cell death pathway.

Discussion

The inventors have demonstrated herein that overexpression of ICE induces Rat-1 cells to undergo apoptosis (Miura, M. et al., Cell 75:653–660 (1993)) and expression of crmA can prevent chicken DRG neurons from cell death induced by trophic factor deprivation (Gagliardini, V. et al., Science 263:826–828 (1994)). These results show that ICE has the ability to induce cell death and that inhibition of ICE activity can prevent programmed cell death. However, the results did not show that ICE was, indeed, activated during programmed cell death. Using pro-IL-1β processing as an indicator, the inventors have demonstrated that ICE is activated when HeLa cells are induced to die with TNF-α and CHX.

ICE has unique substrate specificity which requires an Asp in the P1 position (Sleath et al., J. Biol. Chem 265:14526–14528 (1990)). Only two eukaryotic proteases are reported to cleave after the Asp. The other is granzyme B, a serine protease in the cytotoxic granules of killer T lymphocytes (Odake et al., Biochemistry 30:2217–2227 (1991)). In THP.1 cells and HeLa cells, expression of both ICE and Ich-1 were detected (Wang et al., Cell 78:739–750 (1994)). However, affinity labeling of THP.1 cell lysates with a competitive, irreversible ICE inhibitor, biotinylated tetrapeptide (acyloxy) methyl ketone, resulted in labeling only of ICE (Thornberry et al., Biochemistry 33:3934–3940 (1994)). This suggests that ICE is the only enzyme to cleave proIL-β in the human monocytic cell line, THP.1. The present studies show that crmA cannot prevent cell death induced by Ich-1 in HeLa cells.

How CHX potentiates the TNF cytotoxicity in non-transformed cells is unclear. Most of the cell lines, including HeLa cells, NIH3T3 cells, and TA1 cells, are not killed by TNF alone, but are killed by the combined action of TNF and CHX (Reid et al., J. Biol. Chem. 264:4583–4589 (1991); Reid et al., J. Biol. Chem. 266:16580–16586 (1991)). TNF-α is a pleiotrophic cytokine which may induce more than one cellular response in a single cell. The presence of CHX may inhibit the synthesis of certain signaling molecules and thus, potentiate the killing activity of TNF. Alternatively, CHX may simply inhibit the synthesis of a general cell survival factor(s) and thus, allow cells to become more sensitive to TNF cytotoxicity.

HeLa cells express predominantly p55 TNF receptor, thought to be responsible for cell death signalling (Engelmann et al., *J. Biol. Chem.* 265:14497–14504 (1990); Thoma et al., *J. Exp. Med.* 72:1019–1023 (1990)). TNF p55 receptor triggers the activation of phospholypase A2, protein kinase C, sphingomyelinase, phosphatidylcholine-specific phospholypase C, and NF-kB (Weigmann et al., *J. Biol. Chem.* 267:17997–18001 (1992); Schutze et al., *Cell* 71:765–776 (1992)). In TNF p55 receptor knockout mice, TNF-mediated induction of NF-kB is prevented in thymocytes (Pfeffer et al., *Cell* 73:457–467 (1993)). TNF p55 receptor knockout mice were resistant to lethal doses of either lipopolysaccharides or *S. aureus* enterotoxin B. This suggests that TNF p55 receptor mediated hepatocyte necrosis (Pfeffer et al., *Cell* 73:457–467 (1993)). After the stimulation of HeLa cells by TNF-α/CHX, not all the proIL-1β was converted into mature IL-1β. ICE activity is likely to be tightly controlled within the cells. A small amount of active ICE may be sufficient for induction of apoptosis. Even in the mature IL-1β-producing monocytic cell line, THP.1, most of the ICE is the p45 inactive form. In non-LPS-stimulated THP.1 cells, only 0.02% of ICE is in the active form. In stimulated cells, the maximum amount of active ICE is less than 2% of total ICE (Ayala et al., *J. Immunol.* 153:2592–2599 (1994)). THP.1 cells may have some protective mechanism to prevent the activated ICE from inducing apoptosis. LPS induces the synthesis of a large amount of pro-IL-1β, which may, in fact, confer protection on THP.1 cells, because substrates usually are good competitive inhibitors of enzymes.

In addition to the secretion of mature IL-1β, there was a significant drop of the proIL-1β level in the cell lysates prepared from TNF-α/CHX-treated cells. This could be the result of secretion of mature IL-1β, inhibition of biosynthesis of proIL-1β, or increase of proteolytic activity within the dying cells. If, however, the inventors' hypothesis is correct (i.e., that pro-IL-1β does act as a competitive inhibitor of ICE), a reduction in the level of pro-IL-1β would in fact represent a further reduction in cellular defense against apoptosis and could be one of the reasons that CHX can increase the cytotoxicity of TNF-α.

TNF is a central component in the mammalian host inflammatory response (Tracey, K. G. et al., *Ann. Rev. Cell. Biol.* 9:317–343 (1993)). In models of septic shock, injection of endotoxin (LPS) rapidly induces TNF, IL-1 and IL-6 (Ford, Y. et al., *J. Exp. Med.* 170:1627–1633 (1989)). Under these conditions, the secretion of IL-1β appears to be dependent upon TNF because passive immunization with TNF monoclonal antibodies during endotoxemia in vivo attenuates the appearance of IL-1β (Fong, Y. et al., *J. Exp. Med.* 170:1627–1633 (1989)). The results herein show that TNF plays a role in activating ICE, the key enzyme in processing IL-1β.

Expression of mitochondrial manganese superoxide dismutase has been shown to promote the survival of tumor cells exposed to TNF (Hirose, K. et al., *Mol. Cell. Biol.* 13:3301–3310 (1993)). This suggests that the generation of free radicals plays a role in cell death induced by TNF. There are several reports that TNF cytotoxicity is related to the generation of free radicals and lipid peroxides (Hennet, T. et al., *Biochem. J.* 289:587–592 (1993); Schulze-Osthoff, K. et al., *J. Biol. Chem.* 267:5317–5323 (1992)). If that is the case, ICE may be activated directly or indirectly by free radicals.

The death of Hela cells induced by TNF is also suppressed by bcl-2 overexpression (the viability is 83.7±2.3% under the experimental conditions described for Table 4). Bcl-2 has been suggested to have the ability to either inhibit the production of free radicals (Kane, D. J. et al., *Science* 262:1274–1277 (1993)) or prevent free radicals from damaging cells (Hockenberry, D. M. et al., *Cell* 75:241–251 (1993)). Thus, in HeLa cells, bcl-2 and crmA may suppress cell death induced by TNF through a single biochemical pathway of programmed cell death.

Fas/Apo (ref)-antigen is a member of TNF receptor family (Itoh, N. et al., *Cell* 66:233–243 (1991)). Apoptosis can be induced by stimulation of Fas-antigen by anti-Fas/anti-Apo antibody (Yonehara, S. et al., *J. Exp. Med.* 169:1747–1756 (1989)) or Fas-ligand (Suda, T. et al., *Cell* 75:1169–1178 (1993)), a type II transmembrane protein homologous to TNF. Cell death signalling after the stimulation of Fas-antigen is largely unknown. However, Fas mediated cell death is protected by overexpression of E1b (Hashimoto, S. et al., *Intern. Immun.* 3:343–351 (1991)) or bcl-2 (Itoh, N. et al., *J. Immun.* 151:621–627 (1993)). The data presented herein suggest that stimulation of Fas-antigen may also activate ICE/ced-3 cell death pathway.

What is claimed is:

1. An isolated DNA molecule comprising a cDNA sequence selected from the group consisting of the cDNA sequence shown in FIGS. 10A–10B (SEQ ID No:50) and 10C–10E (SEQ ID No:52).

2. An expression vector having the DNA of claim 1.

3. A host cell transformed with the vector of claim 2.

4. The DNA molecule of claim 1 wherein said sequence is that shown in FIGS. 10A–10B (SEQ ID No:50).

5. The DNA molecule of claim 1 wherein said sequence is that shown in FIGS. 10C–10E (SEQ ID No:52).

6. An expression vector having the DNA of claim 4.

7. An expression vector having the DNA of claim 5.

8. A host cell transformed with the vector of claim 6.

9. A host cell transformed with the vector of claim 7.

10. An isolated DNA molecule encoding the amino acid sequence shown in FIGS. 10A–10B (SEQ ID No:51).

11. An isolated DNA molecule encoding the amino acid sequence shown in FIGS. 10C–10E (SEQ ID No:53).

12. An expression vector having the DNA of claim 10.

13. An expression vector having the DNA of claim 11.

14. A host cell transformed with the vector of claim 12.

15. A host cell transformed with the vector of claim 13.

* * * * *

SEQUENCE LISTING (1) GENERAL INFORMATION:

(iii) NUMBER OF SEQUENCES: 95

(2) INFORMATION FOR SEQ ID NO:1:

(i) SEQUENCE CHARACTERISTICS:
        (A) LENGTH: 7653 base pairs
        (B) TYPE: nucleic acid
        (C) STRANDEDNESS: both
        (D) TOPOLOGY: both (ix) FEATURE:
        (A) NAME/KEY: CDS
        (B) LOCATION: join(2232..2366, 2430..2576, 2855..3109, 4305

-continued

..4634, 5547..5759, 5817..5942, 6298..6537, 7012
..7075)

(xi) SEQUENCE DESCRIPTION: SEQ ID NO:1:

```
AGATCTGAAA TAAGGTGATA AATTAATAAA TTAAGTGTAT TTCTGAGGAA ATTTGACTGT      60

TTTAGCACAA TTAATCTTGT TTCAGAAAAA AAGTCCAGTT TTCTAGATTT TTCCGTCTTA     120

TTGTCGAATT AATATCCCTA TTATCACTTT TTCATGCTCA TCCTCGAGCG GCACGTCCTC     180

AAAGAATTGT GAGAGCAAAC GCGCTCCCAT TGACCTCCAC ACTCAGCCGC CAAAACAAAC     240

GTTCGAACAT TCGTGTGTTG TGCTCCTTTT CCGTTATCTT GCAGTCATCT TTTGTCGTTT     300

TTTTCTTTGT TCTTTTTGTT GAACGTGTTG CTAAGCAATT ATTACATCAA TTGAAGAAAA     360

GGCTCGCCGA TTTATTGTTG CCAGAAAGAT TCTGAGATTC TCGAAGTCGA TTTTATAATA     420

TTTAACCTTG GTTTTTGCAT TGTTTCGTTT AAAAAAACCA CTGTTTATGT GAAAAACGAT     480

TAGTTTACTA ATAAAACTAC TTTTAAACCT TTACCTTTAC CTCACCGCTC CGTGTTCATG     540

GCTCATAGAT TTTCGATACT CAAATCCAAA ATAAATTTA CGAGGGCAAT TAATGTGAAA     600

CAAAAACAAT CCTAAGATTT CCACATGTTT GACCTCTCCG GCACCTTCTT CCTTAGCCCC     660

ACCACTCCAT CACCTCTTTG GCGGTGTTCT TCGAAACCCA CTTAGGAAAG CAGTGTGTAT     720

CTCATTTGGT ATGCTCTTTT CGATTTTATA GCTCTTTGTC GCAATTTCAA TGCTTTAAAC     780

AATCCAAATC GCATTATATT TGTGCATGGA GGCAAATGAC GGGGTTGGAA TCTTAGATGA     840

GATCAGGAGC TTTCAGGGTA AACGCCCGGT TCATTTTGTA CCACATTTCA TCATTTTCCT     900

GTCGTCCTTG GTATCCTCAA CTTGTCCCGG TTTTGTTTTC GGTACACTCT TCCGTGATGC     960

CACCTGTCTC CGTCTCAATT ATCGTTTAGA AATGTGAACT GTCCAGATGG GTGACTCATA    1020

TTGCTGCTGC TACAATCCAC TTTCTTTTCT CATCGGCAGT CTTACGAGCC CATCATAAAC    1080

TTTTTTTTCC GCGAAATTTG CAATAAACCG GCCAAAAACT TTCTCCAAAT TGTTACGCAA    1140

TATATACAAT CCATAAGAAT ATCTTCTCAA TGTTTATGAT TTCTTCGCAG CACTTTCTCT    1200

TCGTGTGCTA ACATCTTATT TTTATAATAT TTCCGCTAAA ATTCCGATTT TTGAGTATTA    1260

ATTTATCGTA AAATTATCAT AATAGCACCG AAAACTACTA AAAATGGTAA AAGCTCCTTT    1320

TAAATCGGCT CGACATTATC GTATTAAGGA ATCACAAAAT TCTGAGAATG CGTACTGCGC    1380

AACATATTTG ACGGCAAAAT ATCTCGTAGC GAAAACTACA GTAATTCTTT AAATGACTAC    1440

TGTAGCGCTT GTGTCGATTT ACGGGCTCAA TTTTTGAAAA TAATTTTTTT TTTCGAATTT    1500

TGATAACCCG TAAATCGTCA CAACGCTACA GTAGTCATTT AAAGGATTAC TGTAGTTCTA    1560

GCTACGAGAT ATTTTGCGCG CCAAATATGA CTGTAATACG CATTCTCTGA ATTTTGTGTT    1620

TCCGTAATAA TTTCACAAGA TTTTGGCATT CCACTTTAAA GGCGCACAGG ATTTATTCCA    1680

ATGGGTCTCG GCACGCAAAA AGTTTGATAG ACTTTTAAAT TCTCCTTGCA TTTTTAATTC    1740

AATTACTAAA ATTTTCGTGA ATTTTTCTGT TAAAATTTTT AAAATCAGTT TTCTAATATT    1800

TTCCAGGCTG ACAAACAGAA ACAAAAACAC AACAAACATT TTAAAAATCA GTTTTCAAAT    1860

TAAAAATAAC GATTTCTCAT TGAAAATTGT GTTTTATGTT TGCGAAAATA AAAGAGAACT    1920

GATTCAAAAC AATTTTAACA AAAAAAAACC CCAAAATTCG CCAGAAATCA AGATAAAAAA    1980

TTCAAGAGGG TCAAAATTTT CCGATTTTAC TGACTTTCAC CTTTTTTTTC GTAGTTCAGT    2040

GCAGTTGTTG GAGTTTTTGA CGAAAACTAG GAAAAAAATC GATAAAAATT ACTCAAATCG    2100

AGCTGAATTT TGAGGACAAT GTTTAAAAAA AAACACTATT TTTCCAATAA TTTCACTCAT    2160

TTTCAGACTA AATCGAAAAT CAAATCGTAC TCTGACTACG GGTCAGTAGA GAGGTCAACC    2220
```

-continued

```
ATCAGCCGAA G ATG ATG CGT CAA GAT AGA AGG AGC TTG CTA GAG AGG AAC        2270
            Met Met Arg Gln Asp Arg Arg Ser Leu Leu Glu Arg Asn
             1               5                  10

ATT ATG ATG TTC TCT AGT CAT CTA AAA GTC GAT GAA ATT CTC GAA GTT         2318
Ile Met Met Phe Ser Ser His Leu Lys Val Asp Glu Ile Leu Glu Val
        15                  20                  25

CTC ATC GCA AAA CAA GTG TTG AAT AGT GAT AAT GGA GAT ATG ATT AAT         2366
Leu Ile Ala Lys Gln Val Leu Asn Ser Asp Asn Gly Asp Met Ile Asn
 30              35                  40                  45

GTGAGTTTTT AATCGAATAA TAATTTTAAA AAAAAATTGA TAATATAAAG AATATTTTTG        2426

CAG TCA TGT GGA ACG GTT CGC GAG AAG AGA CGG GAG ATC GTG AAA GCA         2474
    Ser Cys Gly Thr Val Arg Glu Lys Arg Arg Glu Ile Val Lys Ala
                         50                  55                  60

GTG CAA CGA CGG GGA GAT GTG GCG TTC GAC GCG TTT TAT GAT GCT CTT         2522
Val Gln Arg Arg Gly Asp Val Ala Phe Asp Ala Phe Tyr Asp Ala Leu
                65                  70                  75

CGC TCT ACG GGA CAC GAA GGA CTT GCT GAA GTT CTT GAA CCT CTC GCC         2570
Arg Ser Thr Gly His Glu Gly Leu Ala Glu Val Leu Glu Pro Leu Ala
            80                  85                  90

AGA TCG TAGGTTTTTA AAGTTCGGCG CAAAAGCAAG GGTCTCACGG AAAAAAGAGG          2626
Arg Ser

CGGATCGTAA TTTTGCAACC CACCGGCACG GTTTTTTCCT CCGAAAATCG GAAATTATGC       2686

ACTTTCCCAA ATATTTGAAG TGAAATATAT TTTATTTACT GAAAGCTCGA GTGATTATTT       2746

ATTTTTTAAC ACTAATTTTC GTGGCGCAAA AGGCCATTTT GTAGATTTGC CGAAAATACT       2806

TGTCACACAC ACACACACAC ATCTCCTTCA AATATCCCTT TTTCCAGT GTT GAC TCG        2863
                                                     Val Asp Ser
                                                          95

AAT GCT GTC GAA TTC GAG TGT CCA ATG TCA CCG GCA AGC CAT CGT CGG         2911
Asn Ala Val Glu Phe Glu Cys Pro Met Ser Pro Ala Ser His Arg Arg
            100                 105                 110

AGC CGC GCA TTG AGC CCC GCC GGC TAC ACT TCA CCG ACC CGA GTT CAC         2959
Ser Arg Ala Leu Ser Pro Ala Gly Tyr Thr Ser Pro Thr Arg Val His
    115                 120                 125

CGT GAC AGC GTC TCT TCA GTG TCA TCA TTC ACT TCT TAT CAG GAT ATC         3007
Arg Asp Ser Val Ser Ser Val Ser Ser Phe Thr Ser Tyr Gln Asp Ile
130                 135                 140                 145

TAC TCA AGA GCA AGA TCT CGT TCT CGA TCG CGT GCA CTT CAT TCA TCG         3055
Tyr Ser Arg Ala Arg Ser Arg Ser Arg Ser Arg Ala Leu His Ser Ser
                150                 155                 160

GAT CGA CAC AAT TAT TCA TCT CCT CCA GTC AAC GCA TTT CCC AGC CAA         3103
Asp Arg His Asn Tyr Ser Ser Pro Pro Val Asn Ala Phe Pro Ser Gln
            165                 170                 175

CCT TGT ATGTTGATGC GAACACTAAA TTCTGAGAAT GCGCATTACT CAACATATTT          3159
Pro Ser

GACGCGCAAA TATCTCGTAG CGAAAAATAC AGTAACCCTT TAAATGACTA TTGTAGTGTC       3219

GATTTACGGG CTCGATTTTC GAAACGAATA TATGCTCGAA TTGTGACAAC GAATTTAAT        3279

TTGTCATTTT TGTGTTTTCT TTTGATATTT TTGATCAATT AATAAATTAT TTCCGTAAAC       3339

AGACACCAGC GCTACAGTAC TCTTTTAAAG AGTTACAGTA GTTTTCGCTT CAAGATATTT       3399

TGAAAAGAAT TTTAAACATT TTGAAAAAAA ATCATCTAAC ATGTGCCAAA ACGCTTTTTT       3459

CAAGTTTCGC AGATTTTTTG ATTTTTTTCA TTCAAGATAT GCTTATTAAC ACATATAATT       3519

ATCATTAATG TGAATTTCTT GTAGAAATTT TGGGCTTTTC GTTCTAGTAT GCTCTACTTT       3579

TGAAATTGCT CAACGAAAAA ATCATGTGGT TTGTTCATAT GAATGACGAA AAATAGCAAT       3639

TTTTTATATA TTTTCCCCTA TTCATGTTGT GCAGAAAAAT AGTAAAAAAG CGCATGCATT       3699
```

-continued

```
TTTCGACATT TTTTACATCG AACGACAGCT CACTTCACAT GCTGAAGACG AGAGACGCGG    3759

AGAAATACCA CACATCTTTC TGCGTCTCTC GTCTTCAGCA TGTGAAATGG GATCTCGGTC    3819

GATGTAAAAA AATGTCGAAT AATGTAAAAA ATGCATGCGT TTTTTTACAC TTTTCTGCAC    3879

AAATGAATAG GGGGAAAATG TATTAAAATA CATTTTTTGT ATTTTTCAAC ATCACATGAT    3939

TAACCCCATT ATTTTTTCGT TGAGCAACTT AAAAAGTAGA GAATATTAGA GCGAAAACCA    3999

AAATTTCTTC AAGATATTAC CTTTATTGAT AATTATAGAT GTTAATAAGC ATATCTTGAA    4059

TGAAAGTCAG CAAAAATATG TGCGAAACAC CTGAAAAAAA TCAAAAATTC TGCGAAAATT    4119

GAAAAAATGC ATTAAAATAC ATTTTTGCAT TTTTCTACAT CACATGAATG TAGAAAATTA    4179

AAAGGGAAAT CAAAATTTCT AGAGGATATA ATTGAATGAA ACATTGCGAA ATTAAAATGT    4239

GCGAAACGTC AAAAAGAGG AAATTTGGGT ATCAAAATCG ATCCTAAAAC CAACACATTT    4299

CAGCA TCC GCC AAC TCT TCA TTC ACC GGA TGC TCT TCT CTC GGA TAC        4346
      Ser Ala Asn Ser Ser Phe Thr Gly Cys Ser Ser Leu Gly Tyr
          180             185                 190

AGT TCA AGT CGT AAT CGC TCA TTC AGC AAA GCT TCT GGA CCA ACT CAA      4394
Ser Ser Ser Arg Asn Arg Ser Phe Ser Lys Ala Ser Gly Pro Thr Gln
    195                 200                 205

TAC ATA TTC CAT GAA GAG GAT ATG AAC TTT GTC GAT GCA CCA ACC ATA      4442
Tyr Ile Phe His Glu Glu Asp Met Asn Phe Val Asp Ala Pro Thr Ile
210                 215                 220                 225

AGC CGT GTT TTC GAC GAG AAA ACC ATG TAC AGA AAC TTC TCG AGT CCT      4490
Ser Arg Val Phe Asp Glu Lys Thr Met Tyr Arg Asn Phe Ser Ser Pro
                230                 235                 240

CGT GGA ATG TGC CTC ATC ATA AAT AAT GAA CAC TTT GAG CAG ATG CCA      4538
Arg Gly Met Cys Leu Ile Ile Asn Asn Glu His Phe Glu Gln Met Pro
            245                 250                 255

ACA CGG AAT GGT ACC AAG GCC GAC AAG GAC AAT CTT ACC AAT TTG TTC      4586
Thr Arg Asn Gly Thr Lys Ala Asp Lys Asp Asn Leu Thr Asn Leu Phe
        260                 265                 270

AGA TGC ATG GGC TAT ACG GTT ATT TGC AAG GAC AAT CTG ACG GGA AGG      4634
Arg Cys Met Gly Tyr Thr Val Ile Cys Lys Asp Asn Leu Thr Gly Arg
    275                 280                 285

GTACGGCGAA ATTATATTAC CCAAACGCGA AATTTGCCAT TTTGCGCCGA AAATGTGGCG    4694

CCCGGTCTCG ACACGACAAT TTGTGTTAAA TGCAAAAATG TATAATTTTG CAAAAAACAA    4754

AATTTTGAAC TTCCGCGAAA ATGATTTACC TAGTTTCGAA ATTTTCGTTT TTTCCGGCTA    4814

CATTATGTGT TTTTTCTTAG TTTTTCTATA ATATTTGATG TAAAAAACCG TTTGTAAATT    4874

TTCAGACAAT TTTCCGCATA CAAAACTTGA TAGCACGAAA TCAATTTTCT GAATTTTCAA    4934

AATTATCCAA AAATGCACAA TTTAAAATTT GTGAAAATTG GCAAACGGTG TTTCAATATG    4994

AAATGTATTT TTAAAAACTT TAAAAACCAC TCCGGAAAAG CAATAAAAAT CAAAACAACG    5054

TCACAATTCA AATTCAAAAG TTATTCATCC GATTTGTTTA TTTTTGCAAA ATTTGAAAAA    5114

ATCATGAAGG ATTTAGAAAA GTTTTATAAC ATTTTTTCTA GATTTTTCAA AATTTTTTTT    5174

AACAAATCGA GAAAAAGAGA ATGAAAAATC GATTTTAAAA ATATCCACAG CTTCGAGAGT    5234

TTGAAATTAC AGTACTCCTT AAAGGCGCAC ACCCCATTTG CATTGGACCA AAAATTTGTC    5294

GTGTCGAGAC CAGGTACCGT AGTTTTTGTC GCAAAAATTG CACCATTGGA CAATAAACCT    5354

TCCTAATCAC CAAAAAGTAA AATTGAAATC TTCGAAAAGC CAAAAAATTC AAAAAAAAAG    5414

TCGAATTTCG ATTTTTTTTT TGGTTTTTTG GTCCCAAAAA CCAAAAAAAT CAATTTTCTG    5474

CAAAATACCA AAAAGAAACC CGAAAAAATT TCCCAGCCTT GTTCCTAATG TAAACTGATA    5534
```

```
TTTAATTTCC AG GGA ATG CTC CTG ACA ATT CGA GAC TTT GCC AAA CAC         5582
              Gly Met Leu Leu Thr Ile Arg Asp Phe Ala Lys His
                290             295             300

GAA TCA CAC GGA GAT TCT GCG ATA CTC GTG ATT CTA TCA CAC GGA GAA       5630
Glu Ser His Gly Asp Ser Ala Ile Leu Val Ile Leu Ser His Gly Glu
            305             310             315

GAG AAT GTG ATT ATT GGA GTT GAT GAT ATA CCG ATT AGT ACA CAC GAG       5678
Glu Asn Val Ile Ile Gly Val Asp Asp Ile Pro Ile Ser Thr His Glu
        320             325             330

ATA TAT GAT CTT CTC AAC GCG GCA AAT GCT CCC CGT CTG GCG AAT AAG       5726
Ile Tyr Asp Leu Leu Asn Ala Ala Asn Ala Pro Arg Leu Ala Asn Lys
    335             340             345

CCG AAA ATC GTT TTT GTG CAG GCT TGT CGA GGC G GTTCGTTTT TTATTTAAT     5779
Pro Lys Ile Val Phe Val Gln Ala Cys Arg Gly Glu
350             355             360

TTTAATATAA ATATTTTAAA TAAATTCATT TTCAG AA CGT CGT GAC AAT GGA TTC     5834
                                        Arg Arg Asp Asn Gly Phe
                                                          365

CCA GTC TTG GAT TCT GTC GAC GGA GTT CCT GCA TTT CTT CGT CGT GGA       5882
Pro Val Leu Asp Ser Val Asp Gly Val Pro Ala Phe Leu Arg Arg Gly
            370             375             380

TGG GAC AAT CGA GAC GGG CCA TTG TTC AAT TTT CTT GGA TGT GTG CGG       5930
Trp Asp Asn Arg Asp Gly Pro Leu Phe Asn Phe Leu Gly Cys Val Arg
        385             390             395

CCG CAA GTT CAG GTTGCAATTT AATTTCTTGA ATGAGAATAT TCCTTCAAAA           5982
Pro Gln Val Gln
400

AATCTAAAAT AGATTTTTAT TCCAGAAAGT CCCGATCGAA AAATTGCGAT ATAATTACGA     6042

AATTTGTGAT AAAATGACAA ACCAATCAGC ATCGTCGATC TCCGCCCACT TCATCGGATT     6102

GGTTTGAAAG TGGGCGGAGT GAATTGCTGA TTGGTCGCAG TTTTCAGTTT AGAGGGAATT     6162

TAAAAATCGC CTTTTCGAAA ATTAAAAATT GATTTTTTCA ATTTTTTCGA AAAATATTCC     6222

GATTATTTTA TATTCTTTGG AGCGAAAGCC CCGTCCTGTA ACATTTTTA AATGATAATT      6282

AATAAATTTT TGCAG CAA GTG TGG AGA AAG AAG CCG AGC CAA GCT GAC ATT      6333
                Gln Val Trp Arg Lys Lys Pro Ser Gln Ala Asp Ile
                                405             410             415

CTG ATT CGA TAC GCA ACG ACA GCT CAA TAT GTT TCG TGG AGA AAC AGT       6381
Leu Ile Arg Tyr Ala Thr Thr Ala Gln Tyr Val Ser Trp Arg Asn Ser
            420             425             430

GCT CGT GGA TCA TGG TTC ATT CAA GCC GTC TGT GAA GTG TTC TCG ACA       6429
Ala Arg Gly Ser Trp Phe Ile Gln Ala Val Cys Glu Val Phe Ser Thr
        435             440             445

CAC GCA AAG GAT ATG GAT GTT GTT GAG CTG CTG ACT GAA GTC AAT AAG       6477
His Ala Lys Asp Met Asp Val Val Glu Leu Leu Thr Glu Val Asn Lys
    450             455             460

AAG GTC GCT TGT GGA TTT CAG ACA TCA CAG GGA TCG AAT ATT TTG AAA       6525
Lys Val Ala Cys Gly Phe Gln Thr Ser Gln Gly Ser Asn Ile Leu Lys
465             470             475

CAG ATG CCA GAG GTACTTGAAA CAAACAATGC ATGTCTAACT TTTAAGGACA           6577
Gln Met Pro Glu
480

CAGAAAAATA GGCAGAGGCT CCTTTTGCAA GCCTGCCGCG CGTCAACCTA GAATTTTAGT     6637

TTTTAGCTAA AATGATTGAT TTGAATATT TTATGCTAAT TTTTTTGCGT TAAATTTTGA      6697

AATAGTCACT ATTTATCGGG TTTCCAGTAA AAAATGTTTA TTAGCCATTG GATTTTACTG     6757

AAAACGAAAA TTTGTAGTTT TTCAACGAAA TTTATCGATT TTTAAATGTA AAAAAAAATA     6817

GCGAAAATTA CATCAACCAT CAAGCATTTA AGCCAAAATT GTTAACTCAT TTAAAAATTA     6877
```

-continued

```
ATTCAAAGTT GTCCACGAGT ATTACACGGT TGGCGCGCGG CAAGTTTGCA AAACGACGCT    6937

CCGCCTCTTT TTCTGTGCGG CTTGAAAACA AGGGATCGGT TTAGATTTTT CCCCAAAATT    6997

TAAATTAAAT TTCAG ATG ACA TCC CGC CTG CTC AAA AAG TTC TAC TTT TGG    7048
              Met Thr Ser Arg Leu Leu Lys Lys Phe Tyr Phe Trp
                  485                 490                 495

CCG GAA GCA CGA AAC TCT GCC GTC TAAAATTCAC TCGTGATTCA TTGCCCAATT    7102
Pro Glu Ala Arg Asn Ser Ala Val
               500

GATAATTGTC TGTATCTTCT CCCCCAGTTC TCTTTCGCCC AATTAGTTTA AAACCATGTG    7162

TATATTGTTA TCCTATACTC ATTTCACTTT ATCATTCTAT CATTTCTCTT CCCATTTTCA    7222

CACATTTCCA TTTCTCTACG ATAATCTAAA ATTATGACGT TTGTGTCTCG AACGCATAAT    7282

AATTTTAATA ACTCGTTTTG AATTTGATTA GTTGTTGTGC CCAGTATATA TGTATGTACT    7342

ATGCTTCTAT CAACAAAATA GTTTCATAGA TCATCACCCC AACCCCACCA ACCTACCGTA    7402

CCATATTCAT TTTTGCCGGG AATCAATTTC GATTAATTTT AACCTATTTT TTCGCCACAA    7462

AAAATCTAAT ATTTGAATTA ACGAATAGCA TTCCCATCTC TCCCGTGCCG GAATGCCTCC    7522

CGGCCTTTTA AAGTTCGGAA CATTTGGCAA TTATGTATAA ATTTGTAGGT CCCCCCCATC    7582

ATTTCCCGCC CATCATCTCA AATTGCATTC TTTTTTCGCC GTGATATCCC GATTCTGGTC    7642

AGCAAAGATC T                                                        7653
```

(2) INFORMATION FOR SEQ ID NO:2:

(i) SEQUENCE CHARACTERISTICS:
        (A) LENGTH: 503 amino acids
        (B) TYPE: amino acid
        (D) TOPOLOGY: linear (ii) MOLECULE TYPE: protein (xi) SEQUENCE DESCRIPTION: SEQ ID NO:2:

```
Met Met Arg Gln Asp Arg Arg Ser Leu Leu Glu Arg Asn Ile Met Met
 1               5                  10                  15

Phe Ser Ser His Leu Lys Val Asp Glu Ile Leu Glu Val Leu Ile Ala
                20                  25                  30

Lys Gln Val Leu Asn Ser Asp Asn Gly Asp Met Ile Asn Ser Cys Gly
            35                  40                  45

Thr Val Arg Glu Lys Arg Arg Glu Ile Val Lys Ala Val Gln Arg Arg
        50                  55                  60

Gly Asp Val Ala Phe Asp Ala Phe Tyr Asp Ala Leu Arg Ser Thr Gly
 65                  70                  75                  80

His Glu Gly Leu Ala Glu Val Leu Glu Pro Leu Ala Arg Ser Val Asp
                 85                  90                  95

Ser Asn Ala Val Glu Phe Glu Cys Pro Met Ser Pro Ala Ser His Arg
                100                 105                 110

Arg Ser Arg Ala Leu Ser Pro Ala Gly Tyr Thr Ser Pro Thr Arg Val
            115                 120                 125

His Arg Asp Ser Val Ser Ser Val Ser Ser Phe Thr Ser Tyr Gln Asp
        130                 135                 140

Ile Tyr Ser Arg Ala Arg Ser Arg Ser Arg Ala Leu His Ser
145                 150                 155                 160

Ser Asp Arg His Asn Tyr Ser Pro Pro Val Asn Ala Phe Pro Ser
                165                 170                 175

Gln Pro Ser Ser Ala Asn Ser Ser Phe Thr Gly Cys Ser Ser Leu Gly
```

```
                    180                 185                 190
Tyr Ser Ser Ser Arg Asn Arg Ser Phe Ser Lys Ala Ser Gly Pro Thr
                195                 200                 205

Gln Tyr Ile Phe His Glu Glu Asp Met Asn Phe Val Asp Ala Pro Thr
    210                 215                 220

Ile Ser Arg Val Phe Asp Glu Lys Thr Met Tyr Arg Asn Phe Ser Ser
225                 230                 235                 240

Pro Arg Gly Met Cys Leu Ile Ile Asn Asn Glu His Phe Glu Gln Met
                245                 250                 255

Pro Thr Arg Asn Gly Thr Lys Ala Asp Lys Asp Asn Leu Thr Asn Leu
                260                 265                 270

Phe Arg Cys Met Gly Tyr Thr Val Ile Cys Lys Asp Asn Leu Thr Gly
                275                 280                 285

Arg Gly Met Leu Leu Thr Ile Arg Asp Phe Ala Lys His Glu Ser His
            290                 295                 300

Gly Asp Ser Ala Ile Leu Val Ile Leu Ser His Gly Glu Glu Asn Val
305                 310                 315                 320

Ile Ile Gly Val Asp Asp Ile Pro Ile Ser Thr His Glu Ile Tyr Asp
                325                 330                 335

Leu Leu Asn Ala Ala Asn Ala Pro Arg Leu Ala Asn Lys Pro Lys Ile
                340                 345                 350

Val Phe Val Gln Ala Cys Arg Gly Glu Arg Arg Asp Asn Gly Phe Pro
            355                 360                 365

Val Leu Asp Ser Val Asp Gly Val Pro Ala Phe Leu Arg Arg Gly Trp
        370                 375                 380

Asp Asn Arg Asp Gly Pro Leu Phe Asn Phe Leu Gly Cys Val Arg Pro
385                 390                 395                 400

Gln Val Gln Gln Val Trp Arg Lys Lys Pro Ser Gln Ala Asp Ile Leu
                405                 410                 415

Ile Arg Tyr Ala Thr Thr Ala Gln Tyr Val Ser Trp Arg Asn Ser Ala
            420                 425                 430

Arg Gly Ser Trp Phe Ile Gln Ala Val Cys Glu Val Phe Ser Thr His
        435                 440                 445

Ala Lys Asp Met Asp Val Val Glu Leu Leu Thr Glu Val Asn Lys Lys
    450                 455                 460

Val Ala Cys Gly Phe Gln Thr Ser Gln Gly Ser Asn Ile Leu Lys Gln
465                 470                 475                 480

Met Pro Glu Met Thr Ser Arg Leu Leu Lys Lys Phe Tyr Phe Trp Pro
                485                 490                 495

Glu Ala Arg Asn Ser Ala Val
            500

(2) INFORMATION FOR SEQ ID NO:3:

(i) SEQUENCE CHARACTERISTICS:
        (A) LENGTH: 132 base pairs
        (B) TYPE: nucleic acid
        (C) STRANDEDNESS: both
        (D) TOPOLOGY: both (xi) SEQUENCE DESCRIPTION: SEQ ID NO:3:

GTATTAAGGA ATCACAAAAT TCTGAGAATG CGTACTGCGC AACATATTTG ACGGCAAAAT      60

ATCTCGTAGC GAAAACTACA GTAATTCTTT AAATGACTAC TGTAGCGCTT GTGTCGATTT     120

ACGGGCTCAA TT                                                         132
```

(2) INFORMATION FOR SEQ ID NO:4:

(i) SEQUENCE CHARACTERISTICS:
        (A) LENGTH: 125 base pairs
        (B) TYPE: nucleic acid
        (C) STRANDEDNESS: both
        (D) TOPOLOGY: both (xi) SEQUENCE DESCRIPTION: SEQ ID NO:4:

```
AAAATTCAGA GAATGCGTAT TACAGTCATA TTTGGCGCGC AAAATATCTC GTAGCTAGAA      60

CTACAGTAAT CCTTTAAATG ACTACTGTAG CGTTGTGACG ATTTACGGGT TATCAAAATT     120

CGAAA                                                                 125
```

(2) INFORMATION FOR SEQ ID NO:5:

(i) SEQUENCE CHARACTERISTICS:
        (A) LENGTH: 116 base pairs
        (B) TYPE: nucleic acid
        (C) STRANDEDNESS: both
        (D) TOPOLOGY: both (xi) SEQUENCE DESCRIPTION: SEQ ID NO:5:

```
AAATTCTGAG AATGCGCATT ACTCAACATA TTTGACGCGC AAATATCTCG TAGCGAAAAT      60

ACAGTAACCC TTTAAATGAC TATTGTAGTG TCGATTTACG GGCTCGATTT TCGAAA         116
```

(2) INFORMATION FOR SEQ ID NO:6:

(i) SEQUENCE CHARACTERISTICS:
        (A) LENGTH: 73 base pairs
        (B) TYPE: nucleic acid
        (C) STRANDEDNESS: both
        (D) TOPOLOGY: both (xi) SEQUENCE DESCRIPTION: SEQ ID NO:6:

```
TATCTTGAAG CGAAAACTAC TGTAACTCTT TAAAAGAGTA CTGTAGCGCT GGTGTCTGTT      60

TACGGAAATA ATT                                                        73
```

(2) INFORMATION FOR SEQ ID NO:7:

(i) SEQUENCE CHARACTERISTICS:
        (A) LENGTH: 132 base pairs
        (B) TYPE: nucleic acid
        (C) STRANDEDNESS: both
        (D) TOPOLOGY: both (xi) SEQUENCE DESCRIPTION: SEQ ID NO:7:

```
GTATTACGGC AAGAAATAAT TATGAGAATG CCTATTGCGC ACCATAGTTG ACGCGCAAAA      60

TATCTCGTAG CGAAAACTAC AGTAACTCTT TGAATGACTA CTGTAGCGCT TGTTTCGATT     120

TACGGGCTCG TT                                                         132
```

(2) INFORMATION FOR SEQ ID NO:8:

(i) SEQUENCE CHARACTERISTICS:
        (A) LENGTH: 111 base pairs
        (B) TYPE: nucleic acid
        (C) STRANDEDNESS: both
        (D) TOPOLOGY: both (xi) SEQUENCE DESCRIPTION: SEQ ID NO:8:

```
GTATAACGGT AACACACAAT TCTGAGAATG CGTATTGCAC AACACATTTG ACGCGCAAAA      60

TATCTCGTAG CGAAAACTAC AGTGATTCGC TGAATGAATA CGGTAGGGTC G              111
```

(2) INFORMATION FOR SEQ ID NO:9:

(i) SEQUENCE CHARACTERISTICS:
        (A) LENGTH: 122 base pairs
        (B) TYPE: nucleic acid
        (C) STRANDEDNESS: both
        (D) TOPOLOGY: both (xi) SEQUENCE DESCRIPTION: SEQ ID NO:9:

```
CTATTACGGG AGTACAAAAT TCTGAGAATG CGTACTGCGC AACATATTTG ACGCGCAAAA      60

TATTTCGTAT CGAAAACTAC AGTAATTCGT TTATTGGCTA CTGTGCGTGT TGATTTACGG     120

GC                                                                   122
```

(2) INFORMATION FOR SEQ ID NO:10:

(i) SEQUENCE CHARACTERISTICS:
        (A) LENGTH: 124 base pairs
        (B) TYPE: nucleic acid
        (C) STRANDEDNESS: both
        (D) TOPOLOGY: both (xi) SEQUENCE DESCRIPTION: SEQ ID NO:10:

```
GGGAGCACAA AATTCTGACT ATGAGAATGC GTATAAGCAC AAAATATTTC GTAGCGAAAA      60

CTACAGTAAT TTGTCAAGGG ACTACTGTAG CTAGCGCTTG TGTCGATTTA CGGAGCTCGA     120

TTTT                                                                 124
```

(2) INFORMATION FOR SEQ ID NO:11:

(i) SEQUENCE CHARACTERISTICS:
        (A) LENGTH: 74 base pairs
        (B) TYPE: nucleic acid
        (C) STRANDEDNESS: both
        (D) TOPOLOGY: both (xi) SEQUENCE DESCRIPTION: SEQ ID NO:11:

```
TATAGGAAAA ATTGAATGAT CAATTGCGCA AAATATTGAC AAACTACGTA AGTAGTAGTG      60

TTTTACGGTT GAAA                                                       74
```

(2) INFORMATION FOR SEQ ID NO:12:

(i) SEQUENCE CHARACTERISTICS:
        (A) LENGTH: 270 base pairs
        (B) TYPE: nucleic acid
        (C) STRANDEDNESS: both
        (D) TOPOLOGY: both (xi) SEQUENCE DESCRIPTION: SEQ ID NO:12:

```
TCATTCAAGA TATGCTTATT AACACATATA ATTATCATTA ATGTGAATTT CTTGTAGAAA      60

TTTTGGGCTT TTCGTTCTAG TATGCTCTAC TTTTGAAATT GCTCAACGAA AAAATCATGT     120

GGTTTGTTCA TATGAATGAC GAAAATAGC AATTTTTTAT ATATTTTCCC CTATTCATGT      180

TGTGCAGAAA AATAGTAAAA AAGCGCATGC ATTTTTCGAC ATTTTTTACA TCGAACGACA     240

GCTCACTTCA CATGCTGAAG ACGAGAGACG                                     270
```

(2) INFORMATION FOR SEQ ID NO:13:

(i) SEQUENCE CHARACTERISTICS:
        (A) LENGTH: 281 base pairs
        (B) TYPE: nucleic acid
        (C) STRANDEDNESS: both
        (D) TOPOLOGY: both (xi) SEQUENCE DESCRIPTION: SEQ ID NO:13:

```
TCATTCAAGA TATGCTTATT AACATCTATA ATTATCAATA AAGGTAATAT CTTGAAGAAA      60

TTTTGGTTTT CGCTCTAATA TTCTCTACTT TTTAAGTTGC TCAACGAAAA AATAATGGGG     120

TTAATCATGT GATGTTGAAA AATACAAAAA ATGTATTTTA ATACATTTTC CCCCTATTCA     180

TTTGTGCAGA AAAGTGTAAA AAAACGCATG CATTTTTTAC ATTATTCGAC ATTTTTTTAC     240

ATCGACCGAG ATCCCATTTC ACATGCTGAA GACGAGAGAC G                        281
```

(2) INFORMATION FOR SEQ ID NO:14:

(i) SEQUENCE CHARACTERISTICS:
        (A) LENGTH: 226 base pairs
        (B) TYPE: nucleic acid
        (C) STRANDEDNESS: both
        (D) TOPOLOGY: both (xi) SEQUENCE DESCRIPTION: SEQ ID NO:14:

```
TCATTCAAGA TATGCTTATT AACATATAAT TATCATAAGA ATTCTTGAGA AATTTTGGTT      60

TTCGTCTATA TCTCTACTTT TAATTGCTCA ACGAAAAAAT CATGTGATGG AAAAATAAAT    120

TTTTATAATT TTCCCCTATT CATTTGTGCA GAAAATGTAA AAAACGCATG CATTTTTCGA    180

CATTTTTTAC ATCGACGAAC CATTCACATG CTGAAGACGA GAGACG                  226
```

(2) INFORMATION FOR SEQ ID NO:15:

(i) SEQUENCE CHARACTERISTICS:
        (A) LENGTH: 108 base pairs
        (B) TYPE: nucleic acid
        (C) STRANDEDNESS: both
        (D) TOPOLOGY: both (xi) SEQUENCE DESCRIPTION: SEQ ID NO:15:

```
CTTCGAG AGTTTGAAAT TACAGTACTC CTTAAAGGCG CACACCCCAT TTGCATTGGA       60

CCAAAAATTT GTCGTGTCGA GACCAGGTAC CGTAGTTTTT GTCGCAAA                108
```

(2) INFORMATION FOR SEQ ID NO:16:

(i) SEQUENCE CHARACTERISTICS:
        (A) LENGTH: 31 base pairs
        (B) TYPE: nucleic acid
        (C) STRANDEDNESS: both
        (D) TOPOLOGY: both (xi) SEQUENCE DESCRIPTION: SEQ ID NO:16:

```
ACAAATTGTC GTGTCGAGAC CGGGCGCCAC A                                    31
```

(2) INFORMATION FOR SEQ ID NO:17:

(i) SEQUENCE CHARACTERISTICS:
        (A) LENGTH: 46 base pairs
        (B) TYPE: nucleic acid
        (C) STRANDEDNESS: both
        (D) TOPOLOGY: both (xi) SEQUENCE DESCRIPTION: SEQ ID NO:17:

```
CAGCAACAAA TGTTTGAAAT TACAGTAATC TTTAAAGGCG CACACC                    46
```

(2) INFORMATION FOR SEQ ID NO:18:

(i) SEQUENCE CHARACTERISTICS:
        (A) LENGTH: 49 base pairs
        (B) TYPE: nucleic acid
        (C) STRANDEDNESS: both
        (D) TOPOLOGY: both (xi) SEQUENCE DESCRIPTION: SEQ ID NO:18:

AACAAAACTT TGTCGTGTCG AGACCGGGTA CCGTATTTTT AATTGCAAA            49

(2) INFORMATION FOR SEQ ID NO:19:

(i) SEQUENCE CHARACTERISTICS:
        (A) LENGTH: 44 base pairs
        (B) TYPE: nucleic acid
        (C) STRANDEDNESS: both
        (D) TOPOLOGY: both (xi) SEQUENCE DESCRIPTION: SEQ ID NO:19:

CTGCAACGAA AGTCTGAAAT TACAGTACCC CTTAAAGGCG CATA                 44

(2) INFORMATION FOR SEQ ID NO:20:

(i) SEQUENCE CHARACTERISTICS:
        (A) LENGTH: 95 base pairs
        (B) TYPE: nucleic acid
        (C) STRANDEDNESS: both
        (D) TOPOLOGY: both (xi) SEQUENCE DESCRIPTION: SEQ ID NO:20:

GTTAGAAACT AGAGTACCTC TTAAAGGCGC ACATCCTTTC CCACCTATCG AAAATTTGTC    60

GTGTCGAGAC CGGGTAGCTA ATTTTATGCC AAAAA                               95

(2) INFORMATION FOR SEQ ID NO:21:

(i) SEQUENCE CHARACTERISTICS:
        (A) LENGTH: 114 base pairs
        (B) TYPE: nucleic acid
        (C) STRANDEDNESS: both
        (D) TOPOLOGY: both (xi) SEQUENCE DESCRIPTION: SEQ ID NO:21:

CAGCAACAAA AGTTTGAAAT TACAGTGCTC TTTAAAGGCA CACACCTTTT TACATTTAAC    60

AAAAAAGTGT CGCTTCGAGA CCGGGTACCG TGTTTTTGGC GCAAAAATCG CTAT         114

(2) INFORMATION FOR SEQ ID NO:22:

(i) SEQUENCE CHARACTERISTICS:
        (A) LENGTH: 114 base pairs
        (B) TYPE: nucleic acid
        (C) STRANDEDNESS: both
        (D) TOPOLOGY: both (xi) SEQUENCE DESCRIPTION: SEQ ID NO:22:

CAGAAGCGAA AATTTGAAAT TACAGTACTC TTTAAACGCT CAACCCCGTT TCTATTCAAT    60

AGAAAGTTGT CGTTTCGAGA CCGGACACCG TATTTTGGC GCAAAATATA CCTG          114

(2) INFORMATION FOR SEQ ID NO:23:

(i) SEQUENCE CHARACTERISTICS:
        (A) LENGTH: 107 base pairs
        (B) TYPE: nucleic acid
        (C) STRANDEDNESS: both
        (D) TOPOLOGY: both (xi) SEQUENCE DESCRIPTION: SEQ ID NO:23:

GATTGTTGAA AATTACAGTA ATCTTTAAAG GCGCACACAC GTTTGTATTT TACAGAAAAT    60

TCTCGTTTCG AGACCGAACA CAGTATTTTT GGCGGAGAAA TTCTAAA                 107

```
(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:24:

TTTGTCGTGT CGAGACCTGG                                                    20

(2) INFORMATION FOR SEQ ID NO:25:

(i) SEQUENCE CHARACTERISTICS:
        (A) LENGTH: 103 base pairs
        (B) TYPE: nucleic acid
        (C) STRANDEDNESS: both
        (D) TOPOLOGY: both (xi) SEQUENCE DESCRIPTION: SEQ ID NO:25:

TTTTTAAACT ACAGTACTCT TTAGGAGCGC ACATTTTTTC GCATTTAACA AATTTTTGTC         60

GTGGCGAGAC CTGATACCGT ATTTTTAGGT CAAGATTACT AGG                          103

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: both
        (D) TOPOLOGY: both (xi) SEQUENCE DESCRIPTION: SEQ ID NO:26:

ACCGTTTGAA ACTACAGTAC TCTTTAAAGG CGCGTTTGTC GT                           42

(2) INFORMATION FOR SEQ ID NO:27:

(i) SEQUENCE CHARACTERISTICS:
        (A) LENGTH: 42 base pairs
        (B) TYPE: nucleic acid
        (C) STRANDEDNESS: both
        (D) TOPOLOGY: both (xi) SEQUENCE DESCRIPTION: SEQ ID NO:27:

CGCTAAATAA GTTTAGCCAA TTTAATTCGC GAGACCCTTT AA                           42

(2) INFORMATION FOR SEQ ID NO:28:

(i) SEQUENCE CHARACTERISTICS:
        (A) LENGTH: 77 base pairs
        (B) TYPE: nucleic acid
        (C) STRANDEDNESS: both
        (D) TOPOLOGY: both (xi) SEQUENCE DESCRIPTION: SEQ ID NO:28:

AACCAATCAG CATCGTCGAT CTCCGCCCAC TTCATCGGAT TGGTTTGAAA GTGGGCGGAG         60

TGAATTGCTG ATTGGTC                                                       77

(2) INFORMATION FOR SEQ ID NO:29:

(i) SEQUENCE CHARACTERISTICS:
        (A) LENGTH: 77 base pairs
        (B) TYPE: nucleic acid
        (C) STRANDEDNESS: both
        (D) TOPOLOGY: both (xi) SEQUENCE DESCRIPTION: SEQ ID NO:29:
```

```
AACCAATTAG CGACTTCGGA ATTTCCATAC TTAATCTGAT TGGTTGAAGA ATGGGCAGAG      60

CGAATTGCTG ATTGGCC                                                    77

(2) INFORMATION FOR SEQ ID NO:30:

(i) SEQUENCE CHARACTERISTICS:
        (A) LENGTH: 56 base pairs
        (B) TYPE: nucleic acid
        (C) STRANDEDNESS: both
        (D) TOPOLOGY: both (xi) SEQUENCE DESCRIPTION: SEQ ID NO:30:

AACCAATAGC CTCGTCACTT ATCGATTGGT TAATGGGCGA GGAATTGCTG ATTGGC         56

(2) INFORMATION FOR SEQ ID NO:31:

(i) SEQUENCE CHARACTERISTICS:
        (A) LENGTH: 59 base pairs
        (B) TYPE: nucleic acid
        (C) STRANDEDNESS: both
        (D) TOPOLOGY: both (xi) SEQUENCE DESCRIPTION: SEQ ID NO:31:

TTTTAAGGAC ACAGAAAAAT AGGCAGAGGC TCCTTTTGCA AGCCTGCCGC GCGTCAACC       59

(2) INFORMATION FOR SEQ ID NO:32:

(i) SEQUENCE CHARACTERISTICS:
        (A) LENGTH: 60 base pairs
        (B) TYPE: nucleic acid
        (C) STRANDEDNESS: both
        (D) TOPOLOGY: both (xi) SEQUENCE DESCRIPTION: SEQ ID NO:32:

TTTCAAGCCG CACAGAAAAA GAGGCGGAGC GTCGTTTTGC AAACTTGCCG CGCGCCAACC      60

(2) INFORMATION FOR SEQ ID NO:33:

(i) SEQUENCE CHARACTERISTICS:
        (A) LENGTH: 48 base pairs
        (B) TYPE: nucleic acid
        (C) STRANDEDNESS: both
        (D) TOPOLOGY: both (xi) SEQUENCE DESCRIPTION: SEQ ID NO:33:

TTTAAGCACA GAAAAAGGC GAGTCTTTTG CAACTGCCGC GCGCAACC                   48

(2) INFORMATION FOR SEQ ID NO:34:

(i) SEQUENCE CHARACTERISTICS:
        (A) LENGTH: 2482 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 16..1527

(xi) SEQUENCE DESCRIPTION: SEQ ID NO:34:

AACCATCAGC CGAAG ATG ATG CGT CAA GAT AGA AGG AGC TTG CTA GAG AGG      51
                Met Met Arg Gln Asp Arg Arg Ser Leu Leu Glu Arg
                 1               5                  10

AAC ATT ATG ATG TTC TCT AGT CAT CTA AAA GTC GAT GAA ATT CTC GAA      99
Asn Ile Met Met Phe Ser Ser His Leu Lys Val Asp Glu Ile Leu Glu
         15                  20                  25
```

```
GTT CTC ATC GCA AAA CAA GTG TTG AAT AGT GAT AAT GGA GAT ATG ATT         147
Val Leu Ile Ala Lys Gln Val Leu Asn Ser Asp Asn Gly Asp Met Ile
     30                  35                  40

AAT TCA TGT GGA ACG GTT CGC GAG AAG AGA CGG GAG ATC GTG AAA GCA         195
Asn Ser Cys Gly Thr Val Arg Glu Lys Arg Arg Glu Ile Val Lys Ala
 45                  50                  55                  60

GTG CAA CGA CCG GGA GAT GTG GCG TTC GAC GCG TTT TAT GAT GCT CTT         243
Val Gln Arg Pro Gly Asp Val Ala Phe Asp Ala Phe Tyr Asp Ala Leu
                 65                  70                  75

CGC TCT ACG GGA CAC GAA GGA CTT GCT GAA GTT CTT GAA CCT CTC GCC         291
Arg Ser Thr Gly His Glu Gly Leu Ala Glu Val Leu Glu Pro Leu Ala
             80                  85                  90

AGA TCT GTT GAC TCG AAT GCT GTC GAA TTC GAG TGT CCA ATG TCA CCG         339
Arg Ser Val Asp Ser Asn Ala Val Glu Phe Glu Cys Pro Met Ser Pro
         95                 100                 105

GCA AGC CAT CGT CGG AGC CGC GCA TTG AGC CCC GCC GGC TAC ACT TCA         387
Ala Ser His Arg Arg Ser Arg Ala Leu Ser Pro Ala Gly Tyr Thr Ser
    110                 115                 120

CCG ACC CGA GTT CAC CGT GAC AGC GTC TCT TCA GTG TCA TCA TTC ACT         435
Pro Thr Arg Val His Arg Asp Ser Val Ser Ser Val Ser Ser Phe Thr
125                 130                 135                 140

TCT TAT CAG GAT ATC TAC TCA AGA GCA AGA TCT CGT TCT CGA TCG CGT         483
Ser Tyr Gln Asp Ile Tyr Ser Arg Ala Arg Ser Arg Ser Arg Ser Arg
                145                 150                 155

GCA CTT CAT TCA TCG GAT CGA CAC AAT TAT TCA TCT CCT CCA GTC AAC         531
Ala Leu His Ser Ser Asp Arg His Asn Tyr Ser Ser Pro Pro Val Asn
            160                 165                 170

GCA TTT CCC AGC CAA CCT TCA TCC GCC AAC TCT TCA TTC ACC GGA TGC         579
Ala Phe Pro Ser Gln Pro Ser Ser Ala Asn Ser Ser Phe Thr Gly Cys
        175                 180                 185

TCT TCT CTC GGA TAC AGT TCA AGT CGT AAT CGC TCA TTC AGC AAA GCT         627
Ser Ser Leu Gly Tyr Ser Ser Ser Arg Asn Arg Ser Phe Ser Lys Ala
    190                 195                 200

TCT GGA CCA ACT CAA TAC ATA TTC CAT GAA GAG GAT ATG AAC TTT GTC         675
Ser Gly Pro Thr Gln Tyr Ile Phe His Glu Glu Asp Met Asn Phe Val
205                 210                 215                 220

GAT GCA CCA ACC ATA AGC CGT GTT TTC GAC GAG AAA ACC ATG TAC AGA         723
Asp Ala Pro Thr Ile Ser Arg Val Phe Asp Glu Lys Thr Met Tyr Arg
                225                 230                 235

AAC TTC TCG AGT CCT CGT GGA ATG TGC CTC ATC ATA AAT AAT GAA CAC         771
Asn Phe Ser Ser Pro Arg Gly Met Cys Leu Ile Ile Asn Asn Glu His
            240                 245                 250

TTT GAG CAG ATG CCA ACA CGG AAT GGT ACC AAG GCC GAC AAG GAC AAT         819
Phe Glu Gln Met Pro Thr Arg Asn Gly Thr Lys Ala Asp Lys Asp Asn
        255                 260                 265

CTT ACC AAT TTG TTC AGA TGC ATG GGC TAT ACG GTT ATT TGC AAG GAC         867
Leu Thr Asn Leu Phe Arg Cys Met Gly Tyr Thr Val Ile Cys Lys Asp
    270                 275                 280

AAT CTG ACG GGA AGG GGA ATG CTC CTG ACA ATT CGA GAC TTT GCC AAA         915
Asn Leu Thr Gly Arg Gly Met Leu Leu Thr Ile Arg Asp Phe Ala Lys
285                 290                 295                 300

CAC GAA TCA CAC GGA GAT TCT GCG ATA CTC GTG ATT CTA TCA CAC GGA         963
His Glu Ser His Gly Asp Ser Ala Ile Leu Val Ile Leu Ser His Gly
                305                 310                 315

GAA GAG AAT GTG ATT ATT GGA GTT GAT GAT ATA CCG ATT AGT ACA CAC        1011
Glu Glu Asn Val Ile Ile Gly Val Asp Asp Ile Pro Ile Ser Thr His
            320                 325                 330

GAG ATA TAT GAT CTT CTC AAC GCG GCA AAT GCT CCC CGT CTG GCG AAT        1059
Glu Ile Tyr Asp Leu Leu Asn Ala Ala Asn Ala Pro Arg Leu Ala Asn
        335                 340                 345
```

```
AAG CCG AAA ATC GTT TTT GTG CAG GCT TGT CGA GGC GAA CGT CGT GAC         1107
Lys Pro Lys Ile Val Phe Val Gln Ala Cys Arg Gly Glu Arg Arg Asp
    350             355                 360

AAT GGA TTC CCA GTC TTG GAT TCT GTC GAC GGA GTT CCT GCA TTT CTT         1155
Asn Gly Phe Pro Val Leu Asp Ser Val Asp Gly Val Pro Ala Phe Leu
365             370                 375                 380

CGT CGT GGA TGG GAC AAT CGA GAC GGG CCA TTG TTC AAT TTT CTT GGA         1203
Arg Arg Gly Trp Asp Asn Arg Asp Gly Pro Leu Phe Asn Phe Leu Gly
                385                 390                 395

TGT GTG CGG CCG CAA GTT CAG CAA GTG TGG AGA AAG AAG CCG AGC CAA         1251
Cys Val Arg Pro Gln Val Gln Gln Val Trp Arg Lys Lys Pro Ser Gln
            400                 405                 410

GCT GAC ATT CTG ATT CGA TAC GCA ACG ACA GCT CAA TAT GTT TCG TGG         1299
Ala Asp Ile Leu Ile Arg Tyr Ala Thr Thr Ala Gln Tyr Val Ser Trp
        415                 420                 425

AGA AAC AGT GCT CGT GGA TCA TGG TTC ATT CAA GCC GTC TGT GAA GTG         1347
Arg Asn Ser Ala Arg Gly Ser Trp Phe Ile Gln Ala Val Cys Glu Val
    430                 435                 440

TTC TCG ACA CAC GCA AAG GAT ATG GAT GTT GTT GAG CTG CTG ACT GAA         1395
Phe Ser Thr His Ala Lys Asp Met Asp Val Val Glu Leu Leu Thr Glu
445             450                 455                 460

GTC AAT AAG AAG GTC GCT TGT GGA TTT CAG ACA TCA CAG GGA TCG AAT         1443
Val Asn Lys Lys Val Ala Cys Gly Phe Gln Thr Ser Gln Gly Ser Asn
                465                 470                 475

ATT TTG AAA CAG ATG CCA GAG ATG ACA TCC CGC CTG CTC AAA AAG TTC         1491
Ile Leu Lys Gln Met Pro Glu Met Thr Ser Arg Leu Leu Lys Lys Phe
            480                 485                 490

TAC TTT TGG CCG GAA GCA CGA AAC TCT GCC GTC TAAAATTCAC TCGTGATTCA       1544
Tyr Phe Trp Pro Glu Ala Arg Asn Ser Ala Val
        495                 500

TTGCCCAATT GATAATTGTC TGTATCTTCT CCCCCAGTTC TCTTTCGCCC AATTAGTTTA       1604

AAACCATGTG TATATTGTTA TCCTATACTC ATTTCACTTT ATCATTCTAT CATTTCTCTT       1664

CCCATTTTCA CACATTTCCA TTTCTCTACG ATAATCTAAA ATTATGACGT TGTGTCTCG        1724

AACGCATAAT AATTTTAATA ACTCGTTTTG AATTTGATTA GTTGTTGTGC CCAGTATATA       1784

TGTATGTACT ATGCTTCTAT CAACAAAATA GTTTCATAGA TCATCACCCC AACCCCACCA       1844

ACCTACCGTA CCATATTCAT TTTTGCCGGG AATCAATTTC GATTAATTTT AACCTATTTT       1904

TTCGCCACAA AAAATCTAAT ATTTGAATTA ACGAATAGCA TTCCCATCTC TCCCGTGCCG       1964

GAACTCCCGG CCTTTTAAAG TTCGGAACAT TTGGCCAATT ATGTATAAAA TTTTGTAGGT       2024

CCCCCCCATC ATTTCCCGCC CATCATCTCA AATTGCATTC TTTTTTCGCC GTGATATCCC       2084

GATTCTGGTC AGCAAAGATC TTTCTCATAG CCCATTCCAT TCGAGCTTTC TAATAGGAAT       2144

TTGAAAATTT TCGAAATTCC AGTAAATAAT ATTGGAAAAT GGATTTTTCG AGTTTTCAGC       2204

AACACAAATT TACTTGAAAC CCCATTTTCC AAAATTTCAA TTTTTTCAAA TTTCCCGCTA       2264

TCTTCCAAAA TACTCTTGTA CGTTTATTAT ATTTCCCTCG TTTTTCTTCG ATTCCTCCTC       2324

TCCGCGCACC CAATAAGTTT TATATATGTT GAGATTTATA TAGCTTGTTA TTATAATTAT      2384

ATATTTATAG ATTATTATAG TTGCTTTTCT CGCCGTATGT TTGTGTGTGT GTGATTGGTA       2444

TACATAGATA AAAGAAAACA AGGTAAAAAA AGGAATTC                               2482

(2) INFORMATION FOR SEQ ID NO:35:

(i) SEQUENCE CHARACTERISTICS:
        (A) LENGTH: 503 amino acids
        (B) TYPE: amino acid
```

(D) TOPOLOGY: linear (ii) MOLECULE TYPE: protein (xi) SEQUENCE DESCRIPTION: SEQ ID NO:35:

```
Met Met Arg Gln Asp Arg Arg Ser Leu Leu Glu Arg Asn Ile Met Met
 1               5                  10                  15

Phe Ser Ser His Leu Lys Val Asp Glu Ile Leu Glu Val Leu Ile Ala
             20                  25                  30

Lys Gln Val Leu Asn Ser Asp Asn Gly Asp Met Ile Asn Ser Cys Gly
         35                  40                  45

Thr Val Arg Glu Lys Arg Arg Glu Ile Val Lys Ala Val Gln Arg Pro
 50                  55                  60

Gly Asp Val Ala Phe Asp Ala Phe Tyr Asp Ala Leu Arg Ser Thr Gly
 65                  70                  75                  80

His Glu Gly Leu Ala Glu Val Leu Glu Pro Leu Ala Arg Ser Val Asp
                 85                  90                  95

Ser Asn Ala Val Glu Phe Glu Cys Pro Met Ser Pro Ala Ser His Arg
                100                 105                 110

Arg Ser Arg Ala Leu Ser Pro Ala Gly Tyr Thr Ser Pro Thr Arg Val
            115                 120                 125

His Arg Asp Ser Val Ser Val Ser Ser Phe Thr Ser Tyr Gln Asp
        130                 135                 140

Ile Tyr Ser Arg Ala Arg Ser Arg Ser Arg Ala Leu His Ser
145                 150                 155                 160

Ser Asp Arg His Asn Tyr Ser Ser Pro Pro Val Asn Ala Phe Pro Ser
                165                 170                 175

Gln Pro Ser Ser Ala Asn Ser Ser Phe Thr Gly Cys Ser Ser Leu Gly
            180                 185                 190

Tyr Ser Ser Arg Asn Arg Ser Phe Ser Lys Ala Ser Gly Pro Thr
        195                 200                 205

Gln Tyr Ile Phe His Glu Glu Asp Met Asn Phe Val Asp Ala Pro Thr
    210                 215                 220

Ile Ser Arg Val Phe Asp Glu Lys Thr Met Tyr Arg Asn Phe Ser Ser
225                 230                 235                 240

Pro Arg Gly Met Cys Leu Ile Ile Asn Asn Glu His Phe Glu Gln Met
                245                 250                 255

Pro Thr Arg Asn Gly Thr Lys Ala Asp Lys Asp Asn Leu Thr Asn Leu
            260                 265                 270

Phe Arg Cys Met Gly Tyr Thr Val Ile Cys Lys Asp Asn Leu Thr Gly
        275                 280                 285

Arg Gly Met Leu Leu Thr Ile Arg Asp Phe Ala Lys His Glu Ser His
    290                 295                 300

Gly Asp Ser Ala Ile Leu Val Ile Leu Ser His Gly Glu Glu Asn Val
305                 310                 315                 320

Ile Ile Gly Val Asp Asp Ile Pro Ile Ser Thr His Glu Ile Tyr Asp
                325                 330                 335

Leu Leu Asn Ala Ala Asn Ala Pro Arg Leu Ala Asn Lys Pro Lys Ile
            340                 345                 350

Val Phe Val Gln Ala Cys Arg Gly Glu Arg Arg Asp Asn Gly Phe Pro
        355                 360                 365

Val Leu Asp Ser Val Asp Gly Val Pro Ala Phe Leu Arg Arg Gly Trp
    370                 375                 380

Asp Asn Arg Asp Gly Pro Leu Phe Asn Phe Leu Gly Cys Val Arg Pro
```

-continued

```
385                 390                 395                 400

Gln Val Gln Gln Val Trp Arg Lys Lys Pro Ser Gln Ala Asp Ile Leu
                405                 410                 415

Ile Arg Tyr Ala Thr Thr Ala Gln Tyr Val Ser Trp Arg Asn Ser Ala
            420                 425                 430

Arg Gly Ser Trp Phe Ile Gln Ala Val Cys Glu Val Phe Ser Thr His
        435                 440                 445

Ala Lys Asp Met Asp Val Val Glu Leu Leu Thr Glu Val Asn Lys Lys
    450                 455                 460

Val Ala Cys Gly Phe Gln Thr Ser Gln Gly Ser Asn Ile Leu Lys Gln
465                 470                 475                 480

Met Pro Glu Met Thr Ser Arg Leu Leu Lys Lys Phe Tyr Phe Trp Pro
                485                 490                 495

Glu Ala Arg Asn Ser Ala Val
                500

(2) INFORMATION FOR SEQ ID NO:36:

(i) SEQUENCE CHARACTERISTICS:
        (A) LENGTH: 503 amino acids
        (B) TYPE: amino acid
        (D) TOPOLOGY: both (xi) SEQUENCE DESCRIPTION: SEQ ID NO:36:

Met Met Arg Gln Asp Arg Trp Ser Leu Leu Glu Arg Asn Ile Leu Glu
1               5                  10                  15

Phe Ser Ser Lys Leu Gln Ala Asp Leu Ile Leu Asp Val Leu Ile Ala
                20                  25                  30

Lys Gln Val Leu Asn Ser Asp Asn Gly Asp Met Ile Asn Ser Cys Arg
            35                  40                  45

Thr Glu Arg Asp Asn Glu Lys Glu Ile Val Lys Ala Val Gln Arg Arg
        50                  55                  60

Gly Asp Glu Ala Phe Asp Ala Phe Tyr Asp Ala Leu Arg Asp Thr Gly
65                  70                  75                  80

His Asn Asp Leu Ala Asp Val Leu Met Pro Leu Ser Arg Pro Asn Pro
                85                  90                  95

Val Pro Met Glu Cys Pro Met Ser Pro Ser His Arg Arg Ser Arg
                100                 105                 110

Ala Leu Ser Pro Pro Gly Tyr Ala Ser Pro Thr Arg Val His Arg Asp
            115                 120                 125

Ser Ile Ser Ser Val Ser Ser Phe Thr Ser Thr Tyr Gln Asp Val Tyr
        130                 135                 140

Ser Arg Ala Arg Ser Ser Ser Arg Ser Ser Arg Pro Leu Gln Ser Ser
145                 150                 155                 160

Asp Arg His Asn Tyr Met Ser Ala Ala Thr Ser Phe Pro Ser Gln Pro
                165                 170                 175

Ser Ser Ala Asn Ser Ser Phe Thr Gly Cys Ala Ser Leu Gly Tyr Ser
            180                 185                 190

Ser Ser Arg Asn Arg Ser Phe Ser Lys Thr Ser Ala Gln Ser Gln Tyr
        195                 200                 205

Ile Phe His Glu Glu Asp Met Asn Tyr Val Asp Ala Pro Thr Ile His
    210                 215                 220

Arg Val Phe Asp Glu Lys Thr Met Tyr Arg Asn Phe Ser Ser Pro Arg
225                 230                 235                 240

Gly Leu Cys Leu Ile Ile Asn Asn Glu His Phe Glu Gln Met Pro Thr
```

-continued

```
                 245                 250                 255
Arg Asn Gly Thr Lys Ala Asp Lys Asp Asn Leu Thr Asn Ile Phe Arg
            260                 265                 270
Cys Met Gly Tyr Thr Val Ile Cys Lys Asp Asn Leu Thr Gly Arg Glu
            275                 280                 285
Met Leu Ser Thr Ile Arg Ser Phe Gly Arg Asn Asp Met His Gly Asp
            290                 295                 300
Ser Ala Ile Leu Val Ile Leu Ser His Gly Glu Glu Asn Val Ile Ile
305                 310                 315                 320
Gly Val Asp Asp Val Ser Val Asn Val His Glu Ile Tyr Asp Leu Leu
                325                 330                 335
Asn Ala Ala Asn Ala Pro Arg Leu Ala Asn Lys Pro Lys Leu Val Phe
                340                 345                 350
Val Gln Ala Cys Arg Gly Glu Arg Arg Asp Asn Gly Phe Pro Val Leu
                355                 360                 365
Asp Ser Val Asp Gly Val Pro Ser Leu Ile Arg Arg Gly Trp Asp Asn
                370                 375                 380
Arg Asp Gly Pro Leu Phe Asn Phe Leu Gly Cys Val Arg Pro Gln Val
385                 390                 395                 400
Gln Gln Val Trp Arg Lys Lys Pro Ser Gln Ala Asp Met Leu Ile Ala
                405                 410                 415
Tyr Ala Thr Thr Ala Gln Tyr Val Ser Trp Arg Asn Ser Ala Arg Gly
                420                 425                 430
Ser Trp Phe Ile Gln Ala Val Cys Glu Val Phe Ser Leu His Ala Lys
                435                 440                 445
Asp Met Asp Val Val Glu Leu Leu Thr Glu Val Asn Lys Lys Val Ala
                450                 455                 460
Cys Gly Phe Gln Thr Ser Gln Gly Ser Asn Ile Leu Lys Gln Met Pro
465                 470                 475                 480
Glu Leu Thr Ser Arg Leu Leu Lys Lys Phe Tyr Phe Trp Pro Glu Asp
                485                 490                 495
Arg Gly Arg Asn Ser Ala Val
                500
```

(2) INFORMATION FOR SEQ ID NO:37:

(i) SEQUENCE CHARACTERISTICS:
        (A) LENGTH: 497 amino acids
        (B) TYPE: amino acid
        (D) TOPOLOGY: both (xi) SEQUENCE DESCRIPTION: SEQ ID NO:37:

```
Met Met Arg Gln Asp Arg Arg Asn Leu Leu Glu Arg Asn Ile Leu Val
1               5                   10                  15
Phe Ser Asn Lys Leu Gln Ser Glu Gln Ile Leu Glu Val Leu Ile Ala
                20                  25                  30
Lys Gln Ile Leu Asn Ala Asp Asn Gly Asp Val Ile Asn Ser Cys Arg
            35                  40                  45
Thr Glu Arg Asp Lys Arg Lys Glu Gln Val Lys Ala Val Gln Arg Arg
50                  55                  60
Gly Asp Val Ala Phe Asp Arg Phe Tyr Asp Ala Leu Arg Asp Thr Gly
65                  70                  75                  80
His His Glu Leu Ala Ala Val Leu Glu Pro Leu Ala Arg Thr Asp Leu
                85                  90                  95
Gly Cys Pro Met Ser Pro Ala Ser His Arg Arg Ser Arg Ala Leu Ser
```

-continued

```
                100                 105                 110
Pro Ser Thr Phe Ser Ser Pro Thr Arg Val His Arg Asp Ser Val Ser
            115                 120                 125
Ser Val Ser Ser Phe Thr Ser Thr Tyr Gln Asp Val Tyr Thr Arg Ala
        130                 135                 140
Arg Ser Thr Ser Arg Ser Ser Arg Pro Leu His Thr Ser Asp Arg His
145                 150                 155                 160
Asn Tyr Val Ser Pro Ser Asn Ser Phe Gln Ser Gln Pro Ala Ser Ala
                165                 170                 175
Asn Ser Ser Phe Thr Gly Ser Ser Leu Gly Tyr Ser Ser Ser Arg
            180                 185                 190
Thr Arg Ser Tyr Ser Lys Ala Ser Ala His Ser Gln Tyr Ile Phe His
        195                 200                 205
Glu Glu Asp Met Asn Tyr Val Asp Ala Pro Thr Ile His Arg Val Phe
    210                 215                 220
Asp Glu Lys Thr Met Tyr Arg Asn Phe Ser Thr Pro Arg Gly Leu Cys
225                 230                 235                 240
Leu Ile Ile Asn Asn Glu His Phe Glu Gln Met Pro Thr Arg Asn Gly
                245                 250                 255
Thr Lys Pro Asp Lys Asp Asn Ile Ser Asn Leu Phe Arg Cys Met Gly
            260                 265                 270
Tyr Ile Val His Cys Lys Asp Asn Leu Thr Gly Arg Met Met Leu Thr
        275                 280                 285
Ile Arg Asp Phe Ala Lys Asn Glu Thr His Gly Asp Ser Ala Ile Leu
    290                 295                 300
Val Ile Leu Ser His Gly Glu Glu Asn Val Ile Ile Gly Val Asp Asp
305                 310                 315                 320
Val Ser Val Asn Val His Glu Ile Tyr Asp Leu Leu Asn Ala Ala Asn
                325                 330                 335
Ala Pro Arg Leu Ala Asn Lys Pro Lys Leu Val Phe Val Gln Ala Cys
            340                 345                 350
Arg Gly Glu Arg Arg Asp Val Gly Phe Pro Val Leu Asp Ser Val Asp
        355                 360                 365
Gly Val Pro Ala Leu Ile Arg Arg Gly Trp Asp Lys Gly Asp Gly Pro
    370                 375                 380
Asn Phe Leu Gly Cys Val Arg Pro Gln Ala Gln Gln Val Trp Arg Lys
385                 390                 395                 400
Lys Pro Ser Gln Ala Asp Ile Leu Ile Ala Tyr Ala Thr Thr Ala Gln
                405                 410                 415
Tyr Val Ser Trp Arg Asn Ser Ala Arg Gly Ser Trp Phe Ile Gln Ala
            420                 425                 430
Val Cys Glu Val Phe Ser Leu His Ala Lys Asp Met Asp Val Val Glu
        435                 440                 445
Leu Leu Thr Glu Val Asn Lys Lys Val Ala Cys Gly Phe Gln Thr Ser
    450                 455                 460
Gln Gly Ala Asn Ile Leu Lys Gln Met Pro Glu Leu Thr Ser Arg Leu
465                 470                 475                 480
Leu Lys Lys Phe Tyr Phe Trp Pro Glu Asp Arg Asn Arg Ser Ser Ala
                485                 490                 495
Val
```

(2) INFORMATION FOR SEQ ID NO:38:

(i) SEQUENCE CHARACTERISTICS:
                (A) LENGTH: 402 amino acids
                (B) TYPE: amino acid
                (D) TOPOLOGY: both (xi) SEQUENCE DESCRIPTION: SEQ ID NO:38:

Met Ala Asp Lys Ile Leu Arg Ala Lys Arg Lys Gln Phe Ile Asn Ser
1               5                   10                  15

Val Ser Ile Gly Thr Ile Asn Gly Leu Leu Asp Glu Leu Leu Glu Lys
            20                  25                  30

Arg Val Leu Asn Gln Glu Glu Met Asp Lys Ile Lys Leu Ala Asn Ile
        35                  40                  45

Thr Ala Met Asp Lys Ala Arg Asp Leu Cys Asp His Val Ser Lys Lys
50                  55                  60

Gly Pro Gln Ala Ser Gln Ile Phe Ile Thr Tyr Ile Cys Asn Glu Asp
65                  70                  75                  80

Cys Tyr Leu Ala Gly Ile Leu Glu Leu Gln Ser Ala Pro Ser Ala Glu
                85                  90                  95

Thr Phe Val Ala Thr Glu Asp Ser Lys Gly Gly His Pro Ser Ser Ser
            100                 105                 110

Glu Thr Lys Glu Glu Gln Asn Lys Glu Asp Gly Thr Phe Pro Gly Leu
        115                 120                 125

Thr Gly Thr Leu Lys Phe Cys Pro Leu Glu Lys Ala Gln Lys Leu Trp
130                 135                 140

Lys Glu Asn Pro Ser Glu Ile Tyr Pro Ile Met Asn Thr Thr Thr Arg
145                 150                 155                 160

Thr Arg Leu Ala Leu Ile Ile Cys Asn Thr Glu Phe Gln His Leu Ser
                165                 170                 175

Pro Arg Val Gly Ala Gln Val Asp Leu Arg Glu Met Lys Leu Leu Leu
            180                 185                 190

Glu Asp Leu Gly Tyr Thr Val Lys Val Lys Glu Asn Leu Thr Ala Leu
        195                 200                 205

Glu Met Val Lys Glu Val Lys Glu Phe Ala Ala Cys Pro Glu His Lys
210                 215                 220

Thr Ser Asp Ser Thr Phe Leu Val Phe Met Ser His Gly Ile Gln Glu
225                 230                 235                 240

Gly Ile Cys Gly Thr Thr Tyr Ser Asn Glu Val Ser Asp Ile Leu Lys
                245                 250                 255

Val Asp Thr Ile Phe Gln Met Met Asn Thr Leu Lys Cys Pro Ser Leu
            260                 265                 270

Lys Asp Lys Pro Lys Val Ile Ile Gln Ala Cys Arg Gly Glu Lys
        275                 280                 285         Lys

Gln Gly Val Val Leu Leu Lys Asp Ser Val Arg Asp Ser Glu Glu Asp
290                 295                 300

Phe Leu Thr Asp Ala Ile Phe Glu Asp Asp Gly Ile Lys Lys Ala His
305                 310                 315                 320

Ile Glu Lys Asp Phe Ile Ala Phe Cys Ser Thr Pro Asp Asn Val
                325                 330                 335

Ser Trp Arg His Pro Val Arg Gly Ser Leu Phe Ile Glu Ser Leu Ile
            340                 345                 350

Lys His Met Lys Glu Tyr Ala Trp Ser Cys Asp Leu Glu Asp Ile Phe
        355                 360                 365

Arg Lys Val Arg Phe Ser Phe Glu Gln Pro Glu Phe Arg Leu Gln Met
370                 375                 380

-continued

```
Pro Thr Ala Asp Arg Val Thr Leu Ile Lys Arg Phe Tyr Leu Phe Pro
385                 390                 395                 400

Gly His (2) INFORMATION FOR SEQ ID NO:39:

(i) SEQUENCE CHARACTERISTICS:
        (A) LENGTH: 404 amino acids
        (B) TYPE: amino acid
        (D) TOPOLOGY: both (xi) SEQUENCE DESCRIPTION: SEQ ID NO:39:

Met Ala Asp Lys Val Leu Lys Glu Lys Arg Lys Leu Phe Ile Arg Ser
1               5                   10                  15

Met Gly Glu Gly Thr Ile Asn Gly Leu Leu Asp Glu Leu Leu Gln Thr
                20                  25                  30

Arg Val Leu Asn Lys Glu Glu Met Glu Lys Val Lys Arg Glu Asn Ala
            35                  40                  45

Thr Val Met Asp Lys Thr Arg Ala Leu Ile Asp Ser Val Ile Pro Lys
        50                  55                  60

Gly Ala Gln Ala Cys Gln Ile Cys Ile Thr Tyr Ile Cys Glu Glu Asp
65                  70                  75                  80

Ser Tyr Leu Ala Gly Thr Leu Gly Leu Ser Ala Asp Gln Thr Ser Gly
                85                  90                  95

Asn Tyr Leu Asn Met Gln Asp Ser Gln Gly Val Ile Ser Ser Phe Pro
            100                 105                 110

Ala Pro Gln Ala Val Gln Asp Asn Pro Ala Met Pro Thr Ser Ser Gly
        115                 120                 125

Ser Glu Gly Asn Val Lys Leu Cys Ser Ile Glu Glu Ala Gln Arg Ile
130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Phe Glu Phe Asp Ser Ile
                165                 170                 175

Pro Arg Arg Thr Gly Ala Glu Val Asp Ile Thr Gly Met Thr Met Leu
            180                 185                 190

Leu Gln Asn Leu Gly Tyr Ser Val Asp Val Lys Lys Asn Leu Thr Ala
        195                 200                 205

Ser Asp Met Thr Thr Glu Leu Glu Ala Phe Ala His Arg Pro Glu His
    210                 215                 220                 225

Lys Thr Ser Asp Ser Thr Phe Leu Val Phe Met Ser His Gly Ile Arg
                230                 235                 240

Glu Gly Ile Cys Gly Lys Lys His Ser Glu Gln Val Pro Asp Ile Leu
            245                 250                 255

Gln Leu Asn Ala Ile Phe Asn Met Leu Asn Thr Lys Asn Cys Pro Ser
        260                 265                 270

Leu Lys Asp Lys Pro Lys Val Ile Ile Ile Gln Ala Cys Arg Gly Asp
    275                 280                 285

Ser Pro Gly Val Val Trp Phe Lys Asp Ser Val Gly Val Ser Gly Asn
290                 295                 300                 305

Leu Ser Leu Pro Thr Thr Glu Glu Phe Glu Asp Asp Ala Ile Lys Lys
                310                 315                 320

Ala His Ile Glu Lys Asp Phe Ile Ala Phe Cys Ser Ser Thr Pro Asp
            325                 330                 335

Asn Val Ser Trp Arg His Pro Thr Met Gly Ser Val Phe Ile Gly Arg
```

-continued

```
            340                 345                 350
Leu Ile Glu His Met Gln Glu Tyr Ala Cys Ser Cys Asp Val Glu Glu
            355                 360                 365

Ile Phe Arg Lys Val Arg Phe Ser Phe Glu Gln Pro Asp Gly Arg Ala
370                 375                 380                 385

Gln Met Pro Thr Thr Glu Arg Val Thr Leu Thr Arg Cys Phe Tyr Leu
                390                 395                 400

Phe Pro Gly His
```

(2) INFORMATION FOR SEQ ID NO:40:

(i) SEQUENCE CHARACTERISTICS:
        (A) LENGTH: 171 amino acids
        (B) TYPE: amino acid
        (D) TOPOLOGY: both (xi) SEQUENCE DESCRIPTION: SEQ ID NO:40:

```
Met Leu Thr Val Gln Val Tyr Arg Thr Ser Gln Lys Cys Ser Ser Ser
1               5                   10                  15

Lys His Val Val Glu Val Ile Leu Asp Pro Leu Gly Thr Ser Phe Cys
                20                  25                  30

Ser Leu Leu Pro Pro Pro Leu Leu Leu Tyr Glu Thr Asp Arg Gly Val
                35                  40                  45

Asp Gln Gln Asp Gly Lys Asn His Thr Gln Ser Pro Gly Cys Glu Glu
50                  55                  60

Ser Asp Ala Gly Lys Glu Leu Met Lys Met Arg Leu Pro Thr Arg
65                  70                  75                  80

Ser Asp Met Ile Cys Gly Tyr Ala Cys Leu Lys Gly Asn Ala Ala Met
                85                  90                  95

Arg Asn Thr Lys Arg Gly Ser Trp Tyr Ile Glu Ala Leu Thr Gln Val
                100                 105                 110

Phe Ser Glu Arg Ala Cys Asp Met His Val Ala Asp Met Leu Val Lys
                115                 120                 125

Val Asn Ala Leu Ile Lys Glu Arg Glu Gly Tyr Ala Pro Gly Thr Glu
130                 135                 140

Phe His Arg Cys Lys Glu Met Ser Glu Tyr Cys Ser Thr Leu Cys Gln
145                 150                 155                 160

Gln Leu Tyr Leu Phe Pro Gly Tyr Pro Pro Thr
                165                 170
```

(2) INFORMATION FOR SEQ ID NO:41:

(i) SEQUENCE CHARACTERISTICS:
        (A) LENGTH: 1350 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 35..1156

(xi) SEQUENCE DESCRIPTION: SEQ ID NO:41:

```
TCTTCACAGT GCGAAAGAAC TGAGGCTTTT TCTC ATG GCT GAA AAC AAA CAC        52
                                     Met Ala Glu Asn Lys His
                                     1               5

CCT GAC AAA CCA CTT AAG GTG TTG GAA CAG CTG GGC AAA GAA GTC CTT    100
Pro Asp Lys Pro Leu Lys Val Leu Glu Gln Leu Gly Lys Glu Val Leu
            10              15                  20
```

```
ACG GAG TAC CTA GAA AAA TTA GTA CAA AGC AAT GTA CTG AAA TTA AAG      148
Thr Glu Tyr Leu Glu Lys Leu Val Gln Ser Asn Val Leu Lys Leu Lys
         25                  30                  35

GAG GAA GAT AAA CAA AAA TTT AAC AAT GCT GAA CGC AGT GAC AAG CGT      196
Glu Glu Asp Lys Gln Lys Phe Asn Asn Ala Glu Arg Ser Asp Lys Arg
 40                  45                  50

TGG GTT TTT GTA GAT GCC ATG AAA AAG AAA CAC AGC AAA GTA GGT GAA      244
Trp Val Phe Val Asp Ala Met Lys Lys Lys His Ser Lys Val Gly Glu
 55                  60                  65                  70

ATG CTT CTC CAG ACA TTC TTC AGT GTG GAC CCA GGC AGC CAC CAT GGT      292
Met Leu Leu Gln Thr Phe Phe Ser Val Asp Pro Gly Ser His His Gly
                 75                  80                  85

GAA GCT AAT CTG GAA ATG GAG GAA CCA GAA GAA TCA TTG AAC ACT CTC      340
Glu Ala Asn Leu Glu Met Glu Glu Pro Glu Glu Ser Leu Asn Thr Leu
         90                  95                 100

AAG CTT TGT TCC CCT GAA GAG TTC ACA AGG CTT TGC AGA GAA AAG ACA      388
Lys Leu Cys Ser Pro Glu Glu Phe Thr Arg Leu Cys Arg Glu Lys Thr
        105                 110                 115

CAA GAA ATT TAC CCA ATA AAG GAG GCC AAT GGC CGT ACA CGA AAG GCT      436
Gln Glu Ile Tyr Pro Ile Lys Glu Ala Asn Gly Arg Thr Arg Lys Ala
120                 125                 130

CTT ATC ATA TGC AAT ACA GAG TTC AAA CAT CTC TCA CTG AGG TAT GGG      484
Leu Ile Ile Cys Asn Thr Glu Phe Lys His Leu Ser Leu Arg Tyr Gly
135                 140                 145                 150

GCT AAA TTT GAC ATC ATT GGT ATG AAA GGC CTT CTT GAA GAC TTA GGC      532
Ala Lys Phe Asp Ile Ile Gly Met Lys Gly Leu Leu Glu Asp Leu Gly
                155                 160                 165

TAC GAT GTG GTG GTG AAA GAG GAG CTT ACA GCA GAG GGC ATG GAG TCA      580
Tyr Asp Val Val Val Lys Glu Glu Leu Thr Ala Glu Gly Met Glu Ser
        170                 175                 180

GAG ATG AAA GAC TTT GCT GCA CTC TCA GAA CAC CAG ACA TCA GAC AGC      628
Glu Met Lys Asp Phe Ala Ala Leu Ser Glu His Gln Thr Ser Asp Ser
        185                 190                 195

ACA TTC CTG GTG CTA ATG TCT CAT GGC ACA CTG CAT GGC ATT TGT GGA      676
Thr Phe Leu Val Leu Met Ser His Gly Thr Leu His Gly Ile Cys Gly
        200                 205                 210

ACA ATG CAC AGT GAA AAA ACT CCA GAT GTG CTA CAG TAT GAT ACC ATC      724
Thr Met His Ser Glu Lys Thr Pro Asp Val Leu Gln Tyr Asp Thr Ile
215                 220                 225                 230

TAT CAG ATA TTC AAC AAT TGC CAC TGT CCA GGT CTA CGA GAC AAA CCC      772
Tyr Gln Ile Phe Asn Asn Cys His Cys Pro Gly Leu Arg Asp Lys Pro
                235                 240                 245

AAA GTC ATC ATT GTG CAG GCC TGC AGA GGT GGG AAC TCT GGA GAA ATG      820
Lys Val Ile Ile Val Gln Ala Cys Arg Gly Gly Asn Ser Gly Glu Met
                250                 255                 260

TGG ATC AGA GAG TCT TCA AAA CCC CAG TTG TGC AGA GGT GTA GAT CTA      868
Trp Ile Arg Glu Ser Ser Lys Pro Gln Leu Cys Arg Gly Val Asp Leu
        265                 270                 275

CCT AGG AAT ATG GAA GCT GAT GCT GTC AAG CTG AGC CAC GTG GAG AAG      916
Pro Arg Asn Met Glu Ala Asp Ala Val Lys Leu Ser His Val Glu Lys
280                 285                 290

GAC TTC ATT GCC TTC TAC GCT ACA ACC CCA CAT CAC TTG TCC TAC CGA      964
Asp Phe Ile Ala Phe Tyr Ala Thr Thr Pro His His Leu Ser Tyr Arg
295                 300                 305                 310

GAC AAA ACA GGA GGC TCT TAC TTC ATC ACT AGA CTC ATT TCC TGC TTC     1012
Asp Lys Thr Gly Gly Ser Tyr Phe Ile Thr Arg Leu Ile Ser Cys Phe
                315                 320                 325

CGG AAA CAT GCT TGC TCT TGT CAT CTC TTT GAT ATA TTC CTG AAG GTG     1060
Arg Lys His Ala Cys Ser Cys His Leu Phe Asp Ile Phe Leu Lys Val
        330                 335                 340
```

```
CAA CAA TCA TTT GAA AAG GCA AGT ATT CAT TCC CAG ATG CCC ACC ATT      1108
Gln Gln Ser Phe Glu Lys Ala Ser Ile His Ser Gln Met Pro Thr Ile
            345                 350                 355

GAT CGG GCA ACC TTG ACA AGA TAT TTC TAC CTC TTT CCT GGC AAC TGAGAACA 1163
Asp Arg Ala Thr Leu Thr Arg Tyr Phe Tyr Leu Phe Pro Gly Asn
        360                 365                 370

GCAACAAGCA ACTGAATCTC ATTTCTTCAG CTTGAAGAAG TGATCTTGGC CAAGGATCAC    1223

ATTCTATTCC TGAAATTCCA GAACTAGTGA AATTAAGGAA AGAATACTTA TGAATTCAAG    1283

ACCAGCCTAA GCAACACAGT GGGATTCTGT TCGATAGACA AGCAAACAAG CAAAAATAAA    1343

AAAAAAA                                                              1350

(2) INFORMATION FOR SEQ ID NO:42:

(i) SEQUENCE CHARACTERISTICS:
        (A) LENGTH: 373 amino acids
        (B) TYPE: amino acid
        (D) TOPOLOGY: linear (ii) MOLECULE TYPE: protein (xi) SEQUENCE DESCRIPTION: SEQ ID NO:42:

Met Ala Glu Asn Lys His Pro Asp Lys Pro Leu Lys Val Leu Glu Gln
 1               5                  10                  15

Leu Gly Lys Glu Val Leu Thr Glu Tyr Leu Glu Lys Leu Val Gln Ser
            20                  25                  30

Asn Val Leu Lys Leu Lys Glu Asp Lys Gln Lys Phe Asn Asn Ala
        35                  40                  45

Glu Arg Ser Asp Lys Arg Trp Val Phe Val Asp Ala Met Lys Lys Lys
 50                  55                  60

His Ser Lys Val Gly Glu Met Leu Leu Gln Thr Phe Phe Ser Val Asp
 65                  70                  75                  80

Pro Gly Ser His His Gly Glu Ala Asn Leu Glu Met Glu Glu Pro Glu
                85                  90                  95

Glu Ser Leu Asn Thr Leu Lys Leu Cys Ser Pro Glu Glu Phe Thr Arg
                100                 105                 110

Leu Cys Arg Glu Lys Thr Gln Glu Ile Tyr Pro Ile Lys Glu Ala Asn
            115                 120                 125

Gly Arg Thr Arg Lys Ala Leu Ile Ile Cys Asn Thr Glu Phe Lys His
    130                 135                 140

Leu Ser Leu Arg Tyr Gly Ala Lys Phe Asp Ile Ile Gly Met Lys Gly
145                 150                 155                 160

Leu Leu Glu Asp Leu Gly Tyr Asp Val Val Lys Glu Glu Leu Thr
                165                 170                 175

Ala Glu Gly Met Glu Ser Glu Met Lys Asp Phe Ala Ala Leu Ser Glu
            180                 185                 190

His Gln Thr Ser Asp Ser Thr Phe Leu Val Leu Met Ser His Gly Thr
        195                 200                 205

Leu His Gly Ile Cys Gly Thr Met His Ser Glu Lys Thr Pro Asp Val
    210                 215                 220

Leu Gln Tyr Asp Thr Ile Tyr Gln Ile Phe Asn Asn Cys His Cys Pro
225                 230                 235                 240

Gly Leu Arg Asp Lys Pro Lys Val Ile Val Gln Ala Cys Arg Gly
                245                 250                 255

Gly Asn Ser Gly Glu Met Trp Ile Arg Glu Ser Ser Lys Pro Gln Leu
            260                 265                 270
```

```
Cys Arg Gly Val Asp Leu Pro Arg Asn Met Glu Ala Asp Ala Val Lys
            275                 280                 285

Leu Ser His Val Glu Lys Asp Phe Ile Ala Phe Tyr Ala Thr Thr Pro
290                 295                 300

His His Leu Ser Tyr Arg Asp Lys Thr Gly Gly Ser Tyr Phe Ile Thr
305                 310                 315                 320

Arg Leu Ile Ser Cys Phe Arg Lys His Ala Cys Ser Cys His Leu Phe
                325                 330                 335

Asp Ile Phe Leu Lys Val Gln Gln Ser Phe Glu Lys Ala Ser Ile His
                340                 345                 350

Ser Gln Met Pro Thr Ile Asp Arg Ala Thr Leu Thr Arg Tyr Phe Tyr
            355                 360                 365

Leu Phe Pro Gly Asn
            370

(2) INFORMATION FOR SEQ ID NO:43:

(i) SEQUENCE CHARACTERISTICS:
        (A) LENGTH: 441 amino acids
        (B) TYPE: amino acid
        (D) TOPOLOGY: linear (ii) MOLECULE TYPE: protein (xi) SEQUENCE DESCRIPTION: SEQ ID NO:43:

Ile Pro His Lys Glu Leu Met Ala Ala Asp Arg Gly Arg Arg Ile Leu
1               5                   10                  15

Gly Val Cys Gly Met His Pro His His Gln Glu Thr Leu Lys Lys Asn
            20                  25                  30

Arg Val Val Leu Ala Lys Gln Leu Leu Leu Ser Glu Leu Leu Glu His
            35                  40                  45

Leu Leu Glu Lys Asp Ile Ile Thr Leu Glu Met Arg Glu Leu Ile Gln
        50                  55                  60

Ala Lys Val Gly Ser Phe Ser Gln Asn Val Glu Leu Leu Asn Leu Leu
65                  70                  75                  80

Pro Lys Arg Gly Pro Gln Ala Phe Asp Ala Phe Cys Glu Ala Leu Arg
                85                  90                  95

Glu Thr Lys Gln Gly His Leu Glu Asp Met Leu Leu Thr Thr Leu Ser
            100                 105                 110

Gly Leu Gln His Val Leu Pro Pro Leu Ser Cys Asp Tyr Asp Leu Ser
            115                 120                 125

Leu Pro Phe Pro Val Cys Glu Ser Cys Pro Leu Tyr Lys Lys Leu Arg
130                 135                 140

Leu Ser Thr Asp Thr Val Glu His Ser Leu Asp Asn Lys Asp Gly Pro
145                 150                 155                 160

Val Cys Leu Gln Val Lys Pro Cys Thr Pro Glu Phe Tyr Gln Thr His
                165                 170                 175

Phe Gln Leu Ala Tyr Arg Leu Gln Ser Arg Pro Arg Gly Leu Ala Leu
            180                 185                 190

Val Leu Ser Asn Val His Phe Thr Gly Glu Lys Glu Leu Glu Phe Arg
            195                 200                 205

Ser Gly Gly Asp Val Asp His Ser Thr Leu Val Thr Leu Phe Lys Leu
210                 215                 220

Leu Gly Tyr Asp Val His Val Leu Cys Asp Gln Thr Ala Gln Glu Met
225                 230                 235                 240
```

```
Gln Glu Lys Leu Gln Asn Phe Ala Gln Leu Pro Ala His Arg Val Thr
                245                 250                 255

Asp Ser Cys Ile Val Ala Leu Leu Ser His Gly Val Glu Gly Ala Ile
            260                 265                 270

Tyr Gly Val Asp Gly Lys Leu Leu Gln Leu Gln Glu Val Phe Gln Leu
        275                 280                 285

Phe Asp Asn Ala Asn Cys Pro Ser Leu Gln Asn Lys Pro Lys Met Phe
290                 295                 300

Phe Ile Gln Ala Cys Arg Gly Asp Glu Thr Asp Arg Gly Val Asp Gln
305                 310                 315                 320

Gln Asp Gly Lys Asn His Ala Gly Ser Pro Gly Cys Glu Glu Ser Asp
                325                 330                 335

Ala Gly Lys Glu Lys Leu Pro Lys Met Arg Leu Pro Thr Arg Ser Asp
            340                 345                 350

Met Ile Cys Gly Tyr Ala Cys Leu Lys Gly Thr Ala Ala Met Arg Asn
        355                 360                 365

Thr Lys Arg Gly Ser Trp Tyr Ile Glu Ala Leu Ala Gln Val Phe Ser
    370                 375                 380

Glu Arg Ala Cys Asp Met His Val Ala Asp Met Leu Val Lys Val Asn
385                 390                 395                 400

Ala Leu Ile Lys Asp Arg Glu Gly Tyr Ala Pro Gly Thr Glu Phe His
                405                 410                 415

Arg Cys Lys Glu Met Ser Glu Tyr Cys Ser Thr Leu Cys Arg His Leu
            420                 425                 430

Tyr Leu Phe Pro Gly His Pro Pro Thr
        435                 440
```

(2) INFORMATION FOR SEQ ID NO:44:

(i) SEQUENCE CHARACTERISTICS:
        (A) LENGTH: 120 base pairs
        (B) TYPE: nucleic acid
        (C) STRANDEDNESS: both
        (D) TOPOLOGY: both (ix) FEATURE:
        (A) NAME/KEY: CDS
        (B) LOCATION: join(1..6, 10..118)

(xi) SEQUENCE DESCRIPTION: SEQ ID NO:44:

```
TTC TGG TAG CTC CAA GAG GTT TTT CGA CTT TTT GAC AAT GCT AAC TGT    48
Phe Trp     Leu Gln Glu Val Phe Arg Leu Phe Asp Asn Ala Asn Cys
  1           5                  10                  15

CCA AGT CTA CAG AAC AAG CCA AAA ATG TTC TTC ATC CAA GCA TGT CGT    96
Pro Ser Leu Gln Asn Lys Pro Lys Met Phe Phe Ile Gln Ala Cys Arg
             20                  25                  30

GGA GGT GCT ATT GGA TCC CTT GGG                                   120
Gly Gly Ala Ile Gly Ser Leu Gly
             35
```

(2) INFORMATION FOR SEQ ID NO:45:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:45:

Phe Trp Leu Gln Glu Val Phe Arg Leu Phe Asp Asn Ala Asn Cys Pro

```
              1               5                  10                 15
Ser Leu Gln Asn Lys Pro Lys Met Phe Phe Ile Gln Ala Cys Arg Gly
                        20                  25                  30

Gly Ala Ile Gly Ser Leu Gly
            35
```

(2) INFORMATION FOR SEQ ID NO:46:

(i) SEQUENCE CHARACTERISTICS:
        (A) LENGTH: 120 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 2..119

(xi) SEQUENCE DESCRIPTION: SEQ ID NO:46:

```
T TCT GGT AGC TCC AAG AGG TTT TTC GAC TTT TTG ACA ATG CTA ACT        46
  Ser Gly Ser Ser Lys Arg Phe Phe Asp Phe Leu Thr Met Leu Thr
   1               5                  10                  15

GTC CAA GTC TAC AGA ACA AGC CAA AAA TGT TCT TCA TCC AAG CAT GTC      94
Val Gln Val Tyr Arg Thr Ser Gln Lys Cys Ser Ser Ser Lys His Val
                20                  25                  30

GTG GAG GTG CTA TTG GAT CCC TTG GG                                  120
Val Glu Val Leu Leu Asp Pro Leu Gly
            35
```

(2) INFORMATION FOR SEQ ID NO:47:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO:47:

```
Ser Gly Ser Ser Lys Arg Phe Phe Asp Phe Leu Thr Met Leu Thr Val
 1               5                  10                  15

Gln Val Tyr Arg Thr Ser Gln Lys Cys Ser Ser Ser Lys His Val Val
                20                  25                  30

Glu Val Leu Leu Asp Pro Leu Gly
            35                  40
```

(2) INFORMATION FOR SEQ ID NO:48:

(i) SEQUENCE CHARACTERISTICS:
        (A) LENGTH: 120 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 3..120

(xi) SEQUENCE DESCRIPTION: SEQ ID NO:48:

```
TT CTG GTA GCT CCA AGA GGT TTT TCG ACT TTT TGA CAA TGC TAA CTG       47
   Leu Val Ala Pro Arg Gly Phe Ser Thr Phe     Gln Cys     Leu
    1               5                  10                  15

TCC AAG TCT ACA GAA CAA GCC AAA AAT GTT CTT CAT CCA AGC ATG TCG      95
Ser Lys Ser Thr Glu Gln Ala Lys Asn Val Leu His Pro Ser Met Ser
                20                  25                  30
```

```
TGG AGG TGC TAT TGG ATC CCT TGG G                                             120
Trp Arg Cys Tyr Trp Ile Pro Trp Ala
            35

(2) INFORMATION FOR SEQ ID NO:49:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:49:

Leu Val Ala Pro Arg Gly Phe Ser Thr Phe Gln Cys Leu Ser Lys Ser
 1               5                  10                  15

Thr Glu Gln Ala Lys Asn Val Leu His Pro Ser Met Ser Trp Arg Cys
            20                  25                  30

Tyr Trp Ile Pro Trp Ala
        35

(2) INFORMATION FOR SEQ ID NO:50:

(i) SEQUENCE CHARACTERISTICS:
        (A) LENGTH: 1456 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 14..1316

(xi) SEQUENCE DESCRIPTION: SEQ ID NO:50:

GCACAAGGAG CTG ATG GCC GCT GAC AGG GGA CGC AGG ATA TTG GGA GTG      49
            Met Ala Ala Asp Arg Gly Arg Arg Ile Leu Gly Val
             1               5                  10

TGT GGC ATG CAT CCT CAT CAT CAG GAA ACT CTA AAA AAG AAC CGA GTG     97
Cys Gly Met His Pro His His Gln Glu Thr Leu Lys Lys Asn Arg Val
            15                  20                  25

GTG CTA GCC AAA CAG CTG TTG TTG AGC GAA TTG TTA GAA CAT CTT CTG    145
Val Leu Ala Lys Gln Leu Leu Leu Ser Glu Leu Leu Glu His Leu Leu
    30                  35                  40

GAG AAG GAC ATC ATC ACC TTG GAA ATG AGG GAG CTC ATC CAG GCC AAA    193
Glu Lys Asp Ile Ile Thr Leu Glu Met Arg Glu Leu Ile Gln Ala Lys
 45                  50                  55                  60

GTG GGC AGT TTC AGC CAG AAT GTG GAA CTC CTC AAC TTG CTG CCT AAG    241
Val Gly Ser Phe Ser Gln Asn Val Glu Leu Leu Asn Leu Leu Pro Lys
                65                  70                  75

AGG GGT CCC CAA GCT TTT GAT GCC TTC TGT GAA GCA CTG AGG GAG ACC    289
Arg Gly Pro Gln Ala Phe Asp Ala Phe Cys Glu Ala Leu Arg Glu Thr
            80                  85                  90

AAG CAA GGC CAC CTG GAG GAT ATG TTG CTC ACC ACC CTT TCT GGG CTT    337
Lys Gln Gly His Leu Glu Asp Met Leu Leu Thr Thr Leu Ser Gly Leu
            95                 100                 105

CAG CAT GTA CTC CCA CCG TTG AGC TGT GAC TAC GAC TTG AGT CTC CCT    385
Gln His Val Leu Pro Pro Leu Ser Cys Asp Tyr Asp Leu Ser Leu Pro
        110                 115                 120

TTT CCG GTG TGT GAG TCC TGT CCC CTT TAC AAG AAG CTC CGC CTG TCG    433
Phe Pro Val Cys Glu Ser Cys Pro Leu Tyr Lys Lys Leu Arg Leu Ser
125                 130                 135                 140

ACA GAT ACT GTG GAA CAC TCC CTA GAC AAT AAA GAT GGT CCT GTC TGC    481
```

```
                Thr Asp Thr Val Glu His Ser Leu Asp Asn Lys Asp Gly Pro Val Cys
                                145                 150                 155

CTT CAG GTG AAG CCT TGC ACT CCT GAA TTT TAT CAA ACA CAC TTC CAG              529
Leu Gln Val Lys Pro Cys Thr Pro Glu Phe Tyr Gln Thr His Phe Gln
            160                 165                 170

CTG GCA TAT AGG TTG CAG TCT CGG CCT CGT GGC CTA GCA CTG GTG TTG              577
Leu Ala Tyr Arg Leu Gln Ser Arg Pro Arg Gly Leu Ala Leu Val Leu
        175                 180                 185

AGC AAT GTG CAC TTC ACT GGA GAG AAA GAA CTG GAA TTT CGC TCT GGA              625
Ser Asn Val His Phe Thr Gly Glu Lys Glu Leu Glu Phe Arg Ser Gly
    190                 195                 200

GGG GAT GTG GAC CAC AGT ACT CTA GTC ACC CTC TTC AAG CTT TTG GGC              673
Gly Asp Val Asp His Ser Thr Leu Val Thr Leu Phe Lys Leu Leu Gly
205                 210                 215                 220

TAT GAC GTC CAT GTT CTA TGT GAC CAG ACT GCA CAG GAA ATG CAA GAG              721
Tyr Asp Val His Val Leu Cys Asp Gln Thr Ala Gln Glu Met Gln Glu
                225                 230                 235

AAA CTG CAG AAT TTT GCA CAG TTA CCT GCA CAC CGA GTC ACG GAC TCC              769
Lys Leu Gln Asn Phe Ala Gln Leu Pro Ala His Arg Val Thr Asp Ser
            240                 245                 250

TGC ATC GTG GCA CTC CTC TCG CAT GGT GTG GAG GGC GCC ATC TAT GGT              817
Cys Ile Val Ala Leu Leu Ser His Gly Val Glu Gly Ala Ile Tyr Gly
        255                 260                 265

GTG GAT GGG AAA CTG CTC CAG CTC CAA GAG GTT TTT CAG CTC TTT GAC              865
Val Asp Gly Lys Leu Leu Gln Leu Gln Glu Val Phe Gln Leu Phe Asp
    270                 275                 280

AAC GCC AAC TGC CCA AGC CTA CAG AAC AAA CCA AAA ATG TTC TTC ATC              913
Asn Ala Asn Cys Pro Ser Leu Gln Asn Lys Pro Lys Met Phe Phe Ile
285                 290                 295                 300

CAG GCC TGC CGT GGA GAT GAG ACT GAT CGT GGG GTT GAC CAA CAA GAT              961
Gln Ala Cys Arg Gly Asp Glu Thr Asp Arg Gly Val Asp Gln Gln Asp
                305                 310                 315

GGA AAG AAC CAC GCA GGA TCC CCT GGG TGC GAG GAG AGT GAT GCC GGT             1009
Gly Lys Asn His Ala Gly Ser Pro Gly Cys Glu Glu Ser Asp Ala Gly
            320                 325                 330

AAA GAA AAG TTG CCG AAG ATG AGA CTG CCC ACG CGC TCA GAC ATG ATA             1057
Lys Glu Lys Leu Pro Lys Met Arg Leu Pro Thr Arg Ser Asp Met Ile
        335                 340                 345

TGC GGC TAT GCC TGC CTC AAA GGG ACT GCC GCC ATG CGG AAC ACC AAA             1105
Cys Gly Tyr Ala Cys Leu Lys Gly Thr Ala Ala Met Arg Asn Thr Lys
    350                 355                 360

CGA GGT TCC TGG TAC ATC GAG GCT CTT GCT CAA GTG TTT TCT GAG CGG             1153
Arg Gly Ser Trp Tyr Ile Glu Ala Leu Ala Gln Val Phe Ser Glu Arg
365                 370                 375                 380

GCT TGT GAT ATG CAC GTG GCC GAC ATG CTG GTT AAG GTG AAC GCA CTT             1201
Ala Cys Asp Met His Val Ala Asp Met Leu Val Lys Val Asn Ala Leu
                385                 390                 395

ATC AAG GAT CGG GAA GGT TAT GCT CCT GGC ACA GAA TTC CAC CGG TGC             1249
Ile Lys Asp Arg Glu Gly Tyr Ala Pro Gly Thr Glu Phe His Arg Cys
            400                 405                 410

AAG GAA ATG TCT GAA TAC TGC AGC ACT CTG TGC CGC CAC CTC TAC CTG             1297
Lys Glu Met Ser Glu Tyr Cys Ser Thr Leu Cys Arg His Leu Tyr Leu
        415                 420                 425

TTC CCA GGA CAC CCT CCC ACA TGATGTCACC TCCCCATCAT CCACGCCA                  1346
Phe Pro Gly His Pro Pro Thr
            430

AGTGGAAGCC ACTGGACCAC AGGAGGTGTG ATAGAGCCTT TGATCTTCAG GATGCACGGT           1406

TTCTGTTCTG CCCCCTCAGG GATGTGGGAA TCTCCCAGAC TTGTTTCCTG                      1456
```

(2) INFORMATION FOR SEQ ID NO:51:

(i) SEQUENCE CHARACTERISTICS:
        (A) LENGTH: 435 amino acids
        (B) TYPE: amino acid
        (D) TOPOLOGY: linear (ii) MOLECULE TYPE: protein (xi) SEQUENCE DESCRIPTION: SEQ ID NO:51:

```
Met Ala Ala Asp Arg Gly Arg Arg Ile Leu Gly Val Cys Gly Met His
  1               5                  10                  15

Pro His His Gln Glu Thr Leu Lys Lys Asn Arg Val Val Leu Ala Lys
             20                  25                  30

Gln Leu Leu Leu Ser Glu Leu Leu Glu His Leu Leu Glu Lys Asp Ile
         35                  40                  45

Ile Thr Leu Glu Met Arg Glu Leu Ile Gln Ala Lys Val Gly Ser Phe
     50                  55                  60

Ser Gln Asn Val Glu Leu Leu Asn Leu Leu Pro Lys Arg Gly Pro Gln
 65                  70                  75                  80

Ala Phe Asp Ala Phe Cys Glu Ala Leu Arg Glu Thr Lys Gln Gly His
                 85                  90                  95

Leu Glu Asp Met Leu Leu Thr Thr Leu Ser Gly Leu Gln His Val Leu
            100                 105                 110

Pro Pro Leu Ser Cys Asp Tyr Asp Leu Ser Leu Pro Phe Pro Val Cys
        115                 120                 125

Glu Ser Cys Pro Leu Tyr Lys Lys Leu Arg Leu Ser Thr Asp Thr Val
    130                 135                 140

Glu His Ser Leu Asp Asn Lys Asp Gly Pro Val Cys Leu Gln Val Lys
145                 150                 155                 160

Pro Cys Thr Pro Glu Phe Tyr Gln Thr His Phe Gln Leu Ala Tyr Arg
                165                 170                 175

Leu Gln Ser Arg Pro Arg Gly Leu Ala Leu Val Leu Ser Asn Val His
            180                 185                 190

Phe Thr Gly Glu Lys Glu Leu Glu Phe Arg Ser Gly Gly Asp Val Asp
        195                 200                 205

His Ser Thr Leu Val Thr Leu Phe Lys Leu Leu Gly Tyr Asp Val His
    210                 215                 220

Val Leu Cys Asp Gln Thr Ala Gln Glu Met Gln Glu Lys Leu Gln Asn
225                 230                 235                 240

Phe Ala Gln Leu Pro Ala His Arg Val Thr Asp Ser Cys Ile Val Ala
                245                 250                 255

Leu Leu Ser His Gly Val Glu Gly Ala Ile Tyr Gly Val Asp Gly Lys
            260                 265                 270

Leu Leu Gln Leu Gln Glu Val Phe Gln Leu Phe Asp Asn Ala Asn Cys
        275                 280                 285

Pro Ser Leu Gln Asn Lys Pro Lys Met Phe Phe Ile Gln Ala Cys Arg
    290                 295                 300

Gly Asp Glu Thr Asp Arg Gly Val Asp Gln Gln Asp Gly Lys Asn His
305                 310                 315                 320

Ala Gly Ser Pro Gly Cys Glu Glu Ser Asp Ala Gly Lys Glu Lys Leu
                325                 330                 335

Pro Lys Met Arg Leu Pro Thr Arg Ser Asp Met Ile Cys Gly Tyr Ala
            340                 345                 350

Cys Leu Lys Gly Thr Ala Ala Met Arg Asn Thr Lys Arg Gly Ser Trp
```

```
                  355                 360                 365
Tyr Ile Glu Ala Leu Ala Gln Val Phe Ser Glu Arg Ala Cys Asp Met
    370                 375                 380

His Val Ala Asp Met Leu Val Lys Val Asn Ala Leu Ile Lys Asp Arg
385                 390                 395                 400

Glu Gly Tyr Ala Pro Gly Thr Glu Phe His Arg Cys Lys Glu Met Ser
                405                 410                 415

Glu Tyr Cys Ser Thr Leu Cys Arg His Leu Tyr Leu Phe Pro Gly His
                420                 425                 430

Pro Pro Thr
```

(2) INFORMATION FOR SEQ ID NO:52:

(i) SEQUENCE CHARACTERISTICS:
        (A) LENGTH: 2167 base pairs
        (B) TYPE: nucleic acid
        (C) STRANDEDNESS: both
        (D) TOPOLOGY: both (ii) MOLECULE TYPE: DNA (ix) FEATURE:
        (A) NAME/KEY: CDS
        (B) LOCATION: 89..1019

(xi) SEQUENCE DESCRIPTION: SEQ ID NO:52:

```
AGAGGGAGGG AACGATTTAA GGAGCGAATA CTACTGGTAA ACTAATGGAA GAAATCTGCT        60

GCACCACTGG ATATTGGGAG TGTGTGGC ATG CAT CCT CAT CAT CAG GAA ACT         112
                               Met His Pro His His Gln Glu Thr
                                 1               5

CTA AAA AAG AAC CGA GTG GTG CTA GCC AAA CAG CTG TTG TTG AGC GAA        160
Leu Lys Lys Asn Arg Val Val Leu Ala Lys Gln Leu Leu Leu Ser Glu
 10              15                  20

TTG TTA GAA CAT CTT CTG GAG AAG GAC ATC ATC ACC TTG GAA ATG AGG        208
Leu Leu Glu His Leu Leu Glu Lys Asp Ile Ile Thr Leu Glu Met Arg
 25              30                  35                  40

GAG CTC ATC CAG GCC AAA GTG GGC AGT TTC AGC CAG AAT GTG GAA CTC        256
Glu Leu Ile Gln Ala Lys Val Gly Ser Phe Ser Gln Asn Val Glu Leu
                 45                  50                  55

CTC AAC TTG CTG CCT AAG AGG GGT CCC CAA GCT TTT GAT GCC TTC TGT        304
Leu Asn Leu Leu Pro Lys Arg Gly Pro Gln Ala Phe Asp Ala Phe Cys
             60                  65                  70

GAA GCA CTG AGG GAG ACC AAG CAA GGC CAC CTG GAG GAT ATG TTG CTC        352
Glu Ala Leu Arg Glu Thr Lys Gln Gly His Leu Glu Asp Met Leu Leu
         75                  80                  85

ACC ACC CTT TCT GGG CTT CAG CAT GTA CTC CCA CCG TTG AGC TGT GAC        400
Thr Thr Leu Ser Gly Leu Gln His Val Leu Pro Pro Leu Ser Cys Asp
     90                  95                 100

TAC GAC TTG AGT CTC CCT TTT CCG GTG TGT GAG TCC TGT CCC CTT TAC        448
Tyr Asp Leu Ser Leu Pro Phe Pro Val Cys Glu Ser Cys Pro Leu Tyr
105                 110                 115                 120

AAG AAG CTC CGC CTG TCG ACA GAT ACT GTG GAA CAC TCC CTA GAC AAT        496
Lys Lys Leu Arg Leu Ser Thr Asp Thr Val Glu His Ser Leu Asp Asn
                125                 130                 135

AAA GAT GGT CCT GTC TGC CTT CAG GTG AAG CCT TGC ACT CCT GAA TTT        544
Lys Asp Gly Pro Val Cys Leu Gln Val Lys Pro Cys Thr Pro Glu Phe
            140                 145                 150

TAT CAA ACA CAC TTC CAG CTG GCA TAT AGG TTG CAG TCT CGG CCT CGT        592
Tyr Gln Thr His Phe Gln Leu Ala Tyr Arg Leu Gln Ser Arg Pro Arg
        155                 160                 165
```

```
GGC CTA GCA CTG GTG TTG AGC AAT GTG CAC TTC ACT GGA GAG AAA GAA        640
Gly Leu Ala Leu Val Leu Ser Asn Val His Phe Thr Gly Glu Lys Glu
        170                 175                 180

CTG GAA TTT CGC TCT GGA GGG GAT GTG GAC CAC AGT ACT CTA GTC ACC        688
Leu Glu Phe Arg Ser Gly Gly Asp Val Asp His Ser Thr Leu Val Thr
185                 190                 195                 200

CTC TTC AAG CTT TTG GGC TAT GAC GTC CAT GTT CTA TGT GAC CAG ACT        736
Leu Phe Lys Leu Leu Gly Tyr Asp Val His Val Leu Cys Asp Gln Thr
                205                 210                 215

GCA CAG GAA ATG CAA GAG AAA CTG CAG AAT TTT GCA CAG TTA CCT GCA        784
Ala Gln Glu Met Gln Glu Lys Leu Gln Asn Phe Ala Gln Leu Pro Ala
            220                 225                 230

CAC CGA GTC ACG GAC TCC TGC ATC GTG GCA CTC CTC TCG CAT GGT GTG        832
His Arg Val Thr Asp Ser Cys Ile Val Ala Leu Leu Ser His Gly Val
        235                 240                 245

GAG GGC GCC ATC TAT GGT GTG GAT GGG AAA CTG CTC CAG CTC CAA GAG        880
Glu Gly Ala Ile Tyr Gly Val Asp Gly Lys Leu Leu Gln Leu Gln Glu
    250                 255                 260

GTT TTT CAG CTC TTT GAC AAC GCC AAC TGC CCA AGC CTA CAG AAC AAA        928
Val Phe Gln Leu Phe Asp Asn Ala Asn Cys Pro Ser Leu Gln Asn Lys
265                 270                 275                 280

CCA AAA ATG TTC TTC ATC CAG GCC TGC CGT GGA GGT GCT ATT GGA TCC        976
Pro Lys Met Phe Phe Ile Gln Ala Cys Arg Gly Gly Ala Ile Gly Ser
                285                 290                 295

CTT GGG CAC CTC CTT CTG TTC ACT GCT GCC ACC GCC TCT CTT GCT CTA       1024
Leu Gly His Leu Leu Leu Phe Thr Ala Ala Thr Ala Ser Leu Ala Leu
            300                 305                 310

TGAGACTGAT CGTGGGGTTG ACCAACAAGA TGGAAAGAAC CACGCAGGAT CCCCTGGGTG     1084

CGAGGAGAGT GATGCCGGTA AGAAAAGTT GCCGAAGATG AGACTGCCCA CGCGCTCAGA     1144

CATGATATGC GGCTATGCCT GCCTCAAAGG GACTGCCGCC ATGCGGAACA CCAAACGAGG     1204

TTCCTGGTAC ATCGAGGCTC TTGCTCAAGT GTTTTCTGAG CGGGCTTGTG ATATGCACGT     1264

GGCCGACATG CTGGTTAAGG TGAACGCACT TATCAAGGAT CGGGAAGGTT ATGCTCCTGG     1324

CACAGAATTC CACCGGTGCA AGGAGATGTC TGAATACTGC AGCACTCTGT GCCGCCACCT     1384

CTACCTGTTC CCAGGACACC CTCCCACATG ATGTCACCTC CCCATCATCC ACGCCAAGTG     1444

GAAGCCACTG GACCACAGGA GGTGTGATAG AGCCTTTGAT CTTCAGGATG CACGGTTTCT     1504

GTTCTGCCCC CTCAGGGATG TGGGAATCTC CCAGACTTGT TTCCTGTGCC CATCATCTCT     1564

GCCTTTGAGT GTGGGACTCC AGGCCAGCTC CTTTTCTGTG AAGCCCTTTG CCTGTAGAGC     1624

CAGCCTTGGT TGGACCTATT GCCAGGAATG TTTCAGCTGC AGTTGAAGAG CCTGACAAGT     1684

GAAGTTGTAA ACACAGTGTG GTTATGGGGA GAGGGCATAT AAATTCCCCA TATTTGTGTT     1744

CAGTTCCAGC TTTTGTAGAT GGCACTTTAG TGATTGCTTT TATTACATTA GTTAAGATGT     1804

CTTGAGAGAC CATCTCCTAT CTTTTATTTC ATTCATATCC TCCGCCCTTT TTGTCCTAGA     1864

GTGAGAGTTT GGAAGGTGTC CAAATTTAAT GTAGACATTA TCTTTTGGCT CTGAAGAAGC     1924

AAACATGACT AGAGACGCAC CTTGCTGCAG TGTCCAGAAG CGGCCTGTGC GTTCCCTTCA     1984

GTACTGCAGC GCCACCCAGT GGAAGGACAC TCTTGGCTCG TTTGGGCTCA AGGCACCGCA     2044

GCCTGTCAGC CAACATTGCC TTGCATTTGT ACCTTATTGA TCTTTGCCCA TGGAAGTCTC     2104

AAAGATCTTT CGTTGGTTGT TTCTCTGAGC TTTGTTACTG AAATGAGCCT CGTGGGGAGC     2164

ATC                                                                  2167
```

(2) INFORMATION FOR SEQ ID NO:53:

(i) SEQUENCE CHARACTERISTICS:
            (A) LENGTH: 312 amino acids
            (B) TYPE: amino acid
            (D) TOPOLOGY: linear (ii) MOLECULE TYPE: protein (xi) SEQUENCE DESCRIPTION: SEQ ID NO:53:

Met His Pro His His Gln Glu Thr Leu Lys Lys Asn Arg Val Val Leu
 1               5                  10                  15

Ala Lys Gln Leu Leu Leu Ser Glu Leu Leu Glu His Leu Leu Glu Lys
                20                  25                  30

Asp Ile Ile Thr Leu Glu Met Arg Glu Leu Ile Gln Ala Lys Val Gly
                35                  40                  45

Ser Phe Ser Gln Asn Val Glu Leu Leu Asn Leu Leu Pro Lys Arg Gly
            50                  55                  60

Pro Gln Ala Phe Asp Ala Phe Cys Glu Ala Leu Arg Glu Thr Lys Gln
65                  70                  75                  80

Gly His Leu Glu Asp Met Leu Leu Thr Thr Leu Ser Gly Leu Gln His
                85                  90                  95

Val Leu Pro Pro Leu Ser Cys Asp Tyr Asp Leu Ser Leu Pro Phe Pro
                100                 105                 110

Val Cys Glu Ser Cys Pro Leu Tyr Lys Lys Leu Arg Leu Ser Thr Asp
                115                 120                 125

Thr Val Glu His Ser Leu Asp Asn Lys Asp Gly Pro Val Cys Leu Gln
130                 135                 140

Val Lys Pro Cys Thr Pro Glu Phe Tyr Gln Thr His Phe Gln Leu Ala
145                 150                 155                 160

Tyr Arg Leu Gln Ser Arg Pro Arg Gly Leu Ala Leu Val Leu Ser Asn
                165                 170                 175

Val His Phe Thr Gly Glu Lys Glu Leu Glu Phe Arg Ser Gly Gly Asp
                180                 185                 190

Val Asp His Ser Thr Leu Val Thr Leu Phe Lys Leu Leu Gly Tyr Asp
                195                 200                 205

Val His Val Leu Cys Asp Gln Thr Ala Gln Glu Met Gln Glu Lys Leu
210                 215                 220

Gln Asn Phe Ala Gln Leu Pro Ala His Arg Val Thr Asp Ser Cys Ile
225                 230                 235                 240

Val Ala Leu Leu Ser His Gly Val Glu Gly Ala Ile Tyr Gly Val Asp
                245                 250                 255

Gly Lys Leu Leu Gln Leu Gln Glu Val Phe Gln Leu Phe Asp Asn Ala
                260                 265                 270

Asn Cys Pro Ser Leu Gln Asn Lys Pro Lys Met Phe Phe Ile Gln Ala
                275                 280                 285

Cys Arg Gly Gly Ala Ile Gly Ser Leu Gly His Leu Leu Leu Phe Thr
290                 295                 300

Ala Ala Thr Ala Ser Leu Ala Leu
305                 310

(2) INFORMATION FOR SEQ ID NO:54:

(i) SEQUENCE CHARACTERISTICS:
            (A) LENGTH: 1402 base pairs
            (B) TYPE: nucleic acid
            (C) STRANDEDNESS: both
            (D) TOPOLOGY: both (ii) MOLECULE TYPE: cDNA (ix) FEATURE:
        (A) NAME/KEY: CDS
        (B) LOCATION: 45..1301

(xi) SEQUENCE DESCRIPTION: SEQ ID NO:54:

CTTTTTTTTT TTTTTTTTTT TATGTCCTGG AGTCCTGCAC AGCC ATG GCG GCC AGG        56
                                                Met Ala Ala Arg
                                                  1

AGG ACA CAT GAA AGA GAT CCA ATC TAC AAG ATC AAA GGT TTG GCC AAG        104
Arg Thr His Glu Arg Asp Pro Ile Tyr Lys Ile Lys Gly Leu Ala Lys
  5              10                  15                  20

GAC ATG CTG GAT GGG GTT TTT GAT GAC CTG GTG GAG AAG AAT GTT TTA        152
Asp Met Leu Asp Gly Val Phe Asp Asp Leu Val Glu Lys Asn Val Leu
                 25                  30                  35

AAT GGA GAT GAG TTA CTC AAA ATA GGG GAA AGT GCG AGT TTC ATC CTG        200
Asn Gly Asp Glu Leu Leu Lys Ile Gly Glu Ser Ala Ser Phe Ile Leu
             40                  45                  50

AAC AAG GCT GAG AAT CTG GTT GAG AAC TTC TTA GAG AAA ACA GAC ATG        248
Asn Lys Ala Glu Asn Leu Val Glu Asn Phe Leu Glu Lys Thr Asp Met
         55                  60                  65

GCA GGA AAA ATA TTT GCT GGC CAC ATT GCC AAT TCC CAG GAA CAG CTG        296
Ala Gly Lys Ile Phe Ala Gly His Ile Ala Asn Ser Gln Glu Gln Leu
 70                  75                  80

AGT TTA CAA TTT TCT AAT GAT GAG GAT GAT GGA CCT CAG AAG ATA TGT        344
Ser Leu Gln Phe Ser Asn Asp Glu Asp Asp Gly Pro Gln Lys Ile Cys
 85                  90                  95                 100

ACA CCT TCT TCT CCA TCA GAA TCC AAG AGA AAA GTA GAG GAT GAT GAA        392
Thr Pro Ser Ser Pro Ser Glu Ser Lys Arg Lys Val Glu Asp Asp Glu
                105                 110                 115

ATG GAG GTA AAT GCT GGA TTG GCC CAT GAA TCA CAT CTA ATG CTG ACA        440
Met Glu Val Asn Ala Gly Leu Ala His Glu Ser His Leu Met Leu Thr
            120                 125                 130

GCT CCT CAT GGA CTC CAG AGC TCA GAA GTC CAA GAT ACA CTG AAG CTT        488
Ala Pro His Gly Leu Gln Ser Ser Glu Val Gln Asp Thr Leu Lys Leu
        135                 140                 145

TGT CCA CGT GAT CAG TTT TGT AAG ATA AAG ACA GAA AGG GCA AAA GAG        536
Cys Pro Arg Asp Gln Phe Cys Lys Ile Lys Thr Glu Arg Ala Lys Glu
    150                 155                 160

ATA TAT CCA GTG ATG GAG AAG GAG GGA CGA ACA CGT CTG GCT CTC ATC        584
Ile Tyr Pro Val Met Glu Lys Glu Gly Arg Thr Arg Leu Ala Leu Ile
165                 170                 175                 180

ATC TGC AAC AAA AAG TTT GAC TAC CTT TTT GAT AGA GAT AAT GCT GAT        632
Ile Cys Asn Lys Lys Phe Asp Tyr Leu Phe Asp Arg Asp Asn Ala Asp
                185                 190                 195

ACT GAC ATT TTG AAC ATG CAA GAA CTA CTT GAA AAT CTT GGA TAC TCT        680
Thr Asp Ile Leu Asn Met Gln Glu Leu Leu Glu Asn Leu Gly Tyr Ser
            200                 205                 210

GTG GTG TTA AAA GAA AAC CTT ACA GCT CAG GAA ATG GAG ACA GAG TTA        728
Val Val Leu Lys Glu Asn Leu Thr Ala Gln Glu Met Glu Thr Glu Leu
        215                 220                 225

ATG CAG TTT GCT GGC CGT CCA GAG CAC CAG TCC TCA GAC AGC ACA TTC        776
Met Gln Phe Ala Gly Arg Pro Glu His Gln Ser Ser Asp Ser Thr Phe
    230                 235                 240

CTG GTG TTT ATG TCC CAT GGC ATC CTG GAA GGA ATC TGT GGG GTG AAG        824
Leu Val Phe Met Ser His Gly Ile Leu Glu Gly Ile Cys Gly Val Lys
245                 250                 255                 260

CAC CGA AAC AAA AAG CCA GAT GTT CTT CAT GAT GAC ACT ATC TTC AAA        872
His Arg Asn Lys Lys Pro Asp Val Leu His Asp Asp Thr Ile Phe Lys
                265                 270                 275

```
ATT TTC AAC AAC TCT AAC TGT CGG AGT CTG AGA AAC AAA CCC AAG ATT          920
Ile Phe Asn Asn Ser Asn Cys Arg Ser Leu Arg Asn Lys Pro Lys Ile
            280                 285                 290

CTC ATC ATG CAG GCC TGC AGA GGC AGA TAT AAT GGA ACT ATT TGG GTA          968
Leu Ile Met Gln Ala Cys Arg Gly Arg Tyr Asn Gly Thr Ile Trp Val
        295                 300                 305

TCC ACA AAC AAA GGG ATA GCC ACT GCT GAT ACA GAT GAG GAA CGT GTG         1016
Ser Thr Asn Lys Gly Ile Ala Thr Ala Asp Thr Asp Glu Glu Arg Val
    310                 315                 320

TTG AGC TGT AAA TGG AAT AAT AGT ATA ACA AAG GCC CAT GTG GAG ACA         1064
Leu Ser Cys Lys Trp Asn Asn Ser Ile Thr Lys Ala His Val Glu Thr
325                 330                 335                 340

GAT TTC ATT GCT TTC AAA TCT TCT ACC CCA CAT AAT ATT TCT TGG AAG         1112
Asp Phe Ile Ala Phe Lys Ser Ser Thr Pro His Asn Ile Ser Trp Lys
            345                 350                 355

GTA GGC AAG ACT GGT TCC CTC TTC ATT TCC AAA CTC ATT GAC TGC TTC         1160
Val Gly Lys Thr Gly Ser Leu Phe Ile Ser Lys Leu Ile Asp Cys Phe
        360                 365                 370

AAA AAG TAC TGT TGG TGT TAT CAT TTG GAG GAA ATT TTT CGA AAG GTT         1208
Lys Lys Tyr Cys Trp Cys Tyr His Leu Glu Glu Ile Phe Arg Lys Val
    375                 380                 385

CAA CAC TCA TTT GAG GTC CCA GGT GAA CTG ACC CAG ATG CCC ACT ATT         1256
Gln His Ser Phe Glu Val Pro Gly Glu Leu Thr Gln Met Pro Thr Ile
390                 395                 400

GAG AGA GTA TCC ATG ACA CGC TAT TTC TAC CTT TTT CCC GGG AAT            1301
Glu Arg Val Ser Met Thr Arg Tyr Phe Tyr Leu Phe Pro Gly Asn
405                 410                 415

TAGCACAGGC AACTCTCATG CAGTTCACAG TCAAGTATTG CTGTAGCTGA GAAGAAAGA       1361

AAATTCCAAG ATCCCAGGAT TTTTAAATGT GTAAAACTTT T                          1402

(2) INFORMATION FOR SEQ ID NO:55:

(i) SEQUENCE CHARACTERISTICS:
        (A) LENGTH: 419 amino acids
        (B) TYPE: amino acid
        (D) TOPOLOGY: linear (ii) MOLECULE TYPE: protein (xi) SEQUENCE DESCRIPTION: SEQ ID NO:55:

Met Ala Ala Arg Arg Thr His Glu Arg Asp Pro Ile Tyr Lys Ile Lys
 1               5                  10                  15

Gly Leu Ala Lys Asp Met Leu Asp Gly Val Phe Asp Asp Leu Val Glu
                20                  25                  30

Lys Asn Val Leu Asn Gly Asp Glu Leu Leu Lys Ile Gly Glu Ser Ala
            35                  40                  45

Ser Phe Ile Leu Asn Lys Ala Glu Asn Leu Val Glu Asn Phe Leu Glu
        50                  55                  60

Lys Thr Asp Met Ala Gly Lys Ile Phe Ala Gly His Ile Ala Asn Ser
65                  70                  75                  80

Gln Glu Gln Leu Ser Leu Gln Phe Ser Asn Asp Glu Asp Asp Gly Pro
                85                  90                  95

Gln Lys Ile Cys Thr Pro Ser Ser Pro Ser Glu Ser Lys Arg Lys Val
            100                 105                 110

Glu Asp Asp Glu Met Glu Val Asn Ala Gly Leu Ala His Glu Ser His
        115                 120                 125

Leu Met Leu Thr Ala Pro His Gly Leu Gln Ser Ser Glu Val Gln Asp
    130                 135                 140
```

```
Thr Leu Lys Leu Cys Pro Arg Asp Gln Phe Cys Lys Ile Lys Thr Glu
145                 150                 155                 160

Arg Ala Lys Glu Ile Tyr Pro Val Met Glu Lys Glu Gly Arg Thr Arg
                165                 170                 175

Leu Ala Leu Ile Ile Cys Asn Lys Lys Phe Asp Tyr Leu Phe Asp Arg
                180                 185                 190

Asp Asn Ala Asp Thr Asp Ile Leu Asn Met Gln Glu Leu Leu Glu Asn
                195                 200                 205

Leu Gly Tyr Ser Val Val Leu Lys Glu Asn Leu Thr Ala Gln Glu Met
210                 215                 220

Glu Thr Glu Leu Met Gln Phe Ala Gly Arg Pro Glu His Gln Ser Ser
225                 230                 235                 240

Asp Ser Thr Phe Leu Val Phe Met Ser His Gly Ile Leu Glu Gly Ile
                245                 250                 255

Cys Gly Val Lys His Arg Asn Lys Lys Pro Asp Val Leu His Asp Asp
                260                 265                 270

Thr Ile Phe Lys Ile Phe Asn Asn Ser Asn Cys Arg Ser Leu Arg Asn
                275                 280                 285

Lys Pro Lys Ile Leu Ile Met Gln Ala Cys Arg Gly Arg Tyr Asn Gly
290                 295                 300

Thr Ile Trp Val Ser Thr Asn Lys Gly Ile Ala Thr Ala Asp Thr Asp
305                 310                 315                 320

Glu Glu Arg Val Leu Ser Cys Lys Trp Asn Asn Ser Ile Thr Lys Ala
                325                 330                 335

His Val Glu Thr Asp Phe Ile Ala Phe Lys Ser Ser Thr Pro His Asn
                340                 345                 350

Ile Ser Trp Lys Val Gly Lys Thr Gly Ser Leu Phe Ile Ser Lys Leu
                355                 360                 365

Ile Asp Cys Phe Lys Lys Tyr Cys Trp Cys Tyr His Leu Glu Glu Ile
                370                 375                 380

Phe Arg Lys Val Gln His Ser Phe Glu Val Pro Gly Glu Leu Thr Gln
385                 390                 395                 400

Met Pro Thr Ile Glu Arg Val Ser Met Thr Arg Tyr Phe Tyr Leu Phe
                405                 410                 415

Pro Gly Asn
```

(2) INFORMATION FOR SEQ ID NO:56:

(i) SEQUENCE CHARACTERISTICS:
        (A) LENGTH: 418 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:56:

```
Met Ala Ala Arg Arg Thr His Glu Arg Asp Pro Ile Tyr Lys Ile Lys
1               5                   10                  15

Gly Leu Ala Lys Asp Met Leu Asp Gly Val Phe Asp Asp Leu Val Glu
                20                  25                  30

Lys Asn Val Leu Asn Gly Asp Glu Leu Leu Lys Ile Gly Glu Ser Ala
                35                  40                  45

Ser Phe Ile Leu Asn Lys Ala Glu Asn Leu Val Glu Asn Phe Leu Glu
                50                  55                  60

Lys Thr Asp Met Ala Gly Lys Ile Phe Ala Gly His Ile Ala Asn Ser
```

```
                65                  70                  75                  80
Gln Glu Gln Leu Ser Leu Gln Phe Ser Asn Asp Glu Asp Gly Pro
                    85                  90                  95

Gln Lys Ile Cys Thr Pro Ser Pro Ser Glu Ser Lys Arg Lys Val
                    100                 105                 110

Glu Asp Asp Glu Met Glu Val Asn Ala Gly Leu Ala His Glu Ser His
                    115                 120                 125

Leu Met Leu Thr Ala Pro His Gly Leu Gln Ser Ser Glu Val Gln Asp
                    130                 135                 140

Thr Leu Lys Leu Cys Pro Arg Asp Gln Phe Cys Lys Ile Lys Thr Glu
145                     150                 155                 160

Arg Ala Lys Glu Ile Tyr Pro Val Met Glu Lys Glu Gly Arg Thr Arg
                    165                 170                 175

Leu Ala Leu Ile Ile Cys Asn Lys Lys Phe Asp Tyr Leu Phe Asp Arg
                    180                 185                 190

Asp Asn Ala Asp Thr Asp Ile Leu Asn Met Gln Glu Leu Leu Glu Asn
                    195                 200                 205

Leu Gly Tyr Ser Val Val Leu Lys Glu Asn Leu Thr Ala Gln Glu Met
            210                 215                 220

Glu Thr Glu Leu Met Gln Phe Ala Gly Arg Pro Glu His Gln Ser Ser
225                     230                 235                 240

Asp Ser Thr Pro Gly Val Tyr Val Pro Trp His Pro Gly Arg Asn Leu
                    245                 250                 255

Trp Gly Glu Ala Pro Lys Gln Lys Pro Asp Val Leu His Asp Asp Thr
                    260                 265                 270

Ile Phe Lys Ile Phe Asn Asn Ser Asn Cys Arg Ser Leu Arg Asn Lys
                    275                 280                 285

Pro Lys Ile Leu Ile Met Gln Ala Cys Arg Gly Arg Tyr Asn Gly Thr
            290                 295                 300

Ile Trp Val Ser Thr Asn Lys Gly Ile Ala Thr Ala Asp Thr Asp Glu
305                     310                 315                 320

Glu Arg Val Leu Ser Cys Lys Trp Asn Asn Ser Ile Thr Lys Ala His
                    325                 330                 335

Val Glu Thr Asp Phe Ile Ala Phe Lys Ser Ser Thr Pro His Asn Ile
                    340                 345                 350

Ser Trp Lys Val Gly Lys Thr Gly Ser Leu Phe Ile Ser Lys Leu Ile
                    355                 360                 365

Asp Cys Phe Lys Lys Tyr Cys Trp Cys Tyr His Leu Glu Glu Ile Phe
            370                 375                 380

Arg Lys Val Gln His Ser Phe Glu Val Pro Gly Glu Leu Thr Gln Met
385                     390                 395                 400

Pro Thr Ile Glu Arg Val Ser Met Thr Arg Tyr Phe Tyr Leu Phe Pro
                    405                 410                 415

Gly Asn (2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:57:

ATGCTAACTG TCCAAGTCTA                                                       20
```

(2) INFORMATION FOR SEQ ID NO:58:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:58:

TCCAACAGCA GGAATAGCA                                                19

(2) INFORMATION FOR SEQ ID NO:59:

(i) SEQUENCE CHARACTERISTICS:
        (A) LENGTH: 29 base pairs
        (B) TYPE: nucleic acid
        (C) STRANDEDNESS: both
        (D) TOPOLOGY: both (xi) SEQUENCE DESCRIPTION: SEQ ID NO:59:

TGATCGCCAT CGGGGAAATC GAGGTAGAA                                29

(2) INFORMATION FOR SEQ ID NO:60:

(i) SEQUENCE CHARACTERISTICS:
        (A) LENGTH: 29 base pairs
        (B) TYPE: nucleic acid
        (C) STRANDEDNESS: both
        (D) TOPOLOGY: both (xi) SEQUENCE DESCRIPTION: SEQ ID NO:60:

ATCATATCAT CCAGGCATCG TGCAGAGGG                                29

(2) INFORMATION FOR SEQ ID NO:61:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:61:

GTTGCACTGC TTTCACGATC TCCCGTCTCT                               30

(2) INFORMATION FOR SEQ ID NO:62:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:62:

TCATCGACTT TTAGATGACT AGAGAACATC                               30

(2) INFORMATION FOR SEQ ID NO:63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:63:

GTTTAATTAC CCAAGTTTGA G                                              21

(2) INFORMATION FOR SEQ ID NO:64:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:64:

CCGGTGACAT TGGACACTC                                      19

(2) INFORMATION FOR SEQ ID NO:65:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:65:

ACTATTCAAC ACTTG                                        15

(2) INFORMATION FOR SEQ ID NO:66:

(i) SEQUENCE CHARACTERISTICS:
        (A) LENGTH: 5 amino acids
        (B) TYPE: amino acid
        (D) TOPOLOGY: both (xi) SEQUENCE DESCRIPTION: SEQ ID NO:66:

Gln Ala Cys Arg Gly
1            5

(2) INFORMATION FOR SEQ ID NO:67:

(i) SEQUENCE CHARACTERISTICS:
        (A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:67:

CAACCCTGTA ACTCTTGATT                                  20

(2) INFORMATION FOR SEQ ID NO:68:

(i) SEQUENCE CHARACTERISTICS:
        (A) LENGTH: 21 base pairs
        (B) TYPE: nucleic acid
        (C) STRANDEDNESS: both
        (D) TOPOLOGY: both (xi) SEQUENCE DESCRIPTION: SEQ ID NO:68:

ACCTCTTTGG AGCTACCAGA A                                21

(2) INFORMATION FOR SEQ ID NO:69:

(i) SEQUENCE CHARACTERISTICS:
        (A) LENGTH: 28 base pairs
        (B) TYPE: nucleic acid
        (C) STRANDEDNESS: both
        (D) TOPOLOGY: both (xi) SEQUENCE DESCRIPTION: SEQ ID NO:69:

CCAGATCTAT GCTAACTGTC CAAGTCTA                        28

```
(2) INFORMATION FOR SEQ ID NO:70:

(i) SEQUENCE CHARACTERISTICS:
        (A) LENGTH: 28 base pairs
        (B) TYPE: nucleic acid
        (C) STRANDEDNESS: both
        (D) TOPOLOGY: both (xi) SEQUENCE DESCRIPTION: SEQ ID NO:70:

AAGAGCTCCT CCAACAGCAG GAATAGCA                                              28

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:71:

AGAAGCACTT GTCTCTGCTC                                                       20

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:72:

TTGGCACCTG ATGGCAATAC                                                       20

(2) INFORMATION FOR SEQ ID NO:73:

(i) SEQUENCE CHARACTERISTICS:
        (A) LENGTH: 21 base pairs
        (B) TYPE: nucleic acid
        (C) STRANDEDNESS: both
        (D) TOPOLOGY: both (xi) SEQUENCE DESCRIPTION: SEQ ID NO:73:

GATATCCGCA CAAGGAGCTG A                                                     21

(2) INFORMATION FOR SEQ ID NO:74:

(i) SEQUENCE CHARACTERISTICS:
        (A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:74:

CTATAGGTGG GAGGGTGTCC                                                       20

(2) INFORMATION FOR SEQ ID NO:75:

(i) SEQUENCE CHARACTERISTICS:
        (A) LENGTH: 23 base pairs
        (B) TYPE: nucleic acid
        (C) STRANDEDNESS: both
        (D) TOPOLOGY: both (xi) SEQUENCE DESCRIPTION: SEQ ID NO:75:

GATATCCAGA GGGAGGGAAC GAT                                                   23

(2) INFORMATION FOR SEQ ID NO:76:
```

(i) SEQUENCE CHARACTERISTICS:
            (A) LENGTH: 23 base pairs
            (B) TYPE: nucleic acid
            (C) STRANDEDNESS: both
            (D) TOPOLOGY: both (xi) SEQUENCE DESCRIPTION: SEQ ID NO:76:

GATATCAGAG CAAGAGAGGC GGT                                               23

(2) INFORMATION FOR SEQ ID NO:77:

(i) SEQUENCE CHARACTERISTICS:
            (A) LENGTH: 21 base pairs
            (B) TYPE: nucleic acid
            (C) STRANDEDNESS: both
            (D) TOPOLOGY: both (xi) SEQUENCE DESCRIPTION: SEQ ID NO:77:

GATATCGTGG GAGGGTGTCC T                                                 21

(2) INFORMATION FOR SEQ ID NO:78:

(i) SEQUENCE CHARACTERISTICS:
            (A) LENGTH: 21 base pairs
            (B) TYPE: nucleic acid
            (C) STRANDEDNESS: both
            (D) TOPOLOGY: both (xi) SEQUENCE DESCRIPTION: SEQ ID NO:78:

ATCCAGGCCT CTAGAGGAGA T                                                 21

(2) INFORMATION FOR SEQ ID NO:79:

(i) SEQUENCE CHARACTERISTICS:
            (A) LENGTH: 21 base pairs
            (B) TYPE: nucleic acid
            (C) STRANDEDNESS: both
            (D) TOPOLOGY: both (xi) SEQUENCE DESCRIPTION: SEQ ID NO:79:

ATCTCCTCTA GAGGCCTGGA T                                                 21

(2) INFORMATION FOR SEQ ID NO:80:

(i) SEQUENCE CHARACTERISTICS:
            (A) LENGTH: 21 base pairs
            (B) TYPE: nucleic acid
            (C) STRANDEDNESS: both
            (D) TOPOLOGY: both (xi) SEQUENCE DESCRIPTION: SEQ ID NO:80:

TGCGGCTATA CGTGCCTCAA A                                                 21

(2) INFORMATION FOR SEQ ID NO:81:

(i) SEQUENCE CHARACTERISTICS:
            (A) LENGTH: 21 base pairs
            (B) TYPE: nucleic acid
            (C) STRANDEDNESS: both
            (D) TOPOLOGY: both (xi) SEQUENCE DESCRIPTION: SEQ ID NO:81:

TTTGAGGCAC GTATAGCCGC A                                                 21

(2) INFORMATION FOR SEQ ID NO:82:

(i) SEQUENCE CHARACTERISTICS:
        (A) LENGTH: 24 base pairs
        (B) TYPE: nucleic acid
        (C) STRANDEDNESS: both
        (D) TOPOLOGY: both (xi) SEQUENCE DESCRIPTION: SEQ ID NO:82:

ATTCCGCACA AGGAGCTGAT GGCC                                              24

(2) INFORMATION FOR SEQ ID NO:83:

(i) SEQUENCE CHARACTERISTICS:
        (A) LENGTH: 19 base pairs
        (B) TYPE: nucleic acid
        (C) STRANDEDNESS: both
        (D) TOPOLOGY: both (xi) SEQUENCE DESCRIPTION: SEQ ID NO:83:

GCTGGTCGAC ACCTCTATC                                                    19

(2) INFORMATION FOR SEQ ID NO:84:

(i) SEQUENCE CHARACTERISTICS:
        (A) LENGTH: 23 base pairs
        (B) TYPE: nucleic acid
        (C) STRANDEDNESS: both
        (D) TOPOLOGY: both (xi) SEQUENCE DESCRIPTION: SEQ ID NO:84:

CAAGCTTTTG ATGCCTTCTG TGA                                               23

(2) INFORMATION FOR SEQ ID NO:85:

(i) SEQUENCE CHARACTERISTICS:
        (A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:85:

CTCCAACAGC AGGAATAGCA                                                   20

(2) INFORMATION FOR SEQ ID NO:86:

(i) SEQUENCE CHARACTERISTICS:
        (A) LENGTH: 35 base pairs
        (B) TYPE: nucleic acid
        (C) STRANDEDNESS: both
        (D) TOPOLOGY: both (xi) SEQUENCE DESCRIPTION: SEQ ID NO:86:

GCGATCTTTC GATCGCGATC TTTCTGTCGG AAGGC                                  35

(2) INFORMATION FOR SEQ ID NO:87:

(i) SEQUENCE CHARACTERISTICS:
        (A) LENGTH: 38 base pairs
        (B) TYPE: nucleic acid
        (C) STRANDEDNESS: both
        (D) TOPOLOGY: both (xi) SEQUENCE DESCRIPTION: SEQ ID NO:87:

CAGATCGCCT TGTAGATAGA AAGAACATCT TTGATCGG                               38

(2) INFORMATION FOR SEQ ID NO:88:

(i) SEQUENCE CHARACTERISTICS:

(A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:88:

ATGCTAACTG TCCAAGTCTA                     20

(2) INFORMATION FOR SEQ ID NO:89:

(i) SEQUENCE CHARACTERISTICS:
        (A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:89:

GTCTCATCTT CATCAACTCC                     20

(2) INFORMATION FOR SEQ ID NO:90:

(i) SEQUENCE CHARACTERISTICS:
        (A) LENGTH: 22 base pairs
        (B) TYPE: nucleic acid
        (C) STRANDEDNESS: both
        (D) TOPOLOGY: both (xi) SEQUENCE DESCRIPTION: SEQ ID NO:90:

GTTACCTGCA CACCGAGTCA CG                  22

(2) INFORMATION FOR SEQ ID NO:91:

(i) SEQUENCE CHARACTERISTICS:
        (A) LENGTH: 30 base pairs
        (B) TYPE: nucleic acid
        (C) STRANDEDNESS: both
        (D) TOPOLOGY: both (xi) SEQUENCE DESCRIPTION: SEQ ID NO:91:

GCGTGGTTCT TCTTTCCATC TTGTTGGTCA          30

(2) INFORMATION FOR SEQ ID NO:92:

(i) SEQUENCE CHARACTERISTICS:
        (A) LENGTH: 27 base pairs
        (B) TYPE: nucleic acid
        (C) STRANDEDNESS: both
        (D) TOPOLOGY: both (xi) SEQUENCE DESCRIPTION: SEQ ID NO:92:

ACCTTAATAT GCAAGACTCT CAAGGAG             27

(2) INFORMATION FOR SEQ ID NO:93:

(i) SEQUENCE CHARACTERISTICS:
        (A) LENGTH: 27 base pairs
        (B) TYPE: nucleic acid
        (C) STRANDEDNESS: both
        (D) TOPOLOGY: both (xi) SEQUENCE DESCRIPTION: SEQ ID NO:93:

GCGGCTTGAC TTGTCCATTA TTGGATA             27

(2) INFORMATION FOR SEQ ID NO:94:

(i) SEQUENCE CHARACTERISTICS:
        (A) LENGTH: 20 base pairs

```
        (B) TYPE: nucleic acid
        (C) STRANDEDNESS: both
        (D) TOPOLOGY: both (xi) SEQUENCE DESCRIPTION: SEQ ID NO:94:

GACCTGACAG ACTACCTCAT                                              20

(2) INFORMATION FOR SEQ ID NO:95:

(i) SEQUENCE CHARACTERISTICS:
        (A) LENGTH: 20 base pairs
        (B) TYPE: nucleic acid
        (C) STRANDEDNESS: both
        (D) TOPOLOGY: both (xi) SEQUENCE DESCRIPTION: SEQ ID NO:95:

AGACAGCACT GTGTTGGCAT                                              20
```